United States Patent
Gillis et al.

(10) Patent No.: US 9,334,279 B2
(45) Date of Patent: May 10, 2016

(54) HEPATITIS C VIRUS INHIBITORS

(71) Applicant: BRISTOL-MYERS SQUIBB COMPANY, Princeton, NJ (US)

(72) Inventors: Eric P. Gillis, Cheshire, CT (US); Michael S. Bowsher, Prospect, CT (US); Paul Michael Scola, Glastonbury, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/436,760

(22) PCT Filed: Oct. 31, 2013

(86) PCT No.: PCT/US2013/067745
§ 371 (c)(1),
(2) Date: Apr. 17, 2015

(87) PCT Pub. No.: WO2014/071007
PCT Pub. Date: May 8, 2014

(65) Prior Publication Data
US 2015/0329547 A1    Nov. 19, 2015

Related U.S. Application Data

(60) Provisional application No. 61/721,565, filed on Nov. 2, 2012.

(51) Int. Cl.
| | | |
|---|---|---|
| *C07D 487/04* | (2006.01) | |
| *A61K 31/497* | (2006.01) | |
| *A61K 31/4439* | (2006.01) | |
| *A61K 31/444* | (2006.01) | |
| *A61K 31/506* | (2006.01) | |
| *A61K 45/06* | (2006.01) | |
| *C07D 487/12* | (2006.01) | |

(52) U.S. Cl.
CPC ............ *C07D 487/04* (2013.01); *A61K 31/444* (2013.01); *A61K 31/4439* (2013.01); *A61K 31/497* (2013.01); *A61K 31/506* (2013.01); *A61K 45/06* (2013.01); *C07D 487/12* (2013.01)

(58) Field of Classification Search
None
See application file for complete search history.

(56) References Cited

U.S. PATENT DOCUMENTS

| | | |
|---|---|---|
| 5,223,432 A | 6/1993 | Wirz et al. |
| 7,449,479 B2 | 11/2008 | Wang et al. |
| 7,582,605 B2 | 9/2009 | Moore et al. |
| 7,601,709 B2 | 10/2009 | Miao et al. |
| 7,605,126 B2 | 10/2009 | Niu et al. |
| 7,635,683 B2 | 12/2009 | Gai et al. |
| 7,915,291 B2 | 3/2011 | Wang et al. |
| 8,232,246 B2 | 7/2012 | McDaniel et al. |
| 8,268,776 B2 | 9/2012 | Sun et al. |
| 8,299,094 B2 | 10/2012 | Wang et al. |
| 8,309,685 B2 | 11/2012 | Petter et al. |
| 8,338,606 B2 | 12/2012 | Perrone et al. |
| 8,415,374 B2 | 4/2013 | Lemm et al. |
| 8,507,722 B2 | 8/2013 | Wang |
| 8,710,229 B2 | 4/2014 | Wang et al. |
| 2005/0209135 A1 | 9/2005 | Busacca et al. |
| 2006/0199773 A1 | 9/2006 | Sausker et al. |
| 2006/0257980 A1 | 11/2006 | Li |
| 2007/0078081 A1 | 4/2007 | Casarez et al. |
| 2008/0279821 A1 | 11/2008 | Niu et al. |
| 2013/0302414 A1 | 11/2013 | Perrone |
| 2014/0235617 A1 | 8/2014 | Gao et al. |

FOREIGN PATENT DOCUMENTS

| | | |
|---|---|---|
| WO | WO 98/17679 A1 | 4/1998 |
| WO | WO 98/22106 A1 | 5/1998 |
| WO | WO 99/07733 A2 | 2/1999 |
| WO | WO 99/07734 A2 | 2/1999 |
| WO | WO 00/09543 A2 | 2/2000 |

(Continued)

OTHER PUBLICATIONS

Eley, T. et al., "Improved Bioavailability and Mitigated Food Effect for Asunaprevir (ASV) Utilizing a Lipid-Based Formulation: Similar Exposure with 100mg BID Softgel Capsule (SGC) Relative to 200mg BID of Phase 2 Tablet", Abstract No. A-1247, Interscience Conference on Antimicrobial Agents and Chemotherapy, (Sep. 12, 2012).
Lauer, G.M. et al., "Hepatitis C Virus Infection", The New England Journal of Medicine, vol. 345, No. 1, pp. 41-52 (2001).
Llinàs-Brunet, M. et al., "A Systematic Approach to the Optimization of Substrate-Based Inhibitors of the Hepatitis C Virus NS3 Protease: Discovery of Potent and Specific Tripeptide Inhibitors", Journal of Medicinal Chemistry, vol. 47, No. 26, pp. 6584-6594 (2004).
Poupart, M.-A. et al., "Solid-Phase Synthesis of Peptidomimetic Inhibitors for the Hepatitis C Virus NS3 Protease", The Journal of Organic Chemistry, vol. 66, No. 14, pp. 4743-4751 (2001).

(Continued)

*Primary Examiner* — Yevegeny Valenrod
(74) *Attorney, Agent, or Firm* — Pamela A. Mingo

(57) ABSTRACT

Hepatitis C virus inhibitors having the general formula (I) are disclosed. Compositions comprising the compounds and methods for using the compounds to inhibit HCV are also disclosed.

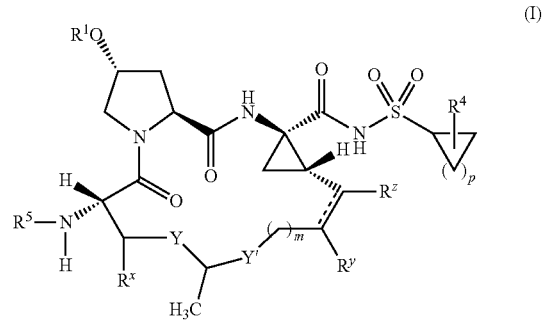

(I)

20 Claims, No Drawings

(56) References Cited

FOREIGN PATENT DOCUMENTS

| | | |
|---|---|---|
| WO | WO 00/09558 A1 | 2/2000 |
| WO | WO 00/59929 A1 | 10/2000 |
| WO | WO 02/08244 A2 | 1/2002 |
| WO | WO 02/060926 A2 | 8/2002 |
| WO | WO 03/053349 A2 | 7/2003 |
| WO | WO 03/062265 A2 | 7/2003 |
| WO | WO 03/064416 A1 | 8/2003 |
| WO | WO 03/064455 A2 | 8/2003 |
| WO | WO 03/064456 A1 | 8/2003 |
| WO | WO 03/066103 A1 | 8/2003 |
| WO | WO 03/099274 A1 | 12/2003 |
| WO | WO 03/099316 A1 | 12/2003 |
| WO | WO 2004/009121 A1 | 1/2004 |
| WO | WO 2004/032827 A2 | 4/2004 |
| WO | WO 2004/037855 A1 | 5/2004 |
| WO | WO 2004/043339 A2 | 5/2004 |
| WO | WO 2004/072243 A2 | 8/2004 |
| WO | WO 2004/093798 A2 | 11/2004 |
| WO | WO 2004/093915 A1 | 11/2004 |
| WO | WO 2004/094452 A2 | 11/2004 |
| WO | WO 2004/101602 A2 | 11/2004 |
| WO | WO 2004/101605 A1 | 11/2004 |
| WO | WO 2004/103996 A1 | 12/2004 |
| WO | WO 2004/113365 A2 | 12/2004 |
| WO | WO 2005/010029 A1 | 2/2005 |
| WO | WO 2005/028501 A1 | 3/2005 |
| WO | WO 2005/037214 A2 | 4/2005 |
| WO | WO 2005/037860 A2 | 4/2005 |
| WO | WO 2005/046712 A1 | 5/2005 |
| WO | WO 2005/051410 A1 | 6/2005 |
| WO | WO 2005/051980 A1 | 6/2005 |
| WO | WO 2005/054430 A2 | 6/2005 |
| WO | WO 2005/070955 A1 | 8/2005 |
| WO | WO 2005/073216 A2 | 8/2005 |
| WO | WO 2005/095403 A2 | 10/2005 |
| WO | WO 2005/116054 A1 | 12/2005 |
| WO | WO 2006/000085 A1 | 1/2006 |
| WO | WO 2006/007700 A1 | 1/2006 |
| WO | WO 2006/007708 A1 | 1/2006 |
| WO | WO 2006/016930 A2 | 2/2006 |
| WO | WO 2006/020276 A2 | 2/2006 |
| WO | WO 2006/026352 A1 | 3/2006 |
| WO | WO 2006/033878 A1 | 3/2006 |
| WO | WO 2006/043145 A1 | 4/2006 |
| WO | WO 2006/086381 A2 | 8/2006 |
| WO | WO 2006/096652 A2 | 9/2006 |
| WO | WO 2006/119061 A2 | 11/2006 |
| WO | WO 2006/122188 A2 | 11/2006 |
| WO | WO 2006/130552 A2 | 12/2006 |
| WO | WO 2006/130553 A2 | 12/2006 |
| WO | WO 2006/130554 A2 | 12/2006 |
| WO | WO 2006/130607 A2 | 12/2006 |
| WO | WO 2006/130626 A2 | 12/2006 |
| WO | WO 2006/130627 A2 | 12/2006 |
| WO | WO 2006/130628 A2 | 12/2006 |
| WO | WO 2006/130666 A2 | 12/2006 |
| WO | WO 2006/130686 A2 | 12/2006 |
| WO | WO 2006/130687 A2 | 12/2006 |
| WO | WO 2006/130688 A2 | 12/2006 |
| WO | WO 2007/001406 A2 | 1/2007 |
| WO | WO 2007/008657 A2 | 1/2007 |
| WO | WO 2007/009109 A2 | 1/2007 |
| WO | WO 2007/009227 A1 | 1/2007 |
| WO | WO 2007/011658 A1 | 1/2007 |
| WO | WO 2007/014918 A1 | 2/2007 |
| WO | WO 2007/014919 A1 | 2/2007 |
| WO | WO 2007/014920 A1 | 2/2007 |
| WO | WO 2007/014921 A1 | 2/2007 |
| WO | WO 2007/014922 A1 | 2/2007 |
| WO | WO 2007/014923 A1 | 2/2007 |
| WO | WO 2007/014924 A1 | 2/2007 |
| WO | WO 2007/014925 A1 | 2/2007 |
| WO | WO 2007/014926 A1 | 2/2007 |
| WO | WO 2007/014927 A2 | 2/2007 |
| WO | WO 2007/015787 A1 | 2/2007 |
| WO | WO 2007/015824 A2 | 2/2007 |
| WO | WO 2007/015855 A1 | 2/2007 |
| WO | WO 2007/016441 A1 | 2/2007 |
| WO | WO 2007/016476 A2 | 2/2007 |
| WO | WO 2007/017144 A2 | 2/2007 |
| WO | WO 2007/025307 A2 | 3/2007 |
| WO | WO 2007/030656 A1 | 3/2007 |
| WO | WO 2007/044893 A2 | 4/2007 |
| WO | WO 2007/044933 A1 | 4/2007 |
| WO | WO 2007/056120 A1 | 5/2007 |
| WO | WO 2007/082131 A1 | 7/2007 |
| WO | WO 2007/106317 A2 | 9/2007 |
| WO | WO 2007/120595 A2 | 10/2007 |
| WO | WO 2007/131966 A1 | 11/2007 |
| WO | WO 2007/143694 A2 | 12/2007 |
| WO | WO 2007/148135 A1 | 12/2007 |
| WO | WO 2008/002924 A2 | 1/2008 |
| WO | WO 2008/005511 A2 | 1/2008 |
| WO | WO 2008/005565 A2 | 1/2008 |
| WO | WO 2008/008502 A1 | 1/2008 |
| WO | WO 2008/008776 A2 | 1/2008 |
| WO | WO 2008/019266 A2 | 2/2008 |
| WO | WO 2008/019289 A2 | 2/2008 |
| WO | WO 2008/019303 A2 | 2/2008 |
| WO | WO 2008/021733 A2 | 2/2008 |
| WO | WO 2008/021871 A2 | 2/2008 |
| WO | WO 2008/021956 A2 | 2/2008 |
| WO | WO 2008/021960 A2 | 2/2008 |
| WO | WO 2008/022006 A2 | 2/2008 |
| WO | WO 2008/051475 A2 | 5/2008 |
| WO | WO 2008/051477 A2 | 5/2008 |
| WO | WO 2008/051514 A2 | 5/2008 |
| WO | WO 2008/057208 A2 | 5/2008 |
| WO | WO 2008/057209 A1 | 5/2008 |
| WO | WO 2008/057871 A2 | 5/2008 |
| WO | WO 2008/057873 A2 | 5/2008 |
| WO | WO 2008/057875 A2 | 5/2008 |
| WO | WO 2008/057995 A2 | 5/2008 |
| WO | WO 2008/059046 A1 | 5/2008 |
| WO | WO 2008/060927 A2 | 5/2008 |
| WO | WO 2008/064057 A1 | 5/2008 |
| WO | WO 2008/064061 A1 | 5/2008 |
| WO | WO 2008/064066 A1 | 5/2008 |
| WO | WO 2008/070358 A2 | 6/2008 |
| WO | WO 2008/086161 A1 | 7/2008 |
| WO | WO 2008/092954 A2 | 8/2008 |
| WO | WO 2008/092955 A1 | 8/2008 |
| WO | WO 2008/095058 A1 | 8/2008 |
| WO | WO 2008/095999 A1 | 8/2008 |
| WO | WO 2008/096001 A1 | 8/2008 |
| WO | WO 2008/096002 A1 | 8/2008 |
| WO | WO 2008/098368 A1 | 8/2008 |
| WO | WO 2008/101665 A1 | 8/2008 |
| WO | WO 2008/106130 A2 | 9/2008 |
| WO | WO 2008/128921 A1 | 10/2008 |
| WO | WO 2008/134395 A1 | 11/2008 |
| WO | WO 2008/134397 A1 | 11/2008 |
| WO | WO 2008/134398 A1 | 11/2008 |
| WO | WO 2008/137779 A2 | 11/2008 |
| WO | WO 2008/141227 A1 | 11/2008 |
| WO | WO 2009/005676 A1 | 1/2009 |
| WO | WO 2009/005677 A2 | 1/2009 |
| WO | WO 2009/005690 A2 | 1/2009 |
| WO | WO 2009/010804 A1 | 1/2009 |
| WO | WO 2009/014730 A1 | 1/2009 |
| WO | WO 2009/047264 A1 | 4/2009 |
| WO | WO 2009/053828 A2 | 4/2009 |
| WO | WO 2009/055335 A2 | 4/2009 |
| WO | WO 2009/064955 A1 | 5/2009 |
| WO | WO 2009/064975 A1 | 5/2009 |
| WO | WO 2009/070689 A1 | 6/2009 |
| WO | WO 2009/070692 A1 | 6/2009 |
| WO | WO 2009/073713 A1 | 6/2009 |
| WO | WO 2009/073719 A1 | 6/2009 |
| WO | WO 2009/073780 A1 | 6/2009 |
| WO | WO 2009/076166 A2 | 6/2009 |
| WO | WO 2009/076173 A2 | 6/2009 |
| WO | WO 2009/079352 A1 | 6/2009 |

(56) References Cited

FOREIGN PATENT DOCUMENTS

| | | |
|---|---|---|
| WO | WO 2009/079353 A1 | 6/2009 |
| WO | WO 2009/080542 A1 | 7/2009 |
| WO | WO 2009/082697 A1 | 7/2009 |
| WO | WO 2009/082701 A1 | 7/2009 |
| WO | WO 2009/085659 A1 | 7/2009 |
| WO | WO 2009/094438 A1 | 7/2009 |
| WO | WO 2009/094443 A1 | 7/2009 |
| WO | WO 2009/108507 A1 | 9/2009 |
| WO | WO 2009/117594 A1 | 9/2009 |
| WO | WO 2009/129109 A1 | 10/2009 |
| WO | WO 2009/134624 A1 | 11/2009 |
| WO | WO 2009/134987 A1 | 11/2009 |
| WO | WO 2009/139792 A1 | 11/2009 |
| WO | WO 2009/140475 A1 | 11/2009 |
| WO | WO 2009/140500 A1 | 11/2009 |
| WO | WO 2009/142842 A2 | 11/2009 |
| WO | WO 2009/146347 A1 | 12/2009 |
| WO | WO 2009/148923 A1 | 12/2009 |
| WO | WO 2010/011566 A1 | 1/2010 |
| WO | WO 2010/015545 A1 | 2/2010 |
| WO | WO 2010/030359 A2 | 3/2010 |
| WO | WO 2010/031829 A1 | 3/2010 |
| WO | WO 2010/031832 A2 | 3/2010 |
| WO | WO 2010/033466 A1 | 3/2010 |
| WO | WO 2010/034105 A1 | 4/2010 |
| WO | WO 2010/036551 A1 | 4/2010 |
| WO | WO 2010/036871 A1 | 4/2010 |
| WO | WO 2010/036896 A1 | 4/2010 |
| WO | WO 2010/059937 A1 | 5/2010 |
| WO | WO 2010/065577 A1 | 6/2010 |
| WO | WO 2010/068760 A2 | 6/2010 |
| WO | WO 2010/068761 A2 | 6/2010 |
| WO | WO 2010/075127 A1 | 7/2010 |
| WO | WO 2010/077783 A1 | 7/2010 |
| WO | WO 2010/080389 A1 | 7/2010 |
| WO | WO 2010/088394 A1 | 8/2010 |
| WO | WO 2010/115981 A1 | 10/2010 |
| WO | WO 2010/116248 A1 | 10/2010 |
| WO | WO 2010/132163 A1 | 11/2010 |
| WO | WO 2010/145523 A1 | 12/2010 |
| WO | WO 2011/002807 A1 | 1/2011 |
| WO | WO 2011/002808 A1 | 1/2011 |
| WO | WO 2011/005646 A2 | 1/2011 |
| WO | WO 2011/014487 A1 | 2/2011 |
| WO | WO 2011/025849 A1 | 3/2011 |
| WO | WO 2011/034518 A1 | 3/2011 |
| WO | WO 2011/038283 A1 | 3/2011 |
| WO | WO 2011/038293 A1 | 3/2011 |
| WO | WO 2011/041551 A1 | 4/2011 |
| WO | WO 2011/046811 A1 | 4/2011 |
| WO | WO 2011/049908 A2 | 4/2011 |
| WO | WO 2011/063501 A1 | 6/2011 |
| WO | WO 2011/063502 A1 | 6/2011 |
| WO | WO 2011/072370 A1 | 6/2011 |
| WO | WO 2011/091757 A1 | 8/2011 |
| WO | WO 2011/112558 A2 | 9/2011 |
| WO | WO 2011/150190 A2 | 12/2011 |
| WO | WO 2011/156337 A2 | 12/2011 |
| WO | WO 2012/018829 A1 | 2/2012 |
| WO | WO2012/019299 * 2/2012 | ............ C07K 5/083 |
| WO | WO 2012/019299 A1 | 2/2012 |
| WO | WO 2012/037259 A1 | 3/2012 |
| WO | WO 2012/040040 A1 | 3/2012 |
| WO | WO 2012/040167 A1 | 3/2012 |
| WO | WO 2012/040242 A1 | 3/2012 |
| WO | WO 2012/047764 A1 | 4/2012 |
| WO | WO 2012/054874 A1 | 4/2012 |
| WO | WO 2012/082672 A2 | 6/2012 |
| WO | WO 2012/092409 A2 | 7/2012 |
| WO | WO 2012/092411 A2 | 7/2012 |
| WO | WO 2012/151195 A1 | 11/2012 |
| WO | WO 2012/166459 A1 | 12/2012 |
| WO | WO 2012/173983 A1 | 12/2012 |
| WO | WO 2013/028465 A1 | 2/2013 |
| WO | WO 2013/028470 A1 | 2/2013 |
| WO | WO 2013/028471 A1 | 2/2013 |
| WO | WO 2013/040568 A1 | 3/2013 |
| WO | WO 2013/066753 A1 | 5/2013 |
| WO | WO 2013/074386 A2 | 5/2013 |
| WO | WO 2013/106689 A1 | 7/2013 |
| WO | WO 2013/120371 A1 | 8/2013 |
| WO | WO 2014/008285 A1 | 1/2014 |
| WO | WO 2014/019344 A1 | 2/2014 |
| WO | WO 2014/025736 A1 | 2/2014 |
| WO | WO 2014/062196 A1 | 4/2014 |
| WO | WO 2014/070964 A1 | 5/2014 |
| WO | WO 2014/070974 A1 | 5/2014 |
| WO | WO 2014/071032 A1 | 5/2014 |
| WO | WO 2014/137869 A1 | 9/2014 |

OTHER PUBLICATIONS

Ribeiro, C.M.R. et al., "Ultrasound in enzymatic resolution of ethyl 3-hydroxy-3-phenylpropanoate", Tetrahedron Letters, vol. 42, pp. 6477-6479 (2001).

Tsantrizos, Y.S. et al., "Olefin ring-closing metathesis as a powerful tool in drug discovery and development—potent macrocyclic inhibitors of the hepatitis C virus NS3 protease", Journal of Organometallic Chemistry, vol. 691, pp. 5163-5174 (2006).

Wirz, B. et al., "Enzymatic preparation of homochiral 2-isobutyl succinic acid derivatives", Tetrahedron: Asymmetry, vol. 8, No. 2, pp. 187-189 (1997).

Yang, S. et al., "Chemoenzymatic Synthesis of (R)-(—)-Citramalic Acid", Synthesis, pp. 365-366 (1992).

* cited by examiner

HEPATITIS C VIRUS INHIBITORS

The present disclosure is generally directed to antiviral compounds, and more specifically directed to compounds which inhibit the function of the NS3 protease (also referred to herein as "serine protease") encoded by Hepatitis C virus (HCV), compositions comprising such compounds, and methods for inhibiting the function of the NS3 protease.

HCV is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma.

Presently, the most effective HCV therapy employs a combination of alpha-interferon and ribavirin, leading to sustained efficacy in 40% of patients. Recent clinical results demonstrate that pegylated alpha-interferon is superior to unmodified alpha-interferon as monotherapy. However, even with experimental therapeutic regimens involving combinations of pegylated alpha-interferon and ribavirin, a substantial fraction of patients do not have a sustained reduction in viral load. Thus, there is a clear and unmet need to develop effective therapeutics for treatment of HCV infection.

HCV is a positive-stranded RNA virus. Based on a comparison of the deduced amino acid sequence and the extensive similarity in the 5' untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. Six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one cleaves at the NS2-NS3 junction; the second one is a serine protease contained within the N-terminal region of NS3 and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a co-factor for the NS3 protease and possibly assisting in the membrane localization of NS3 and other viral replicase components. The complex formation of the NS3 protein with NS4A is essential for efficient polyprotein processing, enhancing the proteolytic cleavage at all of the sites. The NS3 protein also exhibits nucleoside triphosphatase and RNA helicase activities. NS5B is a RNA-dependent RNA polymerase that is involved in the replication of HCV.

The present disclosure provides peptide compounds that can inhibit the functioning of the NS3 protease, e.g., in combination with the NS4A protease. Further, the present disclosure describes the administration of combination therapy to a patient whereby a compound in accordance with the present disclosure, which is effective to inhibit the HCV NS3 protease, can be administered with additional compounds having anti-HCV activity.

In its first aspect the present disclosure provides a compound of formula (I)

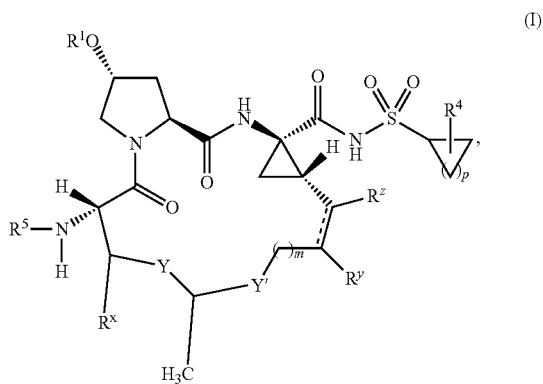

(I)

or a pharmaceutically acceptable salt thereof, wherein
p is 1 or 2;
----- is a single or double bond;
$R^1$ is

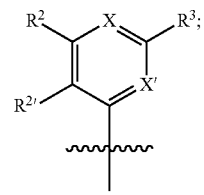

m is 0, 1, or 2;
one of X and X' is N and the other is selected from CH and $CR^{3'}$;
$R^2$, $R^{2'}$, $R^3$, and $R^{3'}$ are independently selected from hydrogen, alkoxy, alkyl, aryl, halo, haloalkyl, and heteroaryl, wherein the aryl and heteroaryl are optionally substituted with one group independently selected from alkoxy and alkyl;
$R^x$ is selected from methyl and ethyl;
$R^y$ and $R^z$ are independently selected from hydrogen and hydroxy; provided that when ----- is a double bond, $R^y$ and $R^z$ are each hydrogen;
$R^4$ is selected from hydrogen, alkyl, and halo, haloalkoxy, haloalkyl, and hydroxyalkyl;
$R^5$ is selected from hydrogen, alkoxyalkoxycarbonyl, alkoxycarbonyl, alkylaminocarbonyl, alkylcarbonyl, cycloalkylalkoxycarbonyl, cycloalkylcarbonyl, cycloalkyloxycarbonyl, deuteroalkoxycarbonyl, deuterohaloalkoxycarbonyl, dialkylaminocarbonyl, dialkylaminocarbonylcarbonyl, haloalkoxycarbonyl, haloalkylaminocarbonyl, haloalkylcarbonyl, heterocyclylcarbonyl, heterocyclyloxycarbonyl, phenylcarbonyl, and phenyloxycarbonyl, wherein the cycloalkyl part of the cycloalkylalkoxycarbonyl, the cycloalkylcarbonyl, and the cycloalkyloxycarbonyl, the heterocyclyl part of the heterocyclylcarbonyl and the heterocyclyloxycarbonyl, and the phenyl part of the phenylcarbonyl and the phenyloxycarbonyl, is optionally substituted with one, two, or three groups independently selected from alkyl, alkylamino, alkylcarbonyl, cycloalkyl, dialkylamino, halo, haloalkoxy, and haloalkyl;

and
one of Y and Y' is CH$_2$ and the other is selected from CH$_2$ and O.

In a first embodiment of the first aspect the present disclosure provides a compound of formula (I), or a pharmaceutically acceptable salt thereof, wherein m is 1. In a second embodiment ----- is a double bond.

In a third embodiment of the first aspect the present disclosure provides a compound of formula (I), or a pharmaceutically acceptable salt thereof, wherein p is 1.

In a fourth embodiment of the first aspect the present disclosure provides a compound of formula (I), or a pharmaceutically acceptable salt thereof, wherein R$^4$ is selected from hydrogen and alkyl.

In a fifth embodiment of the first aspect the present disclosure provides a compound of formula (I), or a pharmaceutically acceptable salt thereof, wherein R$^5$ is selected from alkoxycarbonyl, haloalkoxycarbonyl, heterocyclyloxycarbonyl, and phenyloxycarbonyl, wherein the heterocyclyl part of the heterocyclyloxycarbonyl, and the phenyl part of the phenyloxycarbonyl is optionally substituted with one, two, or three groups independently selected from alkyl, halo, haloalkoxy, and haloalkyl.

In a second aspect the present disclosure provides a compound of formula (II)

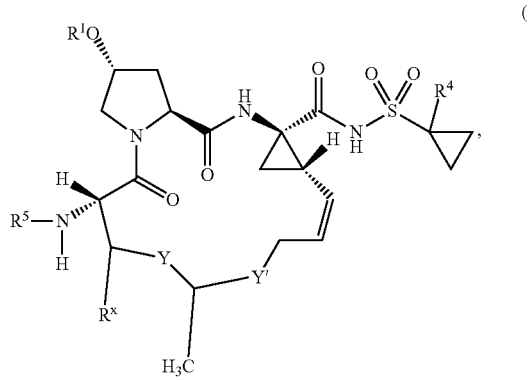

(II)

or a pharmaceutically acceptable salt thereof, wherein R$^1$ is

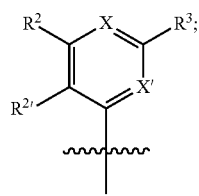

one of X and X' is N and the other is selected from CH and CR$^{3'}$;

R$^2$, R$^{2'}$, R$^3$, and R$^{3'}$ are independently selected from hydrogen, alkoxy, alkyl, aryl, halo, haloalkyl, and heteroaryl, wherein the aryl and heteroaryl are optionally substituted with one group independently selected from alkoxy and alkyl;

R$^x$ is selected from methyl and ethyl;

R$^4$ is selected from hydrogen and alkyl;

R$^5$ is selected from alkoxycarbonyl, cycloalkoxycarbonyl, haloalkoxycarbonyl, and heterocyclyloxycarbonyl, wherein heterocyclyl part of the heterocyclyloxycarbonyl is optionally substituted with one haloalkyl group; and one of Y and Y' is CH$_2$ and the other is selected from CH$_2$ and O.

In a third aspect the present disclosure provides a composition comprising a compound of formula (I), or a pharmaceutically acceptable salt thereof, and a pharmaceutically acceptable carrier. In a first embodiment of the third aspect the present disclosure provides a composition comprising a compound of formula (I), or a pharmaceutically acceptable salt thereof, at least one additional compound having anti-HCV activity, and a pharmaceutical carrier. In a second embodiment at least one of the additional compounds is an interferon or a ribavirin. In a third embodiment the interferon is selected from interferon alpha 2B, pegylated interferon alpha, consensus interferon, interferon alpha 2A, and lymphoblastiod interferon tau. In a fourth embodiment of the third aspect the present disclosure provides a composition comprising a compound of formula (I), or a pharmaceutically acceptable salt thereof, at least one additional compound having anti-HCV activity, and a pharmaceutical carrier, wherein at least one of the additional compounds is selected from interleukin 2, interleukin 6, interleukin 12, Imiquimod, ribavirin, an inosine 5'-monophospate dehydrogenase inhibitor, amantadine, and rimantadine. In a fifth embodiment of the third aspect the present disclosure provides a composition comprising a compound of formula (I), or a pharmaceutically acceptable salt thereof, at least one additional compound having anti-HCV activity, and a pharmaceutical carrier, wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

In a fourth aspect the present disclosure provides a method of treating an HCV infection in a patient, comprising administering to the patient a therapeutically effective amount of a compound of formula (I), or a pharmaceutically acceptable salt thereof. In a first embodiment of the fourth aspect the method further comprises administering at least one additional compound having anti-HCV activity prior to, after, or simultaneously with the compound of formula (I), or a pharmaceutically acceptable salt thereof. In a second embodiment of the fourth aspect at least one of the additional compounds is an interferon or a ribavirin. In a third embodiment the interferon is selected from interferon alpha 2B, pegylated interferon alpha, consensus interferon, interferon alpha 2A, and lymphoblastiod interferon tau. In a fourth embodiment of the fourth aspect the present disclosure provides a method of treating an HCV infection in a patient, comprising administering to the patient a therapeutically effective amount of a compound of formula (I), or a pharmaceutically acceptable salt thereof, and at least one additional compound having anti-HCV activity prior to, after, or simultaneously with the compound of formula (I), or a pharmaceutically acceptable salt thereof, wherein at least one of the additional compounds is selected from interleukin 2, interleukin 6, interleukin 12, Imiquimod, ribavirin, an inosine 5'-monophospate dehydrogenase inhibitor, amantadine, and rimantadine. In a fifth embodiment of the third aspect the present disclosure provides a method of treating an HCV infection in a patient, comprising administering to the patient a therapeutically effective amount of a compound of formula (I), or a pharmaceutically acceptable salt thereof, and at least one additional compound having anti-HCV activity prior to, after, or simultaneously with the compound of formula (I), or a pharmaceutically acceptable salt thereof, wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

Other aspects of the present disclosure may include suitable combinations of embodiments disclosed herein.

Yet other aspects and embodiments may be found in the description provided herein.

The description of the present disclosure herein should be construed in congruity with the laws and principals of chemical bonding. In some instances it may be necessary to remove a hydrogen atom in order to accommodate a substituent at any given location.

It should be understood that the compounds encompassed by the present disclosure are those that are suitably stable for use as pharmaceutical agent.

It is intended that the definition of any substituent or variable at a particular location in a molecule be independent of its definitions elsewhere in that molecule. For example, when n is 2, each of the two $R^1$ groups may be the same or different.

All patents, patent applications, and literature references cited in the specification are herein incorporated by reference in their entirety. In the case of inconsistencies, the present disclosure, including definitions, will prevail.

As used herein, the singular forms "a", "an", and "the" include plural reference unless the context clearly dictates otherwise.

The term "alkoxy," as used herein, refers to an alkyl group attached to the parent molecular moiety through an oxygen atom.

The term "alkoxyalkoxy," as used herein, refers to an alkoxyalkyl group attached to the parent molecular moiety through an oxygen atom.

The term "alkoxyalkoxycarbonyl," as used herein, refers to an alkoxyalkoxy group attached to the parent molecular moiety through a carbonyl group.

The term "alkoxycarbonyl," as used herein, refers to an alkoxy group attached to the parent molecular moiety through a carbonyl group.

The term "alkyl," as used herein, refers to a group derived from a straight or branched chain saturated hydrocarbon containing from one to ten carbon atoms. In one embodiment the hydrocarbon chain has from one to six atoms. In another embodiment the hydrocarbon chain has from one to four atoms.

The term "alkylamino," as used herein, refers to —NHR, wherein R is an alkyl group.

The term "alkylaminocarbonyl," as used herein, refers to an alkylamino group attached to the parent molecular moiety through a carbonyl group.

The term "alkylcarbonyl," as used herein, refers to an alkyl group attached to the parent molecular moiety through a carbonyl group.

The term "aryl," as used herein, refers to a phenyl group, or a bicyclic fused ring system wherein one or both of the rings is a phenyl group. Bicyclic fused ring systems consist of a phenyl group fused to a four- to six-membered aromatic or non-aromatic carbocyclic ring. The aryl groups of the present invention can be attached to the parent molecular moiety through any substitutable carbon atom in the group. Representative examples of aryl groups include, but are not limited to, indanyl, indenyl, naphthyl, phenyl, and tetrahydronaphthyl. In one embodiment the aryl is a phenyl group.

The term "carbonyl," as used herein, refers to —C(O)—.

The term "cycloalkyl," as used herein, refers to a saturated monocyclic or bicyclic hydrocarbon ring system having three to seven carbon atoms and zero heteroatoms. Representative examples of cycloalkyl groups include, but are not limited to, cyclopropyl, cyclobutyl, and cyclopentyl.

The term "cycloalkylalkoxy," as used herein, refers to a (cycloalkyl)alkyl group attached to the parent molecular moiety through an oxygen atom.

The term "cycloalkylalkoxycarbonyl," as used herein, refers to a cycloalkylalkoxy group attached to the parent molecular moiety through a carbonyl group.

The term "cycloalkylcarbonyl," as used herein, refers to a cycloalkyl group attached to the parent molecular moiety through a carbonyl group.

The term "cycloalkyloxy," as used herein, refers to a cycloalkyl group attached to the parent molecular moiety through an oxygen atom.

The term "cycloalkyloxycarbonyl," as used herein, refers to a cycloalkyloxy group attached to the parent molecular moiety through a carbonyl group.

The term "deuteroalkoxycarbonyl," as used herein, refers to an alkoxycarbonyl group wherein one or more of the hydrogen atoms are replaced by deuterium atoms.

The term "deuterohaloalkoxycarbonyl," as used herein, refers to a haloalkoxycarbonyl group wherein one or more of the hydrogen atoms are replaced by deuterium atoms.

The term "dialkylamino," as used herein, refers to —NR$^p$R$^q$, wherein R$^p$ and R$^q$ are alkyl groups. The alkyl groups may be the same or different.

The term "dialkylaminocarbonyl," as used herein, refers to a dialkylamino group attached to the parent molecular moiety through a carbonyl group.

The term "dialkylaminocarbonylcarbonyl," as used herein, refers to a dialkylaminocarbonyl group attached to the parent molecular moiety through a carbonyl group.

The terms "halo" and "halogen," as used herein, refer to F, Cl, Br, and I.

The term "haloalkoxy," as used herein, refers to a haloalkyl group attached to the parent molecular moiety through an oxygen atom.

The term "haloalkoxycarbonyl," as used herein, refers to a haloalkoxy group attached to the parent molecular moiety through a carbonyl group.

The term "haloalkyl," as used herein, refers to an alkyl group substituted with one, two, three, or four halogen atoms.

The term "haloalkylamino," as used herein, refers to an alkyl amino group wherein the alkyl is substituted with one, two, three, or four halogen atoms.

The term "haloalkylaminocarbonyl," as used herein, refers to a haloalkylamino group attached to the parent molecular moiety through a carbonyl group.

The term "haloalkylcarbonyl," as used herein, refers to a haloalkyl group attached to the parent molecular moiety through a carbonyl group.

The term "heteroaryl," as used herein, refers to an aromatic five- or six-membered ring where at least one atom is selected from N, O, and S, and the remaining atoms are carbon. The term "heteroaryl" also includes bicyclic systems where a heteroaryl ring is fused to a four- to six-membered aromatic or non-aromatic ring containing zero, one, or two additional heteroatoms selected from N, O, and S. The heteroaryl groups are attached to the parent molecular moiety through any substitutable carbon or nitrogen atom in the group. Representative examples of heteroaryl groups include, but are not limited to, benzoxadiazolyl, benzoxazolyl, benzofuranyl, benzothienyl, furanyl, imidazolyl, indazolyl, indolyl, isoxazolyl, isoquinolinyl, isothiazolyl, naphthyridinyl, oxadiazolyl, oxazolyl, pyridinyl, pyridazinyl, pyrimidinyl, pyrazinyl, pyrazolyl, pyrrolyl, quinolinyl, thiazolyl, thienopyridinyl, thienyl, triazolyl, thiadiazolyl, and triazinyl. In one embodiment the heteroaryl is selected from pyrazine, pyrazole, pyridine, and thiazole.

The term "heterocyclyl," as used herein, refers to a cyclic, non-aromatic, saturated or partially unsaturated five-, six-, or seven-membered ring where at least one atom is selected from oxygen, nitrogen, and sulfur. The term "heterocyclyl" also includes bicyclic systems where a heterocyclyl ring is fused to a four- to six-membered aromatic or non-aromatic carbocyclic ring or a four- to six-membered non-aromatic ring containing zero, one, or two additional heteroatoms selected from nitrogen, oxygen, and sulfur. The heterocyclyl groups of the invention are attached to the parent molecular group through any substitutable carbon or nitrogen atom in the group. Representative examples of heterocyclyl groups include, but are not limited to, benzodioxolyl, benzothiazolyl, dihydroindolyl, dihydropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, and thiomorpholinyl. In one embodiment the heterocycle is tetrahydropyranyl.

The term "heterocyclylcarbonyl," as used herein, refers to a heterocyclyl group attached to the parent molecular moiety through a carbonyl group.

The term "heterocyclyloxy," as used herein, refers to a heterocyclyl group attached to the parent molecular moiety through an oxygen atom.

The term "heterocyclyloxycarbonyl," as used herein, refers to a heterocyclyloxy group attached to the parent molecular moiety through a carbonyl group.

The term "hydroxy," as used herein, refers to —OH.

The term "hydroxyalkyl," as used herein, refers to an alkyl group substituted with one, two, or three hydroxy groups.

The term "phenylcarbonyl," as used herein, refers to a phenyl group attached to the parent molecular moiety through a carbonyl group.

The term "phenyloxy," as used herein, refers to a phenyl group attached to the parent molecular moiety through an oxygen atom.

The term "phenyloxycarbonyl," as used herein, refers to a phenyloxy group attached to the parent molecular moiety through a carbonyl group.

The present disclosure is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable basic functionality with a suitable acid. Representative acid addition salts include acetate, adipate, alginate, citrate, aspartate, benzoate, benzenesulfonate, bisulfate, butyrate, camphorate, camphorsulfonate; digluconate, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting an acidic group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

As used herein, the term "anti-HCV activity" means the compound is effective to treat the HCV virus.

The term "compounds of the disclosure", and equivalent expressions, are meant to embrace compounds of formula (I), and pharmaceutically acceptable enantiomers, diastereomers, and salts thereof. Similarly, references to intermediates, are meant to embrace their salts where the context so permits.

The term "patient" includes both human and other mammals.

The term "pharmaceutical composition" means a composition comprising a compound of the disclosure in combination with at least one additional pharmaceutical carrier, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Ingredients listed in Remington's Pharmaceutical Sciences, $18^{th}$ ed., Mack Publishing Company, Easton, Pa. (1999) for example, may be used.

The phrase "pharmaceutically acceptable" is employed herein to refer to those compounds, materials, compositions, and/or dosage forms which are, within the scope of sound medical judgment, suitable for use in contact with the tissues of patients without excessive toxicity, irritation, allergic response, or other problem or complication commensurate with a reasonable risk/benefit ratio.

The term "therapeutically effective amount" means the total amount of each active component that is sufficient to show a meaningful patient benefit, e.g., a sustained reduction in viral load. When applied to an individual active ingredient, administered alone, the term refers to that ingredient alone. When applied to a combination, the term refers to combined amounts of the active ingredients that result in the therapeutic effect, whether administered in combination, serially or simultaneously.

The terms "treat" and "treating" refers to: (i) preventing a disease, disorder or condition from occurring in a patient which may be predisposed to the disease, disorder and/or condition but has not yet been diagnosed as having it; (ii) inhibiting the disease, disorder or condition, i.e., arresting its development; and/or (iii) relieving the disease, disorder or condition, i.e., causing regression of the disease, disorder and/or condition.

Where used in naming compounds of the present disclosure, the designations P1', P1, P2, P2*, P3, and P4, as used herein, map the relative positions of the amino acid residues of a protease inhibitor binding relative to the binding of the natural peptide cleavage substrate. Cleavage occurs in the natural substrate between P1 and P1' where the nonprime positions designate amino acids starting from the C-terminus end of the peptide natural cleavage site extending towards the N-terminus; whereas, the prime positions emanate from the N-terminus end of the cleavage site designation and extend toward the C-terminus. For example, P1' refers to the first position away from the right hand end of the C-terminus of the cleavage site (i.e. N-terminus first position); whereas P1 starts the numbering from the left hand side of the C-terminus cleavage site, P2: second position from the C-terminus, etc.). (see Berger A. & Schechter I., Transactions of the Royal Society London series (1970), B257, 249-264].

Asymmetric centers exist in the compounds of the present disclosure. For example, the compounds may include P1 cyclopropyl element of formula

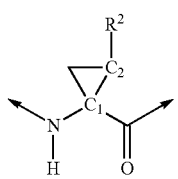

P1 wherein $C_1$ and $C_2$ each represent an asymmetric carbon atom at positions 1 and 2 of the cyclopropyl ring.

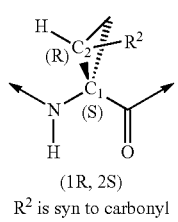

(1R, 2S)
$R^2$ is syn to carbonyl

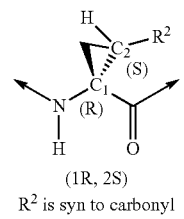

(1R, 2S)
$R^2$ is syn to carbonyl

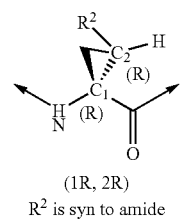

(1R, 2R)
$R^2$ is syn to amide

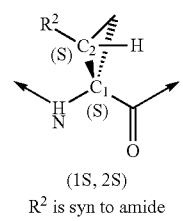

(1S, 2S)
$R^2$ is syn to amide

It should be understood that the disclosure encompasses all stereochemical forms, or mixtures thereof, which possess the ability to inhibit HCV protease.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof Certain compounds of the present disclosure may exist in zwitterionic form and the present disclosure includes each zwitterionic form of these compounds and mixtures thereof.

When it is possible that, for use in therapy, therapeutically effective amounts of a compound of formula (I), as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of compounds of formula (I) or pharmaceutically acceptable salts thereof, and one or more pharmaceutically acceptable carriers, diluents, or excipients. The compounds of formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the disclosure there is also provided a process for the preparation of a pharmaceutical formulation including admixing a compound of formula (I), or a pharmaceutically acceptable salt thereof, with one or more pharmaceutically acceptable carriers, diluents, or excipients.

Pharmaceutical formulations may be presented in unit dose forms containing a predetermined amount of active ingredient per unit dose. Dosage levels of between about 0.01 and about 150 milligram per kilogram ("mg/kg") body weight per day, preferably between about 0.05 and about 100 mg/kg body weight per day of the compounds of the disclosure are typical in a monotherapy for the prevention and treatment of HCV mediated disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Generally, treatment is initiated with small dosages substantially less than the optimum dose of the compound. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this disclosure comprise a combination of a compound of the disclosure and one or more additional therapeutic and/or prophylactic agent, both the compound and the additional agent can be present in a dose that is less than or equal to the dosage normally administered in a monotherapy regimen. The compositions of this disclosure may be co-formulated with one or more additional therapeutic or prophylactic agents, for example, in the form of a monolithic and/or bi/multi-layer tablet or may be administered separately from the therapeutic or prophylactic agent(s).

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phopholipids, such as cholesterol, stearylamine, or phophatidylcholines.

The compounds of formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouth washes.

Pharmaceutical formulations adapted for rectal administration may be presented as suppositories or as enemas.

Pharmaceutical formulations adapted for nasal administration wherein the carrier is a solid include a course powder which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

Table 1 below lists some illustrative examples of compounds that can be administered with the compounds of this disclosure. The compounds of the disclosure can be administered with other anti-HCV activity compounds in combination therapy, either jointly or separately, or by combining the compounds into a composition.

TABLE 1

| Brand Name | Physiological Class | Type of Inhibitor or Target | Source Company |
|---|---|---|---|
| NIM811 | | Cyclophilin Inhibitor | Novartis |
| Zadaxin | | Immunomodulator | Sciclone |
| Suvus | | Methylene blue | Bioenvision |
| Actilon (CPG10101) | | TLR9 agonist | Coley |
| Batabulin (T67) | Anticancer | β-tubulin inhibitor | Tularik Inc., South San Francisco, CA |
| ISIS 14803 | Antiviral | antisense | ISIS Pharmaceuticals Inc, Carlsbad, CA/Elan Phamaceuticals Inc., New York, NY |
| Summetrel | Antiviral | antiviral | Endo Pharmaceuticals Holdings Inc., Chadds Ford, PA |
| GS-9132 (ACH-806) | Antiviral | HCV Inhibitor | Achillion / Gilead |
| Pyrazolopyrimidine compounds and salts From WO-2005047288 26 May 2005 | Antiviral | HCV Inhibitors | Arrow Therapeutics Ltd. |
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |
| XTL-6865 (XTL-002) | Antiviral | monoclonal antibody | XTL Biopharmaceuticals Ltd., Rehovot, Isreal |
| Telaprevir (VX-950, LY-570310) | Antiviral | NS3 serine protease inhibitor | Vertex Pharmaceuticals Inc., Cambridge, MA/ Eli Lilly and Co. Inc., Indianapolis, IN |
| HCV-796 | Antiviral | NS5B Replicase Inhibitor | Wyeth / Viropharma |
| NM-283 | Antiviral | NS5B Replicase Inhibitor | Idenix / Novartis |
| GL-59728 | Antiviral | NS5B Replicase Inhibitor | Gene Labs / Novartis |
| GL-60667 | Antiviral | NS5B Replicase Inhibitor | Gene Labs / Novartis |
| 2'C MeA | Antiviral | NS5B Replicase Inhibitor | Gilead |
| PSI 6130 | Antiviral | NS5B Replicase Inhibitor | Roche |

TABLE 1-continued

| Brand Name | Physiological Class | Type of Inhibitor or Target | Source Company |
|---|---|---|---|
| R1626 | Antiviral | NS5B Replicase Inhibitor | Roche |
| 2'C Methyl adenosine | Antiviral | NS5B Replicase Inhibitor | Merck |
| JTK-003 | Antiviral | RdRp inhibitor | Japan Tobacco Inc., Tokyo, Japan |
| Levovirin | Antiviral | ribavirin | ICN Pharmaceuticals, Costa Mesa, CA |
| Ribavirin | Antiviral | ribavirin | Schering-Plough Corporation, Kenilworth, NJ |
| Viramidine | Antiviral | Ribavirin Prodrug | Ribapharm Inc., Costa Mesa, CA |
| Heptazyme | Antiviral | ribozyme | Ribozyme Pharmaceuticals Inc., Boulder, CO |
| BILN-2061 | Antiviral | serine protease inhibitor | Boehringer Ingelheim Pharma KG, Ingelheim, Germany |
| SCH 503034 | Antiviral | serine protease inhibitor | Schering Plough |
| Zadazim | Immune modulator | Immune modulator | SciClone Pharmaceuticals Inc., San Mateo, CA |
| Ceplene | Immuno-modulator | immune modulator | Maxim Pharmaceuticals Inc., San Diego, CA |
| CellCept | Immuno-suppressant | HCV IgG immuno-suppressant | F. Hoffmann-La Roche LTD, Basel, Switzerland |
| Civacir | Immuno-suppressant | HCV IgG immuno-suppressant | Nabi Biopharmaceuticals Inc., Boca Raton, FL |
| Albuferon - α | Interferon | albumin IFN-α2b | Human Genome Sciences Inc., Rockville, MD |
| Infergen A | Interferon | IFN alfacon-1 | InterMune Pharmaceuticals Inc., Brisbane, CA |
| Omega IFN | Interferon | IFN-ω | Intarcia Therapeutics |
| IFN-β and EMZ701 | Interferon | IFN-β and EMZ701 | Transition Therapeutics Inc., Ontario, Canada |
| Rebif | Interferon | IFN-β1a | Serono, Geneva, Switzerland |
| Roferon A | Interferon | IFN-α2a | F. Hoffmann-La Roche LTD, Basel, Switzerland |
| Intron A | Interferon | IFN-α2b | Schering-Plough Corporation, Kenilworth, NJ |
| Intron A and Zadaxin | Interferon | IFN-α2b/α1-thymosin | RegeneRx Biopharma. Inc., Bethesda, MD/ SciClone Pharmaceuticals Inc, San Mateo, CA |
| Rebetron | Interferon | IFN-α2b/ribavirin | Schering-Plough Corporation, Kenilworth, NJ |
| Actimmune | Interferon | INF-γ | InterMune Inc., Brisbane, CA |
| Interferon-β | Interferon | Interferon-β-1a | Serono |
| Multiferon | Interferon | Long lasting IFN | Viragen/Valentis |
| Wellferon | Interferon | Lympho-blastoid IFN-αn1 | GlaxoSmithKline plc, Uxbridge, UK |
| Omniferon | Interferon | natural IFN-α | Viragen Inc., Plantation, FL |
| Pegasys | Interferon | PEGylated IFN-α2a | F. Hoffmann-La Roche LTD, Basel, Switzerland |
| Pegasys and Ceplene | Interferon | PEGylated IFN-α2a/ immune modulator | Maxim Pharmaceuticals Inc., San Diego, CA |
| Pegasys and Ribavirin | Interferon | PEGylated IFN-α2a/ribavirin | F. Hoffmann-La Roche LTD, Basel, Switzerland |
| PEG-Intron | Interferon | PEGylated IFN-α2b | Schering-Plough Corporation, Kenilworth, NJ |
| PEG-Intron / Ribavirin | Interferon | PEGylated IFN-α2b/ribavirin | Schering-Plough Corporation, Kenilworth, NJ |
| IP-501 | Liver protection | antifibrotic | Indevus Pharmaceuticals Inc., Lexington, MA |
| IDN-6556 | Liver protection | caspase inhibitor | Idun Pharmaceuticals Inc., San Diego, CA |
| ITMN-191 (R-7227) | Antiviral | serine protease inhibitor | InterMune Pharmaceuticals Inc., Brisbane, CA |
| GL-59728 | Antiviral | NS5B Replicase Inhibitor | Genelabs |
| ANA-971 | Antiviral | TLR-7 agonist | Anadys |
| Boceprevir | Antiviral | serine protease inhibitor | Schering Plough |
| TMS-435 | Antiviral | serine protease inhibitor | Tibotec BVBA, Mechelen, Belgium |
| BI-201335 | Antiviral | serine protease inhibitor | Boehringer Ingelheim Pharma KG, Ingelheim, Germany |
| MK-7009 | Antiviral | serine protease inhibitor | Merck |
| PF-00868554 | Antiviral | replicase inhibitor | Pfizer |
| ANA598 | Antiviral | Non-Nucleoside NS5B Polymerase Inhibitor | Anadys Pharmaceuticals, Inc., San Diego, CA, USA |
| IDX375 | Antiviral | Non-Nucleoside Replicase Inhibitor | Idenix Pharmaceuticals, Cambridge, MA, USA |
| BILB 1941 | Antiviral | NS5B Polymerase Inhibitor | Boehringer Ingelheim Canada Ltd R&D, Laval, QC, Canada |
| PSI-7851 | Antiviral | Nucleoside Polymerase Inhibitor | Pharmasset, Princeton, NJ, USA |
| PSI-7977 | Antiviral | Nucleotide NS5B Polymerase Inhibitor | Pharmasset, Princeton, NJ, USA |
| VCH-759 | Antiviral | NS5B Polymerase Inhibitor | ViroChem Pharma |
| VCH-916 | Antiviral | NS5B Polymerase Inhibitor | ViroChem Pharma |
| GS-9190 | Antiviral | NS5B Polymerase Inhibitor | Gilead |
| Peg-interferon lamda | Antiviral | Interferon | ZymoGenetics/Bristol-Myers Squibb |
| daclatasvir | Antiviral | NS5A inhibitor | Bristol-Myers Squibb |
| BMS-791325 | Antiviral | NS5B Polymerase Inhibitor | Bristol-Myers Squibb |
| ACH-3102 | Antiviral | NS5A inhibitor | Bristol-Myers Squibb |
| BMS-984478 | Antiviral | NS5A inhibitor | Bristol-Myers Squibb |

TABLE 1-continued

| Brand Name | Physiological Class | Type of Inhibitor or Target | Source Company |
|---|---|---|---|
| asunaprevir | Antiviral | serine protease inhibitor | Bristol-Myers Squibb |

The compounds of the disclosure may also be used as laboratory reagents. Compounds may be instrumental in providing research tools for designing of viral replication assays, validation of animal assay systems and structural biology studies to further enhance knowledge of the HCV disease mechanisms. Further, the compounds of the present disclosure are useful in establishing or determining the binding site of other antiviral compounds, for example, by competitive inhibition.

The compounds of this disclosure may also be used to treat or prevent viral contamination of materials and therefore reduce the risk of viral infection of laboratory or medical personnel or patients who come in contact with such materials, e.g., blood, tissue, surgical instruments and garments, laboratory instruments and garments, and blood collection or transfusion apparatuses and materials.

This disclosure is intended to encompass compounds having formula (I) when prepared by synthetic processes or by metabolic processes including those occurring in the human or animal body (in vivo) or processes occurring in vitro.

The present disclosure will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what is believed to be the most useful and readily understood description of its procedures and conceptual aspects.

The abbreviations used in the present application, including particularly in the illustrative schemes and examples which follow, are well-known to those skilled in the art. Some of the abbreviations used are as follows: dppf for diphenylphosphinoferrocene; THF for tetrahydrofuran; PPh$_3$ for triphenylphosphine; DMF for N,N-dimethylformamide; MeOH for methanol; TFA for trifluoroacetic acid; EtOAc for ethyl acetate; DMSO for dimethylsulfoxide; h or hr for hours; rt or RT or Rt for room temperature or retention time (context will dictate); Et$_2$O for diethyl ether; HATU for O-(7-azabenzotriazol-1-yl)-N,N,N',N'-tetramethyluronium hexafluorophosphate; MeCN for acetonitrile, LiHMDS for lithium hexamethyldisilazide, and BOC for tert-butoxycarbonyl.

The starting materials useful to synthesize the compounds of the present disclosure are known to those skilled in the art and can be readily manufactured or are commercially available.

The following methods set forth below are provided for illustrative purposes and are not intended to limit the scope of the claims. It will be recognized that it may be necessary to prepare such a compound in which a functional group is protected using a conventional protecting group then to remove the protecting group to provide a compound of the present disclosure. The details concerning the use of protecting groups in accordance with the present disclosure are known to those skilled in the art.

Preparation of 2,4-dichloro-6-(4-isopropoxyphenyl)pyridine

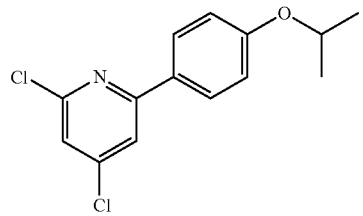 [SMILES: CC(C)Oc1ccc(-c2cc(Cl)cc(Cl)n2)cc1]

To a 40 mL vial equipped with a stir bar was added 2,4,6-trichloropyridine (1.00 g, 5.48 mmol), (4-isopropoxyphenyl)boronic acid (1.00 g, 5.56 mmol), [1,1'-bis(diphenylphosphino)ferrocene]dichloropalladium(II) ("Pd(dppf)Cl$_2$", 200 mg, 0.273 mmol), and K$_3$PO$_4$ (3.49 g, 16.4 mmol). The vial was sealed with a septum screwcap and then placed under N$_2$ atmosphere. To the vial was added degassed THF (30 mL). The vial was placed in a 60° C. heating block with stirring for 60 hours. To the mixture was added diatomaceous earth (Celite®). The mixture was filtered and the filtrate was concentrated in vacuo to afford an amber solid residue. This material was subjected to silica gel chromatography (hexanes:CH$_2$Cl$_2$) to afford 2,4-dichloro-6-(4-isopropoxyphenyl)pyridine as a colorless oil that solidified upon standing (710 mg, 46%). $^1$H-NMR: (400 MHz, CDCl$_3$) δ 7.95-7.90 (m, 2H), 7.58 (d, J=1.5 Hz, 1H), 7.22 (d, J=1.5 Hz, 1H), 6.99-6.93 (m, 2H), 4.64 (spt, J=6.1 Hz, 1H), 1.38 (d, J=6.0 Hz, 6H); MS: MS m/z 281.9 (M$^+$+1).

Preparation of 2-(4,6-dichloropyridin-2-yl)thiazole

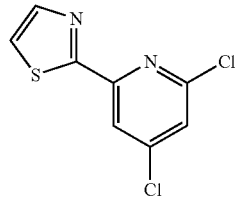 [SMILES: Clc1cc(Cl)nc(-c2nccs2)c1]

To a 15 mL vial equipped with a stir bar was added 2,4,6-trichloropyridine (182 mg, 1.00 mmol) and Pd(dppf)Cl$_2$ (73.2 mg, 0.100 mmol). The vial was sealed with a septum screwcap and was then placed under N$_2$ atmosphere. To the vial was added thiazol-2-ylzinc(II) bromide in THF (8.00 mL, 4.00 mmol). The vial was placed in a 60° C. heating block with stirring for 3 h. The reaction mixture was transferred to a separatory funnel and diluted with water (25 mL) and sat. aq. NaCl ("brine", 25 mL). The mixture was extracted with EtOAc:Et$_2$O (40 mL:20 mL). The organic phase was washed with brine (25 mL); dried over MgSO$_4$; filtered; then concentrated in vacuo to afford an orange solid. This material was subjected to silica gel chromatography (CH$_2$Cl$_2$:MeOH, 100:0 to 99:1) to afford 2-(4,6-dichloropyridin-2-yl)thiazole as a white solid (231 mg, 46%). $^1$H-NMR (400 MHz, CDCl$_3$)

δ 8.16 (d, J=1.8 Hz, 1H), 7.95 (d, J=3.3 Hz, 1H), 7.52 (d, J=3.0 Hz, 1H), 7.37 (d, J=1.8 Hz, 1H).

Preparation of 2-(2-fluoropyridin-4-yl)thiazole

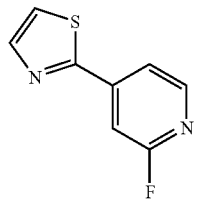 [SMILES: Fc1cc(-c2nccs2)ccn1]

To a two dram vial equipped with a stir bar was added 4-bromo-2-fluoropyridine (132 mg, 0.75 mmol) and Pd(dppf)Cl$_2$ (28 mg, 0.038 mmol). The vial was sealed with a septum screwcap and was then placed under N$_2$ atm. To the vial was added thiazol-2-ylzinc(II) bromide in THF (3.0 mL, 1.5 mmol). The vial was placed in a 60° C. heating block with stirring for 3.5 h. The reaction solution was transfered to a 125 mL reparatory funnel and was diluted with EtOAc (50 mL). The solution was washed with water:brine (25 mL:25 mL); then brine (50 mL). The organic solution was dried over MgSO$_4$; filtered; then concentrated in vacuo. The residue was subjected to silica gel chromatography using hexanes:EtOAc to afford 2-(2-fluoropyridin-4-yl)thiazole as a white solid, 83 mg (61%). $^1$H-NMR (400 MHz, CDCl$_3$) δ 8.32 (d, J=5.3 Hz, 1H), 8.00 (d, J=3.3 Hz, 1H), 7.73 (dt, J=5.3, 1.6 Hz, 1H), 7.53 (d, J=3.3 Hz, 1H), 7.51-7.50 (m, 1H).

Preparation of 2-(6-fluoropyridin-3-yl)thiazole

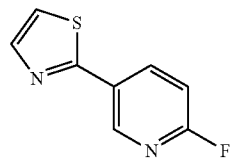 [SMILES: Fc1ccc(-c2nccs2)cn1]

To a 7 mL dram vial equipped with a stir bar was added 5-bromo-2-fluoropyridine (500 mg, 2.84 mmol) and Pd(dppf)Cl$_2$ (104 mg, 0.142 mmol). The vial was sealed with a septum cap and then placed under N$_2$ atm. To the vial was added thiazol-2-ylzinc(II) bromide in THF (6 mL, 3.00 mmol). The vial was placed in a 65° C. heating block with stirring for 2.5 h. The reaction solution was transfered to a 125 mL separatory funnel and was diluted with sat. aq. NaHCO$_3$ (50 mL) upon which a significant amount of a white solid precipitated. The mixture was extracted with EtOAc (2×50 mL). The combined organics were washed with brine (50 mL); dried over MgSO$_4$; filtered; then concentrated in vacuo. The resulting was subjected to silica gel chromatography (hexanes:EtOAc) to afford 2-(6-fluoropyridin-3-yl)thiazole as a white solid, 303 mg (59%). $^1$H-NMR (500 MHz, CDCl$_3$) δ 8.80 (d, J=2.5 Hz, 1H), 8.39 (ddd, J=8.5, 7.4, 2.5 Hz, 1H), 7.92 (d, J=3.3 Hz, 1H), 7.42 (d, J=3.3 Hz, 1H), 7.07-7.03 (m, 1H).

Preparation of 2-(4-chloro-6-(4-isopropoxyphenyl)pyridin-2-yl)pyrazine

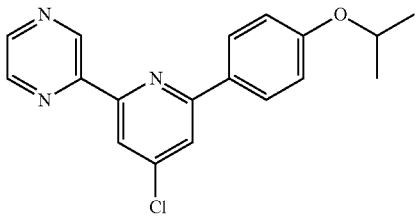 [SMILES: CC(C)Oc1ccc(-c2cc(Cl)cc(-c3cnccn3)n2)cc1]

To a 2 dram vial equipped with a stir bar was added 2,4-dichloro-6-(4-isopropoxyphenyl)pyridine (50 mg, 0.18 mmol), 2-(tributylstannyl)pyrazine (65 mg, 0.18 mmol), CuI (9.0 mg, 0.047 mmol), CsF (82 mg, 0.54 mmol), and Pd(PPh$_3$)$_4$ (10.2 mg, 8.86 μmol). The vial was capped with a septum screw-cap and then placed under N$_2$ atmosphere. To the vial was added degassed DMF (1 mL). The vial was placed in a 80° C. heating block with stirring for 1 hour. The reaction mixture was directly purified by C$_{18}$ chromatography (water:MeOH w/0.1% TFA) to afford 2-(4-chloro-6-(4-isopropoxyphenyl)pyridin-2-yl)pyrazine as a dark solid (37 mg, 64%).
$^1$H-NMR: (400 MHz, CDCl$_3$) δ 9.82 (br. s., 1H), 8.66 (s, 2H), 8.28 (d, J=1.8 Hz, 1H), 8.12-8.03 (m, 2H), 7.75 (d, J=1.5 Hz, 1H), 7.03 (d, J=9.0 Hz, 2H), 4.67 (spt, J=6.1 Hz, 1H), 1.40 (d, J=6.0 Hz, 6H); MS: MS m/z 326.0 (M$^+$+1).

Preparation of 5-(4-chloro-6-(4-isopropoxyphenyl)pyridin-2-yl)thiazole

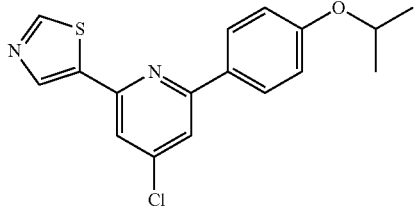 [SMILES: CC(C)Oc1ccc(-c2cc(Cl)cc(-c3cncs3)n2)cc1]

To a 2 dram vial equipped with a stir bar was added 2,4-dichloro-6-(4-isopropoxyphenyl)pyridine (189 mg, 0.668 mmol), 5-(tributylstannyl)thiazole (250 mg, 0.668 mmol), CuI (32 mg, 0.17 mmol), CsF (304 mg, 2.00 mmol), and Pd(PPh$_3$)$_4$ (39 mg, 0.033 mmol). The vial was capped with a septum screw-cap and then placed under N$_2$ atmosphere. To the vial was added degassed DMF (4 mL). The vial was placed in an 80° C. heating block with stirring for 1 hour. The vial was cooled to room temperature and then opened, and to the solution was added an additional charge of 5-(tributylstannyl)thiazole (85 mg, 0.23 mmol) and Pd(PPh$_3$)$_4$ (39 mg, 0.033 mmol). The vial was capped, placed under N$_2$ atmosphere, and then placed in a 80° C. heating block with stirring for an additional 1 hour. The reaction mixture was cooled to room temperature and then transferred to a 125 mL separatory funnel. The mixture was diluted with EtOAc (50 mL) and then washed with saturated aqueous NaCl ("brine", 50 mL). The aqueous phase was extracted with EtOAc (25 mL). The combined organics were washed with brine (25 mL); dried over MgSO$_4$; filtered; then concentrated in vacuo to afford a dark liquid. This material was subjected to silica gel chromatography to afford 5-(4-chloro-6-(4-isopropoxyphenyl)pyridin-2-yl)thiazole as a pale orange liquid (122 mg, 55%). $^1$H-NMR: (400 MHz, CDCl$_3$-d) δ 8.87 (s, 1H), 8.40 (s, 1H), 8.04-7.98 (m, 2H), 7.60 (d, J=1.5 Hz, 1H), 7.55 (d, J=1.8 Hz, 1H), 7.04-6.98 (m, 2H), 4.65 (spt, J=6.1 Hz, 1H), 1.39 (d, J=6.3 Hz, 6H); MS: MS m/z 331.1 (M$^+$+1).

Preparation of 2-(4-fluoro-6-(4-isopropoxyphenyl)pyridin-2-yl)pyrimidine

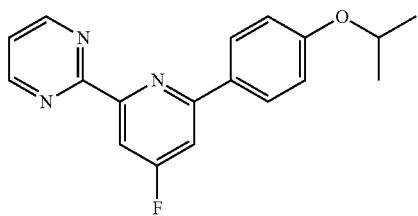 [SMILES: CC(C)Oc1ccc(-c2cc(F)cc(-c3ncccn3)n2)cc1]

Scheme:

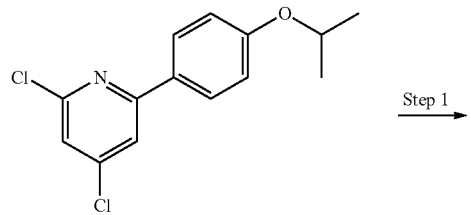

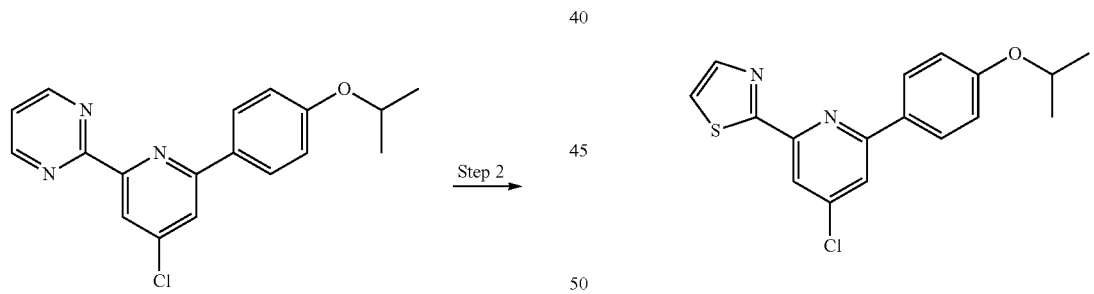

Step 1:

To a 2 dram vial equipped with a stir bar was added 2,4-dichloro-6-(4-isopropoxyphenyl)pyridine (50 mg, 0.18 mmol), 2-(tributylstannyl)pyrimidine (65 mg, 0.18 mmol), CuI (8 mg, 0.04 mmol), CsF (81 mg, 0.53 mmol), and Pd(PPh$_3$)$_4$ (10 mg, 8.9 µmol). The vial was capped with a septum screw-cap and then placed under N$_2$ atmosphere. To the vial was added degassed DMF (1 mL). The vial was placed in a 80° C. heating block with stirring for 1 hour. The mixture was allowed to cool to room temperature, and the reaction mixture was then directly subjected to C$_{18}$ chromatography (water:MeOH w/0.1% TFA) to afford 2-(4-chloro-6-(4-isopropoxyphenyl)pyridin-2-yl)pyrimidine as an amber solid. This material was carried forward into step 2.

Step 2:

To a 2 dram vial equipped with a stir bar and charged with 2-(4-chloro-6-(4-isopropoxyphenyl)pyridin-2-yl)pyrimidine (all material from step 1) was added CsF (200 mg, 1.32 mmol) and DMSO (0.7 mL). The vial was sealed with a septum cap and then placed in a 140° C. heating block with stirring for 18 hours. The reaction mixture was allowed to cool to room temperature and then was transfered to a 125 mL separatory funnel. The mixture was diluted with EtOAc (50 mL) and twice washed with water:brine (25 mL:25 mL). The organic solution was dried over MgSO$_4$; filtered; then concentrated in vacuo to afford a solid amber residue. This material was subjected to silica gel purification (hexanes:EtOAc) to afford 2-(4-fluoro-6-(4-isopropoxyphenyl)pyridin-2-yl)pyrimidine as a white solid (15 mg, 27% over two steps). $^1$H-NMR (400 MHz, CDCl$_3$) δ 8.96 (d, J=5.0 Hz, 2H), 8.12 (dd, J=9.5, 2.3 Hz, 1H), 8.09-8.04 (m, 2H), 7.50 (dd, J=9.8, 2.3 Hz, 1H), 7.36 (t, J=4.9 Hz, 1H), 7.02-6.97 (m, 2H), 4.65 (spt, J=6.0 Hz, 1H), 1.38 (d, J=6.0 Hz, 6H); MS: MS m/z 310.2 (M$^+$+1).

Preparation of 2-(4-chloro-6-(4-isopropoxyphenyl)pyridin-2-yl)thiazole

To a dry 2 dram vial equipped with a stir bar was added 2,4-dichloro-6-(4-isopropoxyphenyl)pyridine (60 mg, 0.21 mmol) and Pd(dppf)Cl$_2$ (8 mg, 10 µmol). The vial was sealed with a septum screw-cap and was then placed under N$_2$ atmosphere. To the vial was added THF (0.5 mL), then thiazol-2-ylzinc(II) bromide in THF (0.5M, 0.53 mL, 0.27 mmol). The vial was placed in a 60° C. heating block with stirring for 2 hours. The vial was opened, and then charged with Pd(dppf)Cl$_2$ (8 mg, 10 µmol). The vial was re-sealed and then placed under N$_2$ atmosphere, and to the vial was added thiazol-2-ylzinc(II) bromide in THF (0.5M, 0.53 mL, 0.27 mmol). The vial was placed in a 60° C. heating block with stirring for 5 hours. The reaction solution was cooled to room temperature and then concentrated under a stream of N$_2$. The resulting solid residue was subjected to silica gel chromatography to afford 2-(4-chloro-6-(4-isopropoxyphenyl)pyridin-2-yl)thiazole as a white solid (24 mg, 34%).

$^1$H-NMR (400 MHz, CDCl$_3$) δ 8.08 (d, J=1.8 Hz, 1H), 8.07-8.02 (m, 2H), 7.95 (d, J=3.0 Hz, 1H), 7.69 (d, J=1.8 Hz, 1H), 7.49 (d, J=3.0 Hz, 1H), 7.04-6.99 (m, 2H), 4.66 (spt, J=6.1 Hz, 1H), 1.40 (d, J=6.0 Hz, 6H); MS: MS m/z 331.1 (M$^+$+1).

Preparation of 4-chloro-6-(4-isopropoxyphenyl)-2,3'-bipyridine

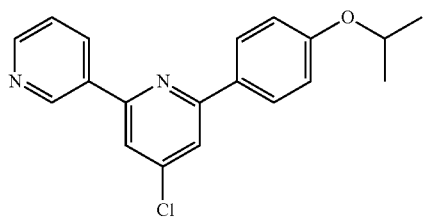 [SMILES: CC(C)Oc1ccc(-c2cc(Cl)cc(-c3cccnc3)n2)cc1]

To a 2 dram vial equipped with a stir bar was added 2,4-dichloro-6-(4-isopropoxyphenyl)pyridine (60 mg, 0.21 mmol), 6-methyl-2-(3-pyridinyl)-1,3,6,2-dioxazaborocane-4,8-dione ("3-pyridyl MIDA boronate", 50 mg, 0.21 mmol), Pd(dppf)Cl$_2$ (8 mg, 10 μmol) and K$_3$PO$_4$ (339 mg, 1.60 mmol). The vial was capped with a septum screw-cap and then placed under N$_2$ atmosphere. To the vial was added deggased THF (5 mL) and degassed water (1 mL). The vial was placed in a 60° C. heating block with stirring for 3 hours. The mixture was cooled to room temperature and the aqueous phase was decanted. The organic phase was concentrated under a stream of N$_2$ and the resulting residue was subjected to silica gel chromatography (hexanes:EtOAc) to afford -chloro-6-(4-isopropoxyphenyl)-2,3'-bipyridine as a white solid (51 mg, 74%). $^1$H-NMR (400 MHz, CDCl$_3$) δ 9.31 (dd, J=2.3, 0.8 Hz, 1H), 8.69 (dd, J=4.8, 1.5 Hz, 1H), 8.44-8.40 (m, 1H), 8.09-8.04 (m, 2H), 7.68 (d, J=1.5 Hz, 1H), 7.64 (d, J=1.5 Hz, 1H), 7.44 (ddd, J=8.0, 4.8, 0.8 Hz, 1H), 7.05-6.97 (m, 2H), 4.66 (spt, J=6.1 Hz, 1H), 1.39 (d, J=6.3 Hz, 6H); MS: MS m/z 325.2 (M$^+$+1).

Preparation of 4-chloro-6-(4-isopropoxyphenyl)-2,4'-bipyridine

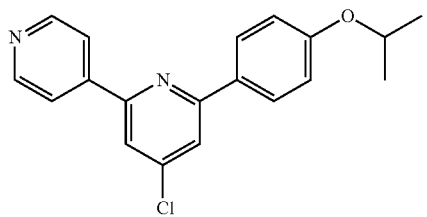 [SMILES: CC(C)Oc1ccc(-c2cc(Cl)cc(-c3ccncc3)n2)cc1]

To a 2 dram vial equipped with a stir bar was added 2,4-dichloro-6-(4-isopropoxyphenyl)pyridine (60 mg, 0.21 mmol), 6-methyl-2-(3-pyridinyl)-1,3,6,2-dioxazaborocane-4,8-dione ("4-pyridyl MIDA boronate", 50 mg, 0.21 mmol), Pd(dppf)Cl$_2$ (8.0 mg, 10 μmol) and K$_3$PO$_4$ (337 mg, 1.59 mmol). The vial was capped with a septum screw-cap and then placed under N$_2$ atmosphere. To the vial was added degassed THF (5 mL) and degassed water (1 mL). The vial was placed in a 60° C. heating block with stirring for 3 hours. The reaction mixture was cooled to room temperature and the aqueous phase was decanted. The organic solution was concentrated under a stream of N$_2$ and the resulting solid residue was subjected to silica gel chromatography (hexanes:EtOAc) to afford 4-chloro-6-(4-isopropoxyphenyl)-2,4'-bipyridine as a white solid (45 mg, 65%). $^1$H-NMR (400 MHz, CDCl$_3$) δ 8.84-8.81 (m, 2H), 8.16-8.11 (m, 2H), 8.00-7.97 (m, 3H), 7.04-6.99 (m, 2H), 4.69 (spt, J=6.0 Hz, 1H), 1.40 (d, J=6.0 Hz, 6H); MS: MS m/z 326.2 (M$^+$+1).

Preparation of 4-chloro-6-(4-isopropoxyphenyl)-6'-methoxy-2,2'-bipyridine

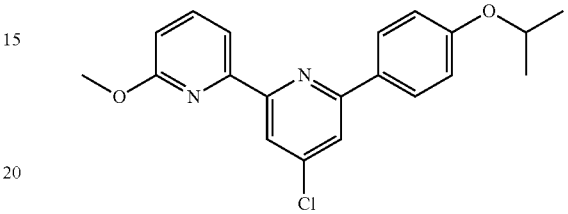

To a 2 dram vial equipped with a stir bar was added 2,4-dichloro-6-(4-isopropoxyphenyl)pyridine (50 mg, 0.18 mmol), 2-methoxy-6-(tributylstannyl)pyridine (701 mg, 0.178 mmol), CuI (9 mg, 0.05 mmol), CsF (82 mg, 0.54 mmol), and Pd(PPh$_3$)$_4$ (10 mg, 8.9 μmol). The vial was sealed with a septum screw-cap and then placed under N$_2$ atmosphere. To the vial was added degassed DMF (1 mL). The vial was placed in a 80° C. heating block with stirring for 1 hour. The reaction mixture was allowed to cool to room temperature and was then directly purified via C$_{18}$ chromatography (water:MeOH w/0.1% TFA) to afford 4-chloro-6-(4-isopropoxyphenyl)-6'-methoxy-2,2'-bipyridine as a dark solid (58 mg, 92%). $^1$H-NMR (500 MHz, CDCl$_3$) 8.29 (d, J=1.7 Hz, 1H), 8.21 (dd, J=7.4, 0.5 Hz, 1H), 8.09-8.04 (m, 2H), 7.74 (t, J=7.8 Hz, 1H), 7.67 (d, J=1.7 Hz, 1H), 7.03-6.99 (m, 2H), 6.82 (dd, J=8.2, 0.5 Hz, 1H), 4.66 (spt, J=6.1 Hz, 1H), 4.08 (s, 3H), 1.40 (d, J=6.0 Hz, 6H); MS: MS m/z 355.2 (M$^+$+1).

Preparation of 4-fluoro-6-(4-isopropoxyphenyl)-2,2'-bipyridine

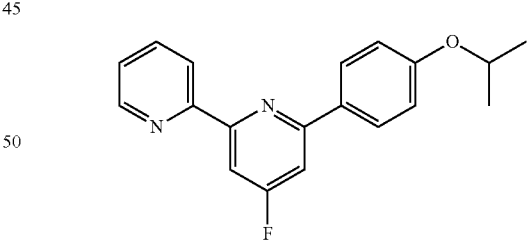

Scheme:

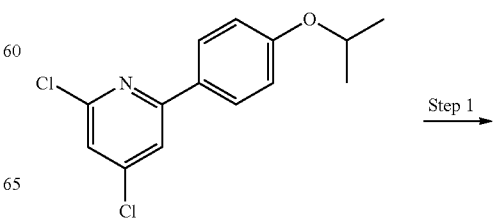

Step 1 →

-continued

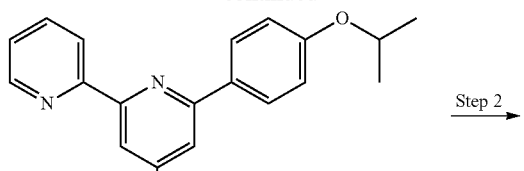

Step 2

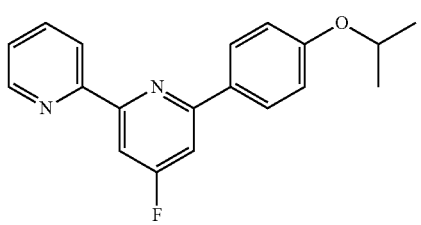 [SMILES: CC(C)Oc1ccc(-c2cc(F)cc(-c3ccccn3)n2)cc1]

Step 1:

To a 2 dram vial equipped with a stir bar was added 2,4-dichloro-6-(4-isopropoxyphenyl)pyridine (50 mg, 0.18 mmol), 2-(tributylstannyl)pyridine (65 mg, 0.18 mmol), CuI (8 mg, 0.04 mmol), CsF (81 mg, 0.53 mmol), and Pd(PPh$_3$)$_4$ (10 mg, 8.9 µmol). The vial was capped and then placed under N$_2$ atmosphere. To the vial was added DMF (1 mL). The vial was placed in a 80° C. heating block with stirring for 1 h. The mixture was allowed to cool to room temperature. The vial was opened and to the reaction was added 2-(tributylstannyl)pyridine (65 mg, 0.18 mmol) and Pd(PPh$_3$)$_4$ (10 mg, 8.9 µmol). The vial was placed under N$_2$ atmosphere and then returned to the 80° C. heating block with stirring for 1 h. The mixture was cooled to room temperature and then adsorbed onto diatomaceous earth (Celite®). The resulting powder was subjected to C$_{18}$ chromatography (water:MeOH w/0.1% TFA) to afford 4-chloro-6-(4-isopropoxyphenyl)-2,2'-bipyridine as an amber solid. This material was carried forward into step 2.

Step 2:

To a 2 dram vial equipped with a stir bar and charged with 4-chloro-6-(4-isopropoxyphenyl)-2,2'-bipyridine (all material from step 1) was added cesium fluoride (200 mg, 1.32 mmol) and DMSO (0.7 mL). The vial was sealed with a septum cap and then placed in a 140° C. heating block with stirring for 18 h. The reaction mixture was allowed to cool to room temperature. The mixture was transferred to a 125 mL separatory funnel and was diluted with EtOAc (50 mL) and then twice washed with water:brine (25 mL:25 mL). The organic solution was dried over MgSO$_4$; filtered; then concentrated in vacuo to afford an amber solid residue which was subjected to silica gel chromatography (hexane:EtOAc) to afford 4-fluoro-6-(4-isopropoxyphenyl)-2,2'-bipyridine as a colorless solid (16 mg, 29% over two steps). $^1$H-NMR (400 MHz, CDCl$_3$) δ 8.72-8.67 (m, 1H), 8.62 (dt, J=7.8, 1.0 Hz, 1H), 8.10-8.05 (m, 3H), 7.86 (td, J=7.8, 1.8 Hz, 1H), 7.41 (dd, J=10.0, 2.3 Hz, 1H), 7.35 (ddd, J=7.5, 4.8, 1.3 Hz, 1H), 7.04-6.99 (m, 2H), 4.66 (spt, J=6.1 Hz, 1H), 1.40 (d, J=6.0 Hz, 6H); MS: MS m/z 309.2 (M$^+$+1).

Preparation of 2,2'-(4-chloropyridine-2,6-diyl)dithiazole

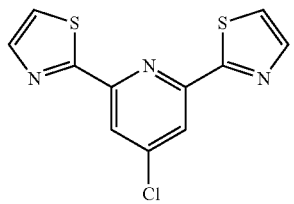 [SMILES: Clc1cc(-c2nccs2)nc(-c2nccs2)c1]

To a 15 mL vial equipped with a stir bar was added 2,4,6-trichloropyridine (365 mg, 2.00 mmol) and Pd(dppf)Cl$_2$ (146 mg, 0.200 mmol). The vial was sealed with a septum screwcap and then was placed under N$_2$ atmosphere. To the vial was added thiazol-2-ylzinc(II) bromide in THF (10.0 mL, 5.00 mmol). The vial was placed in a 60° C. heating block with stirring for 16 h. The reaction mixture was cooled to room temperature, and then was transferred to a 125 mL separatory funnel where it was diluted with Et$_2$O (50 mL) and water (50 mL). The mixture was filtered to remove a significant amount of a yellow-white precipitate and the filtrate was returned to the separatory funnel. The phases were isolated and the aqueous phase was extracted with EtOAc (25 mL). The combined organics were washed with brine (50 mL); dried over MgSO$_4$; filtered; then concentrated in vacuo to afford a pale yellow solid which was subjected to silica gel chromatography (CH$_2$Cl$_2$:MeOH, 100:0 to 90:10) to afford 2,2'-(4-chloropyridine-2,6-diyl)dithiazole as a white solid (294 mg, 53%). $^1$H-NMR (400 MHz, CDCl$_3$) δ 8.23 (s, 2H), 7.97 (d, J=3.0 Hz, 2H), 7.53 (d, J=3.3 Hz, 2H); MS: MS m/z 280.0 (M$^+$+1).

Preparation of 2-(4-fluoropyridin-2-yl)thiazole

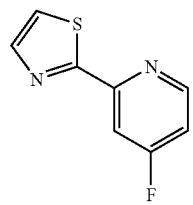 [SMILES: Fc1ccnc(-c2nccs2)c1]

To a 2 dram vial equipped with a stir bar was added 2-chloro-4-fluoropyridine (99 mg, 0.75 mmol) and Pd(dppf)Cl$_2$ (27 mg, 0.038 mmol). The vial was sealed with a septum screwcap and then was placed under N$_2$ atmosphere. To the vial was added thiazol-2-ylzinc(II) bromide in THF (3.0 mL, 1.5 mmol). The vial was placed in a 60° C. heating block with stirring for 3.5 h. The reaction solution was transferred to a 125 mL reparatory funnel and was diluted with EtOAc (50 mL). The solution was washed with water:brine (25 mL:25 mL); then brine (50 mL). The organic solution was dried over MgSO$_4$; filtered; then concentrated in vacuo. The resulting residue was subjected to silica gel chromatography (hexanes: EtOAc) to afford 2-(4-fluoropyridin-2-yl)thiazole as a white solid (106 mg, 78%). $^1$H-NMR (400 MHz, CDCl$_3$-d) δ 8.59

(dd, J=8.3, 5.5 Hz, 1H), 7.98-7.92 (m, 2H), 7.49 (d, J=3.3 Hz, 1H), 7.07 (ddd, J=8.2, 5.6, 2.5 Hz, 1H): MS: MS m/z 181.0 (M⁺+1).

Preparation of 2-(2-fluoropyridin-4-yl)thiazole

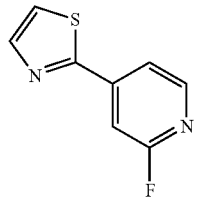 [SMILES: Fc1cc(-c2nccs2)ccn1]

To a 2 dram vial equipped with a stir bar was added 4-bromo-2-fluoropyridine (132 mg, 0.750 mmol) and Pd(dppf)Cl₂ (27 mg, 0.038 mmol). The vial was sealed with a septum screwcap and then was placed under N₂ atmosphere. To the vial was added thiazol-2-ylzinc(II) bromide in THF (3.0 mL, 1.5 mmol). The vial was placed in a 60° C. heating block with stirring for 3.5 h. The reaction solution was transfered to a 125 mL separatory funnel and was diluted with EtOAc (50 mL). The solution was washed with water:brine (25 mL:25 mL); then brine (50 mL). The organic solution was dried over MgSO₄; filtered; then concentrated in vacuo. The residue was subjected to silica gel chromatography (hexanes: EtOAc) to afford 2-(2-fluoropyridin-4-yl)thiazole as a white solid (83 mg, 61%). ¹H-NMR (400 MHz, CDCl₃) δ 8.32 (d, J=5.3 Hz, 1H), 8.00 (d, J=3.3 Hz, 1H), 7.73 (dt, J=5.3, 1.6 Hz, 1H), 7.53 (d, J=3.3 Hz, 1H), 7.51-7.50 (m, 1H): MS: MS m/z 181.0 (M⁺+1).

Preparation of 5-(4-fluoro-6-methylpyridin-2-yl)thiazole

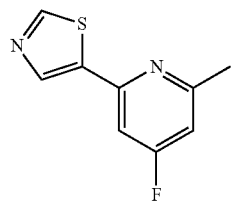

Scheme:

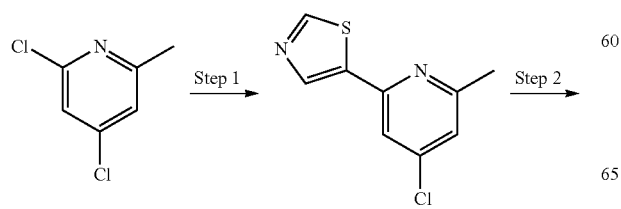

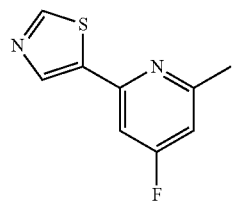

Step 1:
To a 2 dram vial equipped with a stir bar was added 2,4-dichloro-6-methylpyridine (29 mg, 0.18 mmol), 5-(tributylstannyl)thiazole (66 mg, 0.18 mmol), CuI (8 mg, 0.04 mmol), CsF (81 mg, 0.53 mmol), and Pd(PPh₃)₄ (10 mg, 8.9 μmol). The vial was capped with a septum screw-cap and then placed under N₂ atmosphere. To the vial was added degassed DMF (1 mL). The vial was placed in a 80° C. heating block with stirring for 1 hour. The mixture was allowed to cool to room temperature and was then directly purified via C₁₈ chromatography (water:MeOH w/0.1% TFA) to afford 5-(4-chloro-6-methylpyridin-2-yl)thiazole as a white solid. MS: MS m/z 211.1 (M⁺+1). This material was directly carried forward into step 2.

Step 2:
To a 2 dram vial equipped with a stir bar and charged with the entirety of 5-(4-chloro-6-methylpyridin-2-yl)thiazole from step 1 was added CsF (200 mg, 1.32 mmol) and DMSO (0.7 mL). The vial was capped and then placed in a 140° C. heating block with stirring for 16 h. The reaction mixture was transfered to a 125 mL separatory funnel and was diluted with EtOAc (50 mL). The solution was twice washed with brine: water (25 mL:25 mL); dried over MgSO₄; filtered; then concentrated in vacuo to afford an amber solid residue. This material was subjected to silica gel chromatography (hexanes:EtOAc) to afford 5-(4-fluoro-6-methylpyridin-2-yl)thiazole as a colorless solid (7.1 mg, 21% over two steps). ¹H-NMR (500 MHz, CDCl₃) 8.84 (d, J=0.3 Hz, 1H), 8.32 (d, J=0.3 Hz, 1H), 7.22 (dd, J=9.3, 1.7 Hz, 1H), 6.82 (dd, J=9.2, 2.0 Hz, 1H), 2.59 (s, 3H); MS: MS m/z 195.2 (M⁺+1).

Preparation of 2-fluoro-6-(4-isopropoxyphenyl)-4-(1H-pyrazol-1-yl)pyridine

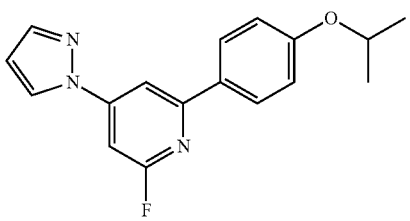 [SMILES: CC(C)Oc1ccc(-c2cc(-n3cccn3)cc(F)n2)cc1]

Scheme:

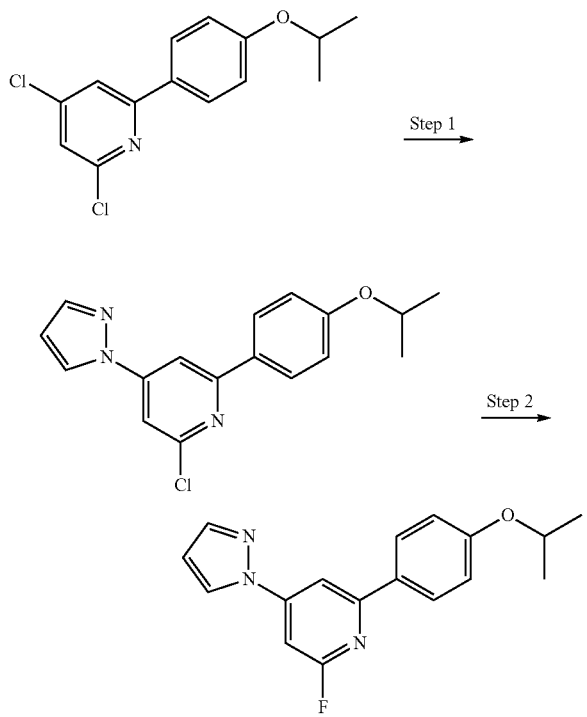

Step 1:

To a dry 2 dram vial equipped with a stir bar was added 1H-pyrazole (16 mg, 0.23 mmol), then DMF (1 mL). To the solution was added sodium hydride (60% disp. in oil, 11 mg, 0.27 mmol) upon which effervesence was immediately observed. The mixture was stirred at room temperature for 15 minutes. To the solution was added 2,4-dichloro-6-(4-isopropoxyphenyl)pyridine (60 mg, 0.21 mmol) as a solution in DMF (0.2 mL). The solution was stirred at room temperature for 3 hours and then at 60° C. for 2.5 hours. The reaction mixture was cooled to room temperature and then directly purified via $C_{18}$ chromatography (water:MeOH w/0.1% TFA) to afford 2-chloro-6-(4-isopropoxyphenyl)-4-(1H-pyrazol-1-yl)pyridine as an off-white solid (41 mg, 62%). $^1$H-NMR (400 MHz, CDCl$_3$) δ 8.05 (d, J=2.5 Hz, 1H), 7.99 (d, J=9.0 Hz, 2H), 7.96 (d, J=1.8 Hz, 1H), 7.81 (d, J=1.5 Hz, 1H), 7.50 (d, J=1.5 Hz, 1H), 6.97 (d, J=8.8 Hz, 2H), 6.56 (dd, J=2.5, 1.8 Hz, 1H), 4.64 (dquin, J=12.2, 6.0 Hz, 1H), 1.40-1.35 (m, 6H); MS: MS m/z 314.2 (M$^+$+1).

Step 2:

To a 2 dram vial equipped with a stir bar and charged with 2-chloro-6-(4-isopropoxyphenyl)-4-(1H-pyrazol-1-yl)pyridine (41 mg, 0.13 mmol) was added CsF (199 mg, 1.31 mmol), then DMSO (0.7 mL). The vial was placed in a 140° C. heating block with vigorous stirring for 18 hours. The reaction mixture was transfered to a separatory funnel and was diluted with EtOAc (50 mL). The organic solution was washed twice with brine:water (25 mL:25 mL); dried over MgSO$_4$; filtered; then concentrated in vacuo to afford 2-fluoro-6-(4-isopropoxyphenyl)-4-(1H-pyrazol-1-yl)pyridine as a yellow solid (25 mg, 63%). $^1$H-NMR (500 MHz, CDCl$_3$) δ 8.07 (dd, J=2.6, 0.4 Hz, 1H), 8.03-7.99 (m, 2H), 7.95 (t, J=1.4 Hz, 1H), 7.81 (d, J=1.4 Hz, 1H), 7.09 (t, J=1.6 Hz, 1H), 7.01-6.97 (m, 2H), 6.57 (dd, J=2.7, 1.7 Hz, 1H), 4.65 (spt, J=6.1 Hz, 1H), 1.39 (d, J=6.1 Hz, 6H); MS: MS m/z 298.2 (M$^+$+1).

Preparation of 2-(4-chloro-[2,3'-bipyridin]-6-yl)thiazole

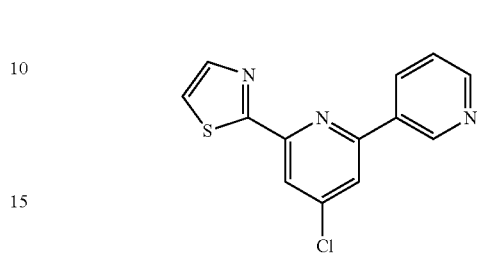

To a 2 dram vial equipped with a stir bar was added 2-(4,6-dichloropyridin-2-yl)thiazole (50 mg, 0.216 mmol), 6-Methyl-2-(3-pyridinyl)-1,3,6,2-dioxazaborocane-4,8-dione ("3-Pyridineboronic acid MIDA ester", 50.6 mg, 0.216 mmol), Pd(dppf)Cl$_2$ (8 mg, 11 μmol) and K$_3$PO$_4$ (344 mg, 1.62 mmol). The vial was capped with a septum screwcap and then placed under N$_2$ atmosphere. To the vial was added THF (1.00 mL) and water (0.20 mL). The mixture was placed in a 60° C. with stirring for 3 h. The reaction mixture was transfered to a 125 mL separatory funnel using EtOAc and water. The mixture was diluted with EtOAc (30 mL), then washed with sat. aq. NaHCO$_3$ (20 mL). The aq. phase was extracted with EtOAc (20 mL). The combined organics were dried over MgSO$_4$; filtered; then concentrated in vacuo to afford a solid yellow residue. This material was subjected to silica gel chromatography (hexanes:EtOAc, 100:0 to 50:50) to afford 2-(4-chloro-[2,3'-bipyridin]-6-yl)thiazole as a white solid (32 mg, 54%). $^1$H-NMR (400 MHz, CDCl$_3$) δ 9.32 (dd, J=2.3, 0.8 Hz, 1H), 8.73 (dd, J=4.9, 1.6 Hz, 1H), 8.43-8.37 (m, 1H), 8.22 (d, J=1.8 Hz, 1H), 7.98 (d, J=3.0 Hz, 1H), 7.79 (d, J=1.8 Hz, 1H), 7.53 (d, J=3.3 Hz, 1H), 7.47 (ddd, J=7.9, 4.9, 1.0 Hz, 1H).

Preparation of 2-(4-chloro-6-(4-(trifluoromethyl)phenyl)pyridin-2-yl)thiazole

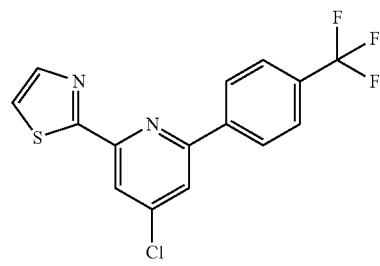 [SMILES: FC(F)(F)c1ccc(-c2cc(Cl)cc(-c3nccs3)n2)cc1]

To a 2 dram vial equipped with a stir bar was added 2-(4,6-dichloropyridin-2-yl)thiazole (50 mg, 0.22 mmol), 4,4,5,5-tetramethyl-2-(4-(trifluoromethyl)phenyl)-1,3,2-dioxaborolane (59 mg, 0.22 mmol), Pd(dppf)Cl$_2$ (8 mg, 11 μmol) and K$_3$PO$_4$ (344 mg, 1.62 mmol). The vial was capped with a septum screwcap and then placed under N$_2$ atmosphere. To the vial was added THF (1 mL) and water (0.5 mL). The mixture was placed in a 60° C. heating block with stirring for 16 h. The reaction mixture was cooled to room temperatured; diluted with MeOH and then concentrated in vacuo. The resulting residue was dissolved/suspended in CH$_2$Cl$_2$ and then filtered through Celite. The filtrate was concentrated to afford a solid orange residue. This material was subjected to silica gel chromatography (hexanes:EtOAc, 100:0 to 95:5) to afford 2-(4-chloro-6-(4-(trifluoromethyl)phenyl)pyridin-2-yl)thiazole as a white solid (46 mg, 62%). $^1$H-NMR (400 MHz, CDCl$_3$) 8.23 (d, J=1.8 Hz, 2H), 8.21 (s, 1H), 7.98 (d, J=3.3 Hz, 1H), 7.80 (d, J=1.5 Hz, 2H), 7.78 (s, 1H), 7.53 (d, J=3.3 Hz, 1H).

Preparation of 2-(4-chloro-6-(p-tolyl)pyridin-2-yl)thiazole

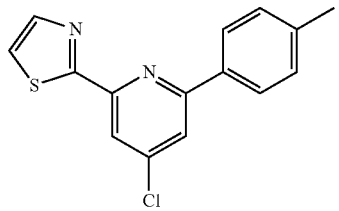 [SMILES: Cc1ccc(-c2cc(Cl)cc(-c3nccs3)n2)cc1]

To a 2 dram vial equipped with a stir bar was added 2-(4,6-dichloropyridin-2-yl)thiazole (50 mg, 0.22 mmol), p-tolylboronic acid (29 mg, 0.22 mmol), Pd(dppf)Cl$_2$ (8 mg, 11 µmol) and K$_3$PO$_4$ (344 mg, 1.62 mmol). The vial was capped with a septum screw-cap and then placed under N$_2$ atmosphere. To the vial was added THF (1 mL) and water (0.5 mL). The mixture was placed in a 60° C. oil bath with stirring for 16 h. The reaction mixture was diluted with EtOAc (5 mL) and brine (1 mL). The mixture was shaken; the aq. phase was decanted away via pipet. The organic phase was dried over MgSO$_4$; filtered; and the filtrate was concentrated in vacuo to afford a dark amber solid. This material was subjected to silica gel chromatography (hexanes:EtOAc, 100:0 to 60:40) to afford 2-(4-chloro-6-(p-tolyl)pyridin-2-yl)thiazole as a white solid (28 mg, 45%). $^1$H-NMR (400 MHz, CDCl$_3$) δ 8.12 (d, J=1.8 Hz, 1H), 8.00 (d, J=8.3 Hz, 2H), 7.96 (d, J=3.3 Hz, 1H), 7.74 (d, J=1.8 Hz, 1H), 7.50 (d, J=3.3 Hz, 1H), 7.33 (d, J=8.0 Hz, 2H), 2.44 (s, 3H).

Preparation of 2-(4-chloro-6'-isopropoxy-[2,3'-bipyridin]-6-yl)thiazole

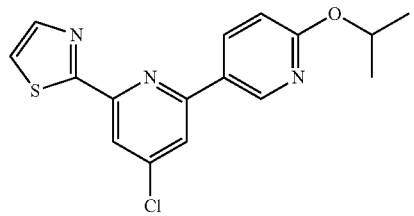 [SMILES: CC(C)Oc1ccc(-c2cc(Cl)cc(-c3nccs3)n2)cn1]

To a 2 dram vial equipped with a stir bar was added 2-(4,6-dichloropyridin-2-yl)thiazole (50 mg, 0.22 mmol), 2-isopropoxy-5-(4,4,5,5-tetramethyl-1,3,2-dioxaborolan-2-yl)pyridine (85 mg, 0.33 mmol), Pd(dppf)Cl$_2$ (8.0 mg, 11 µmol) and K$_3$PO$_4$ (344 mg, 1.62 mmol). The vial was capped with a septum screw-cap and then placed under N$_2$ atmosphere. To the vial was added THF (1 mL) and water (0.50 mL). The mixture was placed in a 60° C. oil bath with stirring for 6 h. The reaction mixture was diluted with EtOAc (4 mL) and the aqueous phase was decanted away. The organic phase was diluted with EtOAc to a volume of 40 mL. The solution was dried over MgSO$_4$; filtered; then concentrated in vacuo to afford a dark residue. This material was subjected to silica gel chromatography (hexanes:EtOAc, 100:0 to 85:15) to afford 2-(4-chloro-6'-isopropoxy-[2,3'-bipyridin]-6-yl)thiazole as a white solid (34 mg, 47%). $^1$H-NMR (400 MHz, CDCl$_3$) δ 8.92-8.87 (m, 1H), 8.32-8.25 (m, 1H), 8.13 (d, J=1.8 Hz, 1H), 7.96 (d, J=3.0 Hz, 1H), 7.68 (d, J=1.8 Hz, 1H), 7.50 (d, J=3.0 Hz, 1H), 6.82 (dd, J=8.8, 0.5 Hz, 1H), 5.41 (spt, J=6.2 Hz, 1H), 1.41 (d, J=6.3 Hz, 6H).

Preparation of 2-(4-fluoro-6-methoxypyridin-2-yl)thiazole

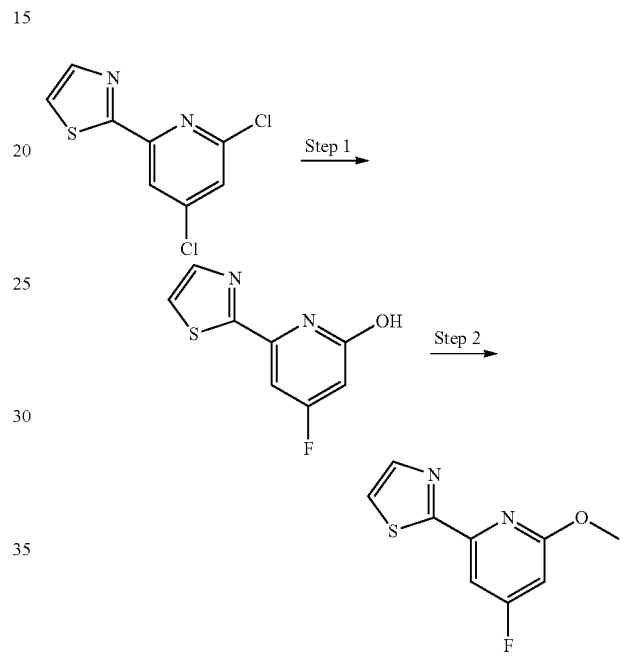

Step 1:

To a 2 dram vial equipped with a stir bar and charged with 2-(4,6-dichloropyridin-2-yl)thiazole (250 mg, 1.08 mmol) was added cesium fluoride (986 mg, 6.49 mmol), then DMSO (5 mL). The vial was placed in a 140° C. heating block with stirring for 16 h. The mixture was cooled to room temperature, transferred to a 125 mL separatory funnel, and then diluted with water (50 mL). The mixture was extracted with EtOAc (2×75 mL). The combined organics were washed with brine (50 mL); dried over MgSO$_4$; filtered; then concentrated in vacuo. The resulting solid residue was subjected to silica gel chromatography (hexanes:EtOAc, 100:0 to 0:100) to afford 2-(4,6-difluoropyridin-2-yl)thiazole as a white solid (102 mg, 48%): $^1$H NMR (500 MHz, CDCl$_3$) δ 7.95 (d, J=3.2 Hz, 1H), 7.86 (dd, J=8.3, 1.8 Hz, 1H), 7.53 (d, J=3.2 Hz, 1H), 6.69 (dt, J=7.9, 2.0 Hz, 1H); and 4-fluoro-6-(thiazol-2-yl)pyridin-2-ol as a white solid (35 mg, 16%): $^1$H NMR (500 MHz, CDCl$_3$) δ 7.92 (d, J=3.2 Hz, 1H), 7.60 (s, 1H), 7.49 (d, J=3.2 Hz, 1H), 6.43 (d, J=1.1 Hz, 1H).

Step 2:

To a 2 dram vial equipped with a stir bar was added 4-fluoro-6-(thiazol-2-yl)pyridin-2-ol (35 mg, 0.18 mmol) as a solution in DMF (1 mL). To the vial was added K$_2$CO$_3$ (49 mg, 0.36 mmol), then iodomethane (25 µL, 0.40 mmol). The vial was capped with a PTFE-lined cap and then placed in a 40° C. heating block with stirring for 2 h. The reaction mixture was transferred to a 125 mL separatory funnel and was diluted with water (25 mL). The mixture was extracted with CH$_2$Cl$_2$ (2×25 mL). The combined organics were dried over MgSO$_4$; filtered; the concentrated in vacuo. The resulting residue was subjected to SiO$_2$ column chromatography (hexanes:EtOAc, 100:0 to 50:50) to afford 2-(4-fluoro-6-methoxypyridin-2-yl)thiazole as a white solid (31 mg, 82%). $^1$H-NMR (500 MHz, CDCl$_3$) δ 7.92 (d, J=3.2 Hz, 1H), 7.66 (dd, J=1.9, 1.1 Hz, 1H), 7.48 (d, J=3.3 Hz, 1H), 6.44 (d, J=2.0 Hz, 1H), 3.97 (s, 3H).

Preparation of
2-(4-chloro-6-phenylpyridin-2-yl)thiazole

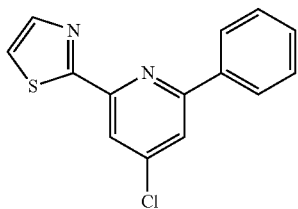 [SMILES: Clc1cc(-c2ccccc2)nc(-c2nccs2)c1]

To a 2 dram vial equipped with a stir bar was added 2-(4,6-dichloropyridin-2-yl)thiazole (50 mg, 0.22 mmol), 6-Methyl-2-phenyl-1,3,6,2-dioxazaborocane-4,8-dione ("phenylboronic acid MIDA ester", 50 mg, 0.22 mmol), Pd(dppf)Cl$_2$ (8 mg, 11 μmol) and K$_3$PO$_4$ (344 mg, 1.62 mmol). The vial was capped with a septum screwcap and then placed under N$_2$ atmosphere. To the vial was added THF (1 mL) and water (0.5 mL). The mixture was placed in a 60° C. oil bath with stirring for 16 h. The reaction mixture was diluted with EtOAc (5 mL) and brine (1 mL). The mixture was shaken; the aq. phase was decanted away via pipet. The organic phase was dried over MgSO$_4$; filtered; and the filtrate was concentrated in vacuo to afford a dark amber solid. This material was subjected to silica gel chromatography to afford 2-(4-chloro-6-phenylpyridin-2-yl)thiazole as a yellow solid (38 mg, 64%). $^1$H-NMR (400 MHz, CDCl$_3$) δ 8.16 (d, J=1.8 Hz, 1H), 8.14-8.08 (m, 2H), 7.97 (d, J=3.0 Hz, 1H), 7.77 (d, J=1.8 Hz, 1H), 7.58-7.45 (m, 4H).

Preparation of
2-(4-fluoropyridin-2-yl)-4-methylthiazole

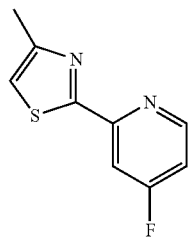

To a dry 10 mL Schlenk flask equipped with a stir bar and placed under N$_2$ atmosphere was added 2-bromo-4-methylthiazole (244 mg, 1.37 mmol) in THF (5 mL). The flask was cooled to −78° C. To the solution was added n-butyllithium in hexanes (0.55 mL, 1.37 mmol). The solution was stirred for 5 minutes. To the solution was added zinc(II) chloride in THF (2.74 mL, 1.37 mmol). A thick ppt. immediately formed which hindered stirring. The flask was immediately transfered to a r.t. water bath and the solution was allowed to warm to r.t. with stirring for 30 min. To the solution was added 2-chloro-4-fluoropyridine (150 mg, 1.14 mmol), then Pd(dppf)Cl$_2$ (42 mg, 0.057 mmol). The vial was placed in a 60° C. heating block with stirring (t=0). The reaction mixture was transfered to a 125 mL separatory funnel and was diluted with Et$_2$O:EtOAc (25 mL:25 mL). The solution was washed with water:brine (25 mL:25 mL). The aq. phase was extracted with EtOAc (25 mL). The combined organics were washed with brine (25 mL); dried over MgSO$_4$; filtered; then concentrated in vacuo. The residue was subjected to silica gel chromatography to afford 2-(4-fluoropyridin-2-yl)-4-methylthiazole as an orange solid (54 mg, 24%).

$^1$H-NMR (400 MHz, CDCl$_3$) δ 8.57 (dd, J=8.2, 5.6 Hz, 1H), 7.91 (dd, J=9.7, 2.4 Hz, 1H), 7.09-7.01 (m, 2H), 2.54 (d, J=1.0 Hz, 3H).

Preparation of
2-(4-fluoropyridin-2-yl)-5-methylthiazole

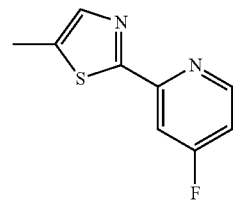

To a dry 10 mL Schlenk flask equipped with a stir bar and placed under N$_2$ atmosphere was added 2-bromo-5-methylthiazole (244 mg, 1.37 mmol) in THF (5 mL). The flask was cooled to −78° C. To the solution was added n-butyllithium in hexanes (0.55 mL, 1.37 mmol). The solution was stirred for 15 minutes. To the solution was added zinc(II) chloride in THF (2.74 mL, 1.37 mmol). The solution was immediately allowed to warm to r.t. (using a r.t. water bath) with stirring for 30 min. To the solution was added 2-chloro-4-fluoropyridine (150 mg, 1.14 mmol), then Pd(dppf)Cl$_2$ (42 mg, 0.057 mmol). The vial was placed in a 60° C. heating block with stirring for 2.25 h. The reaction solution was transfered to a 125 mL separatory funnel and was diluted with Et$_2$O (20 mL). The solution was washed with sat. aq. NaHCO$_3$ (20 mL). The aq. phase was extracted with EtOAc (25 mL). The combined organics were washed with brine (20 mL); dried over MgSO$_4$; filtered; then concentrated in vacuo to afford an orange residue. This material was subjected to silica gel chromatography (hexanes:EtOAc, 100:0 to 80:20) to afford 2-(4-fluoropyridin-2-yl)-5-methylthiazole as a white solid (54 mg, 24%). $^1$H-NMR (400 MHz, CDCl$_3$) δ 8.55 (dd, J=8.2, 5.4 Hz, 1H), 7.91-7.82 (m, 1H), 7.62-7.56 (m, 1H), 7.02 (ddd, J=8.2, 5.6, 2.5 Hz, 1H), 2.55 (d, J=1.3 Hz, 3H).

Preparation of 2,2'-(4-chloropyridine-2,6-diyl)bis(5-methylthiazole

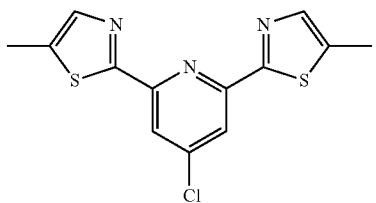

A dry 25 mL schlenk flask equipped with a stir bar and placed under N₂ atmosphere was charged with THF (7 mL) and 2-bromo-5-methylthiazole (610 mg, 3.43 mmol). The solution was cooled to −78° C. To the solution was added n-butyllithium in hexanes (1.37 mL, 3.43 mmol) upon which the solution immediately turned dark/golden. The solution was stirred for 5 minutes. To the solution was added zinc(II) chloride in THF (6.85 mL, 3.43 mmol) upon which the solution lightened to a golden color. The solution was immediately warmed to r.t. with a water bath, with stirring for 30 minutes. To the reaction solution was added 2,4,6-trichloropyridine (250 mg, 1.37 mmol) and Pd(dppf)Cl₂ (100 mg, 0.137 mmol). The flask was sealed and then was placed in a 60° C. oil bath with stirring for 16 h. The reaction solution was transfered to a 500 mL reparatory funnel and was diluted with EtOAc (100 mL), then washed with brine (50 mL). The organic phase was dried over MgSO₄; filtered; then concentrated in vacuo to afford a dark amber solid. This material was subjected to silica gel chromatography to afford 2-(4,6-dichloropyridin-2-yl)-5-methylthiazole as a white solid (33 mg, 8%): ¹H-NMR (500 MHz, CDCl₃) δ 8.07 (d, J=1.7 Hz, 1H), 7.59 (d, J=1.1 Hz, 1H), 7.32 (d, J=1.6 Hz, 1H), 2.55 (d, J=1.1 Hz, 3H); and 2,2'-(4-chloropyridine-2,6-diyl)bis(5-methylthiazole) as a white solid (160 mg, 48%): ¹H-NMR (500 MHz, CDCl₃) 8.10 (s, 2H), 7.60 (d, J=1.3 Hz, 2H), 2.59-2.55 (m, 6H).

Preparation of 4-(4-chloro-6-(4-isopropoxyphenyl)pyridin-2-yl)thiazole

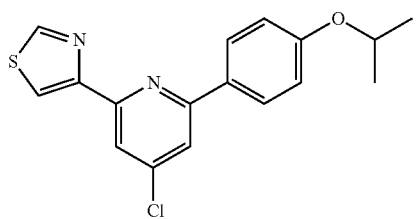 [SMILES: CC(C)Oc1ccc(-c2cc(Cl)cc(-c3cscn3)n2)cc1]

To a 2 dram vial equipped with a stir bar was added 2,4-dichloro-6-(4-isopropoxyphenyl)pyridine (189 mg, 0.668 mmol), 4-(tributylstannyl)thiazole (250 mg, 0.668 mmol), CuI (32 mg, 0.17 mmol), CsF (304 mg, 2.00 mmol), and Pd(PPh₃)₄ (39 mg, 0.033 mmol). The vial was capped and then placed under N₂ atmosphere. To the vial was added DMF (4 mL). The vial was placed in a 80° C. heating block with stirring for 1 h. The mixture was allowed to cool to room temperature. To the reaction was added 4-(tributylstannyl)thiazole (250 mg, 0.668 mmol) and Pd(PPh₃)₄ (10 mg, 8.9 μmol). The vial was placed under N₂ atmosphere and then returned to the 80° C. with stirring for 1 h. The mixture was cooled to room temperature and the mixture was then adsorbed onto diatomaceous earth (Celite®). The resulting powder was subjected to C₁₈ chromatography (water:MeCN, 100:0 to 0:100) to afford 4-(4-chloro-6-(4-isopropoxyphenyl)pyridin-2-yl)thiazole as a dark amber solid (58 mg, 26%). ¹H-NMR (500 MHz, CDCl₃) δ 8.90 (d, J=2.2 Hz, 1H), 8.36 (d, J=2.2 Hz, 1H), 8.09 (d, J=1.7 Hz, 1H), 8.06-8.02 (m, 2H), 7.63 (d, J=1.7 Hz, 1H), 7.03-6.98 (m, 2H), 4.66 (spt, J=6.1 Hz, 1H), 1.41-1.38 (m, 6H).

Preparation of (1R,3r,5S)-bicyclo[3.1.0]hexan-3-yl pyridin-2-yl carbonate

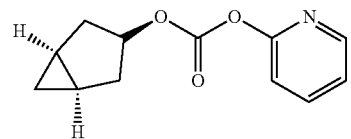

To a round-bottom flask equipped with a stir bar and charged with (1R,3r,5S)-bicyclo[3.1.0]hexan-3-ol (2.50 g, 25.5 mmol) was added CH₂Cl₂ (100 mL), then dipyridin-2-yl carbonate (6.61 g, 30.6 mmol) followed by Et₃N (4.26 mL, 30.6 mmol). The solution was stirred for 16 h. The solvent was removed under vacuum and the resulting residue was subjected to silica gel chromatography (hexanes:EtOAc, 95:5 to 80:20) to afford (1R,3r,5S)-bicyclo[3.1.0]hexan-3-yl pyridin-2-yl carbonate as a colorless oil (3.07 g, 55%). ¹H NMR (400 MHz, CHLOROFORM-d) δ 8.40 (ddd, J=4.8, 2.0, 0.8 Hz, 1H), 7.84-7.76 (m, 1H), 7.24 (ddd, J=7.3, 4.9, 0.9 Hz, 1H), 7.11 (dt, J=8.2, 0.8 Hz, 1H), 5.25 (t, J=6.8 Hz, 1H), 2.31-2.20 (m, 2H), 2.09-2.01 (m, 2H), 1.38-1.31 (m, 2H), 0.53 (tdt, J=8.2, 5.2, 1.3 Hz, 1H), 0.48-0.43 (m, 1H).

Preparation of pyridin-2-yl(3-(trifluoromethyl)tetrahydro-2H-pyran-3-yl)carbonate

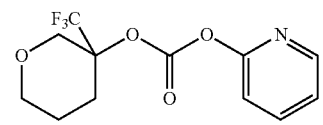 [SMILES: O=C(Oc1ccccn1)OC1(C(F)(F)F)CCCOC1]

Scheme:

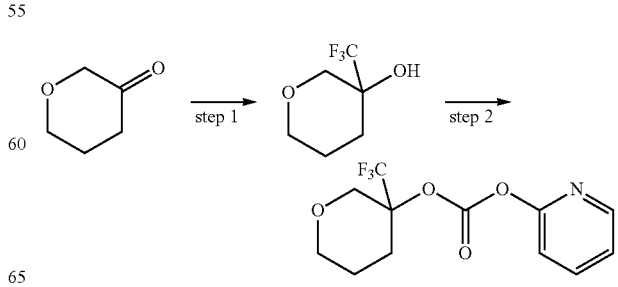

Step 1:

To a round-bottom flask equipped with a stir bar and placed under N₂ atmosphere was added THF (50 mL), then trimethyl (trifluoromethyl)silane (1.03 mL, 6.99 mmol). The solution was cooled to 0° C. and to the solution was added dihydro-2H-pyran-3(4H)-one (500 mg, 4.99 mmol). The solution was stirred for 5 minutes at 0° C. and then was allowed to warm to room temperature with stirring for 30 minutes. The solution was cooled to 0° C. and to the solution was added aq 1M HCl (50 mL). The mixture was stirred at room temperature overnight. The mixture was diluted with water and EtOAc and was transferred to a separatory funnel. The organic phase was isolated; washed with brine; dried over MgSO₄, filtered; then concentrated in vacuo to afford 3-(trifluoromethyl)tetrahydro-2H-pyran-3-ol as a colorless oil (0.40 g, 47%). ¹H-NMR (400 MHz, CDCl₃) δ 4.01-3.93 (m, 1H), 3.82 (dd, J=11.8, 2.5 Hz, 1H), 3.60 (d, J=12.0 Hz, 1H), 3.41 (td, J=11.8, 2.5 Hz, 1H), 2.10-2.08 (m, 2H), 1.97-1.90 (m, 1H), 1.82 (dd, J=12.9, 4.4 Hz, 1H), 1.65-1.55 (m, 1H).

Step 2:

To a round-bottom flask equipped with a stir bar was added sodium hydride (60% w/w in mineral oil, 141 mg, 3.53 mmol) and THF (20 mL). The suspension was cooled to 0° C., and to the mixture was added 3-(trifluoromethyl)tetrahydro-2H-pyran-3-ol (500 mg, 2.94 mmol). After stirring for 30 min. the solution was transferred via cannula to a solution of di(pyridin-2-yl) carbonate (635 mg, 2.94 mmol) in THF (20 mL). The resulting mixture was stirred at 0° C. for 30 min. The mixture was then warmed to room temperature with stirring for 2 h. The mixture was diluted with EtOAc followed and brine and transferred to a separatory funnel. The organic phase was isolated; dried over MgSO₄; filtered; then concentrated in vacuo. The resulting residue was subjected to silica gel chromatography (hexane:EtOAc 95:5 to 60:40) to afford pyridin-2-yl(3-(trifluoromethyl)tetrahydro-2H-pyran-3-yl) carbonate as a colorless oil (195 mg, 23%). ¹H-NMR (400 MHz, CDCl₃) δ 8.43 (dd, J=4.9, 1.4 Hz, 1H), 7.88-7.75 (m, 1H), 7.32-7.24 (m, 1H), 7.19 (d, J=8.3 Hz, 1H), 4.70 (dd, J=12.4, 2.6 Hz, 1H), 4.02-3.92 (m, 1H), 3.67 (d, J=12.3 Hz, 1H), 3.60-3.42 (m, 1H), 2.68-2.53 (m, 1H), 2.08-1.92 (m, 2H), 1.77-1.62 (m, 1H).

Preparation of (2S,4R)-methyl 1-((2S,3R)-2-((tert-butoxycarbonyl)amino)-3,5-dimethylnon-8-enoyl)-4-hydroxypyrrolidine-2-carboxylate

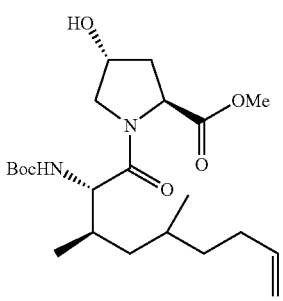 [SMILES: C=CCCC(C)C[C@@H](C)[C@H](NC(=O)OC(C)(C)C)C(=O)N1C[C@H](O)C[C@H]1C(=O)OC]

Scheme:

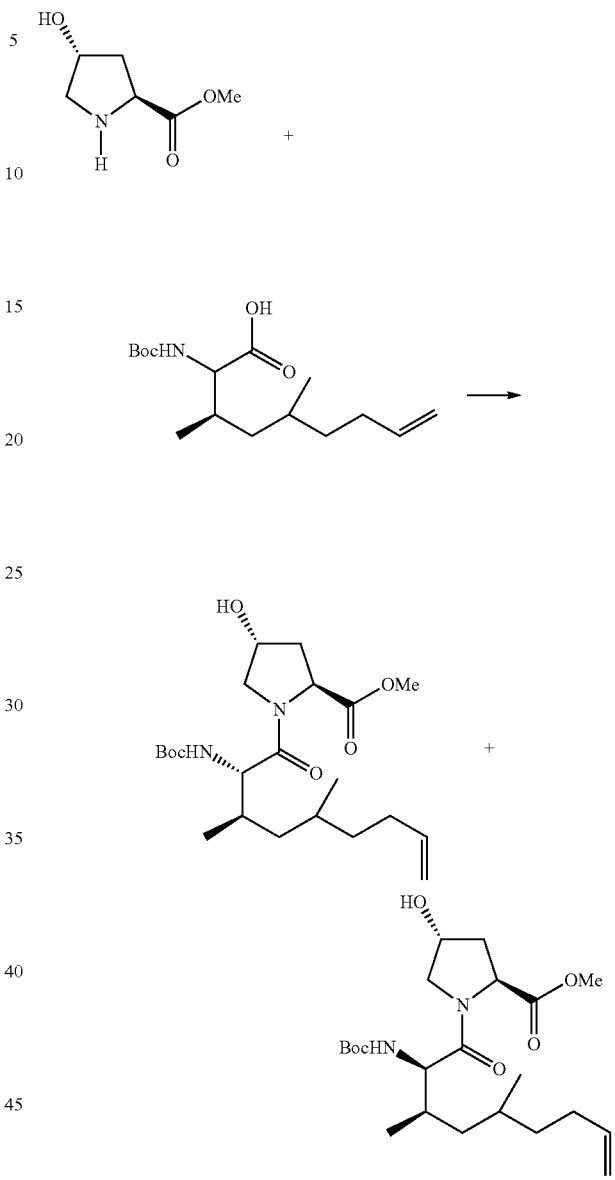

O-(7-Azabenzotriazol-1-yl)-N,N,N',N'-tetramethyluronium hexafluorophosphate ("HATU", 31.7 g, 83.0 mmol) was added to a solution of (2S,4R)-methyl 4-hydroxypyrrolidine-2-carboxylate HCl salt (16.7 g, 92.0 mmol), (3R)-2-((tert-butoxycarbonyl)amino)-3,5-dimethylnon-8-enoic acid (25 g, 83 mmol) and NEt₃ (35 mL, 250 mmol) in CH₂Cl₂ (250 mL) and the solution was stirred at room temperature for 16 h. The reaction solution was transferred to a reparatory funnel and was washed with aqueous 1N HCl (3×) and then brine. The organics were dried over MgSO₄, filtered and concentrated in vacuo. The crude material was purified via silica gel chromatography (hexane:acetone 80:20 to 40:60) to afford the desired product (2S,4R)-methyl 1-((2S,3R)-2-((tert-butoxycarbonyl)amino)-3,5-dimethylnon-8-enoyl)-4-hydroxypyrrolidine-2-carboxylate (10.8 g, 30% yield), MS: MS m/z 427.2 (M⁺+1) and the undesired product (2S,4R)-methyl 1-((2R,3R)-2-((tert-butoxycarbonyl)amino)-3,5-dimethylnon-8-enoyl)-4-hydroxypyrrolidine-2-carboxylate (12 g, 34% yield), MS: MS m/z 427.2 (M++1).

Preparation of tert-butyl ((2R,6S,7R,13aS,14aR, 16aS,Z)-2-hydroxy-7,9-dimethyl-14a-(((1-methylcyclopropyl)sulfonyl)carbamoyl)-5,16-dioxo-1,2,3,5,6, 7,8,9,10,11,13a,14,14a,15,16,16a-hexadecahydrocyclopropa[e]pyrrolo[1,2-a][1,4] diazacyclopentadecin-6-yl)carbamate

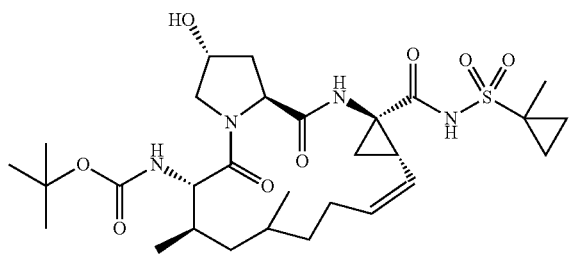 [SMILES: CC1CC/C=C\[C@@H]2C[C@@]2(C(=O)NS(=O)(=O)C2(C)CC2)NC(=O)[C@@H]2C[C@@H](O)CN2C(=O)[C@@H](NC(=O)OC(C)(C)C)[C@H](C)C1]

Scheme:

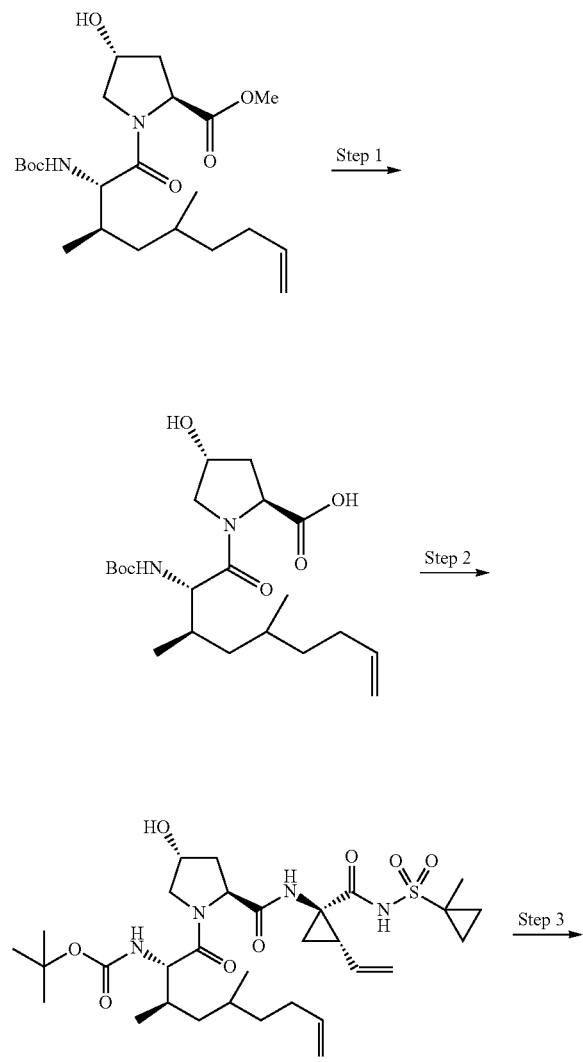

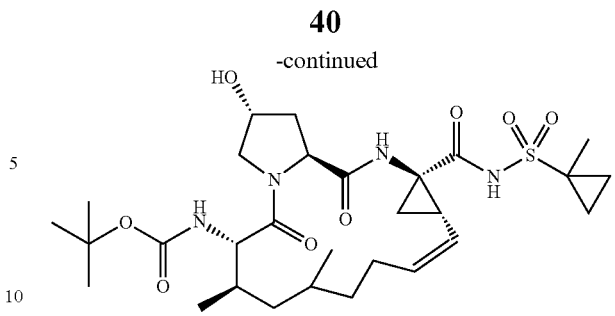

Step 1:

To a 250 mL round-bottom flask equipped with a large stir bar was added (2S,4R)-methyl 1-((2S,3R)-2-((tert-butoxycarbonyl)amino)-3,5-dimethylnon-8-enoyl)-4-hydroxypyrrolidine-2-carboxylate (10.9 g, 25.5 mmol), then THF (75 mL) and methanol (75 mL). To the stirred solution was added aq. lithium hydroxide (2.0 M, 38 mL, 77 mmol). The mixture was vigorously stirred for 1.5 h. The volatiles were removed organics were removed in vacuo and the resulting aqueous solution and solid residue was transferred to a 500 mL separatory funnel. The aqueous phase was adjusted to pH 2.5 using aqueous 2N HCl and was then extracted with EtOAc (3×100 mL). The combined organics were washed with aqueous sat. NaCl adjusted to pH 2.5 with aqueous HCl, dried over MgSO₄; filtered; then concentrated in vacuo to afford (2S, 4R)-1-((2S,3R)-2-((tert-butoxycarbonyl)amino)-3,5-dimethylnon-8-enoyl)-4-hydroxypyrrolidine-2-carboxylic acid as a colorless foam (8.82 g, 84%). MS: MS m/z 413.2 (M++1).

Step 2:

To a 500 mL round-bottom flask charged with (1R,2S)-1-amino-N-((1-methylcyclopropyl)sulfonyl)-2-vinylcyclopropanecarboxamide trifluoroacetic acid salt (7.53 g, 21.0 mmol) was added a solution of (2S,4R)-1-((2S,3R,5R)-2-((tert-butoxycarbonyl)amino)-3,5-dimethylnon-8-enoyl)-4-hydroxypyrrolidine-2-carboxylic acid (8.82 g, 21.38 mmol) in CH₂Cl₂ (100 mL). To the solution was added N,N-diisopropylethylamine (15 mL, 86 mmol) and DMF (15 mL) to afford a homogeneous orange solution. The flask was placed in a room temperature water bath. To the stirred solution was added HATU (9.59 g, 25.2 mmol). The solution was stirred at room temperature for 20 h. The reaction mixture was concentrated in vacuo and the resulting residue was dissolved in EtOAc (300 mL) and transfered to a 1 L separatory funnel. The solution was washed with aq. 1M HCl (4×225 mL). The combined aqueous phases were extracted with EtOAc (150 mL). The combined organics were dried over MgSO₄; filtered, then concentrated in vacuo. The resulting residue was dissolved in MeOH and concentrated onto Celite in vacuo; the resulting powder was subjected to silica gel chromatography (hexanes:acetone, 90:10 to 60:40) to afford tert-butyl ((2S,3R)-1-((2S,4R)-4-hydroxy-2-(((1R,2S)-1-(((1-methylcyclopropyl)sulfonyl)carbamoyl)-2-vinylcyclopropyl)carbamoyl)pyrrolidin-1-yl)-3,5-dimethyl-1-oxonon-8-en-2-yl) carbamate as a colorless solid (5.56 g, 41%). MS: MS m/z 639.5 (M++1).

Step 3:

A solution of tert-butyl ((2S,3R)-1-((2S,4R)-4-hydroxy-2-(((1R,2S)-1-(((1-methylcyclopropyl)sulfonyl)carbamoyl)-2-vinylcyclopropyl)carbamoyl)pyrrolidin-1-yl)-3,5-dimethyl-1-oxonon-8-en-2-yl)carbamate (8.40 g, 13.2 mmol) in 1,2-dichloroethane (1500 ml) was sparged with nitrogen for 30 min. and then 1,3-Bis-(2,4,6-trimethylphenyl)-2-imidazolidinylidene)dichloro(o-isopropoxyphenylmethylene)ruthenium ("Hoveyda-Grubbs Catalyst 2nd Generation", 0.413 g, 0.657 mmol) was added. The reaction solution was heated to 80° C. for 2 h. The reaction solution was cooled to room temperature and then was concentrated in vacuo. The resulting residue was subjected to silica gel chromatography (hexane:acetone 80:20 to 40:60) to afford tert-butyl ((2R,6S,7R,13aS,14aR,16aS,Z)-2-hydroxy-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate as a brown solid (5.6 g, 70% yield). MS: MS m/z 611.3 (M++1).

Preparation of tert-butyl ((2R,6S,7R,13aS,14aR,16aS,Z)-14a-((cyclopropylsulfonyl)carbamoyl)-2-hydroxy-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate

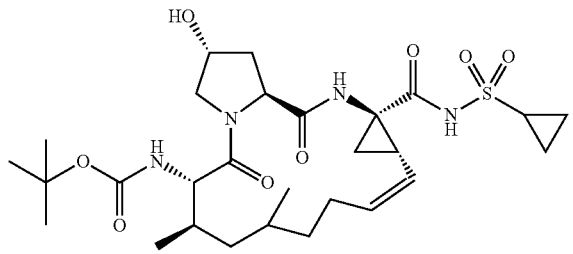

Scheme

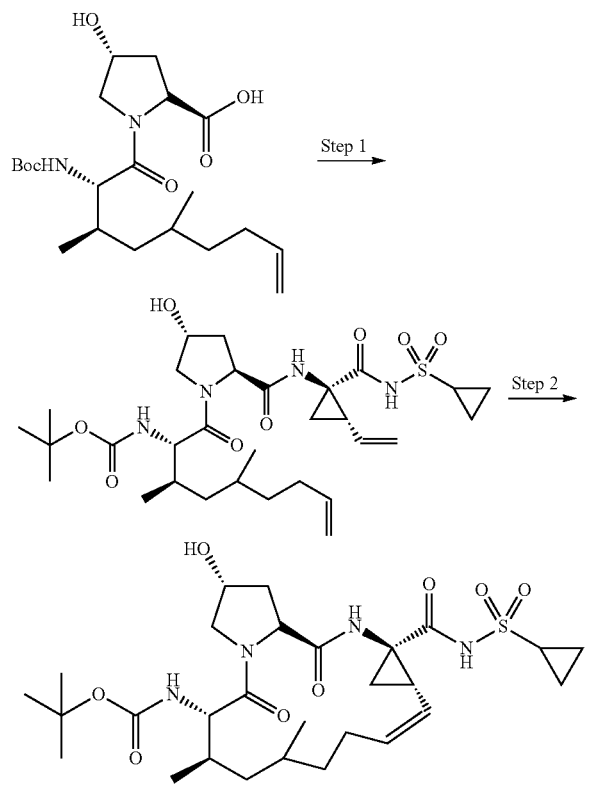

Step 1:
To a solution of (2S,4R)-1-((2S,3R)-2-((tert-butoxycarbonyl)amino)-3,5-dimethylnon-8-enoyl)-4-hydroxypyrrolidine-2-carboxylic acid (10.4 g, 25.3 mmol), (1R,2S)-1-amino-N-(cyclopropylsulfonyl)-2-vinylcyclopropanecarboxamide p-toluenesulfonate salt (11.2 g, 27.8 mmol), and N,N-diisopropylethylamine (17.6 ml, 101 mmol) in CH₂Cl₂ (200 ml) was added HATU (11.5 g, 30.4 mmol). The mixture was stirred at room temperature for 16 h. The mixture was transferred to a separatory funnel and was thrice washed with aq. 1N HCl; then brine. The organic phase was dried over MgSO₄; filtered; then concentrated in vacuo. The resulting residue was subjected to silica gel chromatography to afford tert-butyl ((2S,3R)-1-((2S,4R)-2-(((1R,2S)-1-((cyclopropylsulfonyl)carbamoyl)-2-vinylcyclopropyl)carbamoyl)-4-hydroxypyrrolidin-1-yl)-3,5-dimethyl-1-oxonon-8-en-2-yl)carbamate as a light-orange solid foam (14.8 g, 94%).

Step 2:
A solution of tert-butyl ((2S,3R)-1-((2S,4R)-2-(((1R,2S)-1-((cyclopropylsulfonyl)carbamoyl)-2-vinylcyclopropyl)carbamoyl)-4-hydroxypyrrolidin-1-yl)-3,5-dimethyl-1-oxonon-8-en-2-yl)carbamate (9.50 g, 15.2 mmol) in DCE (2.5 L) was sparged with nitrogen for 30 min. To the solution was added Hoveyda-Grubbs 2nd Generation Catalyst (0.574 g, 0.912 mmol). The solution was heated at 80° C. for 2 h; then cooled to 45° C. and stirred for 2 days. The reaction solution was concentrated in vacuo and the resulting solid residue was then subjected to flash chromatography on silica gel (hexanes:acetone, 80:20 to 40:60) to afford tert-butyl ((2R,6S,7R,13aS,14aR,16aS,Z)-14a-((cyclopropylsulfonyl)carbamoyl)-2-hydroxy-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate as a solid foam (7 g). MS: MS m/z 597.35 (M++1).

Preparation of (2S,3R)-1-tert-butyl 2-methyl 3-ethylaziridine-1,2-dicarboxylate

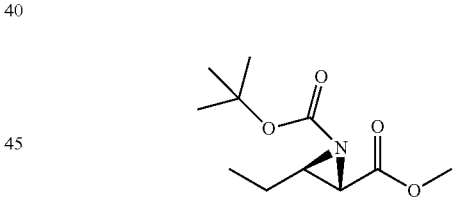

Scheme:

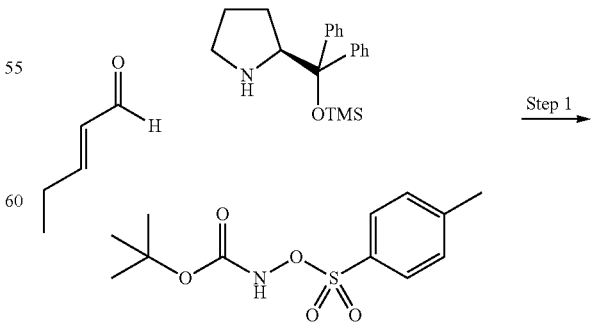

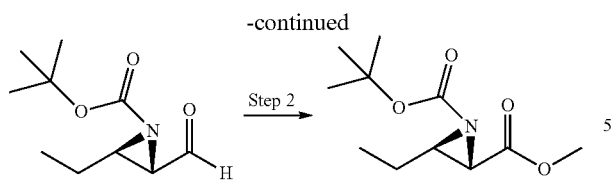

Step 1:

To a 500 mL round-bottom flask equipped with a stir bar was added (S)-2-(diphenyl((trimethylsilyl)oxy)methyl)pyrrolidine (2.60 g, 8.00 mmol) and CHCl$_3$ (200 mL). To the solution was added tert-butyl tosylcarbamate (10.9 g, 40.0 mmol). The flask was placed in a room temperature-water bath. To the stirred solution was added sodium acetate (9.84 g, 120 mmol), then (E)-pent-2-enal (4.04 g, 48.0 mmol). The mixture was stirred at room temperature for 40 minutes. The mixture was filtered, washing the filter cake with a small amount of CHCl$_3$. The filtrate was concentrated in vacuo at 30° C. The resulting orange liquid was dissolved in Et$_2$O (400 mL) and transferred to a 1 L separatory funnel. The solution was washed with water:aq. sat. NaHCO$_3$ (200 mL:200 mL). The aqueous phase was extracted with Et$_2$O (100 mL). The combined organics were washed with brine (200 mL); dried over MgSO$_4$; filtered; then concentrated in vacuo to afford (2R,3S)-tert-butyl 2-ethyl-3-formylaziridine-1-carboxylate as a pale orange liquid.

Step 2:

The following step was run duplicate. To a 250 mL round-bottom flask equipped with a stir bar was added (2R,3S)-tert-butyl 2-ethyl-3-formylaziridine-1-carboxylate (one-half of the material isolated in step 1, assumed 20 mmol) as a solution in MeOH (100 ml). The solution was cooled to 0° C. To the solution was added sodium cyanide (1.96 g, 40.0 mmol). The solution was stirred for 10 minutes. To the solution was added oxidation-grade MnO$_2$ (34.8 g, 400 mmol). The mixture was stirred for 10 minutes, then the ice bath was removed and the solution was allowed to warm to room temperature with stirring for 18 hours. The reaction mixture was filtered through a pad Celite and the filter cake was extracted with EtOAc (100 mL). The filtrate was concentrated in vacuo and the resulting orange solid residue was dissolved in water (100 mL) and EtOAc (100 mL) and transferred to a 1 L separatory funnel where the mixture was further diluted with saturated aq. NaCl ("brine", 100 mL) and EtOAc (100 mL). The mixture was shaken and the phases were separated. The aq. phase was extracted with EtOAc (100 mL). The combined organics were washed with brine (100 mL); dried over MgSO$_4$; filtered; then concentrated in vacuo. The resulting residue was combined with the duplicate run and the combined material was subjected to silica gel chromatography (hexanes:EtOAc, 50:50 to 0:100) to afford (2S,3R)-1-tert-butyl 2-methyl 3-ethylaziridine-1,2-dicarboxylate as a yellow liquid (3.055 g, 33% over two steps).

$^1$H-NMR (500 MHz, CDCl$_3$) δ 3.77 (s, 3H), 2.84 (d, J=2.7 Hz, 1H), 2.77 (td, J=6.0, 2.7 Hz, 1H), 1.63-1.52 (m, 2H), 1.47-1.45 (m, 9H), 1.05 (t, J=7.5 Hz, 3H).

Preparation of (2S,3S)-methyl 2-((tert-butoxycarbonyl)amino)-3-((R)-hex-5-en-2-yloxy)pentanoate

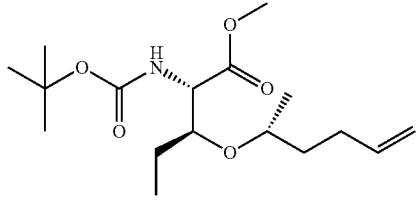 [SMILES: C=CCC[C@@H](C)O[C@@H](CC)[C@H](NC(=O)OC(C)(C)C)C(=O)OC]

To a round-bottom flask equipped with a stir bar was added (2S,3R)-1-tert-butyl 2-methyl 3-ethylaziridine-1,2-dicarboxylate (691, 3.02 mmol) and CH$_2$Cl$_2$ (12 mL). To the solution was added (R)-hex-5-en-2-ol (363 mg, 3.62 mmol), then BF$_3$-OEt$_2$ (1.0M in CH$_2$Cl$_2$, 0.30 mL). The solution was stirred at room temperature for 16 h. The solution was transferred to a separatory funnel and was diluted with CH$_2$Cl$_2$, then the solution was washed with aq. saturated NaHCO$_3$; then brine. The organic phase was dried over Na2SO4; filtered; then concentrated in vacuo. The resulting residue was subjected to silica gel chromatography (hexanes:EtOAc 90:10 to 70:30) to afford (2S,3S)-methyl 2-((tert-butoxycarbonyl)amino)-3-((R)-hex-5-en-2-yloxy)pentanoate as a colorless oil (426 mg, 43%). $^1$H-NMR (500 MHz, CDCl$_3$) δ 5.81 (ddt, J=17.0, 10.4, 6.5 Hz, 1H), 5.19 (d, J=7.7 Hz, 1H), 5.08-5.00 (m, 1H), 4.96 (dd, J=10.2, 1.7 Hz, 1H), 4.50 (dd, J=8.3, 3.5 Hz, 1H), 3.75 (s, 3H), 3.65-3.58 (m, 1H), 3.57-3.50 (m, 1H), 2.19-2.06 (m, 2H), 1.66-1.56 (m, 2H), 1.55-1.38 (m, 11H), 1.13 (d, J=6.1 Hz, 3H), 0.97 (t, J=7.3 Hz, 3H).

Preparation of (2S,4R)-methyl 1-((2S,3S)-2-((tert-butoxycarbonyl)amino)-3-(pent-4-en-1-yloxy)pentanoyl)-4-hydroxypyrrolidine-2-carboxylate

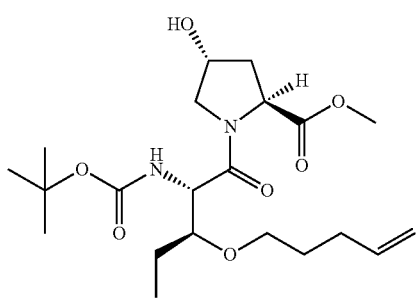 [SMILES: C=CCCCO[C@@H](CC)[C@H](NC(=O)OC(C)(C)C)C(=O)N1C[C@H](O)C[C@H]1C(=O)OC]

To a round-bottom flask equipped with a stir bar was added (2S,3R)-1-tert-butyl 2-methyl 3-ethylaziridine-1,2-dicarboxylate (1.50 g, 6.54 mmol) and CH$_2$Cl$_2$ (30 mL). To the solution was added pent-4-en-1-ol (0.676 g, 7.85 mmol), then BF$_3$-OEt$_2$ (93 mg, 0.083 mL, 0.65 mmol). The solution was stirred at room temperature for 16 h. The solution was transferred to a separatory funnel and was diluted with CH$_2$Cl$_2$. The solution was washed with aq. saturated NaHCO$_3$; then brine. The organic phase was dried over Na$_2$SO$_4$; filtered; then concentrated in vacuo. The resulting residue was subjected to silica gel chromatography (hexane:EtOAc 90:10 to 70:30) to afford (2S,4R)-methyl 1-((2S,3S)-2-((tert-butoxy-carbonyl)amino)-3-(pent-4-en-1-yloxy)pentanoyl)-4-hydroxypyrrolidine-2-carboxylate as as an oil (1.06 g, 51%).
¹H-NMR (500 MHz, CDCl₃) δ 5.87-5.76 (m, 1H), 5.20 (d, J=7.9 Hz, 1H), 5.07-5.01 (m, 1H), 4.99-4.95 (m, 1H), 4.54 (dd, J=8.6, 3.9 Hz, 1H), 3.75 (s, 3H), 3.58-3.51 (m, 1H), 3.50-3.44 (m, 2H), 2.17-2.08 (m, 2H), 1.69-1.61 (m, 2H), 1.61-1.54 (m, 2H), 1.46-1.43 (m, 9H), 0.99 (t, J=7.4 Hz, 3H).

Preparation of tert-butyl ((2R,6S,7S,9R,13aS,14aR,16aS,Z)-7-ethyl-2-hydroxy-9-methyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate Scheme:

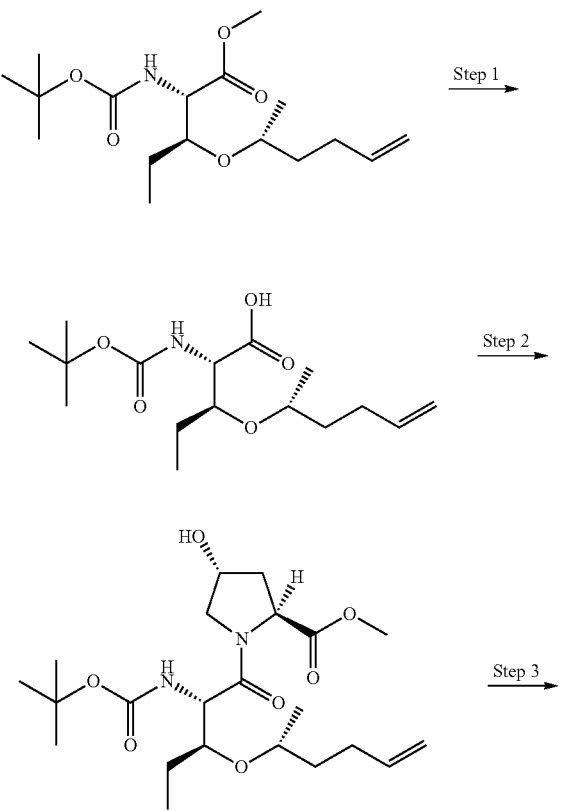

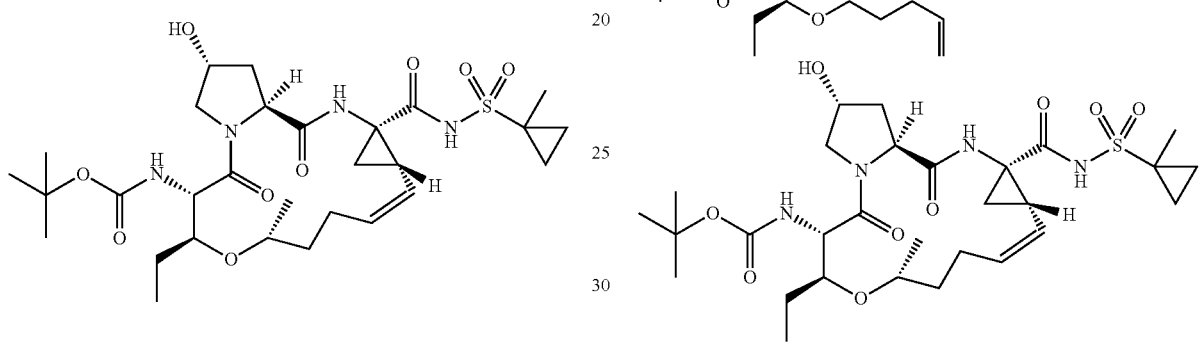

Step 1:
To a round-bottom flask equipped with a stir bar was added (2S,3S)-methyl 2-((tert-butoxycarbonyl)amino)-3-((R)-hex-5-en-2-yloxy)pentanoate (458 mg, 1.39 mmol), THF (5 mL) and MeOH (5 mL). To the stirred solution was added aq. LiOH (2.0 M, 2 mL). The mixture was stirred for 16 h, then was concentrated in vacuo to afford an aqueous solution. The solution was acidified with aq. HCl (1 M) and then transferred to a separatory funnel. The mixture was twice extracted with EtOAc. The combined organics were washed with brine; dried over MgSO₄; filtered; then concentrated in vacuo to afford (2S,3S)-2-((tert-butoxycarbonyl)amino)-3-((R)-hex-5-en-2-yloxy)pentanoic acid as a white foam (438 mg, 100%).

Step 2:
To a round-bottom flask equipped with a stir bar was added (2S,3S)-2-((tert-butoxycarbonyl)amino)-3-(pent-4-en-1-yloxy)pentanoic acid (all material from step 1, 438 mg, 1.39 mmol), (2S,4R)-methyl 4-hydroxypyrrolidine-2-carboxylate-HCl salt (277 mg, 1.53 mmol), 1-[Bis(dimethylamino)methylene]-1H-1,2,3-triazolo[4,5-b]pyridinium 3-oxid hexafluorophosphate ("HATU", 528 mg, 1.39 mmol), and CH₂Cl₂ (10 mL). To the mixture was added N,N-diisopropylethylamine (0.728 mL, 4.17 mmol). The mixture was stirred at room temperature for 16 h. The reaction mixture was transferred to a separatory funnel and was thrice washed with aq. 1N HCl; then brine. The organic phase was dried over MgSO₄; filtered; then concentrated in vacuo to afford (2S,4R)-methyl 1-((2S,3S)-2-((tert-butoxycarbonyl)amino)-3-((R)-hex-5-en-2-yloxy)pentanoyl)-4-hydroxypyrrolidine-2-carboxylate as a yellow oil.

Step 3:
To a round-bottom flask equipped with a stir bar was added (2S,4R)-methyl 1-((2S,3S)-2-((tert-butoxycarbonyl)amino)-

3-((R)-hex-5-en-2-yloxy)pentanoyl)-4-hydroxypyrrolidine-2-carboxylate (all material from step 2, 1.39 mmol), THF (5 mL) and MeOH (5 mL). To the solution was added aq. lithium hydroxide (2.0 M, 4.51 mmol). The mixture was stirred at room temperature for 16 h; then was concentrated to afford an aqueous solution. This solution was acidified and then transferred to a separatory funnel. The solution was twice extracted with EtOAc. The combined organics were washed with brine; dried over MgSO₄; filtered; then concentrated in vacuo to afford (2S,4R)-1-((2S,3S)-2-((tert-butoxycarbonyl)amino)-3-((R)-hex-5-en-2-yloxy)pentanoyl)-4-hydroxypyrrolidine-2-carboxylic acid as a white solid (489 mg).

Step 4:

To a round-bottom flask equipped with a stir bar was added (2S,4R)-1-((2S,3S)-2-((tert-butoxycarbonyl)amino)-3-((R)-hex-5-en-2-yloxy)pentanoyl)-4-hydroxypyrrolidine-2-carboxylic acid (all material from step 3, 489 mg, 1.14 mmol), (1R,2S)-1-amino-N-((1-methylcyclopropyl)sulfonyl)-2-vinylcyclopropanecarboxamide-trifluoroacetic acid salt (450 mg, 1.26 mmol), HATU (456 mg, 1.20 mmol) and DCM (10 mL). To the stirred solution was added N,N-diisopropylethylamine (0.80 mL, 4.56 mmol). The mixture was stirred for 16 h and then was transferred to a separatory funnel. The mixture was thrice washed with aq. 1N HCl; then brine. The solution was dried over MgSO₄; filtered; then concentrated in vacuo to afford tert-butyl ((2S,3S)-3-((R)-hex-5-en-2-yloxy)-1-((2S,4R)-4-hydroxy-2-(((1R,2S)-1-(((1-methylcyclopropyl)sulfonyl)carbamoyl)-2-vinylcyclopropyl)carbamoyl)pyrrolidin-1-yl)-1-oxopentan-2-yl)carbamate as a light-orange solid foam (569 mg).

Step 5:

To a round-bottom flask equipped with a stir bar was added tert-butyl ((2S,3S)-3-((R)-hex-5-en-2-yloxy)-1-((2S,4R)-4-hydroxy-2-(((1R,2S)-1-(((1-methylcyclopropyl)sulfonyl)carbamoyl)-2-vinylcyclopropyl)carbamoyl)pyrrolidin-1-yl)-1-oxopentan-2-yl)carbamate (all material from step 4, 569 mg, 0.869 mmol) and DCE (100 mL). The solution was sparged with nitrogen for 30 min. and then to the solution was added (1,3-Bis-(2,4,6-trimethylphenyl)-2-imidazolidinylidene)dichloro(o-isopropoxyphenylmethylene)ruthenium ("Hoveyda-Grubbs Catalyst 2nd Generation", 27 mg, 0.043 mmol). The solution was stirred at 80° C. for 2 h and then cooled to 45° C. and stirred for 3 days. The solution was concentrated in vacuo and the resulting residue was subjected to silica gel purification (hexanes:acetone 80:20 to 40:60). The product containing fractions were pooled; concentrated; and re-subjected to silica gel chromatography (hexanes:acetone 80:20 to 40:60) to afford tert-butyl ((2R,6S,7S,9R,13aS,14aR,16aS,Z)-7-ethyl-2-hydroxy-9-methyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate as a light-brown solid foam (90 mg, 10% over 5 steps). ¹H-NMR (500 MHz, CD₃OD) δ 8.93 (s, 1H), 5.61 (td, J=10.1, 6.2 Hz, 1H), 5.03 (t, J=10.3 Hz, 1H), 4.58 (br. s., 1H), 4.47-4.37 (m, 2H), 3.92 (br. s., 2H), 3.86-3.79 (m, 1H), 3.58-3.49 (m, 1H), 2.75 (q, J=9.5 Hz, 1H), 2.64-2.52 (m, 1H), 2.23-2.11 (m, 2H), 1.92-1.80 (m, 2H), 1.75 (dd, J=8.5, 5.5 Hz, 1H), 1.66-1.60 (m, 1H), 1.59-1.52 (m, 2H), 1.49 (s, 4H), 1.43 (s, 9H), 1.41-1.32 (m, 2H), 1.15 (d, J=6.3 Hz, 3H), 0.95 (t, J=7.4 Hz, 3H), 0.88-0.84 (m, 2H).

Preparation of tert-butyl ((2R,6S,7S,13aS,14aR,16aS,Z)-7-ethyl-2-hydroxy-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate

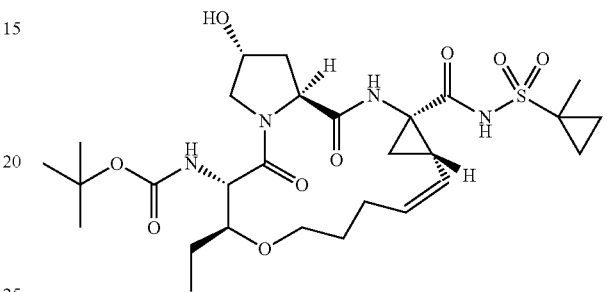

Scheme:

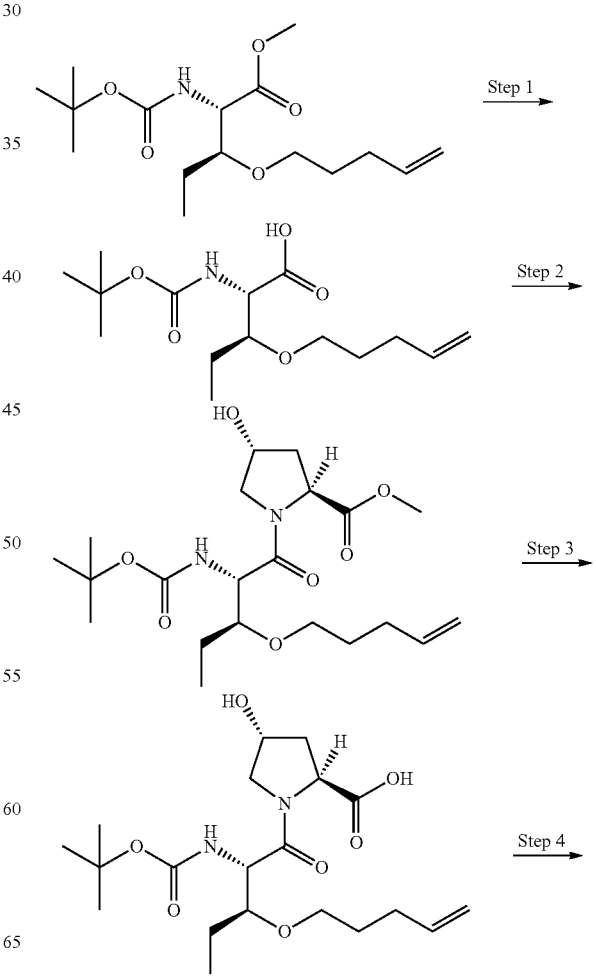

-continued

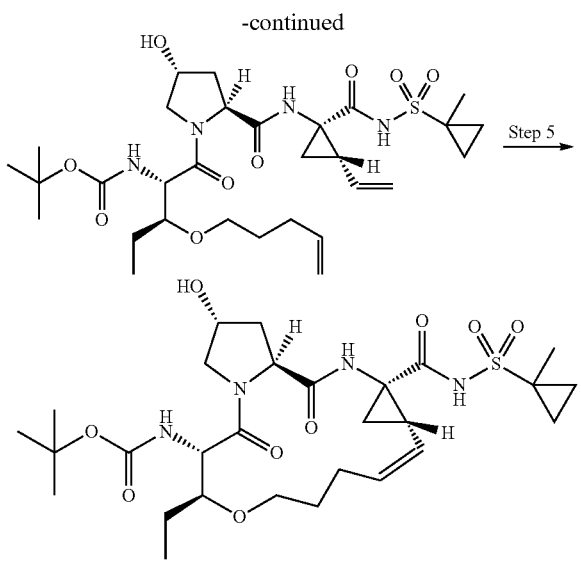

Step 1:
To a round-bottom flask equipped with a stir bar was added (2S,3S)-methyl 2-((tert-butoxycarbonyl)amino)-3-(pent-4-en-1-yloxy)pentanoate (1.06 g, 3.36 mmol), THF (10 mL) and MeOH (10 mL). To the solution was added aq. LiOH (1.0 M, 5.04 mL). The mixture was stirred for 16 h at room temperature. The mixture was concentrated in vacuo, and the resulting aqueous solution was acidified with aq HCl (1.0 M) and then transferred to a separatory funnel. The solution was twice extracted with EtOAc and the combined organics were dried over $MgSO_4$; filtered; then concentrated in vacuo to afford (2S,3S)-2-((tert-butoxycarbonyl)amino)-3-(pent-4-en-1-yloxy)pentanoic acid as a colorless solid foam (1.00 g, 99% yield).

Step 2:
To a round-bottom flask equipped with a stir bar was added (2S,3S)-2-((tert-butoxycarbonyl)amino)-3-(pent-4-en-1-yloxy)pentanoic acid (all material from step 1, 1.00 g, 3.32 mmol), (2S,4R)-methyl 4-hydroxypyrrolidine-2-carboxylate-HCl salt (0.663 g, 3.65 mmol), HATU (1.26 g, 3.32 mmol) and $CH_2Cl_2$ (30 mL). To the mixture was added N,N-diisopropylethylamine (1.75 mL, 9.95 mmol). The mixture was stirred at room temperature for 16 h. The mixture was transferred to a separatory funnel and was thrice washed with aq. HCl (1M); then brine. The organic solution was dried over $MgSO_4$; filtered; then concentrated in vacuo to afford (2S,4R)-methyl 1-((2S,3S)-2-((tert-butoxycarbonyl)amino)-3-(pent-4-en-1-yloxy)pentanoyl)-4-hydroxypyrrolidine-2-carboxylate as a yellow oil (1.53 g).

Step 3:
To a round-bottom flask equipped with a stir bar was added (2S,4R)-methyl 1-((2S,3S)-2-((tert-butoxycarbonyl)amino)-3-(pent-4-en-1-yloxy)pentanoyl)-4-hydroxypyrrolidine-2-carboxylate (all material from step 2, 1.53 g, 3.57 mmol), THF (10 mL) and MeOH (10 mL). To the solution was added aq. LiOH (1.0 M, 5.36 mL). The mixture was stirred at room temperatuer for 16 h; then was concentrated in vacuo to afford an aqueous solution. The solution was acidified with aq HCl (1M) and then transferred to a separatory funnel. The solution was twice extracted with EtOAc. The combined organics were dried over $MgSO_4$; filtered; then concentrated in vacuo to afford (2S,4R)-1-((2S,3S)-2-((tert-butoxycarbonyl)amino)-3-(pent-4-en-1-yloxy)pentanoyl)-4-hydroxypyrrolidine-2-carboxylic acid as a white solid (1.28 g, 86% over two steps).

Step 4:
To a round-bottom flask equipped with a stir bar was added (2S,4R)-1-((2S,3S)-2-((tert-butoxycarbonyl)amino)-3-(pent-4-en-1-yloxy)pentanoyl)-4-hydroxypyrrolidine-2-carboxylic acid (½ of material from step 3, 600 mg, 1.45 mmol), (1R,2S)-1-amino-N-((1-methylcyclopropyl)sulfonyl)-2-vinylcyclopropanecarboxamide-trifluoroacetic acid salt (571 mg, 1.59 mmol), HATU (578 mg, 1.52 mmol) and $CH_2Cl_2$ (10 mL). To the mixture was added N,N-diisopropylethylamine (1.01 mL, 5.79 mmol). The mixture was stirred at room temperature for 16 h. The mixture was transferred to a separatory funnel and was thrice washed with aq. HCl (1M); then brine. The organic solution was dried over $MgSO_4$; filtered; then concentrated in vacuo. The resulting residue was subjected to silica gel chromatography (hexanes:acetone, 94:6 to 60:40) to afford tert-butyl ((2S,3S)-1-((2S,4R)-4-hydroxy-2-(((1R,2S)-1-(((1-methylcyclopropyl)sulfonyl)carbamoyl)-2-vinylcyclopropyl)carbamoyl)pyrrolidin-1-yl)-1-oxo-3-(pent-4-en-1-yloxy)pentan-2-yl)carbamate as a colorless solid foam (480 mg, 52%). MS: MS m/z 641.5 ($M^+$+1).

Step 5:
To a round-bottom flask equipped with a stir bar was added tert-butyl ((2S,3S)-1-((2S,4R)-4-hydroxy-2-(((1R,2S)-1-(((1-methylcyclopropyl)sulfonyl)carbamoyl)-2-vinylcyclopropyl)carbamoyl)pyrrolidin-1-yl)-1-oxo-3-(pent-4-en-1-yloxy)pentan-2-yl)carbamate (all material from step 4, 480 mg, 0.749 mmol) and DCE (100 mL). The solution was sparged with nitrogen for 30 minutes. To the solution was added Hoveyda-Grubbs Catalyst 2nd Generation (23 mg, 0.037 mmol). The solution was stirred at 80° C. for 2 h, then was cooled to 45° C. and was stirred for 3 days. The solution was concentrated in vacuo and the resulting residue was subjected to $C_{18}$ chromatography (water with 0.1% TFA:acetonitrile with 0.1% TFA, 60:40 to 0:100) to afford tert-butyl ((2R,6S,7S,13aS,14aR,16aS,Z)-7-ethyl-2-hydroxy-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate as a brown solid foam (100 mg, 22%). MS: MS m/z 613.4 ($M^+$+1).

Scheme: Preparation of tert-butyl ((2R,6S,7R,13aS,14aR,16aS,Z)-14a-((cyclopropylsulfonyl)carbamoyl)-7-ethyl-2-hydroxy-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate

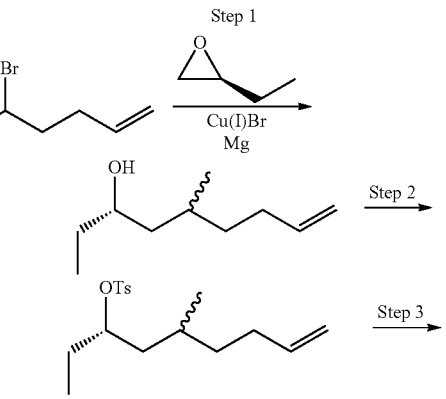

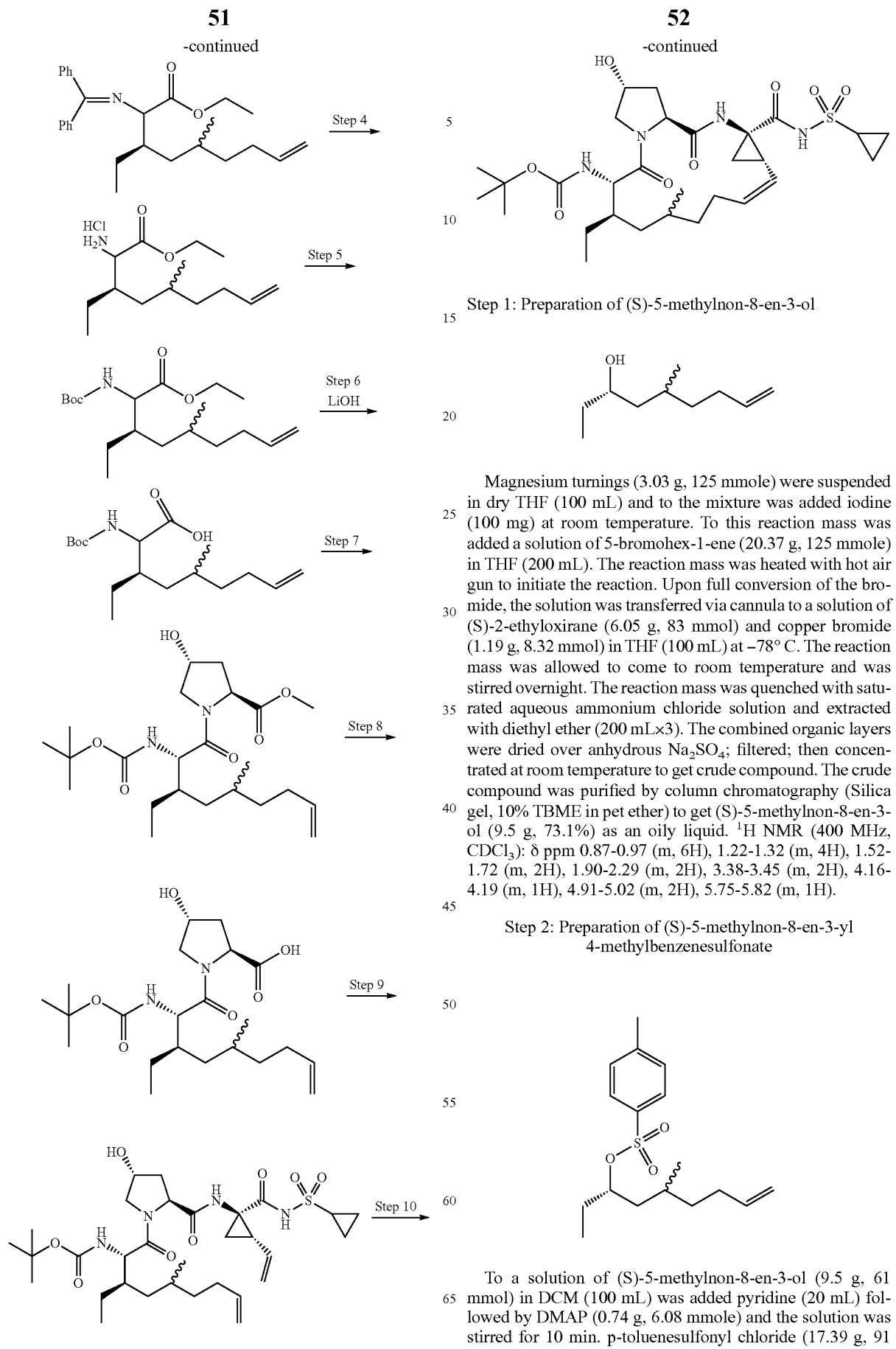

Step 1: Preparation of (S)-5-methylnon-8-en-3-ol

Magnesium turnings (3.03 g, 125 mmole) were suspended in dry THF (100 mL) and to the mixture was added iodine (100 mg) at room temperature. To this reaction mass was added a solution of 5-bromohex-1-ene (20.37 g, 125 mmole) in THF (200 mL). The reaction mass was heated with hot air gun to initiate the reaction. Upon full conversion of the bromide, the solution was transferred via cannula to a solution of (S)-2-ethyloxirane (6.05 g, 83 mmol) and copper bromide (1.19 g, 8.32 mmol) in THF (100 mL) at −78° C. The reaction mass was allowed to come to room temperature and was stirred overnight. The reaction mass was quenched with saturated aqueous ammonium chloride solution and extracted with diethyl ether (200 mL×3). The combined organic layers were dried over anhydrous $Na_2SO_4$; filtered; then concentrated at room temperature to get crude compound. The crude compound was purified by column chromatography (Silica gel, 10% TBME in pet ether) to get (S)-5-methylnon-8-en-3-ol (9.5 g, 73.1%) as an oily liquid. $^1$H NMR (400 MHz, $CDCl_3$): δ ppm 0.87-0.97 (m, 6H), 1.22-1.32 (m, 4H), 1.52-1.72 (m, 2H), 1.90-2.29 (m, 2H), 3.38-3.45 (m, 2H), 4.16-4.19 (m, 1H), 4.91-5.02 (m, 2H), 5.75-5.82 (m, 1H).

Step 2: Preparation of (S)-5-methylnon-8-en-3-yl 4-methylbenzenesulfonate

To a solution of (S)-5-methylnon-8-en-3-ol (9.5 g, 61 mmol) in DCM (100 mL) was added pyridine (20 mL) followed by DMAP (0.74 g, 6.08 mmole) and the solution was stirred for 10 min. p-toluenesulfonyl chloride (17.39 g, 91 mmole) was added to the reaction mass at 0° C. The reaction mass was allowed to come to room temperature and stirred overnight. Solvent was removed under reduced pressure and the residue was diluted with ethyl acetate (100 mL). The organic solution was washed with aqueous 1.5 N HCl solution; saturated bicarbonate solution; brine solution; dried over anhydrous $Na_2SO_4$; filtered; and evaporated under reduced pressure to get crude compound (15 g, 79%). The crude compound was taken to the next step without further purification. MS: MS m/z 328.4 ($M^++18$).

Step 3: Preparation of (3R)-ethyl 2-(diphenylmethyl-eneamino)-3-ethyl-5-methylnon-8-enoate

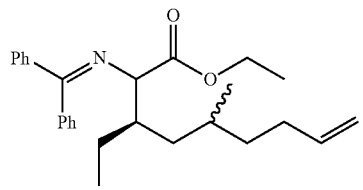 [SMILES: C=CCCC(C)C[C@@H](CC)C(N=C(c1ccccc1)c1ccccc1)C(=O)OCC]

To a solution of (S)-5-methylnon-8-en-3-yl 4-methylbenzenesulfonate (15 g, 48 mmole) and N-(diphenylmethylene) glycinate ethyl ester (15.5 g, 58.0 mmole) in toluene (150 mL) at 0° C. was added lithium bis(trimethylsilyl)amide ("LiHMDS", 72.5 mL, 72.5 mmole, 1 M solution in THF). The reaction mass was allowed to come to room temperature, and then was heated at 110° C. for 2 h. The reaction mass was cooled to room temperature, quenched with water and extracted with ethyl acetate (100 mL×3). The combined organic layers were dried over anhydrous $Na_2SO_4$; filtered; then concentrated under reduced pressure to get crude compound (7.0 g, 35.7%). The crude compound was taken to the next step without further purification. MS: MS m/z 406.4 ($M^++1$).

Step 4: Preparation of (3R)-ethyl 2-amino-3-ethyl-5-methylnon-8-enoate hydrochloride

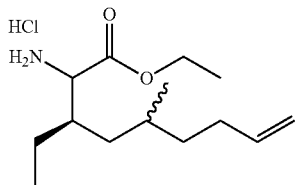 [SMILES: Cl ; C=CCCC(C)C[C@@H](CC)C(N)C(=O)OCC]

A solution of (3R)-ethyl 2-(diphenylmethyleneamino)-3-ethyl-5-methylnon-8-enoate (7.00 g, 17.3 mmole) in diethyl ether (20 mL) was added aqueous 1.5 N HCl solutions (100 mL) and the reaction mass was stirred at room temperature overnight. The reaction mass was washed with diethyl ether (100 mL). The aqueous solution was basified using saturated sodium bicarbonate solution and extracted with ethyl acetate (100 mL×3). The combined organic layers were dried over anhydrous $Na_2SO_4$; filtered; then concentrated under reduced pressure to get crude compound (2.6 g, 62.4%). The crude compound was taken to the next step without further purification. MS: MS m/z 242.4 ($M^++1$).

Step 5: Preparation of (3R)-ethyl 2-(tert-butoxycarbonylamino)-3-ethyl-5-methylnon-8-enoate

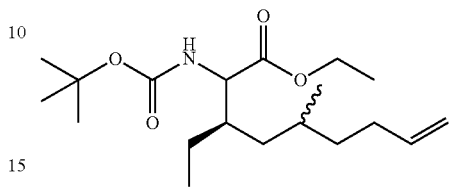

A solution of (3R)-ethyl 2-amino-3-ethyl-5-methylnon-8-enoate hydrochloride (2.99 g, 10.8 mmole) in DCM (20 mL) was added N,N-diisopropylethylamine ("DIPEA", 1.08 mL, 10.8 mmole) followed by $(Boc)_2O$ (2.39 mL, 10.8 mmole) at room temperature. The reaction mass was stirred at room temperature overnight. The reaction mass was diluted with DCM and washed with water. The organic layer was dried over anhydrous $Na_2SO_4$; filtered; then concentrated under reduced pressure to get crude compound. The crude compound was purified by column chromatography (Silica gel, 20% ethyl acetate in pet-ether) to get 2.3 g, (62.5%) of (3R)-ethyl 2-(tert-butoxycarbonylamino)-3,5-dimethylnon-8-enoate as an oily liquid. MS: MS m/z 342.4 ($M^++1$).

Step 6: Preparation of (3R)-2-(tert-butoxycarbonylamino)-3-ethyl-5-methylnon-8-enoic acid

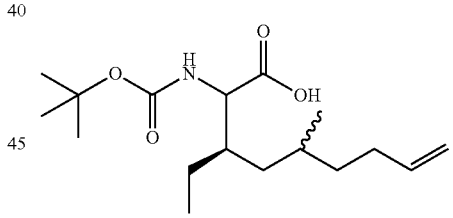

To a solution of (3R)-ethyl 2-(tert-butoxycarbonylamino)-3-ethyl-5-methylnon-8-enoate (2.30 g, 6.74 mmole) in THF/water (50 mL, 1:1) was added methanol (10 mL) followed by LiOH (0.84 g, 20 mmol) at room temperature. The reaction mass was stirred at room temperature overnight. Solvent was evaporated under reduced pressure and the residue was diluted with water (10 mL). The aqueous solution was acidified with aqueous 1.5 N HCl solutions to pH ~3 and extracted with ethyl acetate (100 mL×3). The combined organic layer was dried over anhydrous $Na_2SO_4$; filtered; then concentrated under reduce pressure to get crude compound. The crude compound was purified by column chromatography (Silica gel, 2% methanol in DCM) to get 1.5 g (71%) of Intermediate 9 as an off-white solid. $^1H$ NMR (400 MHz, DMSO-$d_6$): δ ppm 1.27-1.09 (m, 8H), 1.02-1.35 (m, 3H), 1.39 (s, 11H), 1.91-1.97 (m, 1H), 1.99-2.02 (m, 2H), 4.03-4.12 (m, 1H), 4.90-5.03 (m, 2H), 5.74-5.84 (m, 1H), 6.80-6.83 (m, 1H), 12.47 (sb, 1H).

Step 7: Preparation of (2S,4R)-methyl 1-((2S,3R)-2-(tert-butoxycarbonylamino)-3-ethyl-5-methylnon-8-enoyl)-4-hydroxypyrrolidine-2-carboxylate

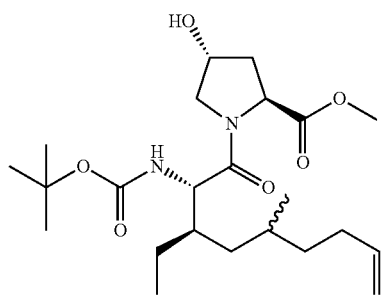 [SMILES: C=CCCC(C)C[C@@H](CC)[C@H](NC(=O)OC(C)(C)C)C(=O)N1C[C@H](O)C[C@H]1C(=O)OC]

To a solution of (3R)-2-(tert-butoxycarbonylamino)-3-ethyl-5-methylnon-8-enoic acid (2.0 g, 6.4 mmole) in dichloromethane (20 mL) was added DIPEA (1.93 mL, 19.2 mmole) and HATU (2.42 g, 6.38 mmole) followed by (2S,4R)-methyl 4-hydroxypyrrolidine-2-carboxylate (1.15 g, 6.38 mmole) at room temperature. The reaction mixture was stirred at room temperature for 2 h. The reaction mass was diluted with DCM and washed with water. The organic layer was dried over anhydrous $Na_2SO_4$; filtered; then concentrated under reduced pressure to get crude compound as mixture of diastereomers. The material was subjected to SFC purification to afford (2S,4R)-methyl 1-((2S,3R)-2-(tert-butoxycarbonylamino)-3-ethyl-5-methylnon-8-enoyl)-4-hydroxypyrrolidine-2-carboxylate (1.5 g, 53%). MS: MS m/z 441.6 ($M^+$+1).

Step 8: Preparation of (2S,4R)-1-((2S,3R)-2-(tert-butoxycarbonylamino)-3-ethyl-5-methylnon-8-enoyl)-4-hydroxypyrrolidine-2-carboxylic acid

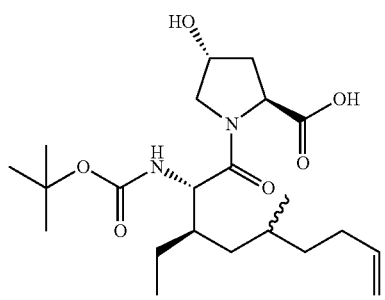 [SMILES: C=CCCC(C)C[C@@H](CC)[C@H](NC(=O)OC(C)(C)C)C(=O)N1C[C@H](O)C[C@H]1C(=O)O]

To a solution of (2S,4R)-methyl 1-((2S,3R)-2-(tert-butoxycarbonylamino)-3-ethyl-5-methylnon-8-enoyl)-4-hydroxypyrrolidine-2-carboxylate (1.5 g, 3.40 mmole) in THF:water (16 mL, 1:1) was added LiOH (286 mg, 6.80 mmole) followed by 3 mL of methanol at room temperature. The reaction mass was stirred at room temperature overnight. The solvent was evaporated under reduced pressure and the residue was diluted with water and acidified with aqueous 1.5 N HCl solutions. The aqueous solution was extracted with ethyl acetate (20 mL×3). The combined organic layers were dried over anhydrous $Na_2SO_4$; filtered; then concentrated under reduced pressure to afford (2S,4R)-1-((2S,3R)-2-(tert-butoxycarbonylamino)-3-ethyl-5-methylnon-8-enoyl)-4-hydroxypyrrolidine-2-carboxylic acid (1.3 g, 90%) as a white solid. $^1$H NMR (400 MHz, DMSO-$d_6$): δ ppm 0.81-0.93 (m, 6H), 1.12-1.29 (m, 5H), 1.30-1.50 (m, 11H), 1.71-1.80 (m, 2H), 1.91-2.51 (m, 4H), 3.57-3.59 (m, 1H), 4.27-4.35 (m, 3H), 4.92-4.97 (m, 2H), 5.01-5.15 (m, 1H), 5.74-5.79 (m, 1H), 6.30-6.80 (m, 1H), 12.50 (sb, 1H). MS: MS m/z 427.6 ($M^+$+1).

Step 9: Preparation of tert-butyl (2S,3R)-1-((2S,4R)-2-((1R,2S)-1-(cyclopropylsulfonylcarbamoyl)-2-vinylcyclopropylcarbamoyl)-4-hydroxypyrrolidin-1-yl)-3-ethyl-5-methyl-1-oxonon-8-en-2-ylcarbamate

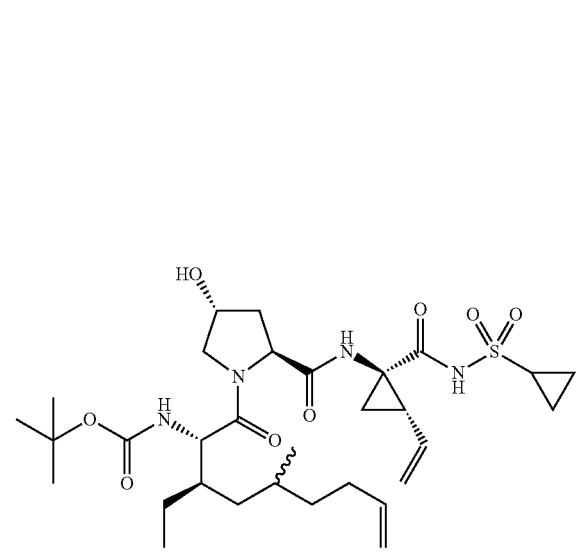 [SMILES: C=CCCC(C)C[C@@H](CC)[C@H](NC(=O)OC(C)(C)C)C(=O)N1C[C@H](O)C[C@H]1C(=O)N[C@]1(C(=O)NS(=O)(=O)C2CC2)C[C@H]1C=C]

To a solution of (2S,4R)-1-((2S,3R)-2-(tert-butoxycarbonylamino)-3-ethyl-5-methylnon-8-enoyl)-4-hydroxypyrrolidine-2-carboxylic acid (1.3 g, 3.05 mmole) in dichloromethane (50 mL) was added HATU (1.15 g, 3.05 mmole) followed by DIPEA (1.6 mL, 9.13 mmole) at room temperature. The reaction mass was stirred at the same temperature for 10 min. (1R,2S)-1-amino-N-(cyclopropylsulfonyl)-2-vinylcyclopropanecarboxamide (1.22 g, 3.05 mmole) was added to the reaction mass and the mixture was stirred at room temperature for 1 h. The reaction mass was diluted with dichloromethane and washed with water. The organic layer was dried over anhydrous $Na_2SO_4$; filtered; then concentrated under reduced pressure to get the crude compound. The crude compound was purified by silica gel chromatography (6% methanol in chloroform) to get 1.7 g (87%) of tert-butyl (2S,3R)-1-((2S,4R)-2-((1R,2S)-1-(cyclopropylsulfonylcarbamoyl)-2-vinylcyclopropylcarbamoyl)-4-hydroxypyrrolidin-1-yl)-3-ethyl-5-methyl-1-oxonon-8-en-2-ylcarbamate as a white solid. MS: MS m/z 639.55 (M⁺+1).

Step 10: Preparation of tert-butyl (2R,6S,7R,13aS, 14aR,16aS,Z)-14a-(cyclopropylsulfonylcarbamoyl)-7-ethyl-2-hydroxy-9-methyl-5,16-dioxo-1,2,3,5,6,7, 8,9,10,11,13a,14,14a,15,16,16a-hexadecahydrocyclopropa[e]pyrrolo[1,2-a][1,4]diazacyclopentadecin-6-ylcarbamate

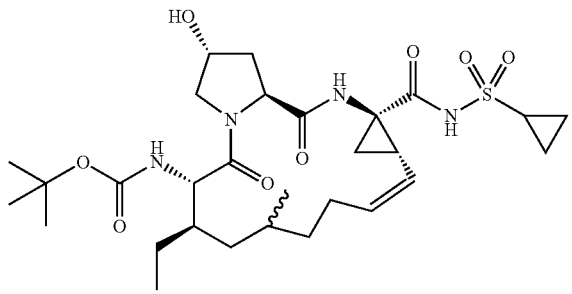 [SMILES: CC[C@@H]1CC(C)CC/C=C\[C@@H]2C[C@@]2(C(=O)NS(=O)(=O)C2CC2)NC(=O)[C@@H]2C[C@@H](O)CN2C(=O)[C@H]1NC(=O)OC(C)(C)C]

To a degassed solution of tert-butyl (2S,3R)-1-((4S,4R)-2-((1R,2S)-1-(cyclopropylsulfonylcarbamoyl)-2-vinylcyclopropylcarbamoyl)-4-hydroxypyrrolidin-1-yl)-3-ethyl-5-methyl-1-oxonon-8-en-2-ylcarbamate (1.7 g, 2.66 mmole) in dichloroethane (100 mL) was added (1,3-Bis-(2,4,6-trimethylphenyl)-2-imidazolidinylidene)dichloro(o-isopropoxyphenylmethylene)ruthenium ("Hoveyda-Grubbs II generation catalyst", 266 mg) at room temperature under nitrogen atmosphere. The reaction mass was heated at 95° C. overnight. The solvent was evaporated under reduced pressure and the residue was purified by silica gel chromatography (5% methanol in chloroform) to afford tert-butyl (2R,6S, 7R,13aS,14aR,16aS,Z)-14a-(cyclopropylsulfonylcarbamoyl)-7-ethyl-2-hydroxy-9-methyl-5,16-dioxo-1,2,3,5,6,7,8,9,10,11,13a,14,14a,15,16, 16a-hexadecahydrocyclopropa[e]pyrrolo[1,2-a][1,4]diazacyclopentadecin-6-ylcarbamate (770 mg, 47%) as a pale yellow crystalline solid. MS: MS m/z 609.20 (M⁺−1).

Preparation of tert-butyl ((2S,3R)-3-ethyl-1-((2S, 4R)-4-hydroxy-2-(((1R,2S)-1-(((1-methylcyclopropyl)sulfonyl)carbamoyl)-2-vinylcyclopropyl)carbamoyl)pyrrolidin-1-yl)-5-methyl-1-oxonon-8-en-2-yl)carbamate

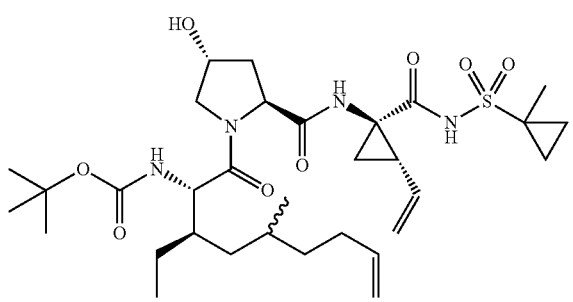 [SMILES: C=CCCC(C)C[C@@H](CC)[C@H](NC(=O)OC(C)(C)C)C(=O)N1C[C@H](O)C[C@H]1C(=O)N[C@]1(C(=O)NS(=O)(=O)C2(C)CC2)C[C@H]1C=C]

The same procedure was used as described for the preparation of tert-butyl ((2S,3R)-1-((2S,4R)-4-hydroxy-2-(((1R, 2S)-1-(((1-methylcyclopropyl)sulfonyl)carbamoyl)-2-vinyl-cyclopropyl)carbamoyl)pyrrolidin-1-yl)-3,5-dimethyl-1-oxonon-8-en-2-yl)carbamate but (2S,4R)-1-((2S,3R)-2-(tert-butoxycarbonylamino)-3-ethyl-5-methylnon-8-enoyl)-4-hydroxypyrrolidine-2-carboxylic acid was used as starting material instead of (2S,4R)-1-((3R)-2-((tert-butoxycarbonyl)amino)-3,5-dimethylnon-8-enoyl)-4-hydroxypyrrolidine-2-carboxylic acid. ¹H NMR (400 MHz, DMSO-d₆): δ ppm 10.42 (d, J=4.02 Hz, 1H) 8.83 (d, J=8.53 Hz, 1H) 6.24 (m, 1H) 5.81 (m, 1H) 5.57 (m, 1H) 5.05 (m, 5H) 4.32 (m, 3H) 3.59 (m, 2H) 1.92 (m, 8H) 1.25 (m, 21H) 0.84 (m, 8H) MS: MS m/z 653.4 (M⁺+1)

Preparation of tert-butyl ((2R,6S,7R,9R,13aS,14aR, 16aS,Z)-7-ethyl-2-hydroxy-9-methyl-14a-(((1-methylcyclopropyl)sulfonyl)carbamoyl)-5,16-dioxo-1,2,3, 5,6,7,8,9,10,11,13a,14,14a,15,16,16a-hexadecahydrocyclopropa[e]pyrrolo[1,2-a][1,4]diazacyclopentadecin-6-yl)carbamate

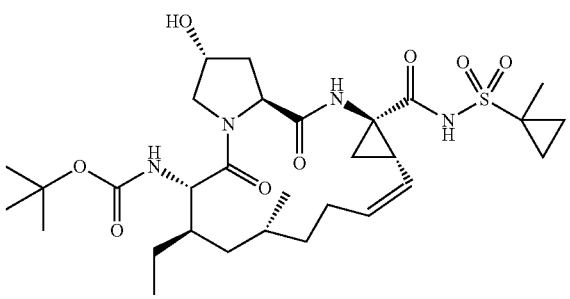 [SMILES: CC[C@@H]1C[C@H](C)CC/C=C\[C@@H]2C[C@@]2(C(=O)NS(=O)(=O)C2(C)CC2)NC(=O)[C@@H]2C[C@@H](O)CN2C(=O)[C@H]1NC(=O)OC(C)(C)C]

The same procedure was used as described for of tert-butyl ((2R,6S,7R,9R,13aS,14aR,16aS,Z)-2-hydroxy-7,9-dimethyl-14a-(((1-methylcyclopropyl)sulfonyl)carbamoyl)-5, 16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate but tert-butyl ((2S, 3R)-3-ethyl-1-((2S,4R)-4-hydroxy-2-(((1R,2S)-1-(((1-methylcyclopropyl)sulfonyl)carbamoyl)-2-vinylcyclopropyl)carbamoyl)pyrrolidin-1-yl)-5-methyl-1-oxonon-8-en-2-yl)carbamate was used as a starting material instead of tert-butyl ((2S,3R)-1-((2S,4R)-4-hydroxy-2-(((1R, 2S)-1-(((1-methylcyclopropyl)sulfonyl)carbamoyl)-2-vinyl-cyclopropyl)carbamoyl)pyrrolidin-1-yl)-3,5-dimethyl-1-oxonon-8-en-2-yl)carbamate. ¹H NMR (400 MHz, DMSO-d₆): δ ppm 8.32 (s, 1H) 7.01 (d, J=9.54 Hz, 1H) 5.38 (m, 2H) 5.08 (m, 1H) 4.40 (br. s., 1H) 4.20 (t, J=7.78 Hz, 1H) 4.00 (m, 1H)

3.67 (m, 2H) 2.85 (q, J=7.53 Hz, 3H) 2.22 (d, J=8.03 Hz, 1H) 1.84 (m, 4H) 1.29 (m, 22H) 0.84 (m, 6H) 0.48 (m, 2H). MS: MS m/z 625.4 (M++1).
Preparation of Compound 1001 and 1002
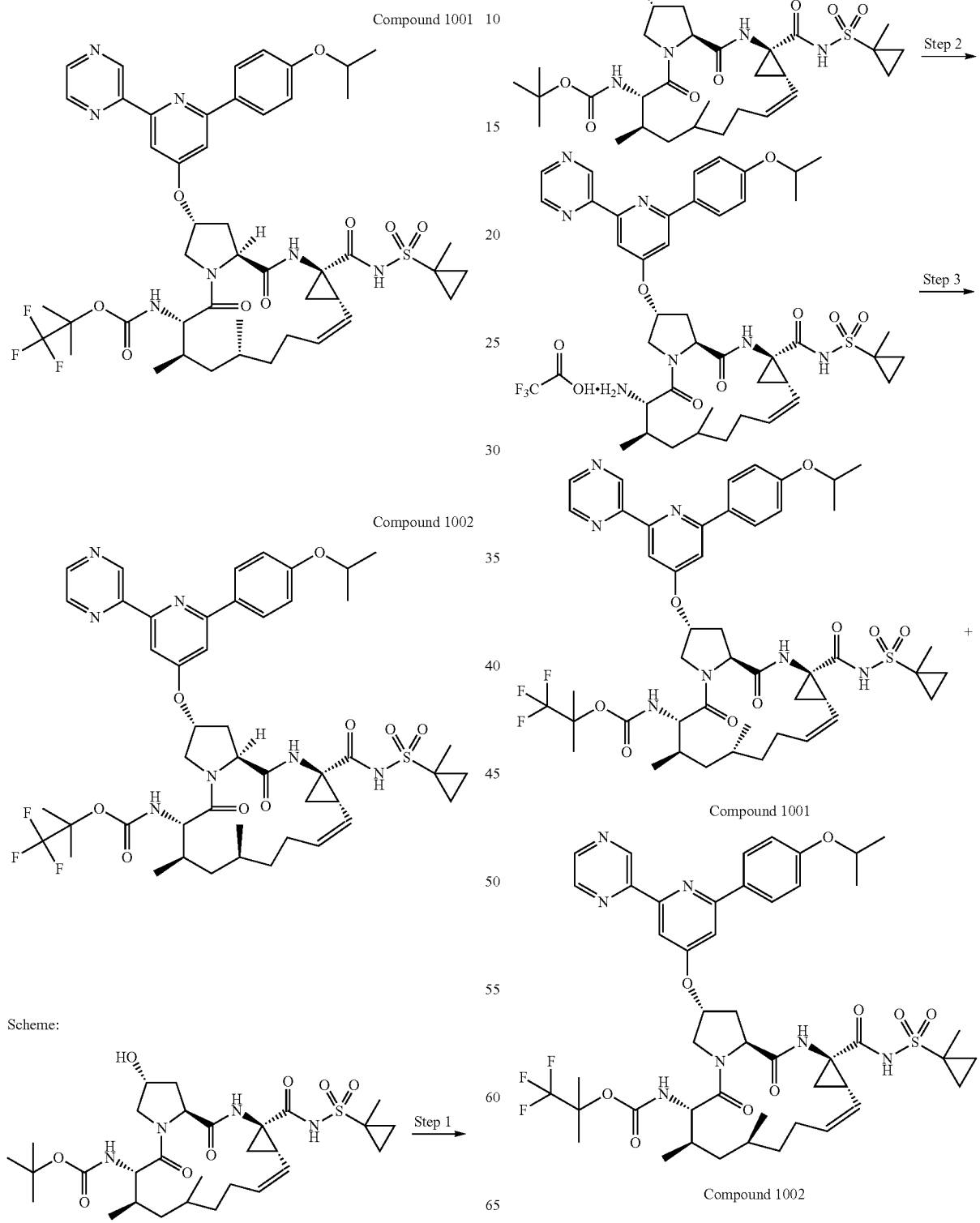

Step 1:

To a dry 2 dram vial equipped with a stir bar and charged with 2-(4-chloro-6-(4-isopropoxyphenyl)pyridin-2-yl)pyrazine (37 mg, 0.11 mmol) was added tert-butyl ((2R,6S,7R,13aS,14aR,16aS,Z)-2-hydroxy-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (46 mg, 0.076 mmol). To the vial was added DMSO (1.25 mL). The mixture was stirred for 2 minutes to afford a red, homogeneous solution. To the solution was added potassium tert-butoxide (43 mg, 0.38 mmol) to afford a very deep amber solution. The solution was stirred at room temperature for 2 h. To the solution was added aq. 1M HCl (3 mL) upon which a solid precipitated. The mixture was transfered to a 125 mL reparatory funnel and was diluted with water:brine (20 mL:20 mL). The mixture was extracted with EtOAc (2×30 mL). The combined organics were dried over $MgSO_4$; filtered; then concentrated in vacuo to afford tert-butyl ((2R,6S,7R,13aS,14aR,16aS,Z)-2-((2-(4-isopropoxyphenyl)-6-(pyrazin-2-yl)pyridin-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate as a solid residue. MS: MS m/z 900.6 ($M^+$+1).

Step 2:

To a 25 mL round-bottom flask equipped with a stir bar and charged with tert-butyl ((2R,6S,7R,13aS,14aR,16aS,Z)-2-((2-(4-isopropoxyphenyl)-6-(pyrazin-2-yl)pyridin-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (all material from Step 1) was added $CH_2Cl_2$ (1 mL), then trifluoroacetic acid (1.0 mL, 13 mmol). The solution was stirred at room temperature for 2 h. The reaction solution was diluted with toluene (2 mL) and then concentrated in vacuo to afford (2R,6S,7R,13aS,14aR,16aS,Z)-6-amino-2-((2-(4-isopropoxyphenyl)-6-(pyrazin-2-yl)pyridin-4-yl)oxy)-7,9-dimethyl-N-((1-methylcyclopropyl)sulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide trifluoroacetic acid salt as an amber solid residue. MS: MS m/z 800.5 ($M^+$+1).

Step 3:

To a vial equipped with a stir bar and charged with (2R,6S,7R,13aS,14aR,16aS,Z)-6-amino-2-((2-(4-isopropoxyphenyl)-6-(pyrazin-2-yl)pyridin-4-yl)oxy)-7,9-dimethyl-N-((1-methylcyclopropyl)sulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide trifluoroacetic acid salt (all material from Step 2) in $CH_2Cl_2$ (0.75 mL) was added pyridin-2-yl(1,1,1-trifluoro-2-methylpropan-2-yl) carbonate (28.4 mg, 0.114 mmol), then N,N-Diisopropylethylamine (0.11 mL, 0.61 mmol). The solution was stirred at room temperature for 1 h. The volatiles were removed under a stream of $N_2$. The resulting residue was subjected to HPLC purification as follows: Column=Waters XBridge C18, 19×200 mm, 5-µm particles; Guard Column=Waters XBridge C18, 19×10 mm, 5-µm particles; Mobile Phase A=water with 20-mM ammonium acetate; Mobile Phase B=95:5 acetonitrile:water with 20-mM ammonium acetate; Gradient=70-100% B over 20 minutes, then a 4-minute hold at 100% B; Flow=20 mL/min. Fractions containing Compound 1001 were combined and dried via centrifugal evaporation to afford Compound 1001 as a solid (7.0 mg, 19% over three steps); fractions containing Compound 1002 were combined and dried via centrifugal evaporation to afford Compound 1002 as a solid (1.9 mg, 5% over three steps).

Compound 1001: 1,1,1-trifluoro-2-methylpropan-2-yl ((2R,6S,7R,9R,13aS,14aR,16aS,Z)-2-((2-(4-isopropoxyphenyl)-6-(pyrazin-2-yl)pyridin-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H-NMR (500 MHz, $CD_3OD$) δ 9.71-9.68 (m, 1H), 8.73-8.70 (m, 1H), 8.64 (d, J=2.4 Hz, 1H), 8.13-8.08 (m, J=8.9 Hz, 2H), 7.84 (d, J=2.1 Hz, 1H), 7.41 (d, J=2.1 Hz, 1H), 7.08-7.02 (m, J=8.9 Hz, 2H), 5.61-5.54 (m, 1H), 5.49 (br. s., 1H), 5.17 (br. s., 1H), 4.76-4.54 (m, 4H), 4.04 (dd, J=11.4, 3.2 Hz, 1H), 3.85 (d, J=10.7 Hz, 1H), 2.72-2.58 (m, 2H), 2.46 (ddd, J=13.8, 10.1, 4.1 Hz, 1H), 2.42-2.34 (m, 1H), 2.03-1.94 (m, 1H), 1.88 (d, J=6.4 Hz, 1H), 1.80-1.71 (m, 2H), 1.63-1.53 (m, 2H), 1.50 (s, 3H), 1.45 (d, J=7.9 Hz, 2H), 1.43-1.38 (m, 2H), 1.37 (d, J=6.1 Hz, 6H), 1.34 (s, 3H), 1.32-1.19 (m, 2H), 1.17 (s, 3H), 0.99 (d, J=6.7 Hz, 3H), 0.95 (d, J=6.4 Hz, 3H), 0.84-0.77 (m, 3H); MS: MS m/z 954.5 ($M^+$+1).

Compound 1002: 1,1,1-trifluoro-2-methylpropan-2-yl ((2R,6S,7R,9S,13aS,14aR,16aS,Z)-2-((2-(4-isopropoxyphenyl)-6-(pyrazin-2-yl)pyridin-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 954.5 ($M^+$+1).

Regarding the general synthesis of Compound 1001: The following intermediates are interchangeable with tert-butyl ((2R,6S,7R,13aS,14aR,16aS,Z)-2-hydroxy-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate in step 1 of the synthesis pathway: tert-butyl ((2R,6S,7R,13aS,14aR,16aS,Z)-2-hydroxy-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; tert-butyl ((2R,6S,7R,13aS,14aR,16aS,Z)-2-hydroxy-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; tert-butyl ((2R,6S,7R,13aS,14aR,16aS,Z)-14a-((cyclopropylsulfonyl)carbamoyl)-7-ethyl-2-hydroxy-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; tert-butyl ((2R,6S,7R,13aS,14aR,16aS,Z)-14a-((cyclopropylsulfonyl)carbamoyl)-2-hydroxy-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. Compounds containing a tert-butyl carbamate moiety can be accessed by following the general procedure of Compound 1001 but stopping after the first step.

Preparation of Compound 1003 and 1004

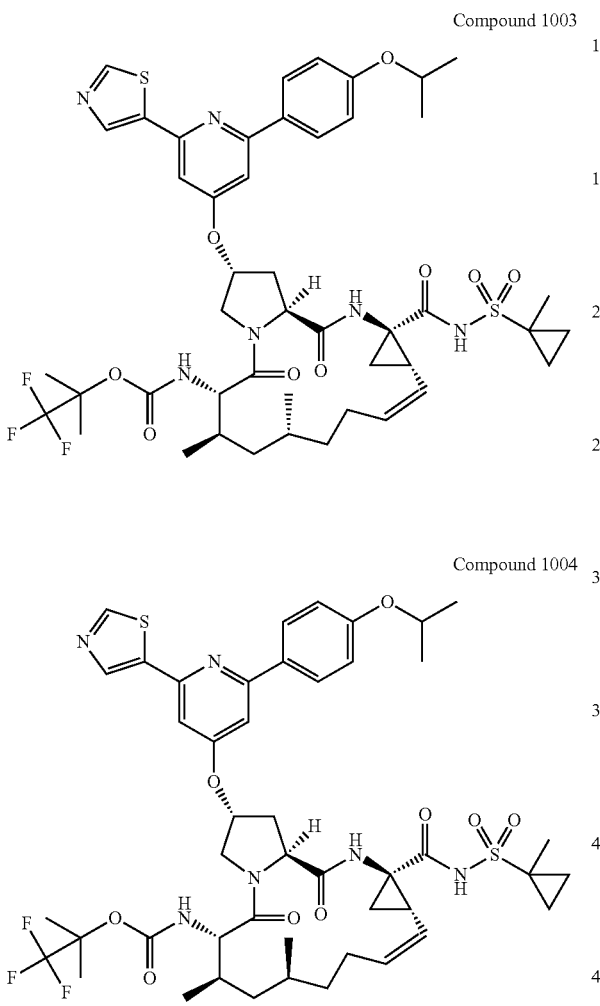

Compound 1003

Compound 1004

Compounds 1003 and 1004 were prepared using the intermediates described above and by following the general procedure described for the synthesis of Compound 1001.

Compound 1003: 1,1,1-trifluoro-2-methylpropan-2-yl ((2R,6S,7R,9R,13aS,14aR,16aS,Z)-2-((2-(4-isopropoxyphenyl)-6-(thiazol-5-yl)pyridin-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H-NMR (500 MHz, CD$_3$OD) δ 9.71-9.68 (m, 1H), 8.73-8.70 (m, 1H), 8.64 (d, J=2.4 Hz, 1H), 8.13-8.08 (m, J=8.9 Hz, 2H), 7.84 (d, J=2.1 Hz, 1H), 7.41 (d, J=2.1 Hz, 1H), 7.08-7.02 (m, J=8.9 Hz, 2H), 5.61-5.54 (m, 1H), 5.49 (br. s., 1H), 5.17 (br. s., 1H), 4.76-4.54 (m, 4H), 4.04 (dd, J=11.4, 3.2 Hz, 1H), 3.85 (d, J=10.7 Hz, 1H), 2.72-2.58 (m, 2H), 2.46 (ddd, J=13.8, 10.1, 4.1 Hz, 1H), 2.42-2.34 (m, 1H), 2.03-1.94 (m, 1H), 1.88 (d, J=6.4 Hz, 1H), 1.80-1.71 (m, 2H), 1.63-1.53 (m, 2H), 1.50 (s, 3H), 1.45 (d, J=7.9 Hz, 2H), 1.43-1.38 (m, 2H), 1.37 (d, J=6.1 Hz, 6H), 1.34 (s, 3H), 1.32-1.19 (m, 2H), 1.17 (s, 3H), 0.99 (d, J=6.7 Hz, 3H), 0.95 (d, J=6.4 Hz, 3H), 0.84-0.77 (m, 3H); MS: MS m/z 959.5 (M$^+$+1).

Compound 1004: 1,1,1-trifluoro-2-methylpropan-2-yl ((2R,6S,7R,9S,13aS,14aR,16aS,Z)-2-((2-(4-isopropoxyphenyl)-6-(thiazol-5-yl)pyridin-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 959.5 (M$^+$+1).

Preparation of Compound 1005 and 1006

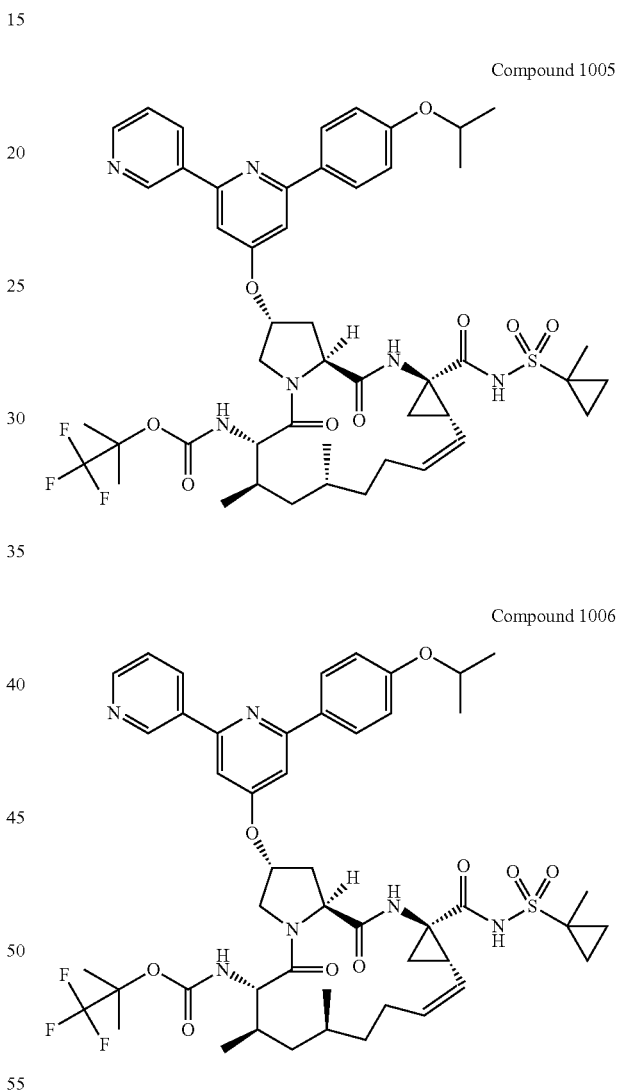

Compound 1005

Compound 1006

Compounds 1005 and 1006 were prepared using the intermediates described above and by following the general procedure for the synthesis of Compound 1001.

Compound 1005: 1,1,1-trifluoro-2-methylpropan-2-yl ((2R,6S,7R,9R,13aS,14aR,16aS,Z)-2-((6-(4-isopropoxyphenyl)-[2,3'-bipyridin]-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H-NMR (500 MHz, DMSO-d$_6$) δ 11.03 (s, 1H), 9.39-9.36 (m, 1H), 9.20 (br. s., 1H), 8.67 (d, J=4.0 Hz, 1H), 8.56 (d, J=7.9 Hz, 1H), 8.16 (d, J=8.9 Hz, 2H), 7.84 (d, J=8.9 Hz, 1H), 7.56 (dd, J=7.8, 4.7 Hz, 1H), 7.50 (s, 1H), 7.42 (s, 1H), 7.05 (d, J=8.5 Hz, 2H), 5.62 (br. s., 1H), 5.54 (d, J=5.5 Hz, 1H), 4.98 (t, J=9.9 Hz, 1H), 4.73 (dt, J=12.1, 6.0 Hz, 1H), 4.51-4.39 (m, 2H), 3.95-3.90 (m, 1H), 3.75 (t, J=9.6 Hz, 1H), 2.73-2.64 (m, 1H), 2.60 (d, J=7.3 Hz, 1H), 2.35-2.24 (m, 2H), 1.92 (s, 1H), 1.86 (d, J=4.6 Hz, 1H), 1.63 (br. s., 2H), 1.56-1.44 (m, 3H), 1.42 (s, 4H), 1.37 (br. s., 1H), 1.32 (d, J=6.1 Hz, 6H), 1.28 (s, 4H), 1.19 (d, J=7.0 Hz, 1H), 1.14 (s, 3H), 0.92 (d, J=7.0 Hz, 3H), 0.91-0.89 (m, 1H), 0.85 (d, J=6.1 Hz, 3H), 0.73 (t, J=12.7 Hz, 1H); MS: MS m/z 953.5 (M$^+$+1).

Compound 1006: 1,1,1-trifluoro-2-methylpropan-2-yl ((2R,6S,7R,9S,13aS,14aR,16aS,Z)-2-((6-(4-isopropoxyphenyl)-[2,3'-bipyridin]-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 953.5 (M$^+$+1).

Preparation of Compound 1007 and 1008

Compounds 1007 and 1008 were prepared using the intermediates described above and by following the general procedure described for the synthesis of Compound 1001.

Compound 1007: 1,1,1-trifluoro-2-methylpropan-2-yl ((2R,6S,7R,9R,13aS,14aR,16aS,Z)-2-((2-(4-isopropoxyphenyl)-6-(thiazol-2-yl)pyridin-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H-NMR (500 MHz, DMSO-d$_6$) δ 11.01 (br. s., 1H), 9.18 (br. s., 1H), 8.10 (d, J=8.9 Hz, 2H), 8.00 (d, J=3.4 Hz, 1H), 7.89 (d, J=3.1 Hz, 1H), 7.82 (d, J=7.3 Hz, 1H), 7.47 (s, 1H), 7.50 (s, 1H), 7.06 (d, J=8.9 Hz, 2H), 5.59 (br. s., 1H), 5.51 (br. s., 1H), 4.97 (br. s., 1H), 4.73 (dt, J=12.2, 6.1 Hz, 1H), 4.50-4.39 (m, 2H), 3.92-3.87 (m, 1H), 3.68 (t, J=9.6 Hz, 1H), 2.71-2.61 (m, 1H), 2.58 (br. s., 1H), 2.33-2.23 (m, 2H), 1.93-1.86 (m, 1H), 1.82 (br. s., 1H), 1.61 (br. s., 2H), 1.52 (br. s., 1H), 1.48 (br. s., 1H), 1.40 (br. s., 3H), 1.34 (br. s., 1H), 1.30 (d, J=6.1 Hz, 6H), 1.29-1.25 (m, 1H), 1.23 (s, 3H), 1.22-1.12 (m, 4H), 0.90 (d, J=6.7 Hz, 3H), 0.83 (d, J=6.1 Hz, 3H), 0.71 (t, J=12.4 Hz, 1H); MS: MS m/z 959.5 (M$^+$+1).

Compound 1008: 1,1,1-trifluoro-2-methylpropan-2-yl ((2R,6S,7R,9S,13aS,14aR,16aS,Z)-2-((2-(4-isopropoxyphenyl)-6-(thiazol-2-yl)pyridin-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 959.5 (M$^+$+1).

Preparation of Compound 1009 and 1010

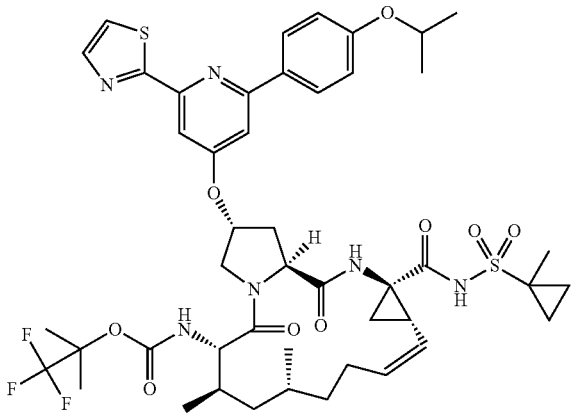

Compund 1007

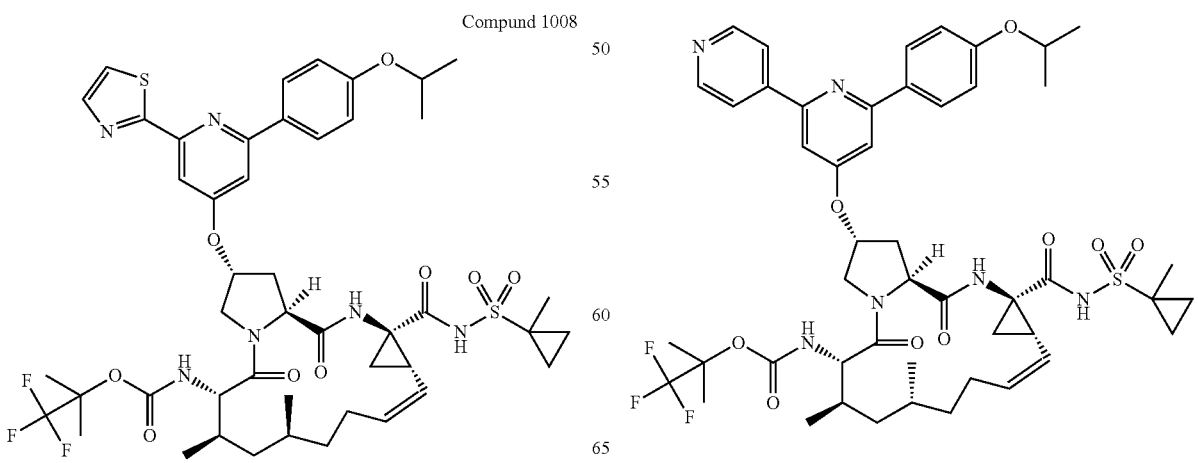

Compund 1008

Compound 1009

Preparation of Compound 1011 and 1012

Compound 1010

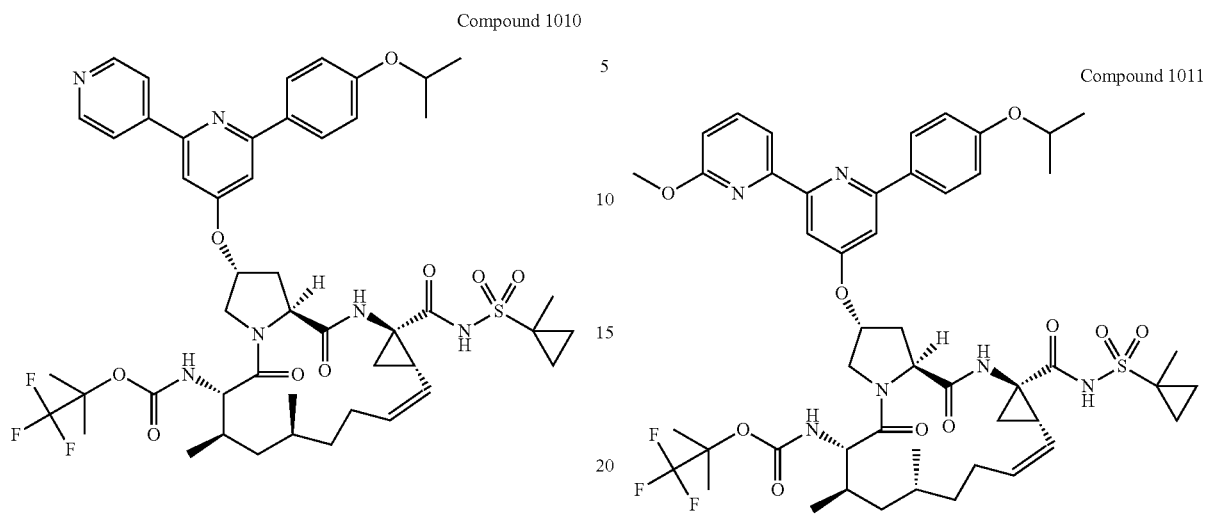

Compounds 1009 and 1010 were prepared using the intermediates described above and by following the general procedure described for the synthesis of Compound 1001.

Compound 1009: 1,1,1-trifluoro-2-methylpropan-2-yl ((2R,6S,7R,9R,13aS,14aR,16aS,Z)-2-((6-(4-isopropoxyphenyl)-[2,4'-bipyridin]-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H-NMR (500 MHz, DMSO-$d_6$) δ 11.03 (s, 1H), 9.20 (br. s., 1H), 8.74 (d, J=5.5 Hz, 2H), 8.22-8.15 (m, 4H), 7.84 (d, J=8.2 Hz, 1H), 7.55 (s, 1H), 7.48 (s, 1H), 7.06 (d, J=8.9 Hz, 2H), 5.64 (br. s., 1H), 5.54 (d, J=7.3 Hz, 1H), 4.98 (t, J=9.6 Hz, 1H), 4.74 (dt, J=12.1, 6.0 Hz, 1H), 4.51-4.39 (m, 2H), 3.93 (d, J=10.1 Hz, 1H), 3.74 (t, J=9.8 Hz, 1H), 2.74-2.63 (m, 1H), 2.60 (d, J=6.7 Hz, 1H), 2.35-2.24 (m, 2H), 1.96-1.81 (m, 2H), 1.63 (br. s., 2H), 1.53 (br. s., 1H), 1.51-1.44 (m, 2H), 1.42 (s, 4H), 1.36 (br. s., 1H), 1.32 (d, J=5.8 Hz, 6H), 1.31-1.28 (m, 2H), 1.27 (s, 3H), 1.21-1.15 (m, 1H), 1.13 (s, 3H), 0.92 (d, J=7.0 Hz, 3H), 0.85 (d, J=6.4 Hz, 3H), 0.72 (t, J=12.2 Hz, 1H); MS: MS m/z 953.5 (M$^+$+1).

Compound 1010: 1,1,1-trifluoro-2-methylpropan-2-yl ((2R,6S,7R,9S,13aS,14aR,16aS,Z)-2-((6-(4-isopropoxyphenyl)-[2,4'-bipyridin]-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 953.5 (M$^+$+1).

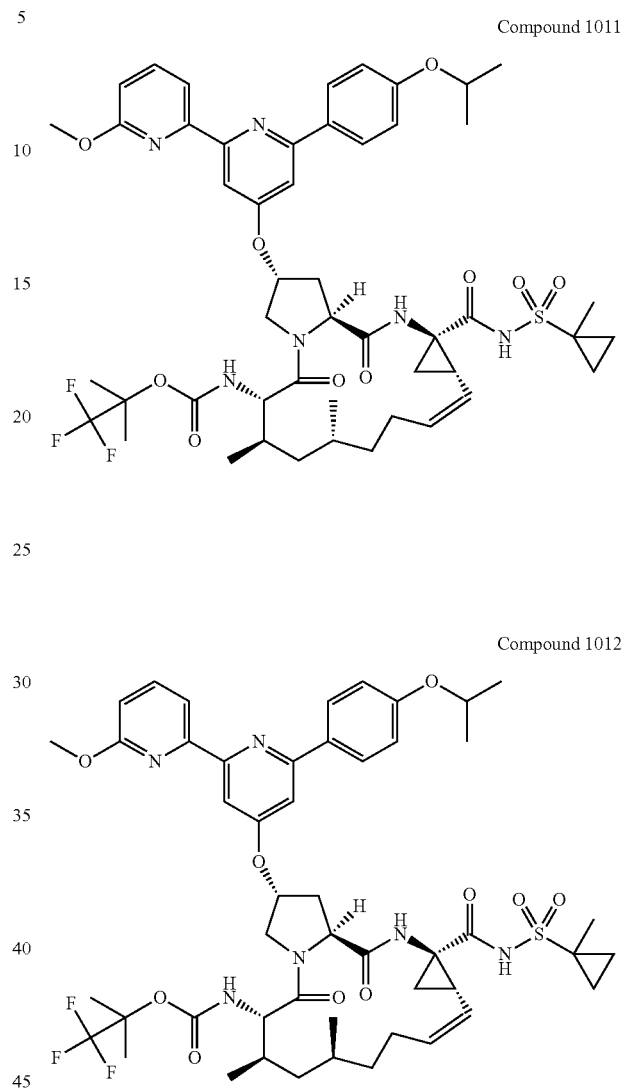

Compounds 1011 and 1012 were prepared using the intermediates described above and by following the general procedure described for the synthesis of Compound 1001.

Compound 1011: 1,1,1-trifluoro-2-methylpropan-2-yl ((2R,6S,7R,9R,13aS,14aR,16aS,Z)-2-((6-(4-isopropoxyphenyl)-6'-methoxy-[2,2'-bipyridin]-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H-NMR (500 MHz, DMSO-$d_6$) δ 11.03 (s, 1H), 9.16 (s, 1H), 8.21-8.14 (m, 3H), 7.91-7.84 (m, 2H), 7.72 (d, J=1.8 Hz, 1H), 7.49 (s, 1H), 7.07 (d, J=8.5 Hz, 2H), 6.92 (d, J=8.2 Hz, 1H), 5.61 (br. s., 1H), 5.53 (d, J=5.5 Hz, 1H), 4.98 (t, J=9.8 Hz, 1H), 4.74 (dt, J=12.0, 6.1 Hz, 1H), 4.51-4.43 (m, 2H), 3.99 (s, 3H), 3.93 (d, J=9.5 Hz, 1H), 3.75-3.70 (m, 1H), 2.73-2.58 (m, 2H), 2.35-2.24 (m, 2H), 1.95-1.81 (m, 2H), 1.63 (d, J=6.1 Hz, 2H), 1.55-1.49 (m, 1H), 1.46 (d, J=9.5 Hz, 2H), 1.42 (s, 3H), 1.36 (br. s., 1H), 1.33 (d, J=6.1 Hz, 5H), 1.30 (br. s., 1H), 1.28 (s, 3H), 1.23 (br. s., 1H), 1.18 (s, 2H), 1.14 (br. s., 1H), 0.99-0.88 (m, 4H), 0.85 (d, J=6.1 Hz, 3H), 0.73 (t, J=11.7 Hz, 1H); MS: MS m/z 983.6 (M⁺+1).

Compound 1012: 1,1,1-trifluoro-2-methylpropan-2-yl ((2R,6S,7R,9R,13aS,14aR,16aS,Z)-2-((6-(4-isopropoxyphenyl)-6'-methoxy-[2,2'-bipyridin]-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 983.5 (M⁺+1).

Preparation of Compound 1013 and 1014

Compound 1013

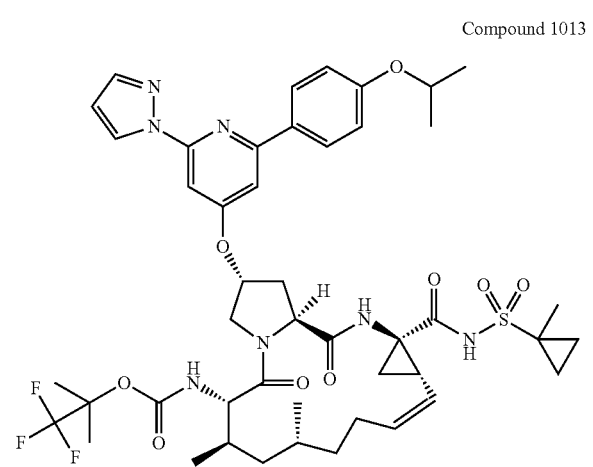 [SMILES: CC(C)Oc1ccc(-c2cc(O[C@@H]3C[C@H]4C(=O)N[C@]5(C(=O)NS(=O)(=O)C6(C)CC6)C[C@H]5/C=C\CC[C@@H](C)C[C@@H](C)[C@H](NC(=O)OC(C)(C)C(F)(F)F)C(=O)N4C3)cc(-n3cccn3)n2)cc1]

Compound 1014

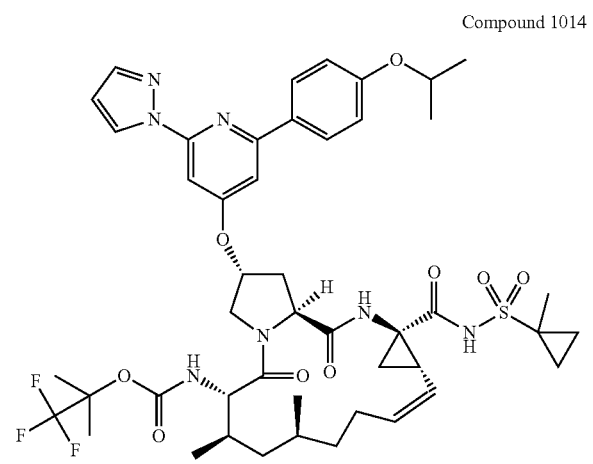 [SMILES: CC(C)Oc1ccc(-c2cc(O[C@@H]3C[C@H]4C(=O)N[C@]5(C(=O)NS(=O)(=O)C6(C)CC6)C[C@H]5/C=C\CC[C@H](C)C[C@@H](C)[C@H](NC(=O)OC(C)(C)C(F)(F)F)C(=O)N4C3)cc(-n3cccn3)n2)cc1]

Compounds 1013 and 1014 were prepared using the intermediates described above and by following the general procedure described for the synthesis of Compound 1001.

Compound 1013: 1,1,1-trifluoro-2-methylpropan-2-yl ((2R,6S,7R,9R,13aS,14aR,16aS,Z)-2-((2-(4-isopropoxyphenyl)-6-(1H-pyrazol-1-yl)pyridin-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. ¹H-NMR (500 MHz, DMSO-d₆) δ 11.07 (s, 1H), 9.18 (s, 1H), 8.84 (d, J=2.4 Hz, 1H), 8.13 (d, J=8.5 Hz, 2H), 7.99 (d, J=1.2 Hz, 1H), 7.87-7.81 (m, 2H), 7.12-7.04 (m, 3H), 6.66-6.64 (m, 1H), 5.88 (br. s., 1H), 5.57-5.51 (m, 1H), 4.97 (t, J=10.1 Hz, 1H), 4.75 (quin, J=6.0 Hz, 1H), 4.52 (dd, J=9.8, 7.3 Hz, 1H), 4.42 (d, J=11.3 Hz, 1H), 3.98-3.91 (m, 1H), 3.69 (dd, J=10.7, 8.5 Hz, 1H), 2.70 (q, J=9.1 Hz, 1H), 2.56 (dd, J=13.7, 6.7 Hz, 1H), 2.39-2.27 (m, 2H), 1.96-1.81 (m, 2H), 1.69-1.61 (m, 2H), 1.56-1.44 (m, 3H), 1.42 (s, 4H), 1.37 (br. s., 1H), 1.33 (d, J=6.1 Hz, 6H), 1.31 (br. s., 1H), 1.29 (s, 3H), 1.18 (s, 3H), 1.13 (d, J=12.2 Hz, 1H), 0.95-0.89 (m, 4H), 0.85 (d, J=6.4 Hz, 3H), 0.74 (t, J=12.2 Hz, 1H); MS: MS m/z 940.8 (M⁺+1).

Compound 1014: 1,1,1-trifluoro-2-methylpropan-2-yl ((2R,6S,7R,9S,13aS,14aR,16aS,Z)-2-((2-(4-isopropoxyphenyl)-6-(1H-pyrazol-1-yl)pyridin-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 940.8 (M⁺+1).

Preparation of Compound 1015 and 1016

Compound 1015

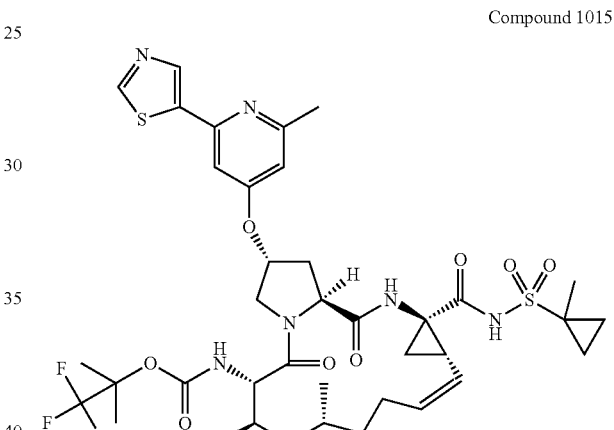

Compound 1016

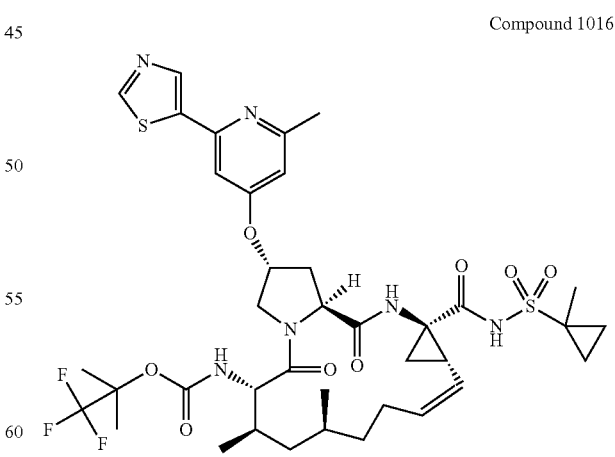

Compounds 1015 and 1016 were prepared using the intermediates described above and by following the general procedure described for the synthesis of Compound 1001.

Compound 1015: 1,1,1-trifluoro-2-methylpropan-2-yl ((2R,6S,7R,9R,13aS,14aR,16aS,Z)-7,9-dimethyl-2-((2-methyl-6-(thiazol-5-yl)pyridin-4-yl)oxy)-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H-NMR (500 MHz, DMSO-$d_6$) δ 11.02 (br. s., 1H), 9.18-9.10 (m, 2H), 8.63-8.59 (m, 1H), 7.38 (s, 1H), 7.18 (d, J=7.9 Hz, 1H), 6.82 (s, 1H), 5.52 (br. s., 1H), 5.40 (br. s., 1H), 4.98 (br. s., 1H), 4.38 (d, J=9.8 Hz, 2H), 3.92-3.87 (m, 1H), 3.75 (t, J=9.9 Hz, 1H), 2.72 (br. s., 1H), 2.44 (s, 4H), 2.35-2.19 (m, 3H), 1.92 (s, 1H), 1.83 (br. s., 1H), 1.61 (br. s., 2H), 1.51 (br. s., 1H), 1.41 (br. s., 4H), 1.37 (br. s., 1H), 1.29 (br. s., 1H), 1.17 (s, 10H), 1.15-1.04 (m, 2H), 0.92 (d, J=7.0 Hz, 3H), 0.85 (d, J=6.4 Hz, 3H), 0.70 (d, J=11.3 Hz, 1H); MS: MS m/z 785.5 (M$^+$+1).

Compound 1016: 1,1,1-trifluoro-2-methylpropan-2-yl ((2R,6S,7R,9S,13aS,14aR,16aS,Z)-7,9-dimethyl-2-((2-methyl-6-(thiazol-5-yl)pyridin-4-yl)oxy)-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 785.5 (M$^+$+1).

Preparation of Compound 1017 and 1018

Compounds 1017 and 1018 were prepared using the intermediates described above and by following the general procedure described for the synthesis of Compound 1001.

Compound 1017: 3-(trifluoromethyl)tetrahydro-2H-pyran-3-yl ((2R,6S,7R,9R,13aS,14aR,16aS,Z)-2-((2-(4-isopropoxyphenyl)-6-(thiazol-5-yl)pyridin-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H-NMR (500 MHz, DMSO-$d_6$) δ 11.02 (s, 1H), 9.19-9.14 (m, 2H), 8.65 (s, 1H), 8.14-8.05 (m, 2H), 7.94 (d, J=8.9 Hz, 1H), 7.46 (d, J=1.8 Hz, 1H), 7.34 (d, J=1.8 Hz, 1H), 7.05 (d, J=8.9 Hz, 2H), 5.61-5.50 (m, 2H), 5.00 (t, J=9.8 Hz, 1H), 4.73 (quin, J=6.1 Hz, 1H), 4.47-4.38 (m, 2H), 4.08 (d, J=11.9 Hz, 1H), 3.97-3.92 (m, 1H), 3.82-3.75 (m, 1H), 3.56 (d, J=10.7 Hz, 1H), 3.40 (d, J=11.6 Hz, 1H), 3.34-3.28 (m, 1H), 2.75-2.67 (m, 1H), 2.58 (dd, J=13.6, 6.6 Hz, 1H), 2.39-2.22 (m, 3H), 2.12 (d, J=13.7 Hz, 1H), 1.98-1.83 (m, 2H), 1.76-1.67 (m, 1H), 1.67-1.56 (m, 2H), 1.53 (dd, J=9.0, 5.0 Hz, 1H), 1.45 (br. s., 2H), 1.42 (s, 3H), 1.40-1.33 (m, 1H), 1.32 (d, J=5.8 Hz, 6H), 1.29 (d, J=4.9 Hz, 1H), 1.13 (d, J=12.2 Hz, 1H), 0.93 (d, J=6.7 Hz, 4H), 0.91-0.88 (m, 2H), 0.87 (d, J=6.4 Hz, 3H), 0.74 (t, J=11.9 Hz, 1H); MS: MS m/z 1002.0 (M$^+$+1).

Compound 1018: 3-(trifluoromethyl)tetrahydro-2H-pyran-3-yl ((2R,6S,7R,9S,13aS,14aR,16aS,Z)-2-((2-(4-isopropoxyphenyl)-6-(thiazol-5-yl)pyridin-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 1002.0 (M$^+$+1).

Preparation of Compound 1019 and 1020

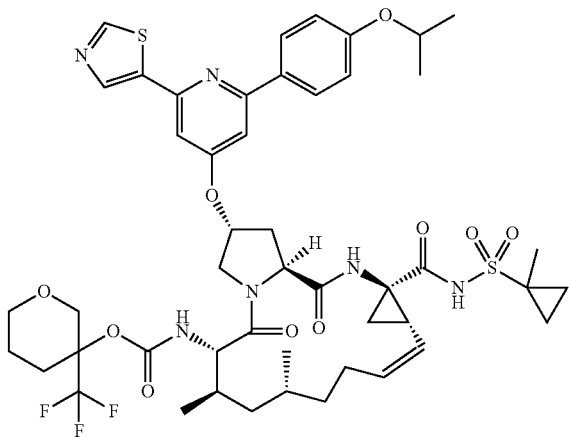

Compound 1017

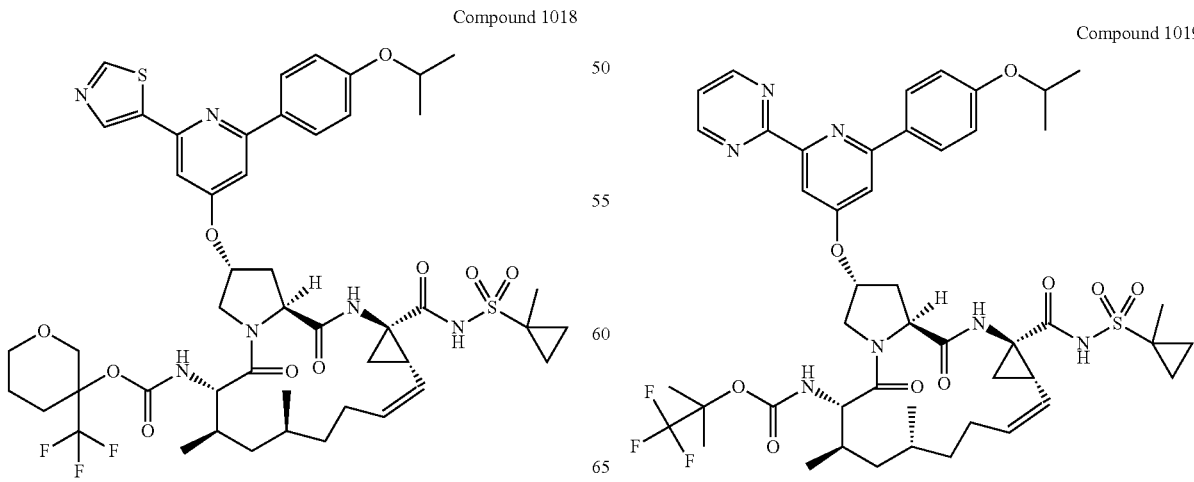

Compound 1018

Compound 1019

Compound 1020

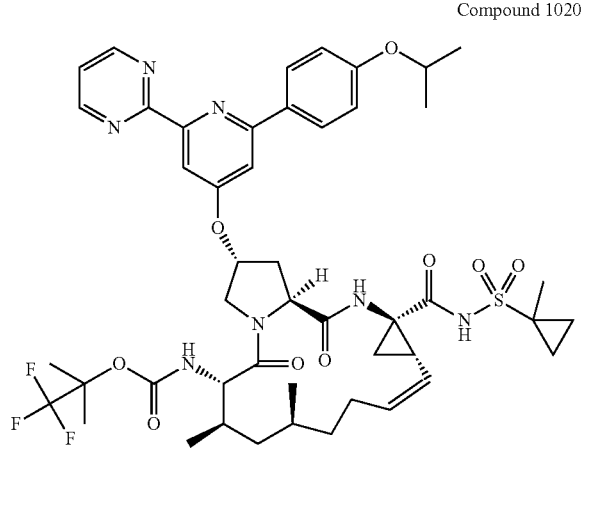 [SMILES: CC(C)Oc1ccc(-c2cc(O[C@@H]3C[C@H]4C(=O)N[C@]5(C(=O)NS(=O)(=O)C6(C)CC6)C[C@H]5/C=C\CC[C@H](C)C[C@@H](C)[C@H](NC(=O)OC(C)(C)C(F)(F)F)C(=O)N4C3)cc(-c3ncccn3)n2)cc1]

Compounds 1019 and 1020 were prepared using the intermediates described above and by following the general procedure described for the synthesis of Compound 1001.

Compound 1019: 1,1,1-trifluoro-2-methylpropan-2-yl ((2R,6S,7R,9R,13aS,14aR,16aS,Z)-2-((2-(4-isopropoxyphenyl)-6-(pyrimidin-2-yl)pyridin-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H-NMR (500 MHz, DMSO-$d_6$) δ 11.03 (s, 1H), 9.17 (s, 1H), 9.04-9.01 (m, 2H), 8.16 (d, J=8.9 Hz, 2H), 7.87-7.80 (m, 2H), 7.60 (t, J=4.9 Hz, 1H), 7.54 (d, J=2.1 Hz, 1H), 7.06 (d, J=8.9 Hz, 2H), 5.60 (br. s., 1H), 5.58-5.49 (m, 1H), 4.99 (t, J=9.8 Hz, 1H), 4.74 (dt, J=12.0, 6.1 Hz, 1H), 4.51-4.38 (m, 2H), 3.95-3.90 (m, 1H), 3.72 (dd, J=10.4, 8.9 Hz, 1H), 2.73-2.57 (m, 2H), 2.35-2.25 (m, 2H), 1.96-1.81 (m, 2H), 1.62 (d, J=7.6 Hz, 2H), 1.55-1.49 (m, 1H), 1.49-1.43 (m, 2H), 1.42 (s, 3H), 1.37 (d, J=11.0 Hz, 2H), 1.32 (d, J=6.1 Hz, 7H), 1.28 (s, 3H), 1.18 (s, 3H), 1.17-1.08 (m, 1H), 0.94-0.90 (m, 4H), 0.85 (d, J=6.1 Hz, 3H), 0.73 (t, J=12.4 Hz, 1H); MS: MS m/z 953.0 (M$^-$–1).

Compound 1020: 1,1,1-trifluoro-2-methylpropan-2-yl ((2R,6S,7R,9S,13aS,14aR,16aS,Z)-2-((2-(4-isopropoxyphenyl)-6-(pyrimidin-2-yl)pyridin-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 955.0 (M$^+$+1).

Preparation of Compound 1021 and 1022

Compound 1021

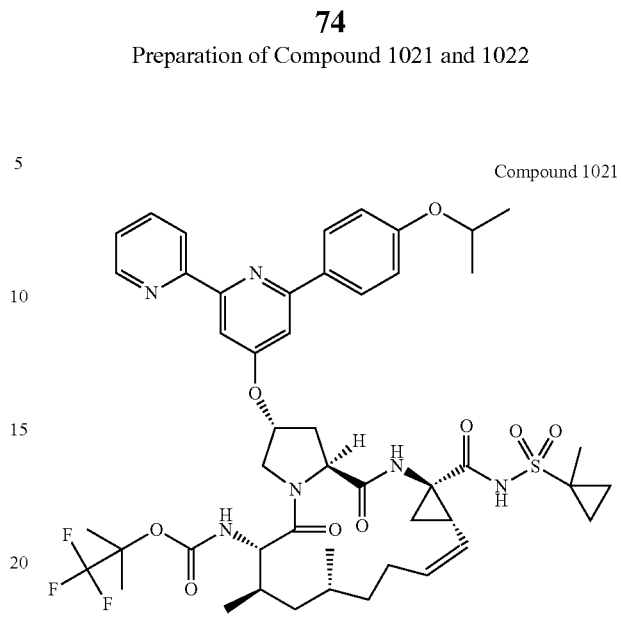

Compound 1022

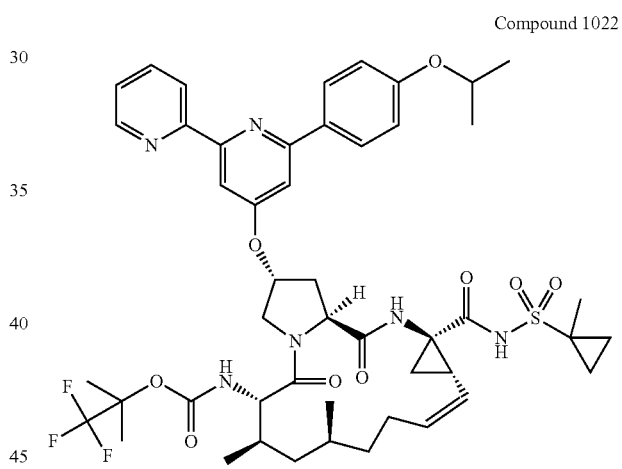

Compounds 1021 and 1022 were prepared using the intermediates described above and by following the general procedure described for the synthesis of Compound 1001.

Compound 1021: 1,1,1-trifluoro-2-methylpropan-2-yl ((2R,6S,7R,9R,13aS,14aR,16aS,Z)-2-((6-(4-isopropoxyphenyl)-[2,2'-bipyridin]-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H-NMR (500 MHz, DMSO-$d_6$) δ 11.03 (s, 1H), 9.18 (s, 1H), 8.71 (d, J=4.3 Hz, 1H), 8.56 (d, J=7.9 Hz, 1H), 8.21-8.16 (m, J=8.9 Hz, 2H), 8.00 (td, J=7.8, 1.8 Hz, 1H), 7.86-7.81 (m, 2H), 7.50 (dd, J=6.7, 5.2 Hz, 1H), 7.45 (d, J=1.8 Hz, 1H), 7.08-7.04 (m, J=8.9 Hz, 2H), 5.61-5.50 (m, 2H), 4.99 (t, J=9.9 Hz, 1H), 4.74 (dt, J=12.0, 6.1 Hz, 1H), 4.51-4.40 (m, 2H), 3.93 (d, J=7.6 Hz, 1H), 3.74-3.69 (m, 1H), 2.73-2.64 (m, 1H), 2.60 (dd, J=13.3, 6.6 Hz, 1H), 2.35-2.25 (m, 2H), 1.96-1.81 (m, 2H), 1.67-1.60 (m, 2H), 1.53 (dd, J=9.3, 5.3 Hz, 1H), 1.51-1.43 (m, 2H), 1.42

(s, 3H), 1.36 (br. s., 2H), 1.32 (d, J=6.1 Hz, 6H), 1.29 (d, J=5.8 Hz, 1H), 1.26 (s, 3H), 1.15 (s, 3H), 1.12 (d, J=13.1 Hz, 1H), 0.93-0.88 (m, 4H), 0.84 (d, J=6.4 Hz, 3H), 0.73 (t, J=12.2 Hz, 1H); MS: MS m/z 953.7 (M$^+$+1).

Compound 1022: 1,1,1-trifluoro-2-methylpropan-2-yl ((2R,6S,7R,9S,13aS,14aR,16aS,Z)-2-((6-(4-isopropoxyphenyl)-[2,2'-bipyridin]-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 951.7 (M$^-$−1).

Preparation of Compound 1023 and 1024

Compound 1023: 1,1,1-trifluoro-2-methylpropan-2-yl ((2R,6S,7R,9R,13aS,14aR,16aS,Z)-2-((2,6-di(thiazol-2-yl)pyridin-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H-NMR (500 MHz, DMSO-d$_6$) δ 11.03 (br. s., 1H), 9.20 (br. s., 1H), 8.06 (d, J=3.1 Hz, 2H), 7.96 (d, J=3.1 Hz, 2H), 7.84 (d, J=7.6 Hz, 1H), 7.67 (s, 2H), 5.62 (br. s., 1H), 5.52 (br. s., 1H), 4.99 (br. s., 1H), 4.49 (d, J=9.5 Hz, 2H), 3.94-3.89 (m, 1H), 3.66 (dd, J=10.4, 8.2 Hz, 1H), 2.65 (br. s., 1H), 2.61 (br. s., 1H), 2.35-2.25 (m, 2H), 1.94-1.78 (m, 2H), 1.63 (br. s., 2H), 1.54 (br. s., 1H), 1.49 (br. s., 2H), 1.42 (s, 3H), 1.34 (d, J=14.0 Hz, 2H), 1.28 (br. s., 1H), 1.20 (s, 3H), 1.15 (s, 3H), 1.13-1.07 (m, 1H), 0.92 (d, J=6.7 Hz, 4H), 0.84 (d, J=6.1 Hz, 3H), 0.74 (t, J=12.4 Hz, 1H); MS: MS m/z 908.5 (M$^+$+1).

Compound 1024: 1,1,1-trifluoro-2-methylpropan-2-yl ((2R,6S,7R,9S,13aS,14aR,16aS,Z)-2-((2,6-di(thiazol-2-yl)pyridin-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 908.5 (M$^+$+1).

Preparation of Compound 1025

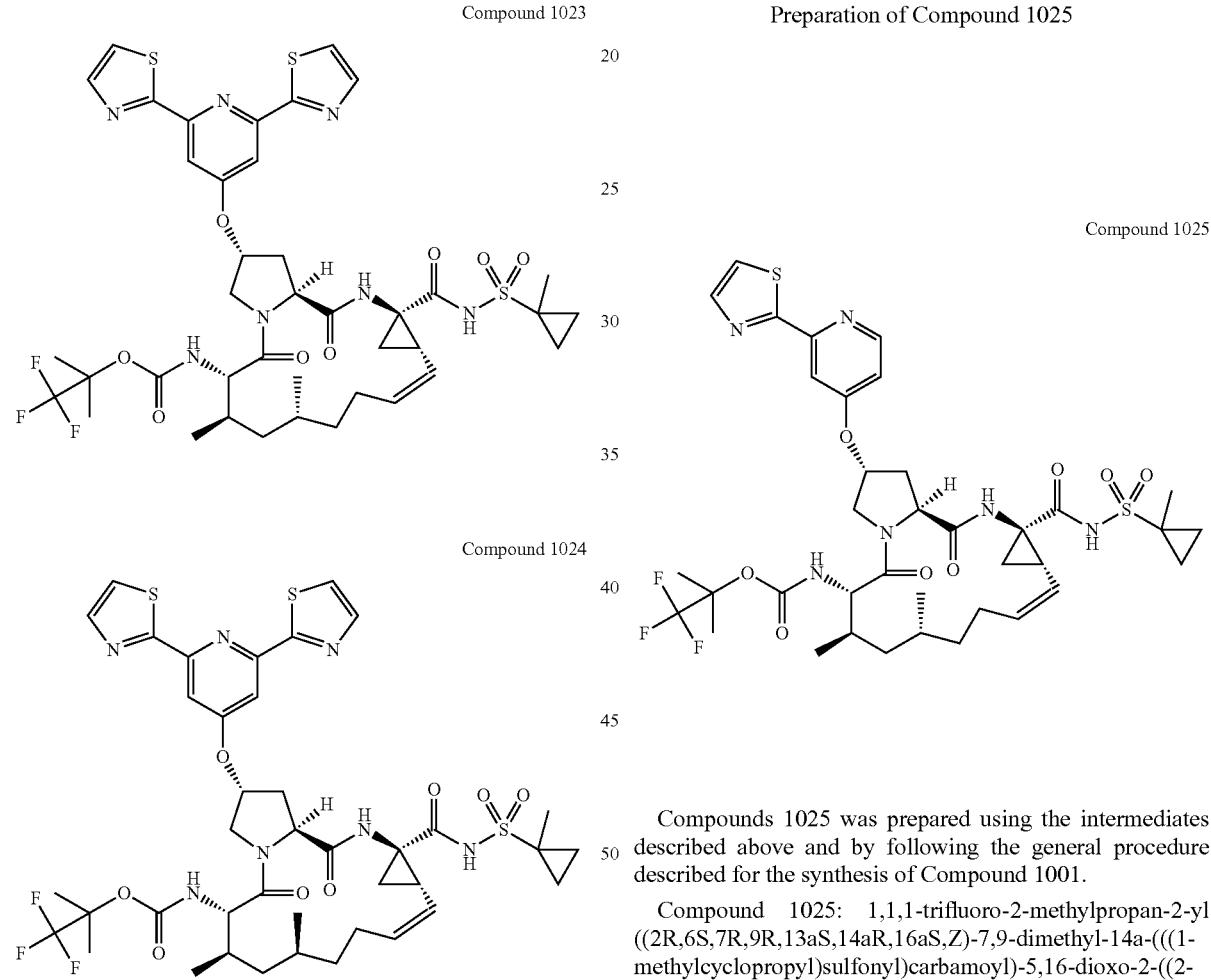

Compound 1023

Compound 1024

Compound 1025

Compounds 1023 and 1024 were prepared using the intermediates described above and by following the general procedure described for the synthesis of Compound 1001.

Compounds 1025 was prepared using the intermediates described above and by following the general procedure described for the synthesis of Compound 1001.

Compound 1025: 1,1,1-trifluoro-2-methylpropan-2-yl ((2R,6S,7R,9R,13aS,14aR,16aS,Z)-7,9-dimethyl-14a-(((1-methylcyclopropyl)sulfonyl)carbamoyl)-5,16-dioxo-2-((2-(thiazol-2-yl)pyridin-4-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H-NMR (500 MHz, DMSO-d$_6$) δ 11.01 (s, 1H), 9.16 (br. s., 1H), 8.47 (d, J=5.8 Hz, 1H), 8.00 (d, J=3.1 Hz, 1H), 7.89 (d, J=3.1 Hz, 1H), 7.86 (d, J=7.9 Hz, 1H), 7.61 (d, J=2.1 Hz, 1H), 7.07 (dd, J=5.8, 2.4 Hz, 1H), 5.53 (d, J=6.1 Hz, 1H), 5.47 (br. s., 1H), 4.98 (t, J=9.5 Hz, 1H), 4.48-4.40 (m, 2H), 3.90 (d, J=8.9 Hz, 1H), 3.69 (dd, J=10.7, 8.5 Hz, 1H), 2.72-2.64 (m, 1H), 2.57 (dd, J=13.6, 6.3 Hz, 1H), 2.34-2.22 (m, 2H), 1.95-1.81 (m, 2H), 1.63 (d, J=5.5 Hz, 2H), 1.53 (br. s., 1H), 1.45 (br. s., 2H), 1.41 (s, 3H), 1.36 (br. s., 1H), 1.32 (s, 3H), 1.29 (d, J=10.4 Hz, 2H), 1.23 (s, 3H), 1.12 (d, J=11.9 Hz, 1H), 0.93-0.88 (m, 4H), 0.86 (d, J=6.4 Hz, 3H), 0.73 (t, J=11.9 Hz, 1H); MS: MS m/z 825.5 (M$^+$+1).

1.90-2.01 (2H, m), 1.60 (1H, dd, J=9.54, 5.52 Hz), 1.45-1.52 (5H, m), 1.40 (3H, s), 1.29-1.35 (2H, m), 0.81-1.09 (11H, m); MS: MS m/z 762.2 (M$^+$+1).

Preparation of Compound 1026

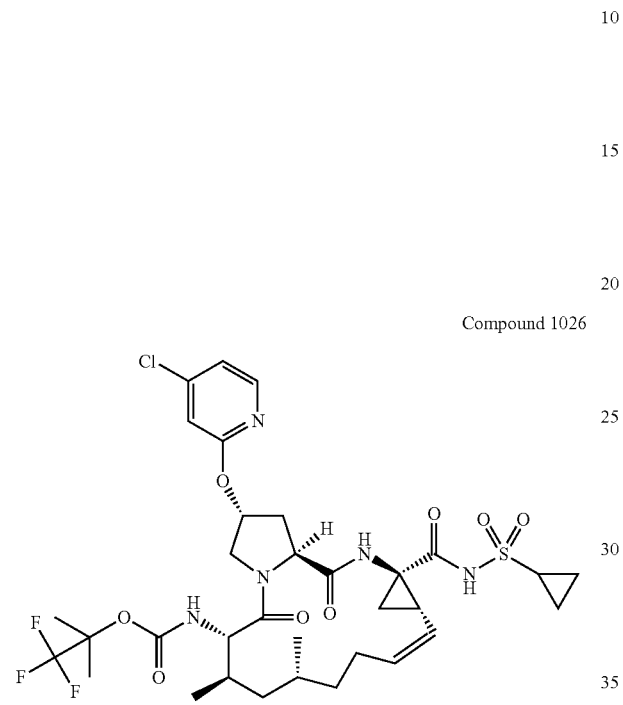

Compound 1026

Preparation of Compound 1027 and 1028

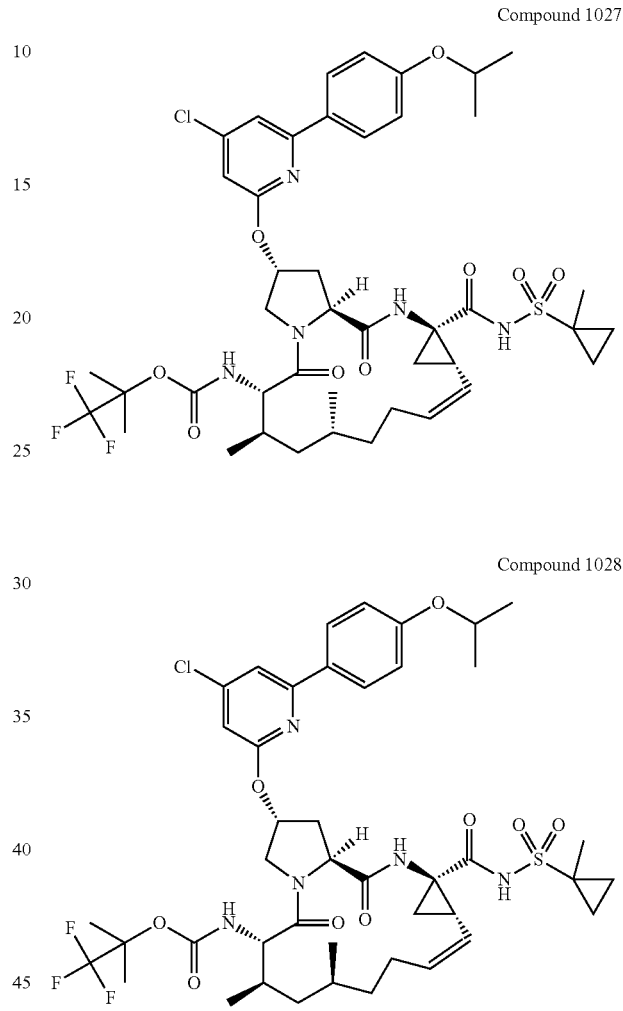

Compound 1027

Compound 1028

Compounds 1026 was prepared by following the general procedure described for the synthesis of Compound 1001 using the intermediates described above, 2,4-dichloropyridine.

Compound 1026: 1,1,1-trifluoro-2-methylpropan-2-yl ((2R,6S,7R,9R,13aS,14aR,16aS,Z)-2-((4-chloropyridin-2-yl)oxy)-14a-((cyclopropylsulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD) δ 8.21 (1H, d, J=5.77 Hz), 7.09 (1H, d, J=2.26 Hz), 7.00 (1H, dd, J=6.02, 2.26 Hz), 5.63 (1H, td, J=10.10, 5.65 Hz), 5.35 (1H, br. s.), 5.01-5.10 (1H, m), 4.61 (1H, d, J=11.80 Hz), 4.52 (1H, dd, J=10.16, 7.15 Hz), 3.94-4.01 (1H, m), 3.80-3.86 (1H, m), 2.91-2.98 (1H, m), 2.61-2.70 (2H, m), 2.39 (2H, ddd, J=13.99, 10.10, 4.27 Hz), 2.32-2.47 (2H, m), Compounds 1027 and 1028 were prepared using the intermediates described above and by following the general procedure described for the synthesis of Compound 1001.

Compound 1027: 1,1,1-trifluoro-2-methylpropan-2-yl ((2R,6S,7R,9R,13aS,14aR,16aS,Z)-2-((4-chloro-6-(4-isopropoxyphenyl)pyridin-2-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H-NMR (500 MHz, DMSO-d$_6$) δ 11.01 (br. s., 1H), 9.19 (br. s., 1H), 8.00 (d, J=8.9 Hz, 2H), 7.86 (d, J=8.2 Hz, 1H), 7.40 (d, J=1.5 Hz, 1H), 7.05-6.99 (m, 3H), 5.51 (br. s., 2H), 5.03-4.95 (m, 1H), 4.72 (quin, J=6.0 Hz, 1H), 4.47-4.36 (m, 2H), 3.87 (d, J=9.5 Hz, 1H), 3.72 (dd, J=10.5, 8.7 Hz, 1H), 2.67 (d, J=7.9 Hz, 1H), 2.60-2.53 (m, 1H), 2.33-2.19 (m, 2H), 1.95-1.81 (m, 2H), 1.63 (br. s., 2H), 1.53 (d, J=6.7 Hz, 1H), 1.48-1.44 (m, 1H), 1.41 (s, 3H), 1.36 (s, 3H), 1.30 (d, J=6.1 Hz, 7H), 1.24 (s, 3H), 1.20-1.08 (m, 1H), 0.92 (d, J=7.0 Hz, 4H), 0.86 (d, J=6.4 Hz, 3H), 0.72 (t, J=12.5 Hz, 1H); MS: MS m/z 910.5 (M$^+$+1).

Compound 1028: 1,1,1-trifluoro-2-methylpropan-2-yl ((2R,6S,7R,9S,13aS,14aR,16aS,Z)-2-((4-chloro-6-(4-isopropoxyphenyl)pyridin-2-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 910.5 (M$^+$+1).

Preparation of Compound 1029 and 1030

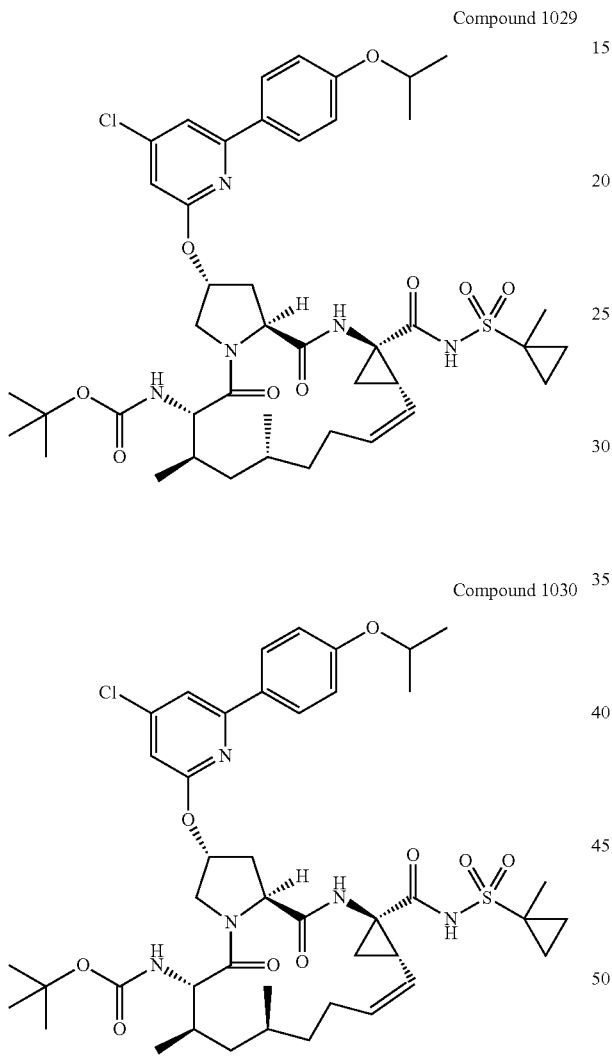

Compound 1029

Compound 1030

Compounds 1029 and 1030 were prepared using the intermediates described above and by following the general procedure described for the synthesis of Compound 1001.

Compound 1029: tert-butyl ((2R,6S,7R,9R,13aS,14aR,16aS,Z)-2-((4-chloro-6-(4-isopropoxyphenyl)pyridin-2-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H-NMR (500 MHz, CD$_3$OD) δ 7.94-7.87 (m, J=8.9 Hz, 2H), 7.27 (d, J=1.8 Hz, 1H), 7.01-6.97 (m, J=8.9 Hz, 2H), 6.97-6.92 (m, 1H), 5.71 (q, J=8.6 Hz, 1H), 5.38 (br. s., 1H), 5.08 (t, J=8.7 Hz, 1H), 4.69 (dt, J=12.0, 6.1 Hz, 1H), 4.59 (t, J=8.4 Hz, 1H), 4.40 (d, J=11.6 Hz, 1H), 4.14 (d, J=6.7 Hz, 1H), 4.06 (d, J=10.1 Hz, 1H), 2.61 (dd, J=14.0, 7.3 Hz, 2H), 2.49-2.32 (m, 2H), 2.03-1.88 (m, 2H), 1.71 (dd, J=8.2, 5.5 Hz, 1H), 1.60 (d, J=8.9 Hz, 3H), 1.49 (s, 3H), 1.47-1.37 (m, 3H), 1.35 (d, J=6.1 Hz, 7H), 1.28 (s, 8H), 1.27-1.14 (m, 3H), 1.07 (d, J=6.7 Hz, 2H), 0.91 (d, J=7.0 Hz, 3H), 0.89-0.81 (m, 2H); MS: MS m/z 856.1 (M$^+$+1).

Compound 1030: tert-butyl ((2R,6S,7R,9S,13aS,14aR,16aS,Z)-2-((4-chloro-6-(4-isopropoxyphenyl)pyridin-2-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 856.5 (M$^+$+1).

Preparation of Compound 1031 and 1032

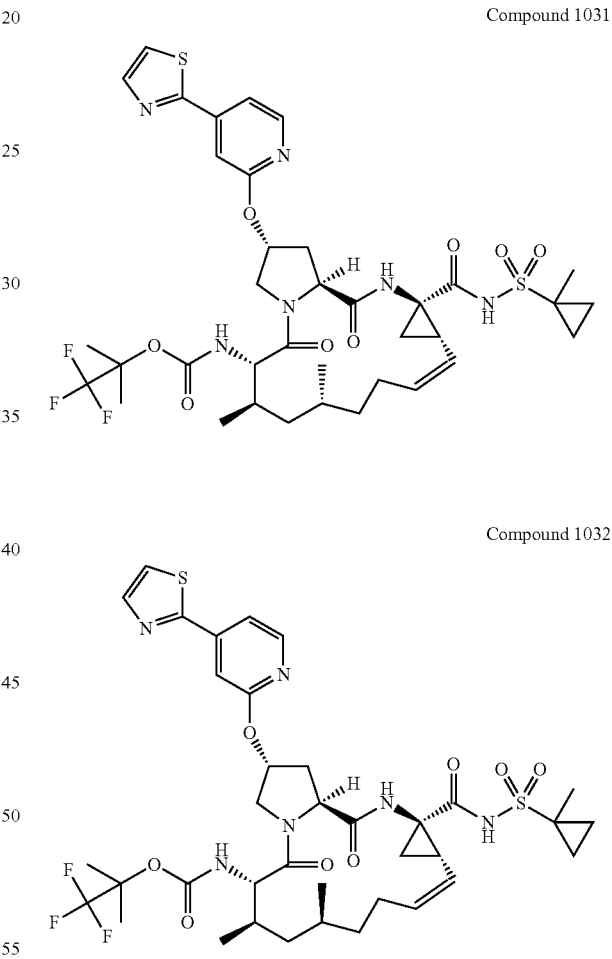

Compound 1031

Compound 1032

Compounds 1031 and 1032 were prepared using the intermediates described above and by following the general procedure described for the synthesis of Compound 1001.

Compound 1031: 1,1,1-trifluoro-2-methylpropan-2-yl ((2R,6S,7R,9R,13aS,14aR,16aS,Z)-7,9-dimethyl-14a-(((1-methylcyclopropyl)sulfonyl)carbamoyl)-5,16-dioxo-2-((4-(thiazol-2-yl)pyridin-2-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H-NMR (500 MHz, DMSO-d$_6$) δ 11.06 (s, 1H), 9.19 (br. s., 1H), 8.33 (d, J=5.2 Hz, 1H), 8.06 (d, J=3.4 Hz, 1H), 7.99 (d, J=3.4 Hz, 1H), 7.83 (d, J=8.2 Hz, 1H), 7.54 (dd, J=5.3, 1.4 Hz, 1H), 7.20 (s, 1H), 5.71 (br. s., 1H), 5.54 (d, J=6.4 Hz, 1H), 4.99-4.93 (m, 1H), 4.54-4.46 (m, 1H), 4.41 (d, J=11.3 Hz, 1H), 3.89 (dd, J=11.6, 3.4 Hz, 1H), 3.67 (dd, J=10.7, 8.5 Hz, 1H), 2.70 (d, J=8.2 Hz, 1H), 2.37-2.24 (m, 3H), 1.95-1.80 (m, 2H), 1.63 (d, J=5.8 Hz, 2H), 1.53 (d, J=8.5 Hz, 1H), 1.47 (d, J=10.1 Hz, 1H), 1.42 (s, 4H), 1.36 (br. s., 2H), 1.29 (s, 5H), 1.18 (s, 3H), 1.12 (d, J=12.5 Hz, 1H), 0.92 (d, J=7.0 Hz, 4H), 0.86 (d, J=6.1 Hz, 3H), 0.73 (t, J=12.2 Hz, 1H); MS: MS m/z 825.4 (M$^+$+1).

Compound 1032: 1,1,1-trifluoro-2-methylpropan-2-yl ((2R,6S,7R,9S,13aS,14aR,16aS,Z)-7,9-dimethyl-14a-(((1-methylcyclopropyl)sulfonyl)carbamoyl)-5,16-dioxo-2-((4-(thiazol-2-yl)pyridin-2-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 825.5 (M$^+$+1).

Preparation of Compound 1033

Compound 1033

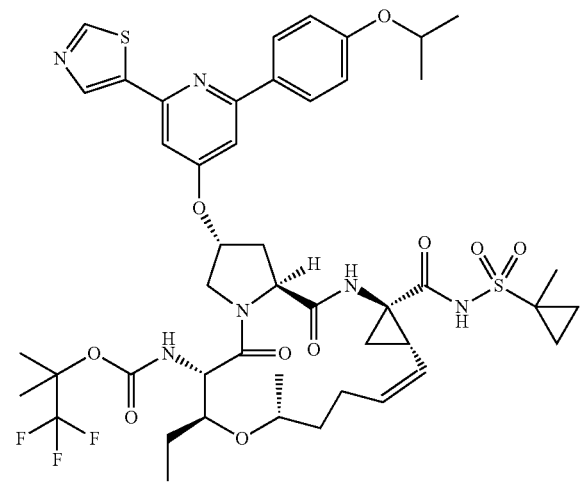

Compound 1033 was prepared using the intermediates described above and by following the general procedure described for the synthesis of Compound 1001.

Compound 1033: 1,1,1-trifluoro-2-methylpropan-2-yl ((2R,6S,7S,9R,13aS,14aR,16aS,Z)-7-ethyl-2-((2-(4-isopropoxyphenyl)-6-(thiazol-5-yl)pyridin-4-yl)oxy)-9-methyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. $^1$H-NMR (500 MHz, DMSO-d$_6$) δ 11.14 (br. s., 1H), 9.18 (br. s., 1H), 9.14-9.11 (m, 1H), 8.65 (s, 1H), 8.05 (d, J=8.9 Hz, 2H), 7.87 (d, J=9.8 Hz, 1H), 7.46 (d, J=1.5 Hz, 1H), 7.34 (s, 1H), 7.03 (d, J=8.9 Hz, 2H), 5.59-5.52 (m, 2H), 5.02 (br. s., 1H), 4.70 (dt, J=12.1, 6.0 Hz, 1H), 4.43-4.38 (m, 1H), 4.23 (d, J=11.6 Hz, 1H), 4.12 (t, J=9.6 Hz, 1H), 3.96 (d, J=9.2 Hz, 1H), 3.85 (br. s., 1H), 2.72-2.64 (m, 1H), 2.55 (br. s., 1H), 2.36 (br. s., 1H), 2.28-2.22 (m, 1H), 1.87 (br. s., 1H), 1.67 (br. s., 1H), 1.61 (br. s., 1H), 1.52 (d, J=13.7 Hz, 2H), 1.46 (d, J=12.5 Hz, 2H), 1.41 (s, 3H), 1.34 (s, 3H), 1.30 (d, J=6.1 Hz, 7H), 1.28-1.24 (m, 2H), 1.10 (s, 3H), 1.05 (d, J=6.1 Hz, 3H), 0.90 (br. s., 2H), 0.83 (br. s., 1H), 0.78 (t, J=7.3 Hz, 3H); MS: MS m/z 975.8 (M$^+$+1).

Preparation of Compound 1034

Compound 1034

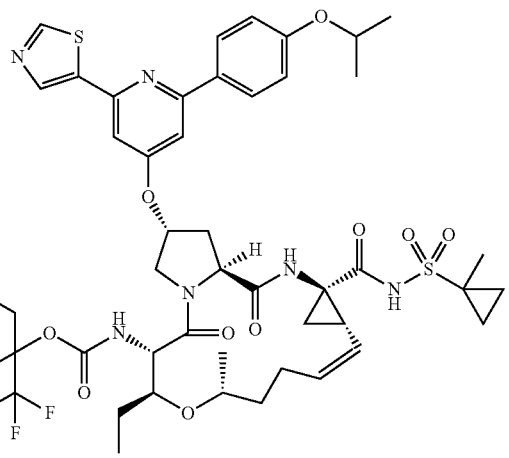

Compound 1034 was prepared using the intermediates described above and by following the general procedure described for the synthesis of Compound 1001.

Compound 1034: 3-(trifluoromethyl)tetrahydro-2H-pyran-3-yl ((2R,6S,7S,9R,13aS,14aR,16aS,Z)-7-ethyl-2-((2-(4-isopropoxyphenyl)-6-(thiazol-5-yl)pyridin-4-yl)oxy)-9-methyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. $^1$H-NMR (500 MHz, DMSO-d$_6$) δ 11.66-10.30 (m, 1H), 9.14 (s, 1H), 9.06 (br. s., 1H), 8.64 (s, 1H), 8.08-8.03 (m, 2H), 8.01 (d, J=9.5 Hz, 1H), 7.45 (s, 1H), 7.32 (s, 1H), 7.04 (d, J=8.9 Hz, 2H), 5.58-5.50 (m, 2H), 5.09 (br. s., 1H), 4.71 (quin, J=6.0 Hz, 1H), 4.39-4.34 (m, 1H), 4.29 (d, J=11.3 Hz, 1H), 4.16 (t, J=9.8 Hz, 1H), 4.06-3.94 (m, 2H), 3.91-3.85 (m, 1H), 3.59-3.50 (m, 3H), 2.66 (br. s., 1H), 2.37 (br. s., 1H), 2.27 (t, J=10.4 Hz, 1H), 2.14 (d, J=12.2 Hz, 1H), 1.90 (d, J=17.7 Hz, 1H), 1.78-1.65 (m, 2H), 1.65-1.51 (m, 4H), 1.46 (br. s., 2H), 1.41 (s, 3H), 1.36 (d, J=12.5 Hz, 3H), 1.31 (s, 3H), 1.27-1.20 (m, 1H), 1.07 (d, J=6.1 Hz, 3H), 0.87 (br. s., 2H), 0.80 (t, J=7.3 Hz, 3H); MS: MS m/z 1017.8 (M⁺+1).

J=6.1 Hz, 7H), 1.28-1.23 (m, 1H), 1.07 (d, J=6.1 Hz, 3H), 0.88 (br. s., 2H), 0.80 (t, J=7.5 Hz, 3H); MS: MS m/z 1018.0 (M⁺+1).

Preparation of Compound 1035

Preparation of Compound 1036

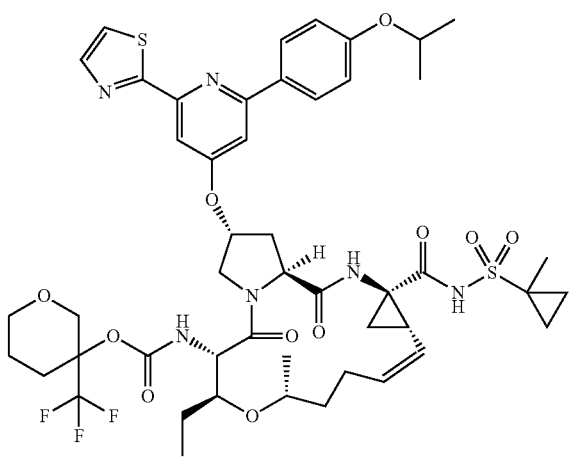

Compound 1035

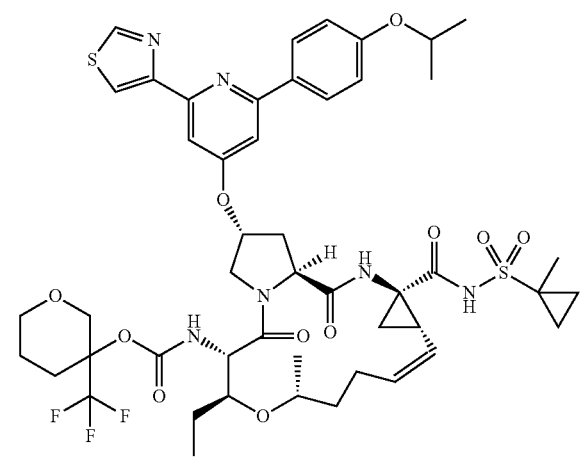

Compound 1036

Compound 1035 was prepared using the intermediates described above and by following the general procedure described for the synthesis of Compound 1001.

Compound 1035: 3-(trifluoromethyl)tetrahydro-2H-pyran-3-yl ((2R,6S,7S,9R,13aS,14aR,16aS,Z)-7-ethyl-2-((2-(4-isopropoxyphenyl)-6-(thiazol-2-yl)pyridin-4-yl)oxy)-9-methyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. ¹H-NMR (500 MHz, DMSO-d₆) δ 11.11 (br. s., 1H), 9.07 (br. s., 1H), 8.10 (d, J=8.9 Hz, 2H), 8.03 (d, J=9.8 Hz, 1H), 8.00 (d, J=3.1 Hz, 1H), 7.87 (d, J=3.1 Hz, 1H), 7.51 (d, J=1.8 Hz, 1H), 7.45 (d, J=1.8 Hz, 1H), 7.06 (d, J=8.9 Hz, 2H), 5.54 (br. s., 2H), 5.07 (br. s., 1H), 4.72 (quin, J=6.0 Hz, 1H), 4.37 (t, J=8.1 Hz, 1H), 4.28 (d, J=11.0 Hz, 1H), 4.14 (t, J=9.8 Hz, 1H), 3.99 (t, J=12.5 Hz, 2H), 3.91-3.85 (m, 1H), 3.57-3.45 (m, 4H), 2.74 (s, 1H), 2.55 (br. s., 1H), 2.37 (br. s., 1H), 2.27 (br. s., 1H), 2.14 (d, J=12.8 Hz, 1H), 1.92-1.84 (m, 1H), 1.77-1.65 (m, 2H), 1.59 (br. s., 2H), 1.53 (br. s., 2H), 1.41 (s, 4H), 1.36 (br. s., 2H), 1.31 (d, Compound 1036 was prepared using the intermediates described above and by following the general procedure described for the synthesis of Compound 1001.

Compound 1036: 3-(trifluoromethyl)tetrahydro-2H-pyran-3-yl ((2R,6S,7S,9R,13aS,14aR,16aS,Z)-7-ethyl-2-((2-(4-isopropoxyphenyl)-6-(thiazol-4-yl)pyridin-4-yl)oxy)-9-methyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. ¹H-NMR (500 MHz, DMSO-d₆) δ 11.11 (br. s., 1H), 9.23 (d, J=1.8 Hz, 1H), 9.05 (br. s., 1H), 8.45 (d, J=1.5 Hz, 1H), 8.15 (d, J=8.5 Hz, 2H), 8.05 (d, J=9.8 Hz, 1H), 7.53 (s, 1H), 7.36 (s, 1H), 7.03 (d, J=8.5 Hz, 2H), 5.58-5.49 (m, 2H), 5.06 (br. s., 1H), 4.75-4.70 (m, 1H), 4.39-4.33 (m, 1H), 4.26 (d, J=10.4 Hz, 1H), 4.16 (t, J=9.8 Hz, 1H), 4.07 (d, J=11.9 Hz, 1H), 3.98 (d, J=9.2 Hz, 1H), 3.91 (br. s., 1H), 3.58-3.46 (m, 3H), 2.74 (s, 1H), 2.55 (br. s., 1H), 2.39 (br. s., 1H), 2.28 (d, J=10.4 Hz, 1H), 2.17 (d, J=13.4 Hz, 1H), 1.92 (br. s., 1H), 1.80-1.66 (m, 3H), 1.59 (br. s., 2H), 1.52 (br. s., 2H), 1.47 (d, J=15.0 Hz, 2H), 1.41 (s, 3H), 1.38 (br. s., 1H), 1.31 (d, J=5.8 Hz, 8H), 1.08 (d, J=6.1 Hz, 3H), 0.89 (br. s., 2H), 0.81 (t, J=7.3 Hz, 3H); MS: MS m/z 1017.9 (M$^+$+1).

Preparation of Compound 1037

Preparation of Compound 1038

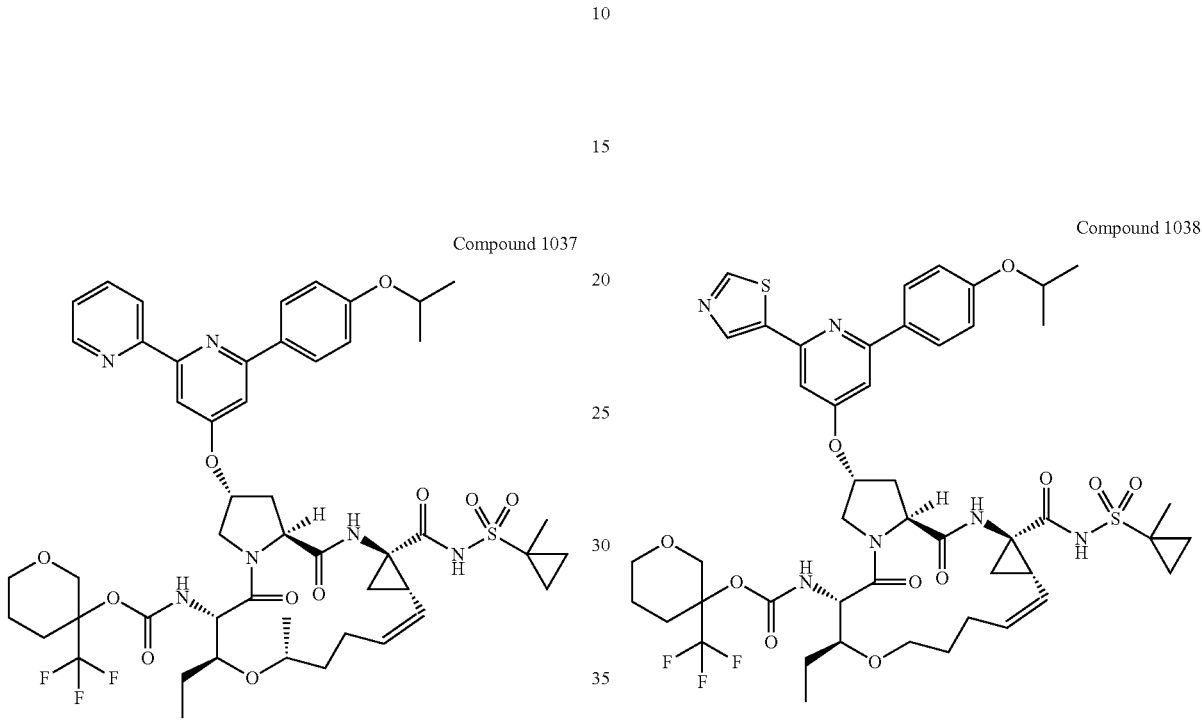

Compound 1037

Compound 1038

Compound 1037 was prepared using the intermediates described above and by following the general procedure described for the synthesis of Compound 1001.

Compound 1037: 3-(trifluoromethyl)tetrahydro-2H-pyran-3-yl ((2R,6S,7S,9R,13aS,14aR,16aS,Z)-7-ethyl-2-((6-(4-isopropoxyphenyl)-[2,2'-bipyridin]-4-yl)oxy)-9-methyl-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. $^1$H-NMR (500 MHz, DMSO-d$_6$) δ 11.10 (br. s., 1H), 9.05 (br. s., 1H), 8.70 (d, J=4.3 Hz, 1H), 8.55 (d, J=7.9 Hz, 1H), 8.16 (d, J=8.9 Hz, 2H), 8.05 (d, J=9.8 Hz, 1H), 8.02-7.95 (m, 1H), 7.82 (d, J=1.8 Hz, 1H), 7.50-7.45 (m, 1H), 7.44 (d, J=1.8 Hz, 1H), 7.05 (d, J=8.9 Hz, 2H), 5.59-5.50 (m, 2H), 5.06 (br. s., 1H), 4.73 (dt, J=12.0, 6.1 Hz, 1H), 4.39-4.34 (m, 1H), 4.27 (d, J=11.6 Hz, 1H), 4.16 (t, J=9.8 Hz, 1H), 4.06 (d, J=11.6 Hz, 1H), 3.99 (d, J=7.9 Hz, 1H), 3.92-3.87 (m, 1H), 3.58-3.40 (m, 3H), 2.74 (s, 1H), 2.59-2.53 (m, 1H), 2.40 (br. s., 1H), 2.28 (t, J=9.8 Hz, 1H), 2.20-2.13 (m, 1H), 1.93-1.86 (m, 1H), 1.82-1.65 (m, 2H), 1.59 (d, J=7.6 Hz, 2H), 1.56-1.50 (m, 2H), 1.50-1.43 (m, 2H), 1.41 (s, 3H), 1.36 (s, 3H), 1.32 (d, J=6.1 Hz, 6H), 1.28 (br. s., 1H), 1.12-1.03 (m, 3H), 0.89 (br. s., 2H), 0.81 (t, J=7.3 Hz, 3H); MS: MS m/z 1011.9 (M$^+$+1).

Compound 1038 was prepared using the intermediates described above and by following the general procedure described for the synthesis of Compound 1001.

Compound 1038: 3-(trifluoromethyl)tetrahydro-2H-pyran-3-yl ((2R,6S,7S,13aS,14aR,16aS,Z)-7-ethyl-2-((2-(4-isopropoxyphenyl)-6-(thiazol-5-yl)pyridin-4-yl)oxy)-14a-(((1-methylcyclopropyl)sulfonyl)carbamoyl)-5,16-dioxo-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. $^1$H-NMR (500 MHz, DMSO-d$_6$) δ 11.03 (br. s., 1H), 9.14 (s, 1H), 9.02 (br. s., 1H), 8.65 (s, 1H), 8.10-8.02 (m, 4H), 7.46 (s, 1H), 7.33 (s, 1H), 7.04 (d, J=8.9 Hz, 3H), 5.62-5.55 (m, 1H), 5.53 (br. s., 1H), 5.08 (br. s., 1H), 4.72 (dt, J=12.1, 6.0 Hz, 1H), 4.41-4.36 (m, 1H), 4.27 (d, J=12.2 Hz, 1H), 4.16 (t, J=9.6 Hz, 1H), 4.04-3.95 (m, 2H), 3.78 (d, J=10.4 Hz, 1H), 3.59-3.42 (m, 3H), 3.23 (br. s., 1H), 2.55 (br. s., 1H), 2.30 (br. s., 2H), 2.14 (d, J=14.6 Hz, 1H), 2.05 (d, J=8.2 Hz, 1H), 1.73 (d, J=8.9 Hz, 2H), 1.64-1.58 (m, 2H), 1.55 (dd, J=9.5, 4.9 Hz, 2H), 1.44 (br.

s., 3H), 1.41 (s, 3H), 1.36 (d, J=8.9 Hz, 1H), 1.31 (d, J=6.1 Hz, 6H), 1.24 (br. s., 1H), 0.88 (br. s., 2H), 0.79 (t, J=7.3 Hz, 3H); MS: MS m/z 1003.9 (M⁺+1).

Preparation of Compound 1039

1H), 1.09 (s, 3H), 1.06 (d, J=6.1 Hz, 3H), 0.89 (br. s., 2H), 0.78 (t, J=7.2 Hz, 3H); MS: MS m/z 985.9 (M⁺+1).

Preparation of Compound 1040

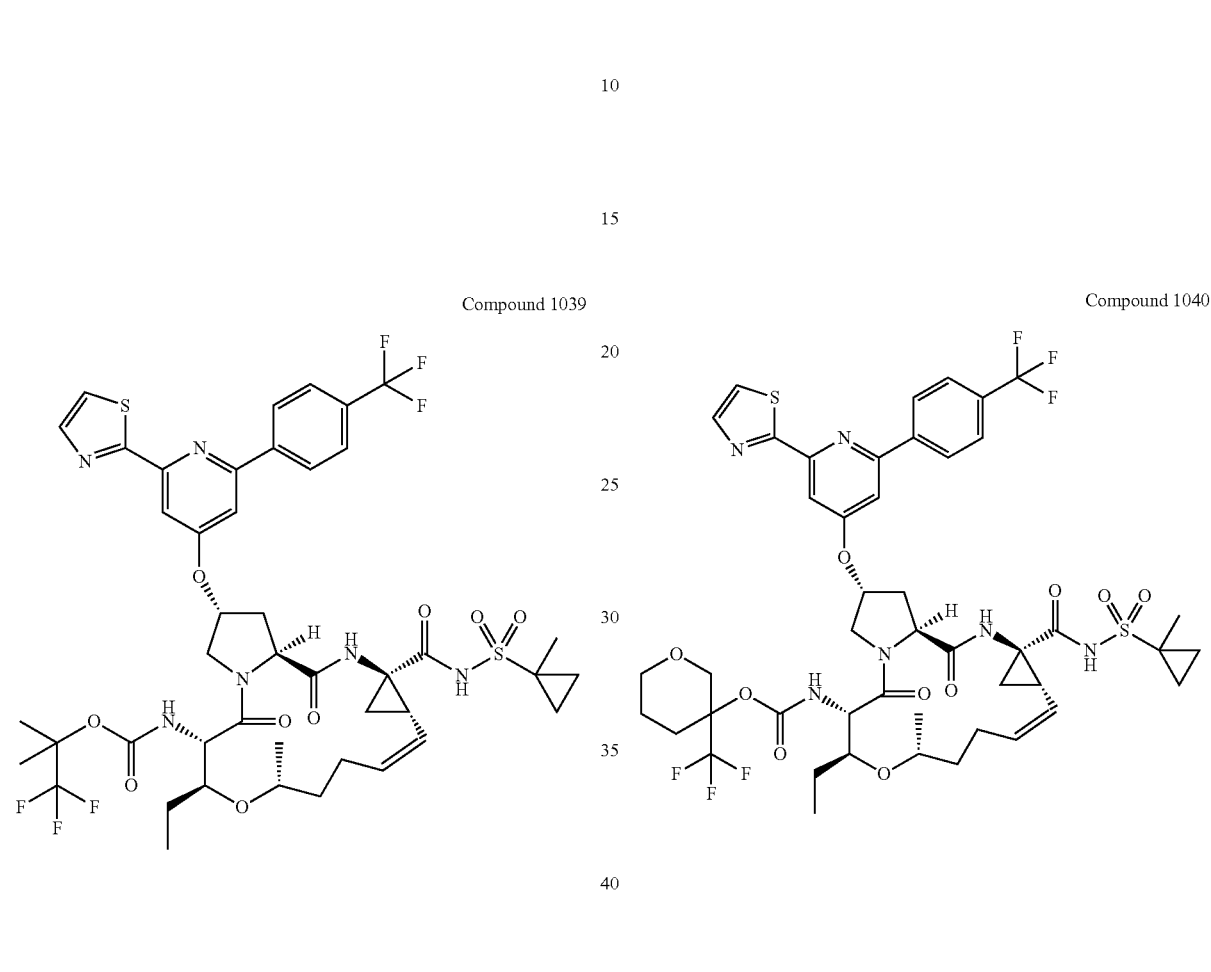

Compound 1039

Compound 1040

Compound 1039 was prepared using the intermediates described above and by following the general procedure described for the synthesis of Compound 1001.

Compound 1039: 1,1,1-trifluoro-2-methylpropan-2-yl ((2R,6S,7S,9R,13aS,14aR,16aS,Z)-7-ethyl-9-methyl-14a-(((1-methylcyclopropyl)sulfonyl)carbamoyl)-5,16-dioxo-2-((2-(thiazol-2-yl)-6-(4-(trifluoromethyl)phenyl)pyridin-4-yl)oxy)-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. ¹H-NMR (500 MHz, DMSO-d₆) δ 11.13 (br. s., 1H), 9.15 (br. s., 1H), 8.38 (d, J=7.9 Hz, 2H), 8.03 (br. s., 1H), 7.95-7.88 (m, 4H), 7.70 (s, 1H), 7.64 (s, 1H), 5.62 (br. s., 1H), 5.55 (d, J=8.9 Hz, 1H), 5.03 (br. s., 1H), 4.42 (t, J=8.2 Hz, 1H), 4.27 (d, J=11.6 Hz, 1H), 4.10 (t, J=9.6 Hz, 1H), 3.98 (d, J=9.8 Hz, 1H), 3.85 (d, J=10.7 Hz, 1H), 3.47 (br. s., 1H), 2.72 (d, J=13.4 Hz, 1H), 2.62-2.54 (m, 1H), 2.37 (br. s., 1H), 2.31-2.24 (m, 1H), 1.87 (br. s., 1H), 1.67 (br. s., 1H), 1.62 (br. s., 1H), 1.54 (br. s., 2H), 1.46 (br. s., 1H), 1.42 (s, 3H), 1.32 (br. s., 5H), 1.23 (br. s., Compound 1040 was prepared using the intermediates described above and by following the general procedure described for the synthesis of Compound 1001.

Compound 1040: 3-(trifluoromethyl)tetrahydro-2H-pyran-3-yl ((2R,6S,7S,9R,13aS,14aR,16aS,Z)-7-ethyl-9-methyl-14a-(((1-methylcyclopropyl)sulfonyl)carbamoyl)-5,16-dioxo-2-((2-(thiazol-2-yl)-6-(4-(trifluoromethyl)phenyl)pyridin-4-yl)oxy)-2,3,5,6,7,9,10,11,13a,14,14a,15,16,16a-tetradecahydro-1H-cyclopropa[i]pyrrolo[1,2-e][1,5,8]oxadiazacyclopentadecin-6-yl)carbamate. ¹H-NMR (500 MHz, DMSO-d₆) δ 11.11 (br. s., 1H), 9.11 (br. s., 1H), 8.37 (d, J=8.2 Hz, 2H), 8.05-8.00 (m, 2H), 7.94-7.88 (m, 3H), 7.65 (s, 2H), 5.60-5.51 (m, 2H), 5.05 (br. s., 1H), 4.39 (t, J=8.2 Hz, 1H), 4.33 (d, J=11.3 Hz, 1H), 4.14 (t, J=10.1 Hz, 1H), 3.98 (d, J=10.4 Hz, 2H), 3.91-3.85 (m, 1H), 3.51 (br. s., 2H), 3.33-3.27 (m, 1H), 2.74 (br. s., 1H), 2.57 (br. s., 1H), 2.41 (br. s., 1H), 2.28 (t, J=10.4 Hz, 1H), 2.12 (d, J=12.2 Hz, 1H), 1.89 (br. s., 1H), 1.70 (d, J=9.5 Hz, 2H), 1.61 (br. s., 1H), 1.54 (br. s., 3H), 1.47-1.44 (m, 2H), 1.41 (s, 4H), 1.39-1.27 (m, 3H), 1.07 (d, J=5.8 Hz, 3H), 0.89 (br. s., 2H), 0.79 (t, J=7.2 Hz, 3H); MS: MS m/z 1027.9 (M⁺+1).

Preparation of Compound 1041 and Compound 1042

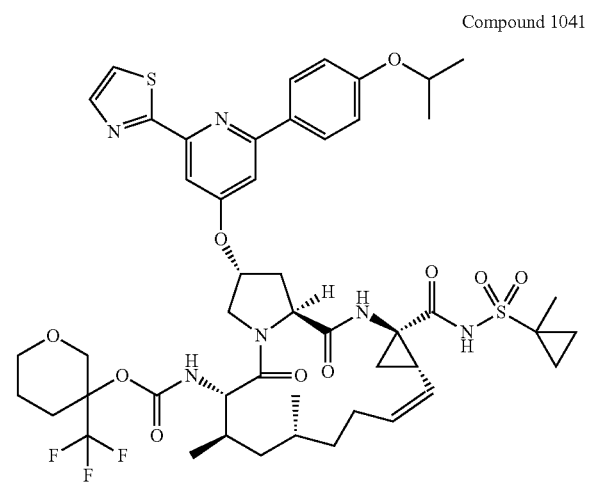 [SMILES: CC(C)Oc1ccc(-c2cc(O[C@@H]3C[C@H]4C(=O)N[C@]5(C(=O)NS(=O)(=O)C6(C)CC6)C[C@H]5/C=C\CC[C@@H](C)C[C@@H](C)[C@H](NC(=O)OC5(C(F)(F)F)CCCOC5)C(=O)N4C3)cc(-c3nccs3)n2)cc1]

Compound 1041

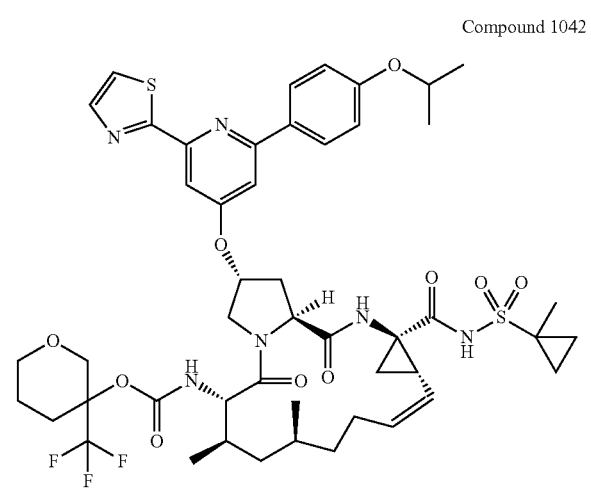 [SMILES: CC(C)Oc1ccc(-c2cc(O[C@@H]3C[C@H]4C(=O)N[C@]5(C(=O)NS(=O)(=O)C6(C)CC6)C[C@H]5/C=C\CC[C@H](C)C[C@@H](C)[C@H](NC(=O)OC5(C(F)(F)F)CCCOC5)C(=O)N4C3)cc(-c3nccs3)n2)cc1]

Compound 1042

Compound 1041 and Compound 1042 were prepared using the intermediates described above and by following the general procedure described for the synthesis of Compound 1001.

Compound 1041: 3-(trifluoromethyl)tetrahydro-2H-pyran-3-yl ((2R,6S,7R,9R,13aS,14aR,16aS,Z)-2-((2-(4-isopropoxyphenyl)-6-(thiazol-2-yl)pyridin-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. ¹H-NMR (500 MHz, CD₃OD) δ 8.10-8.06 (m, J=8.9 Hz, 2H), 7.94 (d, J=3.4 Hz, 1H), 7.72-7.69 (m, 1H), 7.60 (d, J=2.1 Hz, 1H), 7.36 (d, J=2.1 Hz, 1H), 7.04-7.00 (m, J=8.9 Hz, 2H), 5.57 (d, J=4.6 Hz, 1H), 5.44 (br. s., 1H), 5.15 (br. s., 1H), 4.75-4.68 (m, 1H), 4.68-4.60 (m, 1H), 4.56 (d, J=10.1, 7.3 Hz, 1H), 4.15 (d, J=11.9 Hz, 1H), 4.05 (dd, J=11.7, 3.2 Hz, 1H), 3.89 (d, J=11.0 Hz, 1H), 3.55 (d, J=10.7 Hz, 1H), 3.38-3.33 (m, 1H), 3.31-3.26 (m, 1H), 2.71-2.62 (m, 2H), 2.49-2.35 (m, 2H), 2.19 (d, J=11.0 Hz, 1H), 2.02-1.89 (m, 2H), 1.80-1.71 (m, 2H), 1.71-1.62 (m, 2H), 1.56 (dd, J=9.0, 5.3 Hz, 2H), 1.50 (s, 3H), 1.50-1.38 (m, 5H), 1.37 (d, J=6.1 Hz, 6H), 1.30-1.19 (m, 2H), 1.00 (d, J=7.0 Hz, 3H), 0.97 (d, J=6.4 Hz, 3H), 0.86-0.78 (m, 3H); MS: MS m/z 1001.7 (M⁺+1).

Compound 1042: 3-(trifluoromethyl)tetrahydro-2H-pyran-3-yl ((2R,6S,7R,9S,13aS,14aR,16aS,Z)-2-(((2-(4-isopropoxyphenyl)-6-(thiazol-2-yl)pyridin-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 1001.7 (M⁺+1).

Preparation of Compound 1043

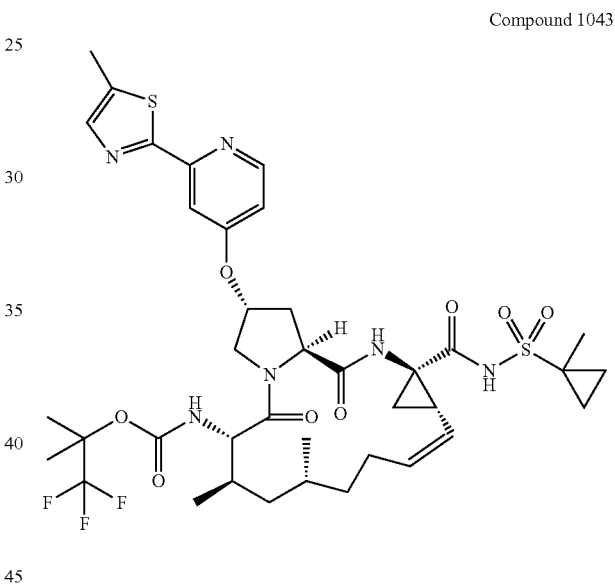

Compound 1043

Compound 1043 was prepared using the intermediates described above and by following the general procedure described for the synthesis of Compound 1001.

Compound 1043: 1,1,1-trifluoro-2-methylpropan-2-yl ((2R,6S,7R,9R,13aS,14aR,16aS,Z)-7,9-dimethyl-14a-(((1-methylcyclopropyl)sulfonyl)carbamoyl)-2-((2-(5-methylthiazol-2-yl)pyridin-4-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. ¹H-NMR (500 MHz, DMSO-d₆) δ 11.00 (br. s., 1H), 9.14 (br. s., 1H), 8.42 (d, J=5.5 Hz, 1H), 7.81 (d, J=7.6 Hz, 1H), 7.67 (d, J=1.2 Hz, 1H), 7.53 (d, J=2.4 Hz, 1H), 7.01 (dd, J=5.8, 2.4 Hz, 1H), 5.51 (br. s., 1H), 5.43 (br. s., 1H), 4.97 (br. s., 1H), 4.45-4.35 (m, 2H), 3.88 (d, J=9.2 Hz, 1H), 3.72-3.65 (m, 1H), 2.64 (br. s., 1H), 2.31-2.21 (m, 2H), 1.93-1.87 (m, 1H), 1.83 (d, J=6.7 Hz, 1H), 1.61 (br. s., 2H), 1.51 (br. s., 3H), 1.39 (br. s., 5H), 1.33 (s, 4H), 1.26 (br. s., 2H), 1.23 (s, 4H), 1.13 (br. s., 2H), 0.91 (d, J=6.7 Hz, 4H), 0.84 (d, J=6.4 Hz, 3H), 0.70 (br. s., 1H); MS: MS m/z 839.6 (M⁺+1).

Preparation of Compound 1044

Preparation of Compound 1045

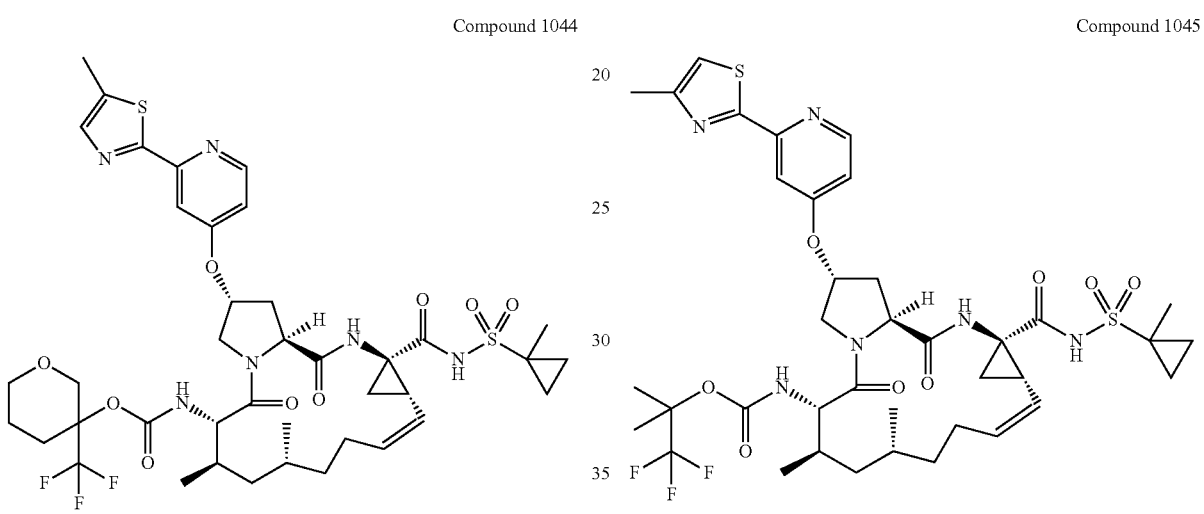

Compound 1044

Compound 1045

Compound 1044 was prepared using the intermediates described above and by following the general procedure described for the synthesis of Compound 1001.

Compound 1044: 3-(trifluoromethyl)tetrahydro-2H-pyran-3-yl ((2R,6S,7R,9R,13aS,14aR,16aS,Z)-7,9-dimethyl-14a-(((1-methylcyclopropyl)sulfonyl)carbamoyl)-2-((2-(5-methylthiazol-2-yl)pyridin-4-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. ¹H-NMR (500 MHz, DMSO-d₆) δ 10.99 (br. s., 1H), 9.13 (br. s., 1H), 8.40 (d, J=5.8 Hz, 1H), 7.90 (d, J=8.2 Hz, 1H), 7.67-7.63 (m, 1H), 7.53 (d, J=2.4 Hz, 1H), 6.98 (dd, J=5.8, 2.4 Hz, 1H), 5.51 (br. s., 1H), 5.41 (br. s., 1H), 4.97 (br. s., 1H), 4.43-4.35 (m, 2H), 4.03 (d, J=12.2 Hz, 1H), 3.91 (d, J=7.3 Hz, 1H), 3.76-3.71 (m, 1H), 3.58 (d, J=11.0 Hz, 1H), 2.68 (br. s., 1H), 2.25 (d, J=13.4 Hz, 2H), 2.23-2.11 (m, 2H), 1.91 (br. s., 1H), 1.87 (br. s., 2H), 1.79-1.71 (m, 2H), 1.63 (d, J=12.8 Hz, 4H), 1.48 (br. s., 5H), 1.40 (br. s., 4H), 1.36-1.32 (m, 1H), 1.27 (br. s., 1H), 1.12 (br.

s., 1H), 0.91 (d, J=6.7 Hz, 4H), 0.86 (d, J=6.4 Hz, 4H), 0.75-0.69 (m, 1H); MS: MS m/z 881.7 (M⁺+1).

Compound 1045 was prepared using the intermediates described above and by following the general procedure described for the synthesis of Compound 1001.

Compound 1045: 1,1,1-trifluoro-2-methylpropan-2-yl ((2R,6S,7R,9R,13aS,14aR,16aS,Z)-7,9-dimethyl-14a-(((1-methylcyclopropyl)sulfonyl)carbamoyl)-2-((2-(4-methylthiazol-2-yl)pyridin-4-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate.
¹H-NMR (500 MHz, DMSO-d₆) δ 10.98 (br. s., 1H), 9.12 (br. s., 1H), 8.43 (d, J=5.8 Hz, 1H), 7.82 (d, J=8.2 Hz, 1H), 7.55 (d, J=2.4 Hz, 1H), 7.42-7.40 (m, 1H), 7.03 (dd, J=5.8, 2.4 Hz, 1H), 5.55-5.48 (m, 1H), 5.46 (br. s., 1H), 5.00 (br. s., 1H), 4.43 (dd, J=10.5, 7.2 Hz, 1H), 4.38 (d, J=11.6 Hz, 1H), 3.91-3.85 (m, 1H), 3.71-3.66 (m, 1H), 2.65 (br. s., 1H), 2.55 (d, J=6.7 Hz, 1H), 2.44 (s, 3H), 2.32-2.21 (m, 2H), 1.94-1.87 (m, 1H), 1.84 (d, J=6.4 Hz, 1H), 1.65-1.56 (m, 2H), 1.51 (d, J=9.2 Hz, 1H), 1.40 (s, 4H), 1.33 (s, 4H), 1.28 (br. s., 1H), 1.25 (s, 4H), 1.11 (d, J=12.2 Hz, 1H), 0.91 (d, J=7.0 Hz, 3H), 0.88-0.87 (m, 2H), 0.84 (br. s., 3H), 0.71 (t, J=11.9 Hz, 1H); MS: MS m/z 839.7 (M⁺+1).

Preparation of Compound 1046

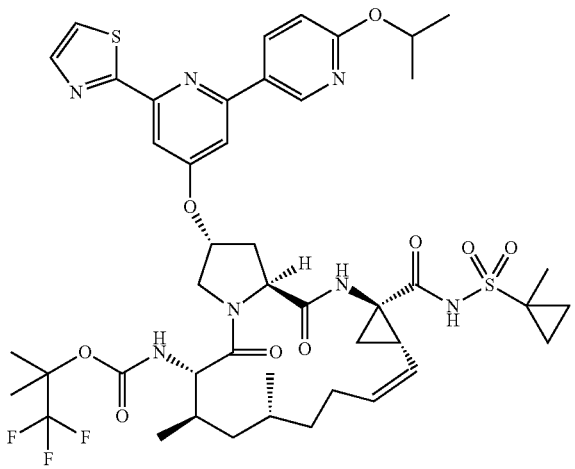

Compound 1046

Compound 1046 was prepared using the intermediates described above and by following the general procedure described for the synthesis of Compound 1001.

Compound 1046: 1,1,1-trifluoro-2-methylpropan-2-yl ((2R,6S,7R,9R,13aS,14aR,16aS,Z)-2-((6'-isopropoxy-6-(thiazol-2-yl)-[2,3'-bipyridin]-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. ¹H-NMR (500 MHz, DMSO-d₆) δ 11.01 (br. s., 1H), 9.20 (br. s., 1H), 8.94 (d, J=2.1 Hz, 1H), 8.42 (dd, J=8.7, 2.3 Hz, 1H), 8.00 (d, J=3.1 Hz, 1H), 7.88 (d, J=3.1 Hz, 1H), 7.77 (d, J=8.9 Hz, 1H), 7.56-7.51 (m, 2H), 6.90 (d, J=8.9 Hz, 1H), 5.57 (br. s., 1H), 5.50 (br. s., 1H), 5.33 (quin, J=6.2 Hz, 1H), 4.96 (br. s., 1H), 4.51-4.45 (m, 1H), 4.43 (d, J=12.8 Hz, 1H), 3.90 (d, J=9.5 Hz, 1H), 3.67 (d, J=9.8 Hz, 1H), 2.56 (d, J=12.5 Hz, 2H), 2.27 (br. s., 2H), 1.90 (d, J=11.0 Hz, 1H), 1.81 (br. s., 1H), 1.60 (br. s., 2H), 1.50 (br. s., 1H), 1.46 (br. s., 1H), 1.39 (s, 5H), 1.33 (d, J=6.1 Hz, 7H), 1.28 (br. s., 2H), 1.21 (s, 3H), 1.10 (s, 4H), 0.90 (d, J=6.7 Hz, 3H), 0.82 (d, J=6.1 Hz, 3H), 0.70 (t, J=11.9 Hz, 1H); MS: MS m/z 960.9 (M⁺+1).

Preparation of Compound 1047

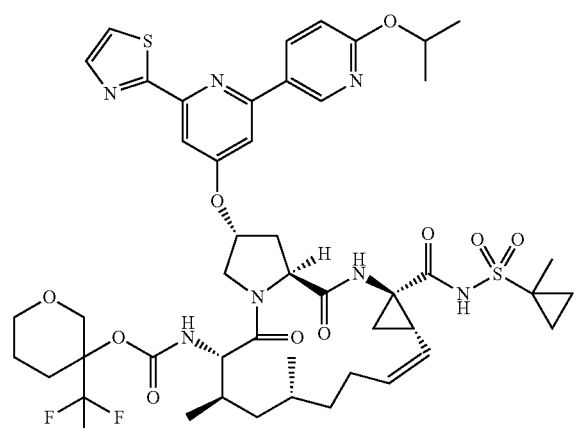

Compound 1047

Compound 1047 was prepared using the intermediates described above and by following the general procedure described for the synthesis of Compound 1001.

Compound 1047: 3-(trifluoromethyl)tetrahydro-2H-pyran-3-yl ((2R,6S,7R,9R,13aS,14aR,16aS,Z)-2-((6'-isopropoxy-6-(thiazol-2-yl)-[2,3'-bipyridin]-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. ¹H-NMR (500 MHz, DMSO-d₆) δ 10.99 (s, 1H), 9.08 (br. s., 1H), 8.92 (s, 1H), 8.42-8.38 (m, 1H), 8.00 (d, J=3.1 Hz, 1H), 7.87 (d, J=3.4 Hz, 1H), 7.85 (d, J=8.5 Hz, 1H), 7.53 (s, 1H), 7.49 (s, 1H), 6.90 (d, J=8.9 Hz, 1H), 5.53 (br. s., 1H), 5.48 (br. s., 1H), 5.33 (dt, J=12.3, 6.2 Hz, 1H), 5.05 (br. s., 1H), 4.43 (d, J=9.5 Hz, 2H), 3.93 (d, J=12.2 Hz, 3H), 3.72 (t, J=9.5 Hz, 1H), 3.29 (d, J=11.9 Hz, 1H), 3.24 (t, J=9.2 Hz, 1H), 2.55 (br. s., 1H), 2.27 (br. s., 2H), 2.05 (br. s., 1H), 1.93-1.81 (m, 2H), 1.63 (d, J=9.5 Hz, 3H), 1.57 (br. s., 1H), 1.52 (br. s., 1H), 1.46 (br. s., 2H), 1.38 (br. s., 5H), 1.33 (d, J=6.1 Hz, 8H), 1.22 (s, 2H), 1.12 (br.

s., 1H), 0.90 (d, J=6.7 Hz, 3H), 0.83 (br. s., 3H), 0.71 (d, J=11.9 Hz, 1H); MS: MS m/z 1002.9 (M⁺+1).

Preparation of Compound 1048

Preparation of Compound 1049

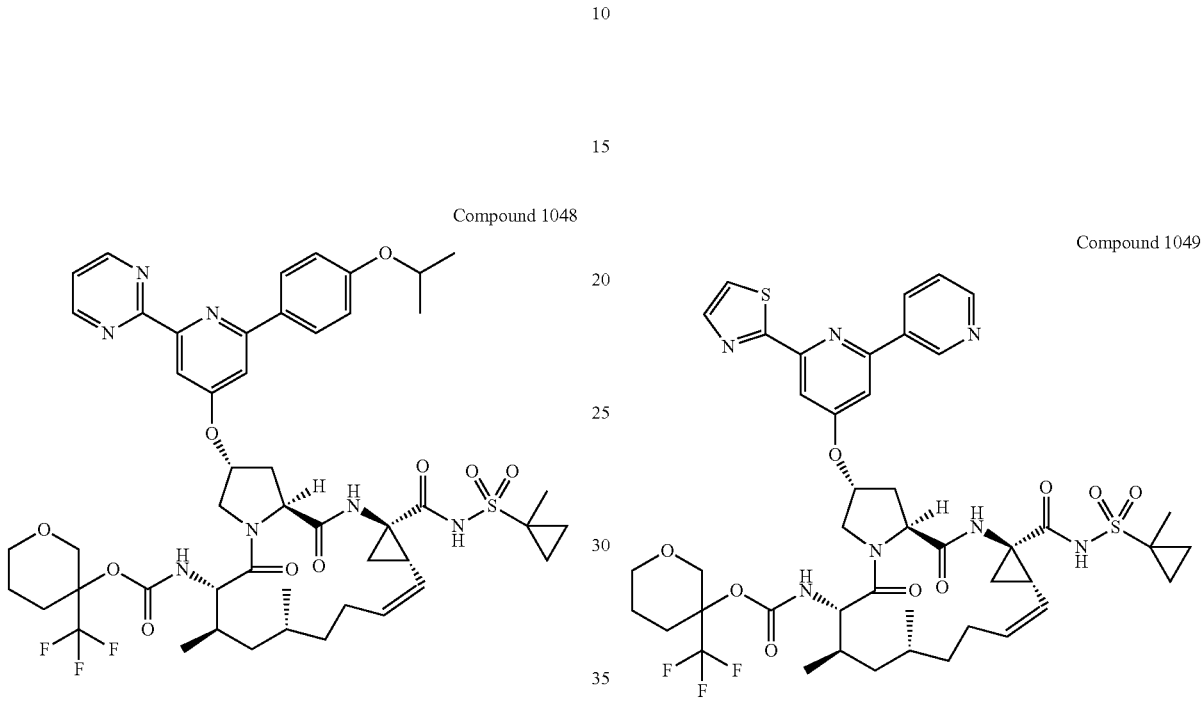

Compound 1048

Compound 1049

Compound 1048 was prepared using the intermediates described above and by following the general procedure described for the synthesis of Compound 1001.

Compound 1048: 3-(trifluoromethyl)tetrahydro-2H-pyran-3-yl ((2R,6S,7R,9R,13aS,14aR,16aS,Z)-2-((2-(4-isopropoxyphenyl)-6-(pyrimidin-2-yl)pyridin-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. ¹H-NMR (500 MHz, DMSO-d₆) δ 9.18-9.04 (m, 1H), 8.98 (d, J=4.6 Hz, 2H), 8.12 (d, J=8.5 Hz, 2H), 7.84 (d, J=8.2 Hz, 1H), 7.78 (s, 1H), 7.56 (t, J=4.9 Hz, 1H), 7.47 (s, 1H), 7.03 (d, J=8.9 Hz, 2H), 5.53 (br. s., 1H), 5.50 (br. s., 1H), 5.05 (br. s., 1H), 4.70 (dt, J=12.0, 6.1 Hz, 1H), 4.44-4.36 (m, 2H), 4.02 (d, J=11.9 Hz, 1H), 3.92 (d, J=8.5 Hz, 1H), 3.75 (d, J=9.8 Hz, 1H), 3.35 (d, J=12.2 Hz, 1H), 3.27 (t, J=9.3 Hz, 1H), 2.55 (br. s., 1H), 2.26 (br. s., 2H), 2.10 (d, J=13.1 Hz, 1H), 1.91 (s, 1H), 1.84 (br. s., 1H), 1.69-1.60 (m, 2H), 1.56 (br. s., 2H), 1.47 (br. s., 1H), 1.43-1.40 (m, 1H), 1.38 (s, 5H), 1.35-1.32 (m, 1H), 1.30 (d, J=5.8 Hz, 7H), 1.27-1.18 (m, 2H), 1.12 (br. s., 2H), 0.90 (d, J=6.7 Hz, 3H), 0.84 (d, J=6.4 Hz, 3H), 0.82-0.79 (m, 1H), 0.70 (t, J=12.1 Hz, 1H); MS: MS m/z 996.9 (M⁺+1).

Compound 1049 was prepared using the intermediates described above and by following the general procedure described for the synthesis of Compound 1001.

Compound 1049: 3-(trifluoromethyl)tetrahydro-2H-pyran-3-yl ((2R,6S,7R,9R,13aS,14aR,16aS,Z)-7,9-dimethyl-14a-(((1-methylcyclopropyl)sulfonyl)carbamoyl)-5,16-dioxo-2-((6-(thiazol-2-yl)-[2,3'-bipyridin]-4-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. ¹H-NMR (500 MHz, DMSO-d₆) δ 9.30 (s, 1H), 9.18-8.86 (m, 1H), 8.67 (d, J=4.9 Hz, 1H), 8.48 (d, J=7.9 Hz, 1H), 8.01 (d, J=3.1 Hz, 1H), 7.88 (d, J=3.4 Hz, 1H), 7.83 (d, J=9.2 Hz, 1H), 7.60 (d, J=3.7 Hz, 2H), 7.59-7.56 (m, 1H), 5.55 (br. s., 1H), 5.48 (br. s., 1H), 5.18-4.89 (m, 1H), 4.44 (t, J=8.4 Hz, 2H), 3.95-3.88 (m, 3H), 3.72 (d, J=10.4 Hz, 1H), 3.24 (d, J=11.9 Hz, 1H), 3.22-3.16 (m, 1H), 2.55 (s, 1H), 2.31-2.24 (m, 2H), 2.04 (d, J=14.0 Hz, 1H), 1.84 (br. s., 2H), 1.61 (br. s., 2H), 1.56 (br. s., 1H), 1.50 (br. s., 2H), 1.42-1.39 (m, 1H), 1.38 (s, 4H), 1.35-1.29 (m, 2H), 1.22 (br. s., 1H), 1.14 (d, J=15.0 Hz, 1H), 0.90 (d, J=6.7 Hz, 3H), 0.83 (d, J=6.4 Hz, 3H), 0.70 (d, J=12.2 Hz, 1H); MS: MS m/z 944.9 (M⁺+1).

Preparation of Compound 1050

(br. s., 3H), 1.20-1.15 (m, 1H), 1.12 (br. s., 3H), 0.93-0.89 (m, 3H), 0.89-0.86 (m, 1H), 0.84 (br. s., 4H), 0.71 (br. s., 1H); MS: MS m/z 902.7 (M⁺+1).

Preparation of Compound 1051

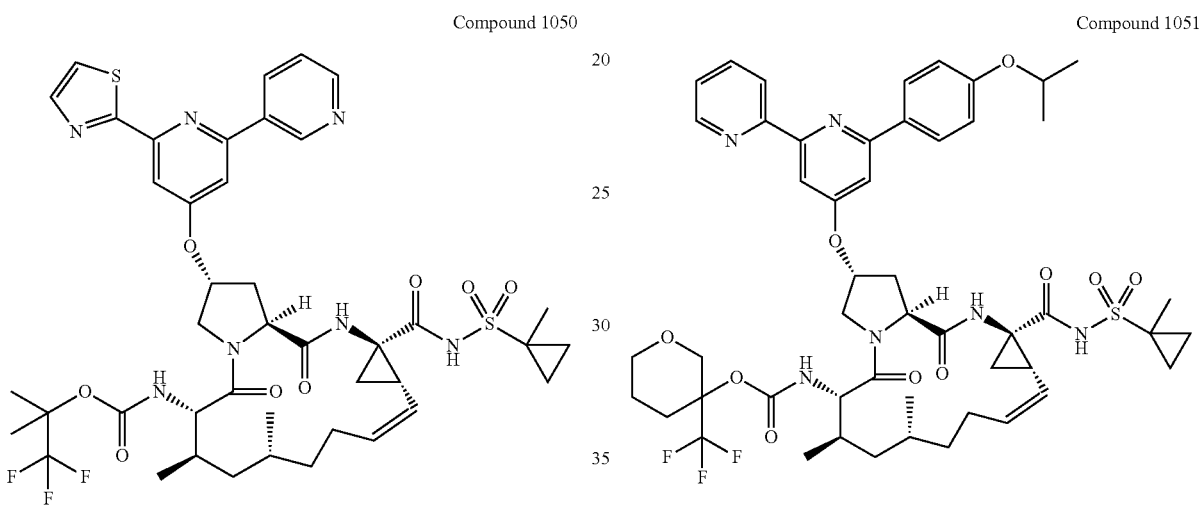

Compound 1050

Compound 1051

Compound 1050 was prepared using the intermediates described above and by following the general procedure described for the synthesis of Compound 1001.

Compound 1050: 1,1,1-trifluoro-2-methylpropan-2-yl ((2R,6S,7R,9R,13aS,14aR,16aS,Z)-7,9-dimethyl-14a-(((1-methylcyclopropyl)sulfonyl)carbamoyl)-5,16-dioxo-2-((6-(thiazol-2-yl)-[2,3'-bipyridin]-4-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. ¹H-NMR (500 MHz, DMSO-d₆) δ 11.00 (br. s., 1H), 9.36 (br. s., 1H), 9.17 (br. s., 1H), 8.70 (br. s., 1H), 8.52 (d, J=6.1 Hz, 1H), 8.03 (d, J=3.1 Hz, 1H), 7.96-7.91 (m, 1H), 7.82 (d, J=7.0 Hz, 1H), 7.69 (br. s., 1H), 7.62 (br. s., 1H), 7.59 (br. s., 1H), 5.62 (br. s., 1H), 5.51 (br. s., 1H), 5.00 (br. s., 1H), 4.46 (d, J=11.0 Hz, 2H), 3.91 (d, J=11.0 Hz, 1H), 3.73-3.66 (m, 1H), 2.61 (br. s., 2H), 2.29 (br. s., 2H), 1.91 (br. s., 1H), 1.83 (br. s., 1H), 1.61 (br. s., 2H), 1.49 (d, J=10.7 Hz, 1H), 1.46-1.43 (m, 1H), 1.40 (br. s., 4H), 1.34 (br. s., 1H), 1.26 (br. s., 1H), 1.22

Compound 1051 was prepared using the intermediates described above and by following the general procedure described for the synthesis of Compound 1001.

Compound 1051: 3-(trifluoromethyl)tetrahydro-2H-pyran-3-yl ((2R,6S,7R,9R,13aS,14aR,16aS,Z)-2-((6-(4-isopropoxyphenyl)-[2,2'-bipyridin]-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. ¹H-NMR (500 MHz, DMSO-d₆) δ 11.01 (br. s., 1H), 9.10 (br. s., 1H), 8.70 (d, J=3.7 Hz, 1H), 8.55 (d, J=7.9 Hz, 1H), 8.15 (d, J=8.9 Hz, 2H), 7.99 (t, J=6.9 Hz, 1H), 7.91 (d, J=8.9 Hz, 1H), 7.81 (s, 1H), 7.48 (t, J=5.6 Hz, 1H), 7.41 (s, 1H), 7.05 (d, J=8.9 Hz, 2H), 5.56-5.48 (m, 2H), 5.02 (br. s., 1H), 4.75-4.70 (m, 1H), 4.46-4.38 (m, 2H), 4.06 (d, J=12.8 Hz, 1H), 3.97-3.90 (m, 1H), 3.77 (t, J=9.9 Hz, 1H), 3.53 (d, J=10.7 Hz, 1H), 2.67 (br. s., 1H), 2.61-2.53 (m, 1H), 2.34-2.24 (m, 2H), 2.12 (d, J=13.7 Hz, 1H), 1.96-1.84 (m, 1H), 1.74-1.63 (m, 2H), 1.59 (br. s., 2H), 1.50 (br. s., 1H), 1.46-1.42 (m, 2H), 1.40 (s, 4H), 1.37 (br. s., 1H), 1.32 (d, J=6.1 Hz, 7H), 1.27 (br. s., 2H), 1.14 (br. s., 1H), 0.92 (d, J=6.7 Hz, 3H), 0.86 (d, J=6.1 Hz, 3H), 0.73 (t, J=12.2 Hz, 1H); MS: MS m/z 995.9 (M⁺+1).

Preparation of Compound 1052

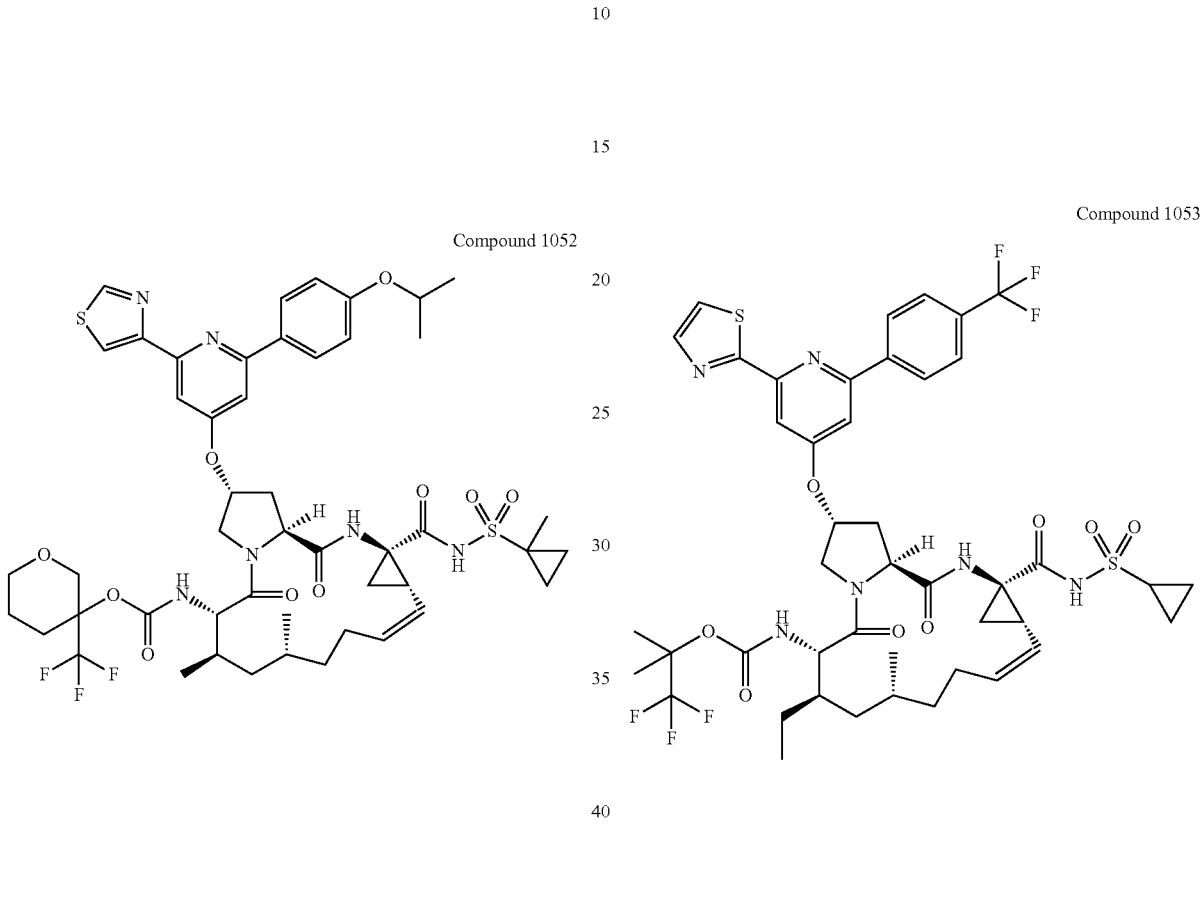

Compound 1052

Compound 1053

Compound 1052 was prepared using the intermediates described above and by following the general procedure described for the synthesis of Compound 1001.

Compound 1052: 3-(trifluoromethyl)tetrahydro-2H-pyran-3-yl ((2R,6S,7R,9R,13aS,14aR,16aS,Z)-2-((2-(4-isopropoxyphenyl)-6-(thiazol-4-yl)pyridin-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. ¹H-NMR (500 MHz, DMSO-d₆) δ 10.99 (br. s., 1H), 9.23 (d, J=1.8 Hz, 1H), 9.11 (br. s., 1H), 8.47-8.43 (m, 1H), 8.18-8.11 (m, 2H), 7.90 (d, J=8.5 Hz, 1H), 7.52 (s, 1H), 7.34 (s, 1H), 7.05-7.01 (m, J=8.9 Hz, 2H), 5.52 (br. s., 2H), 5.00 (br. s., 1H), 4.72 (dt, J=12.1, 6.2 Hz, 1H), 4.45-4.37 (m, 2H), 4.07 (d, J=11.3 Hz, 1H), 3.96-3.90 (m, 1H), 3.77 (t, J=9.8 Hz, 1H), 3.54 (d, J=11.3 Hz, 1H), 2.69 (br. s., 1H), 2.55 (br. s., 1H), 2.33-2.23 (m, 2H), 2.14 (d, J=13.4 Hz, 1H), 1.96-1.84 (m, 2H), 1.75-1.67 (m, 1H), 1.59 (br. s., 3H), 1.51 (br. s., 1H), 1.45-1.42 (m, 2H), 1.40 (s, 5H), 1.36 (br. s., 1H), 1.31 (d, J=6.1 Hz, 7H), 1.24 (s, 3H), 1.14 (br. s., 1H), 0.92 (d, J=6.7 Hz, 3H), 0.86 (d, J=6.4 Hz, 3H), 0.73 (t, J=12.1 Hz, 1H); MS: MS m/z 1001.9 (M⁺+1).

Preparation of Compound 1053

Compound 1053 was prepared using the intermediates described above and by following the general procedure described for the synthesis of Compound 1001.

Compound 1053: 1,1,1-trifluoro-2-methylpropan-2-yl ((2R,6S,7R,9R,13aS,14aR,16aS,Z)-14a-((cyclopropylsulfonyl)carbamoyl)-7-ethyl-9-methyl-5,16-dioxo-2-((2-(thiazol-2-yl)-6-(4-(trifluoromethyl)phenyl)pyridin-4-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. ¹H-NMR (500 MHz, DMSO-d₆) δ 8.95 (br. s., 1H), 8.38 (d, J=7.9 Hz, 2H), 8.03 (d, J=3.1 Hz, 1H), 7.94-7.89 (m, 3H), 7.84 (d, J=8.9 Hz, 1H), 7.69 (s, 1H), 7.65 (s, 1H), 5.61 (br. s., 1H), 5.50 (d, J=5.8 Hz, 1H), 5.15 (br. s., 1H), 4.44 (d, J=10.1 Hz, 2H), 3.95-3.84 (m, 2H), 2.88 (d, J=9.2 Hz, 1H), 2.57 (br. s., 2H), 2.34-2.20 (m, 2H), 1.92 (d, J=7.9 Hz, 2H), 1.58 (br. s., 1H), 1.49 (br. s., 1H), 1.43 (d, J=9.5 Hz, 3H), 1.33 (d, J=12.8 Hz, 2H), 1.26 (s, 3H), 1.18 (br. s., 2H), 1.11 (s, 3H), 1.06 (br. s., 1H), 1.01 (br. s., 1H), 0.94 (br. s., 3H), 0.91 (d, J=5.8 Hz, 3H), 0.69 (t, J=7.3 Hz, 3H); MS: MS m/z 969.7 (M⁺+1).

Preparation of Compound 1054

Compound 1054

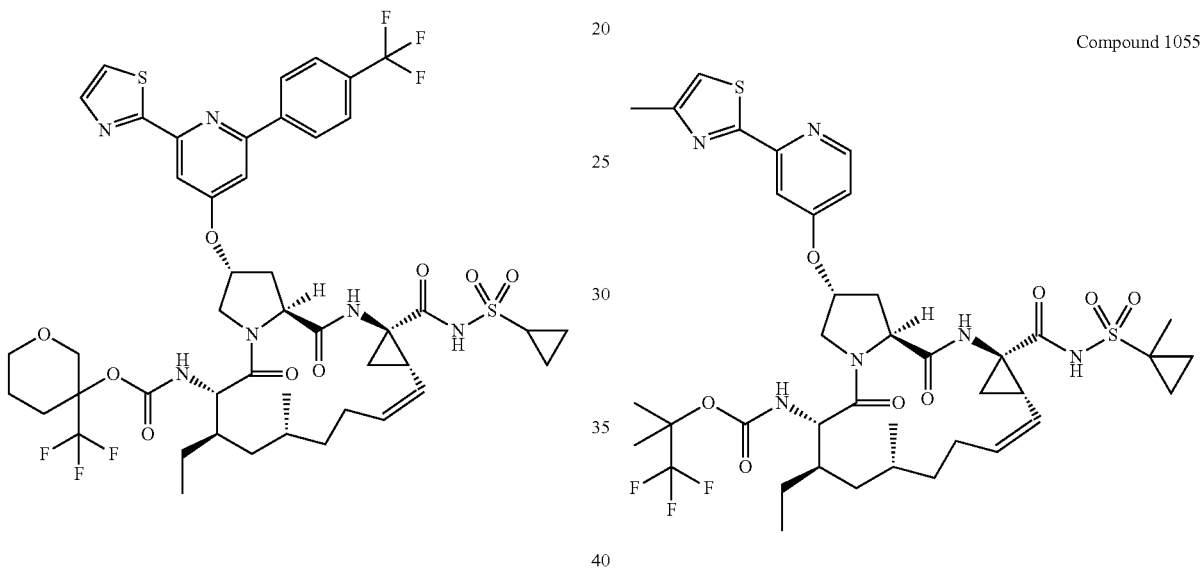

Compound 1055

Compound 1054 was prepared using the intermediates described above and by following the general procedure described for the synthesis of Compound 1001.

Compound 1054: 3-(trifluoromethyl)tetrahydro-2H-pyran-3-yl ((2R,6S,7R,9R,13aS,14aR,16aS,Z)-14a-((cyclopropylsulfonyl)carbamoyl)-7-ethyl-9-methyl-5,16-dioxo-2-((2-(thiazol-2-yl)-6-(4-(trifluoromethyl)phenyl)pyridin-4-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. ¹H-NMR (500 MHz, DMSO-d₆) δ 8.90 (br. s., 1H), 8.37 (d, J=8.2 Hz, 2H), 8.03 (d, J=3.1 Hz, 1H), 7.96-7.89 (m, 4H), 7.65 (d, J=5.8 Hz, 2H), 5.58 (br. s., 1H), 5.49 (d, J=5.8 Hz, 1H), 5.16 (br. s., 1H), 4.48 (d, J=11.3 Hz, 1H), 4.44-4.38 (m, 1H), 3.98 (d, J=12.5 Hz, 1H), 3.95-3.89 (m, 2H), 3.52 (d, J=10.1 Hz, 1H), 3.26 (t, J=9.6 Hz, 1H), 2.87 (br. s., 1H), 2.57 (br. s., 2H), 2.33-2.20 (m, 2H), 2.09 (d, J=13.7 Hz, 1H), 2.00-1.89 (m, 2H), 1.72-1.64 (m, 1H), 1.57 (br. s., 2H), 1.53-1.38 (m, 6H), 1.33 (br. s., 2H), 1.23 (br. s., 1H), 1.18 (br. s., 1H), 1.04 (br. s., 3H), 0.95 (br. s., 2H), 0.92 (d, J=5.5 Hz, 3H), 0.71 (t, J=7.2 Hz, 3H); MS: MS m/z 1011.8 (M⁺+1).

Preparation of Compound 1055

Compound 1055

Compound 1055 was prepared using the intermediates described above and by following the general procedure described for the synthesis of Compound 1001.

Compound 1055: 1,1,1-trifluoro-2-methylpropan-2-yl ((2R,6S,7R,9R,13aS,14aR,16aS,Z)-7-ethyl-9-methyl-14a-(((1-methylcyclopropyl)sulfonyl)carbamoyl)-2-((2-(4-methylthiazol-2-yl)pyridin-4-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate.
¹H-NMR (500 MHz, DMSO-d₆) δ 10.99 (s, 1H), 9.09 (br. s., 1H), 8.44 (d, J=5.8 Hz, 1H), 7.86 (d, J=8.5 Hz, 1H), 7.56-7.53 (m, 1H), 7.41 (s, 1H), 7.06-7.02 (m, 1H), 5.51 (d, J=6.7 Hz, 1H), 5.46 (br. s., 1H), 5.02 (br. s., 1H), 4.44-4.36 (m, 2H), 3.93-3.84 (m, 2H), 2.62 (br. s., 1H), 2.44 (s, 3H), 2.25 (d, J=9.8 Hz, 2H), 1.93 (d, J=19.2 Hz, 2H), 1.59 (br. s., 1H), 1.48 (br. s., 4H), 1.39 (s, 5H), 1.35 (s, 3H), 1.26 (d, J=10.1 Hz, 2H), 1.23 (s, 3H), 1.15 (br. s., 1H), 1.00-0.93 (m, 1H), 0.90 (d, J=6.4 Hz, 3H), 0.86 (br. s., 2H), 0.71 (t, J=7.3 Hz, 3H); MS: MS m/z 853.9 (M⁺+1).

Preparation of Compound 1056

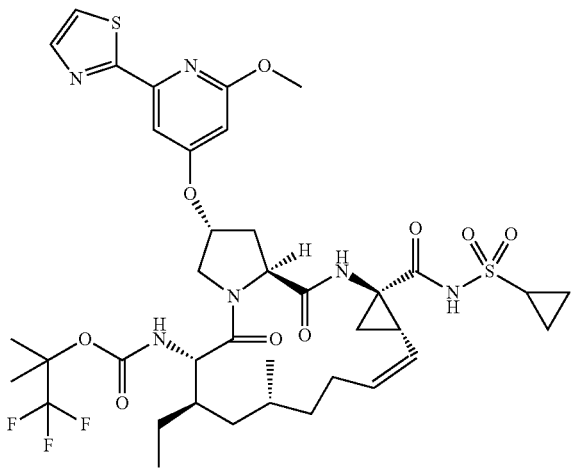

Compound 1056

Compound 1056 was prepared using the intermediates described above and by following the general procedure described for the synthesis of Compound 1001.

Compound 1056: 1,1,1-trifluoro-2-methylpropan-2-yl ((2R,6S,7R,9R,13aS,14aR,16aS,Z)-14a-((cyclopropylsulfonyl)carbamoyl)-7-ethyl-2-((2-methoxy-6-(thiazol-2-yl)pyridin-4-yl)oxy)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. ¹H-NMR (500 MHz, DMSO-d₆) δ 8.84 (br. s., 1H), 7.98-7.91 (m, 1H), 7.82 (d, J=3.1 Hz, 1H), 7.75 (d, J=9.2 Hz, 1H), 7.29 (s, 1H), 6.36 (s, 1H), 5.63 (br. s., 1H), 5.51-5.44 (m, 1H), 5.16 (br. s., 1H), 4.38 (t, J=8.1 Hz, 1H), 4.27 (d, J=11.3 Hz, 1H), 4.03-3.98 (m, 1H), 3.91 (t, J=10.1 Hz, 1H), 3.57 (br. s., 3H), 2.82 (br. s., 1H), 2.47 (br. s., 2H), 2.35-2.27 (m, 1H), 2.21 (d, J=12.2 Hz, 1H), 1.90 (br. s., 3H), 1.57-1.51 (m, 1H), 1.47 (d, J=16.8 Hz, 4H), 1.40 (s, 3H), 1.35 (br. s., 2H), 1.33 (s, 3H), 1.21 (br. s., 1H), 1.15 (d, J=7.0 Hz, 1H), 1.01 (br. s., 1H), 0.96 (d, J=11.3 Hz, 3H), 0.90 (d, J=6.4 Hz, 3H), 0.68 (t, J=7.5 Hz, 3H); MS: MS m/z 855.8 (M⁺+1).

Preparation of Compound 1057

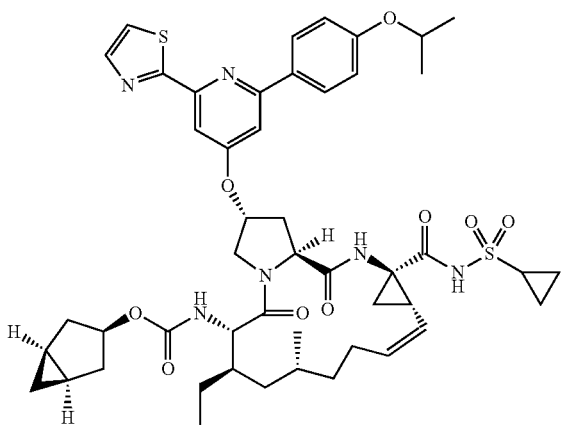

Compound 1057

Compound 1057 was prepared using the intermediates described above and by following the general procedure described for the synthesis of Compound 1001.

Compound 1057: (1R,3r,5S)-bicyclo[3.1.0]hexan-3-yl ((2R,6S,7R,9R,13aS,14aR,16aS,Z)-14a-((cyclopropylsulfonyl)carbamoyl)-7-ethyl-2-((2-(4-isopropoxyphenyl)-6-(thiazol-2-yl)pyridin-4-yl)oxy)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. ¹H-NMR (500 MHz, DMSO-d₆) δ 11.16 (br. s., 1H), 9.02 (br. s., 1H), 8.12-8.08 (m, J=8.5 Hz, 2H), 7.98 (d, J=3.4 Hz, 1H), 7.84 (d, J=3.1 Hz, 1H), 7.50 (s, 1H), 7.44 (s, 1H), 7.32 (d, J=9.2 Hz, 1H), 7.06-7.02 (m, J=8.9 Hz, 2H), 5.54-5.48 (m, 2H), 5.05 (br. s., 1H), 4.70 (dt, J=11.9, 6.0 Hz, 1H), 4.57 (t, J=6.6 Hz, 1H), 4.42-4.35 (m, 2H), 3.94-3.88 (m, 1H), 2.88 (br. s., 1H), 2.60 (br. s., 1H), 2.58-2.53 (m, 1H), 2.28-2.19 (m, 2H), 1.89 (d, J=13.1 Hz, 2H), 1.85-1.78 (m, 1H), 1.65-1.55 (m, 2H), 1.53 (br. s., 1H), 1.46 (d, J=14.3 Hz, 1H), 1.40 (br. s., 2H), 1.37-1.30 (m, 3H), 1.29 (d, J=6.1 Hz, 7H), 1.25 (s, 1H), 1.09 (d, J=5.8 Hz, 4H), 0.98-0.91 (m, 4H), 0.89 (d, J=6.7 Hz, 3H), 0.66 (t, J=7.5 Hz, 3H), 0.27-0.23 (m, 2H); MS: MS m/z 929.9 (M⁺+1).

Preparation of Compound 1058

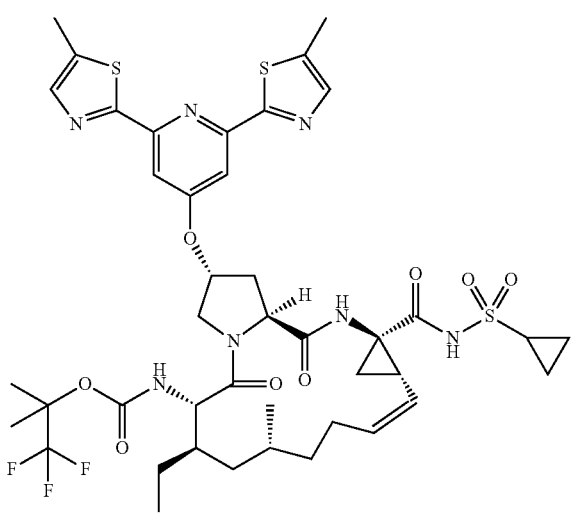

Compound 1058

Compound 1058 was prepared using the intermediates described above and by following the general procedure described for the synthesis of Compound 1001.

Compound 1058: 1,1,1-trifluoro-2-methylpropan-2-yl ((2R,6S,7R,9R,13aS,14aR,16aS,Z)-2-((2,6-bis(5-methylthiazol-2-yl)pyridin-4-yl)oxy)-14a-((cyclopropylsulfonyl)carbamoyl)-7-ethyl-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. ¹H-NMR (400 MHz, CD₃OD) δ 7.63 (s, 3H), 5.64-5.55 (m, 1H), 5.44 (br. s., 1H), 5.10 (br. s., 1H), 4.74 (d, J=11.5 Hz, 1H), 4.56 (dd, J=9.9, 6.9 Hz, 1H), 4.06-3.98 (m, 2H), 2.96-2.89 (m, 1H), 2.74-2.63 (m, 2H), 2.57 (s, 6H), 2.45 (ddd, J=14.1, 10.5, 4.3 Hz, 1H), 2.37 (d, J=13.6 Hz, 1H), 2.02-1.92 (m, 2H), 1.76 (dd, J=8.3, 5.5 Hz, 1H), 1.59 (dd, J=9.7, 5.4 Hz, 1H), 1.56-1.48 (m, 4H), 1.48-1.37 (m, 2H), 1.32 (s, 3H), 1.31-1.21 (m, 3H), 1.17 (s, 3H), 1.16-1.04 (m, 3H), 1.00 (d, J=6.3 Hz, 3H), 0.78 (t, J=7.4 Hz, 3H); MS: MS m/z 936.5 (M⁺+1).

Preparation of Compound 1059

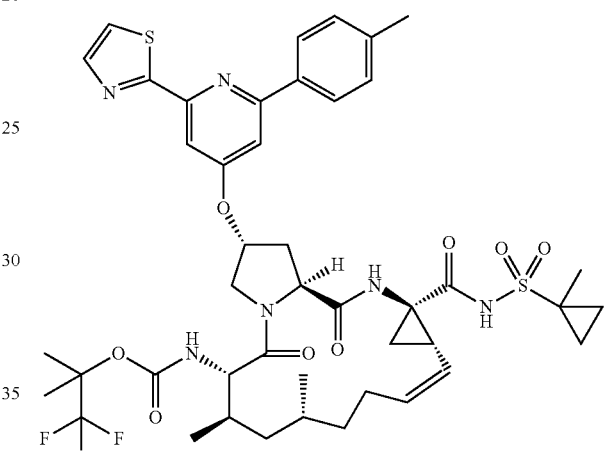

Compound 1059

Compound 1059 was prepared using the intermediates described above and by following the general procedure described for the synthesis of Compound 1001.

Compound 1059: 1,1,1-trifluoro-2-methylpropan-2-yl ((2R,6S,7R,9R,13aS,14aR,16aS,Z)-7,9-dimethyl-14a-(((1-methylcyclopropyl)sulfonyl)carbamoyl)-5,16-dioxo-2-((2-(thiazol-2-yl)-6-(p-tolyl)pyridin-4-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. ¹H-NMR (500 MHz, DMSO-d₆) δ 9.04 (br. s., 1H), 8.06 (d, J=7.6 Hz, 2H), 8.00 (d, J=2.4 Hz, 1H), 7.87 (br. s., 1H), 7.77 (d, J=8.2 Hz, 1H), 7.50 (s, 1H), 7.54 (s, 1H), 7.35 (d, J=7.3 Hz, 2H), 5.58 (br. s., 1H), 5.48 (br. s., 1H), 5.07 (br. s., 1H), 4.48-4.39 (m, 2H), 3.90 (d, J=8.9 Hz, 1H), 3.69 (d, J=9.8 Hz, 1H), 2.55 (br. s., 2H), 2.38 (br. s., 3H), 2.26 (d, J=10.1 Hz, 2H), 1.91 (br. s., 1H), 1.81 (br. s., 1H), 1.64 (br. s., 1H), 1.58 (br. s., 1H), 1.46 (br. s., 1H), 1.39 (br. s., 5H), 1.34-1.30 (m, 2H), 1.23 (br. s., 4H), 1.16 (br. s., 2H), 1.11 (br. s., 3H), 0.90 (d, J=6.4 Hz, 3H), 0.82 (d, J=5.2 Hz, 3H), 0.69 (br. s., 1H); MS: MS m/z 915.6 (M⁺+1).

Preparation of Compound 1060

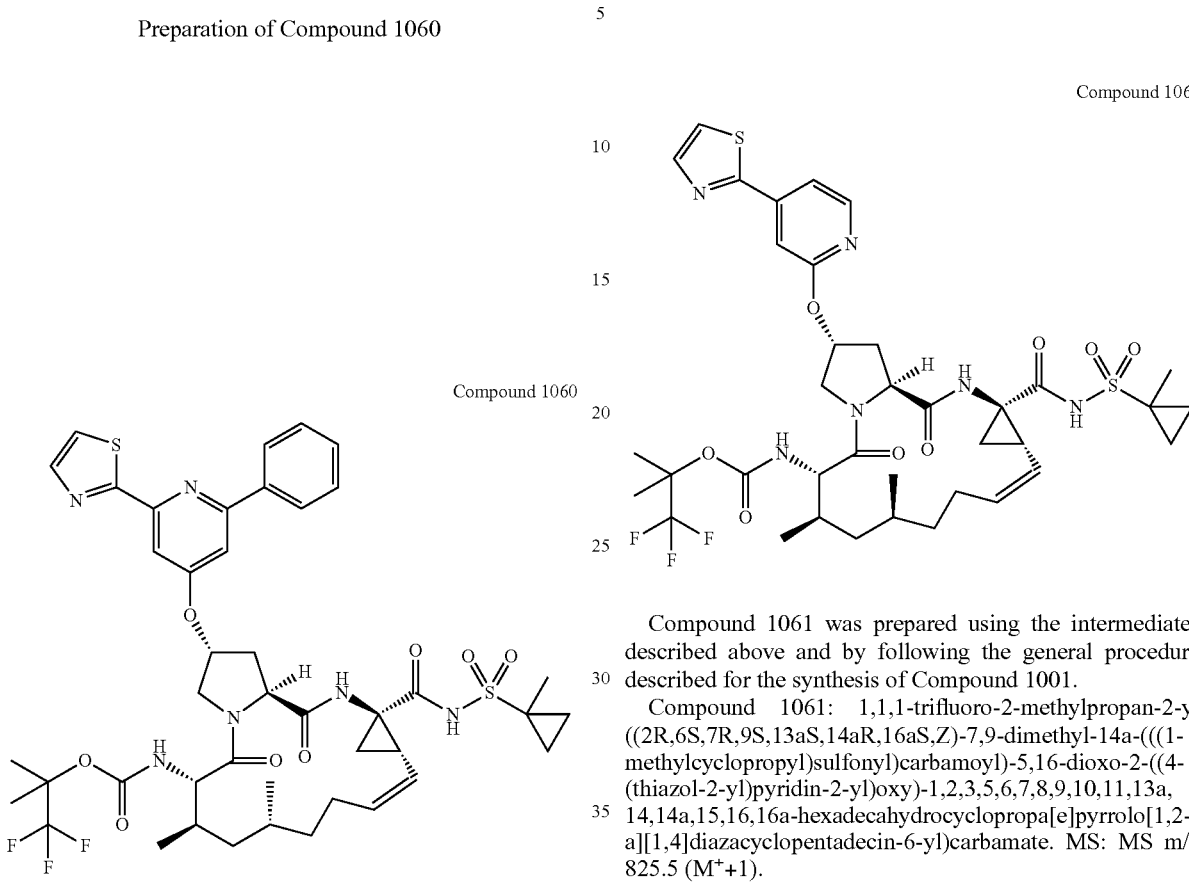

Compound 1060

Compound 1060 was prepared using the intermediates described above and by following the general procedure described for the synthesis of Compound 1001.

Compound 1060: 1,1,1-trifluoro-2-methylpropan-2-yl ((2R,6S,7R,9R,13aS,14aR,16aS,Z)-7,9-dimethyl-14a-(((1-methylcyclopropyl)sulfonyl)carbamoyl)-5,16-dioxo-2-((2-phenyl-6-(thiazol-2-yl)pyridin-4-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate.
¹H-NMR (500 MHz, DMSO-d₆) δ 9.14 (br. s., 1H), 8.15 (d, J=7.3 Hz, 2H), 8.01 (br. s., 1H), 7.88 (br. s., 1H), 7.77 (d, J=8.2 Hz, 1H), 7.58-7.46 (m, 5H), 5.59 (br. s., 1H), 5.50 (br. s., 1H), 5.00 (br. s., 1H), 4.51-4.41 (m, 2H), 3.90 (d, J=11.9 Hz, 1H), 3.68 (br. s., 1H), 2.60 (br. s., 2H), 2.27 (br. s., 2H), 1.91 (br. s., 1H), 1.81 (br. s., 1H), 1.60 (br. s., 2H), 1.48 (d, J=15.0 Hz, 3H), 1.39 (br. s., 3H), 1.34 (br. s., 2H), 1.25 (br. s., 2H), 1.21 (br. s., 3H), 1.14-1.11 (m, 1H), 1.09 (br. s., 3H), 0.90 (d, J=6.4 Hz, 3H), 0.82 (d, J=5.5 Hz, 3H), 0.71 (d, J=12.8 Hz, 1H); MS: MS m/z 901.5 (M⁺+1).

Preparation of Compound 1061

Compound 1061

Compound 1061 was prepared using the intermediates described above and by following the general procedure described for the synthesis of Compound 1001.

Compound 1061: 1,1,1-trifluoro-2-methylpropan-2-yl ((2R,6S,7R,9S,13aS,14aR,16aS,Z)-7,9-dimethyl-14a-(((1-methylcyclopropyl)sulfonyl)carbamoyl)-5,16-dioxo-2-((4-(thiazol-2-yl)pyridin-2-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 825.5 (M⁺+1).

Preparation of Compound 1062

Compound 1062

Compound 1062 was prepared using the intermediates described above and by following the general procedure described for the synthesis of Compound 1001.

Compound 1062: 1,1,1-trifluoro-2-methylpropan-2-yl ((2R,6S,7R,9R,13aS,14aR,16aS,Z)-7,9-dimethyl-14a-(((1- methylcyclopropyl)sulfonyl)carbamoyl)-5,16-dioxo-2-((4-(thiazol-2-yl)pyridin-2-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^{1}$H-NMR (500 MHz, DMSO-d$_6$) δ 11.06 (s, 1H), 9.19 (br. s., 1H), 8.33 (d, J=5.2 Hz, 1H), 8.06 (d, J=3.4 Hz, 1H), 7.99 (d, J=3.4 Hz, 1H), 7.83 (d, J=8.2 Hz, 1H), 7.54 (dd, J=5.3, 1.4 Hz, 1H), 7.20 (s, 1H), 5.71 (br. s., 1H), 5.54 (d, J=6.4 Hz, 1H), 4.96 (t, J=9.9 Hz, 1H), 4.54-4.46 (m, 1H), 4.41 (d, J=11.3 Hz, 1H), 3.92-3.87 (m, 1H), 3.67 (dd, J=10.7, 8.5 Hz, 1H), 2.73-2.65 (m, 1H), 2.39-2.24 (m, 2H), 1.95-1.80 (m, 2H), 1.63 (d, J=5.8 Hz, 2H), 1.53 (d, J=8.5 Hz, 1H), 1.47 (d, J=10.1 Hz, 1H), 1.42 (s, 4H), 1.36 (br. s., 2H), 1.29 (s, 4H), 1.18 (s, 3H), 1.12 (d, J=12.5 Hz, 1H), 0.92 (d, J=7.0 Hz, 4H), 0.90-0.88 (m, 1H), 0.86 (d, J=6.1 Hz, 3H), 0.73 (t, J=12.2 Hz, 1H). MS: MS m/z 825.4 (M$^+$+1).

Preparation of Compound 1063

Compound 1063

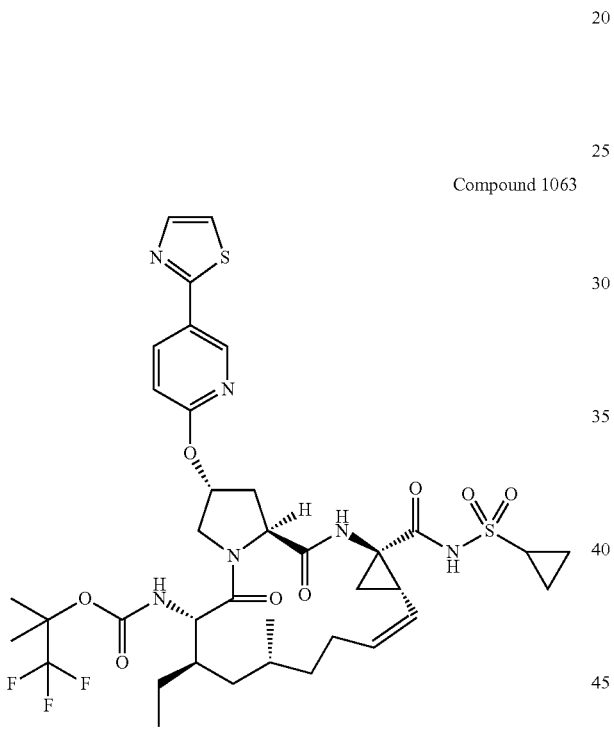

Preparation of Compound 1064

Compound 1064

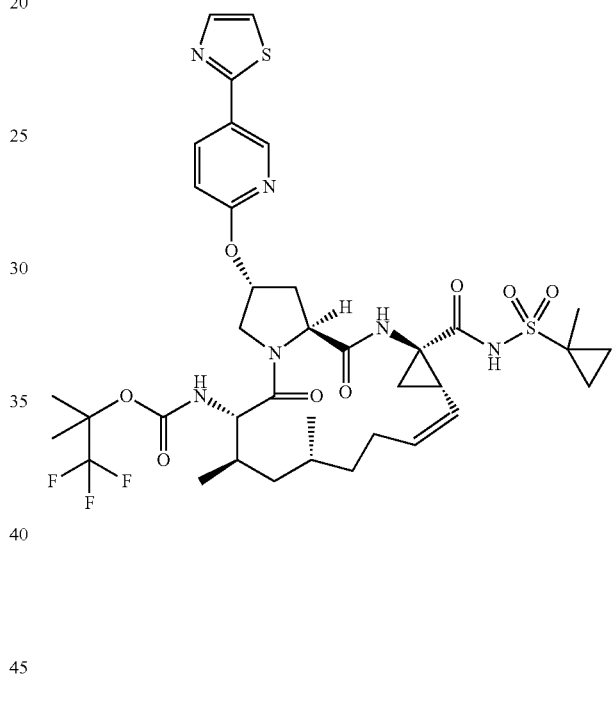

Compound 1063 was prepared using the intermediates described above and by following the general procedure described for the synthesis of Compound 1001.

Compound 1063: 1,1,1-trifluoro-2-methylpropan-2-yl ((2R,6S,7R,9R,13aS,14aR,16aS,Z)-14a-((cyclopropylsulfonyl)carbamoyl)-7-ethyl-9-methyl-5,16-dioxo-2-((5-(thiazol-2-yl)pyridin-2-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^{1}$H-NMR (500 MHz, DMSO-d$_6$) δ 8.80 (br. s., 1H), 8.73 (s, 1H), 8.21 (d, J=8.5 Hz, 1H), 7.97-7.82 (m, 1H), 7.82-7.67 (m, 2H), 6.88 (d, J=8.5 Hz, 1H), 5.64 (br. s., 1H), 5.46 (br. s., 1H), 5.28-5.09 (m, 1H), 4.37 (d, J=12.2 Hz, 2H), 2.80 (br. s., 2H), 2.46 (br. s., 2H), 2.24 (d, J=13.1 Hz, 3H), 1.52 (d, J=18.6 Hz, 2H), 1.45 (br. s., 2H), 1.38 (br. s., 3H), 1.33 (br. s., 4H), 1.28 (br. s., 1H), 1.22 (br. s., 3H), 1.16 (br. s., 1H), 1.00 (br. s., 1H), 0.89 (br. s., 6H), 0.68 (t, J=7.0 Hz, 3H). MS: MS m/z 826.0 (M$^+$+1).

Compound 1064 was prepared using the intermediates described above and by following the general procedure described for the synthesis of Compound 1001.

Compound 1064: 1,1,1-trifluoro-2-methylpropan-2-yl ((2R,6S,7R,9R,13aS,14aR,16aS,Z)-7,9-dimethyl-14a-(((1-methylcyclopropyl)sulfonyl)carbamoyl)-5,16-dioxo-2-((5-(thiazol-2-yl)pyridin-2-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^{1}$H-NMR (500 MHz, DMSO-d$_6$) δ 11.03 (br. s., 1H), 9.14 (br. s., 1H), 8.74 (s, 1H), 8.22 (d, J=8.9 Hz, 1H), 7.94-7.89 (m, 1H), 7.75 (d, J=3.1 Hz, 2H), 6.88 (d, J=8.5 Hz, 1H), 5.66 (br. s., 1H), 5.50 (br. s., 1H), 4.96 (br. s., 1H), 4.47-4.34 (m, 2H), 3.89 (d, J=12.2 Hz, 2H), 2.61 (br. s., 1H), 2.24 (br. s., 2H), 1.89 (d, J=10.7 Hz, 1H), 1.82 (br. s., 1H), 1.59 (br. s., 2H), 1.50 (br. s., 1H), 1.38 (br. s., 5H), 1.33 (s, 4H), 1.25 (s, 4H), 1.17-1.06 (m, 1H), 0.89

(d, J=6.7 Hz, 3H), 0.88-0.85 (m, 1H), 0.83 (d, J=6.1 Hz, 4H), 0.69 (t, J=13.0 Hz, 1H). MS: MS m/z 825.7 (M$^+$+1).

Preparation of Compound 1065

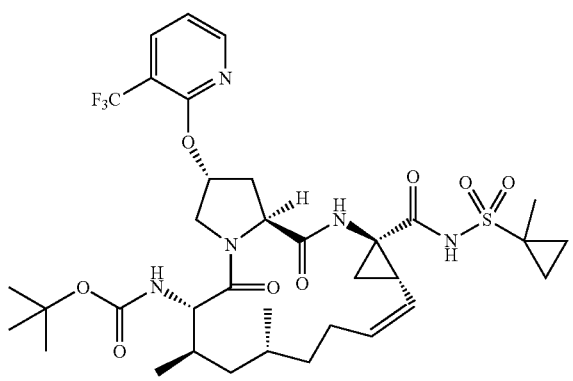

Compound 1065

Compound 1065 was prepared using the intermediates described above and by following the general procedure described for the synthesis of Compound 1001.

Compound 1065: tert-butyl ((2R,6S,7R,9R,13aS,14aR,16aS,Z)-7,9-dimethyl-14a-(((1-methylcyclopropyl)sulfonyl)carbamoyl)-5,16-dioxo-2-((3-(trifluoromethyl)pyridin-2-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H-NMR (500 MHz, DMSO-d$_6$) δ 8.93 (br. s., 1H), 8.47 (d, J=4.6 Hz, 1H), 8.07 (d, J=7.6 Hz, 1H), 7.22-7.17 (m, 1H), 7.08 (d, J=8.9 Hz, 1H), 5.77 (br. s., 1H), 5.46 (d, J=5.2 Hz, 1H), 5.15 (br. s., 1H), 4.47-4.35 (m, 2H), 3.91 (d, J=8.9 Hz, 1H), 3.67 (t, J=9.9 Hz, 1H), 2.55 (d, J=8.9 Hz, 1H), 2.44 (dd, J=13.3, 6.9 Hz, 2H), 2.34-2.23 (m, 2H), 1.88 (br. s., 1H), 1.84-1.76 (m, 1H), 1.71-1.64 (m, 1H), 1.54 (d, J=5.2 Hz, 1H), 1.45 (br. s., 1H), 1.38 (s, 3H), 1.34 (br. s., 3H), 1.26-1.21 (m, 1H), 1.17 (s, 9H), 1.13 (br. s., 3H), 0.92 (d, J=6.7 Hz, 3H), 0.84 (d, J=6.4 Hz, 3H), 0.67 (t, J=12.5 Hz, 1H). MS: MS m/z 756.5 (M$^+$+1).

Preparation of Compound 1066

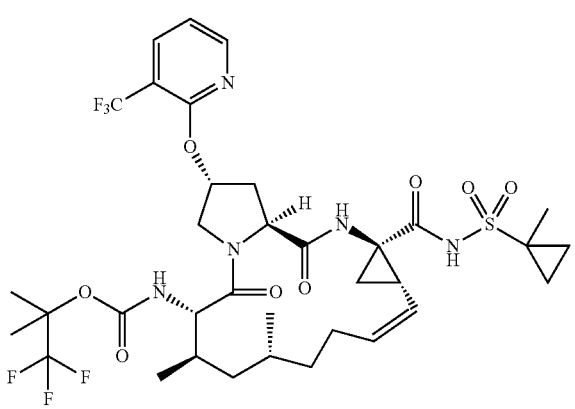

Compound 1066

Compound 1066 was prepared using the intermediates described above and by following the general procedure described for the synthesis of Compound 1001.

Compound 1066: 1,1,1-trifluoro-2-methylpropan-2-yl ((2R,6S,7R,9R,13aS,14aR,16aS,Z)-7,9-dimethyl-14a-(((1-methylcyclopropyl)sulfonyl)carbamoyl)-5,16-dioxo-2-((3-(trifluoromethyl)pyridin-2-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H-NMR (500 MHz, CD$_3$OD) δ 8.42-8.39 (m, 1H), 8.03-7.97 (m, 1H), 7.13 (dd, J=7.3, 5.3 Hz, 1H), 5.85 (t, J=3.1 Hz, 1H), 5.59 (td, J=10.4, 5.6 Hz, 1H), 5.03 (t, J=10.2 Hz, 1H), 4.62-4.52 (m, 2H), 3.99 (dd, J=11.8, 3.5 Hz, 1H), 3.80 (d, J=10.8 Hz, 1H), 2.73-2.58 (m, 2H), 2.47-2.35 (m, 2H), 2.04-1.82 (m, 2H), 1.82-1.71 (m, 2H), 1.67-1.59 (m, 1H), 1.55 (dd, J=9.4, 5.4 Hz, 1H), 1.52-1.46 (m, 6H), 1.46-1.37 (m, 2H), 1.36-1.31 (m, 3H), 1.29-1.16 (m, 1H), 0.99 (d, J=6.8 Hz, 3H), 0.96 (d, J=6.5 Hz, 3H), 0.87-0.84 (m, 2H), 0.84-0.76 (m, 1H). MS: MS m/z 808.5 (M$^-$−1).

Preparation of Compound 1067

Compound 1067

Compound 1067 was prepared using the intermediates described above and by following the general procedure described for the synthesis of Compound 1001.

Compound 1067: 1,1,1-trifluoro-2-methylpropan-2-yl ((2R,6S,7R,9R,13aS,14aR,16aS,Z)-2-((4-chloro-3-(trifluoromethyl)pyridin-2-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H-NMR (500 MHz, CD$_3$OD) δ 8.00 (d, J=7.8 Hz, 1H), 7.20 (d, J=8.0 Hz, 1H), 5.80 (t, J=3.3 Hz, 1H), 5.60 (td, J=10.3, 5.8 Hz, 1H), 5.02 (t, J=9.8 Hz, 1H), 4.66 (d, J=12.0 Hz, 1H), 4.56 (dd, J=10.4, 6.9 Hz, 1H), 4.00 (dd, J=12.0, 3.3 Hz, 1H), 3.80 (d, J=10.8 Hz, 1H), 2.73-2.58 (m, 2H), 2.48-2.35 (m, 2H), 2.01-1.82 (m, 2H), 1.82-1.71 (m, 2H), 1.55 (dd, J=9.5, 5.5 Hz, 1H), 1.52-1.47 (m, 7H), 1.45 (d, J=2.3 Hz, 1H), 1.43-1.38 (m, 2H), 1.35 (s, 3H), 1.29-1.15 (m, 1H), 0.98 (t, J=6.3 Hz, 6H), 0.90-0.77 (m, 3H). MS: MS m/z 842.4 (M⁻−1).

Preparation of Compound 1068

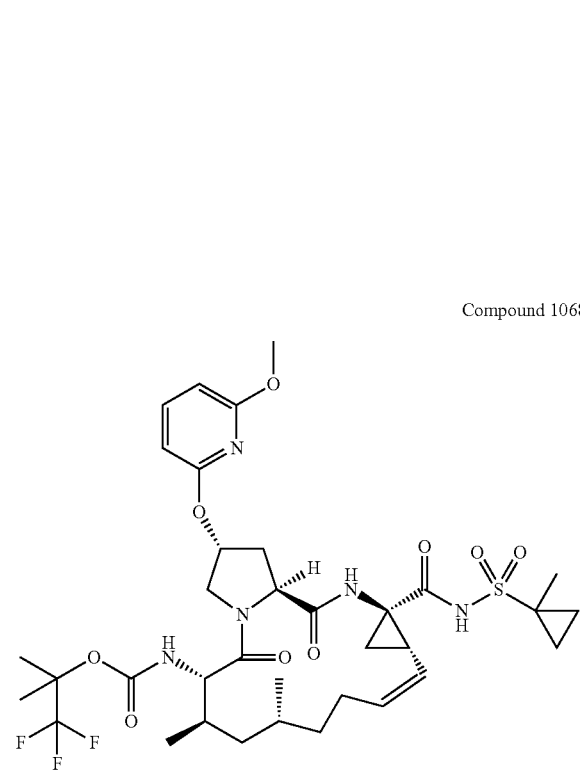 [SMILES: COc1cccc(O[C@@H]2C[C@H]3C(=O)N[C@]4(C(=O)NS(=O)(=O)C5(C)CC5)C[C@H]4/C=C\CC[C@@H](C)C[C@@H](C)[C@H](NC(=O)OC(C)(C)C(F)(F)F)C(=O)N3C2)n1]

Compound 1068

Compound 1068 was prepared using the intermediates described above and by following the general procedure described for the synthesis of Compound 1001.

Compound 1068: 1,1,1-trifluoro-2-methylpropan-2-yl ((2R,6S,7R,9R,13aS,14aR,16aS,Z)-2-((6-methoxypyridin-2-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. ¹H-NMR (500 MHz, CD₃OD) δ 7.53 (t, J=7.9 Hz, 1H), 6.34 (d, J=7.8 Hz, 1H), 6.28 (d, J=7.8 Hz, 1H), 5.67-5.57 (m, 2H), 5.00 (br. s., 1H), 4.55-4.49 (m, 2H), 4.04 (dd, J=11.7, 3.6 Hz, 1H), 3.95-3.91 (m, 3H), 3.89 (s, 1H), 2.70 (d, J=7.8 Hz, 1H), 2.57 (dd, J=13.6, 7.0 Hz, 1H), 2.43-2.33 (m, 2H), 2.02-1.87 (m, 2H), 1.75 (dd, J=8.5, 5.5 Hz, 2H), 1.64 (d, J=7.8 Hz, 1H), 1.57-1.51 (m, 4H), 1.50 (s, 3H), 1.47 (br. s., 1H), 1.44-1.39 (m, 2H), 1.38 (s, 3H), 1.26-1.18 (m, 1H), 0.99 (d, J=6.8 Hz, 3H), 0.96 (d, J=6.3 Hz, 3H), 0.89-0.74 (m, 3H). MS: MS m/z 770.7 (M⁻−1).

Preparation of Compound 1069

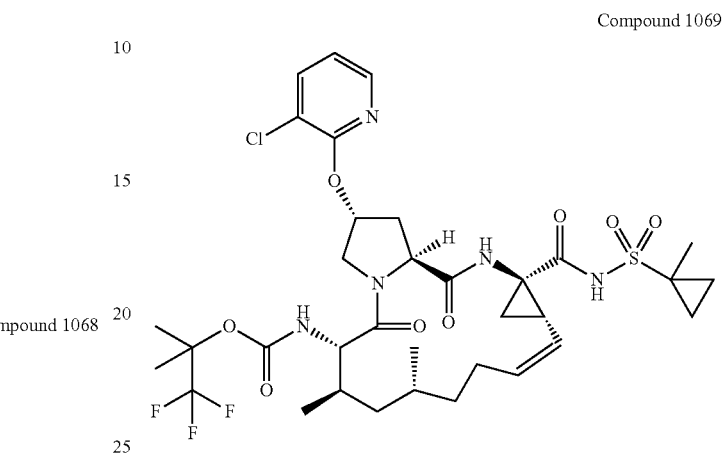

Compound 1069

Compound 1069 was prepared using the intermediates described above and by following the general procedure described for the synthesis of Compound 1001.

Compound 1069: 1,1,1-trifluoro-2-methylpropan-2-yl ((2R,6S,7R,9R,13aS,14aR,16aS,Z)-2-((3-chloropyridin-2-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. ¹H-NMR (500 MHz, CD₃OD) δ 1H NMR (400 MHz, METHANOL-d4) Shift 8.10 (dd, J=4.9, 1.6 Hz, 1H), 7.74 (dd, J=7.7, 1.6 Hz, 1H), 6.97 (dd, J=7.7, 4.9 Hz, 1H), 5.76 (br. s., 1H), 5.64-5.57 (m, 1H), 5.00 (br. s., 1H), 4.63-4.58 (m, 2H), 3.99 (dd, J=11.8, 3.5 Hz, 1H), 3.81 (d, J=11.3 Hz, 1H), 2.71 (d, J=7.8 Hz, 1H), 2.63 (dd, J=13.8, 7.0 Hz, 1H), 2.45-2.35 (m, 2H), 2.00-1.85 (m, 2H), 1.80-1.72 (m, 2H), 1.64 (d, J=9.3 Hz, 1H), 1.55 (dd, J=9.4, 5.6 Hz, 1H), 1.52-1.47 (m, 7H), 1.47-1.40 (m, 2H), 1.40-1.36 (m, 3H), 1.27-1.19 (m, 1H), 0.99 (d, J=6.8 Hz, 3H), 0.97 (d, J=6.3 Hz, 3H), 0.89-0.77 (m, 3H). MS: MS m/z 774.6 (M⁻−1).

Biological Studies

HCV NS3/4A protease complex enzyme assays and cell-based HCV replicon assays were utilized in the present disclosure, and were prepared, conducted and validated as follows:

Generation of Recombinant HCV NS3/4A Protease Complex

HCV NS3 protease complexes, derived from the BMS strain, H77 strain or J4L6S strain, were generated, as described below. These purified recombinant proteins were generated for use in a homogeneous assay (see below) to provide an indication of how effective compounds of the present disclosure would be in inhibiting HCV NS3 proteolytic activity.

Serum from an HCV-infected patient was obtained from Dr. T. Wright, San Francisco Hospital. An engineered full-length cDNA (compliment deoxyribonucleic acid) template of the HCV genome (BMS strain) was constructed from DNA fragments obtained by reverse transcription-PCR (RT-PCR) of serum RNA (ribonucleic acid) and using primers selected on the basis of homology between other genotype 1a strains. From the determination of the entire genome sequence, a genotype 1a was assigned to the HCV isolate according to the classification of Simmonds et al. (See P Simmonds, K A Rose, S Graham, S W Chan, F McOmish, B C Dow, E A Follett, P L Yap and H Marsden, J. Clin. Microbiol., 31(6), 1493-1503 (1993)). The amino acid sequence of the nonstructural region, NS2-5B, was shown to be >97% identical to HCV genotype 1a (H77) and 87% identical to genotype 1b (J4L6S). The infectious clones, H77 (1a genotype) and J4L6S (1b genotype) were obtained from R. Purcell (NIH) and the sequences are published in Genbank (AAB67036, see Yanagi, M., Purcell, R. H., Emerson, S. U. and Bukh, *J. Proc. Natl. Acad. Sci. U.S.A.* 94(16), 8738-8743 (1997); AF054247, see Yanagi, M., St Claire, M., Shapiro, M., Emerson, S. U., Purcell, R. H. and Bukh, J., *Virology* 244 (1), 161-172. (1998)).

The H77 and J4L6S strains were used for production of recombinant NS3/4A protease complexes. DNA encoding the recombinant HCV NS3/4A protease complex (amino acids 1027 to 1711) for these strains was manipulated as described by P. Gallinari et al. (see Gallinari P, Paolini C, Brennan D, Nardi C, Steinkuhler C, De Francesco R. *Biochemistry.* 38(17):5620-32, (1999)). Briefly, a three-lysine solubilizing tail was added at the 3'-end of the NS4A coding region. The cysteine in the P1 position of the NS4A-NS4B cleavage site (amino acid 1711) was changed to a glycine to avoid the proteolytic cleavage of the lysine tag. Furthermore, a cysteine to serine mutation was introduced by PCR at amino acid position 1454 to prevent the autolytic cleavage in the NS3 helicase domain. The variant DNA fragment was cloned in the pET21b bacterial expression vector (Novagen) and the NS3/4A complex was expressed in *Escherichia. coli* strain BL21 (DE3) (Invitrogen) following the protocol described by P. Gallinari et al. (see Gallinari P, Brennan D, Nardi C, Brunetti M, Tomei L, Steinkuhler C, De Francesco R., *J Virol.* 72(8):6758-69 (1998)) with modifications. Briefly, the NS3/4A protease complex expression was induced with 0.5 millimolar (mM) Isopropyl β-D-1-thiogalactopyranoside (IPTG) for 22 hours (h) at 20° C. A typical fermentation (1 Liter (L)) yielded approximately 10 grams of wet cell paste. The cells were resuspended in lysis buffer (10 mL/gram) consisting of 25 mM N-(2-Hydroxyethyl)Piperazine-N'-(2-Ethane Sulfonic acid) (HEPES) pH 7.5, 20% glycerol, 500 mM Sodium Chloride (NaCl), 0.5% Triton X-100, 1 microgram/milliliter ("μg/mL") lysozyme, 5 mM Magnesium Chloride (MgCl$_2$), 1 μg/ml DnaseI, 5 mM β-Mercaptoethanol (βME), Protease inhibitor-Ethylenediamine Tetraacetic acid (EDTA) free (Roche). The mixture was homogenized and incubated for 20 minutes (min) at 4° C. The homogenate was sonicated and clarified by ultra-centrifugation at 235,000 g for 1 hour (h) at 4° C. Imidazole was added to the supernatant to a final concentration of 15 mM and the pH was adjusted to 8.0. The crude protein extract was loaded on a Nickel-Nitrilotriacetic acid (Ni-NTA) column pre-equilibrated with buffer B (25 mM HEPES, pH 8.0, 20% glycerol, 500 mM NaCl, 0.5% Triton X-100, 15 mM imidazole, 5 mM βME). The sample was loaded at a flow rate of 1 mL/min. The column was washed with 15 column volumes of buffer C (same as buffer B except with 0.2% Triton X-100). The protein was eluted with 5 column volumes of buffer D (same as buffer C except with 200 mM Imidazole).

NS3/4A protease complex-containing fractions were pooled and loaded on a desalting column Superdex-S200 pre-equilibrated with buffer E (25 mM HEPES, pH 7.5, 20% glycerol, 300 mM NaCl, 0.2% Triton X-100, 10 mM βME). Sample was loaded and eluted with buffer E at a flow rate of 1 mL/min. NS3/4A protease complex-containing fractions were pooled and concentrated to approximately 0.5 mg/ml. The purity of the NS3/4A protease complexes, derived from the BMS, H77 and J4L6S strains, were judged to be greater than 90% by SDS-PAGE and mass spectrometry analyses. The enzyme was stored at −80° C., thawed on ice and diluted prior to use in assay buffer.

FRET Peptide Assay to Monitor HCV NS3/4A Proteolytic Activity

The purpose of this in vitro assay was to measure the inhibition of HCV NS3 protease complexes, derived from the BMS strain, H77 strain or J4L6S strain, as described above, by compounds of the present disclosure. This assay provides an indication of how effective compounds of the present disclosure would be in inhibiting HCV NS3 proteolytic activity.

In order to monitor HCV NS3/4A protease activity, an NS3/4A peptide substrate was used. The substrate was RET S1 (Resonance Energy Transfer Depsipeptide Substrate; AnaSpec, Inc. cat #22991)(FRET peptide), described by Taliani et al. in *Anal. Biochem.* 240(2):60-67 (1996). The sequence of this peptide is loosely based on the NS4A/NS4B natural cleavage site for the HCV NS3 protease except there is an ester linkage rather than an amide bond at the cleavage site. The peptide also contains a fluorescence donor, EDANS, near one end of the peptide and an acceptor, DABCYL, near the other end. The fluorescence of the peptide is quenched by intermolecular resonance energy transfer (RET) between the donor and the acceptor, but as the NS3 protease cleaves the peptide the products are released from RET quenching and the fluorescence of the donor becomes apparent.

The peptide substrate was incubated with one of the three recombinant NS3/4A protease complexes, in the absence or presence of a compound of the present disclosure. The inhibitory effects of a compound were determined by monitoring the formation of fluorescent reaction product in real time using a Cytofluor Series 4000.

The reagents were as follow: HEPES and Glycerol (Ultrapure) were obtained from GIBCO-BRL. Dimethyl Sulfoxide (DMSO) was obtained from Sigma. β-Mercaptoethanol was obtained from Bio Rad.

Assay buffer: 50 mM HEPES pH 7.5; 0.15 M NaCl; 0.1% Triton; 15% Glycerol; 10 mM βME. Substrate: 2 μM final concentration (from a 2 mM stock solution in DMSO stored at −20° C.). HCV NS3/4A protease type 1a (1b), 2-3 nM final concentration (from a 5 μM stock solution in 25 mM HEPES pH 7.5, 20% glycerol, 300 mM NaCl, 0.2% Triton-X100, 10 mM βME). For compounds with potencies approaching the assay limit, the assay was made more sensitive by adding 50 μg/ml Bovine Serum Albumin (Sigma) to the assay buffer and reducing the end protease concentration to 300 pM.

The assay was performed in a 96-well polystyrene black plate from Falcon. Each well contained 25 μl NS3/4A protease complex in assay buffer, 50 μl of a compound of the present disclosure in 10% DMSO/assay buffer and 25 μl substrate in assay buffer. A control (no compound) was also prepared on the same assay plate. The enzyme complex was mixed with compound or control solution for 1 min before initiating the enzymatic reaction by the addition of substrate. The assay plate was read immediately using the Cytofluor Series 4000 (Perspective Biosystems). The instrument was set to read an emission of 340 nm and excitation of 490 nm at 25° C. Reactions were generally followed for approximately 15 min.

The percent inhibition was calculated with the following equation:

$$100-[(\delta F_{inh}/\delta F_{con})\times 100]$$

where δF is the change in fluorescence over the linear range of the curve. A non-linear curve fit was applied to the inhibition-concentration data, and the 50% effective concentration ($IC_{50}$) was calculated by the use of Excel XLfit software using the equation, $y=A+4B-A)/(1+((C/x)^{\wedge}D)))$.

Compounds of the present disclosure, which were tested against more than one type of NS3/4A complex, were found to have similar inhibitory properties though the compounds uniformly demonstrated greater potency against the 1b strains as compared to the 1a strains.

Generation of HCV Replicon

An HCV GT1b(Con1) replicon cell system was established as described by Lohmann V, Korner F, Koch J, Herian U, Theilmann L, Bartenschlager R., Science 285(5424):110-3 (1999) and modified to introduce a luciferase reporter (Krieger N, Lohmann V, and Bartenschlager R, J. Virol. 75(10):4614-4624 (2001)). cDNA encoding a humanized form of the Renilla luciferase gene, and a linker sequence fused directly to the 3'-end of the luciferase gene were introduced into the replicon construct using an Asc1 restriction site located in core, directly upstream of the neomycin marker gene. The adaptive mutation at position 1179 (serine to isoleucine) was also introduced (Blight K J, Kolykhalov, A A, Rice, C M, Science 290(5498):1972-1974). A stable cell line constitutively expressing this HCV replicon construct was generated by first linearizing plasmid DNAs with ScaI. RNA transcripts were synthesized in vitro using the T7 MegaScript transcription kit (Ambion, Austin, Tex.) according to manufacturer's directions. In vitro transcripts of the cDNA were transfected into the human hepatoma cell line, HUH-7. Selection for cells constitutively expressing the HCV replicon was achieved in the presence of the selectable marker, neomycin (G418). Resulting cell lines were characterized for positive and negative strand RNA production and protein production over time.

A stable HCV GT1a(H77) replicon luciferase reporter cell line (Yanagi M, Purcell RH, Emerson S U, et al. Transcripts from a single full-length cDNA clone of hepatitis C virus are infectious when directly transfected into the liver of a chimpanzee. Proc Natl Acad Sci USA 1997; 94(16):8738-8743) was generated as described previously for the genotype 1b(Con1) replicon luciferase cell line. The replicon construct was modified by introducing mutations into the genes encoding the NS3 helicase domain (proline replaced by leucine at position 1496) and NS5A (serine to isoleucine at position 2204) to improve replication in cell culture.

HCV Replicon Luciferase Reporter Assay

HCV replicon luciferase assays were developed to monitor the inhibitory effects of compounds described in the disclosure on HCV genotypes 1a and 1b viral replication. HUH-7 cells, constitutively expressing the HCV replicon, were grown in Dulbecco's Modified Eagle Media (DMEM) (Gibco-BRL) containing 10% Fetal calf serum (FCS) (Sigma) and 1 mg/mL G418 (Gibco-BRL). Compounds were serially diluted 3 folds in DMSO for a twenty-point titration and subsequently transferred to sterile 384-well tissue-culture treated plates (Corning cat #3571). The plates were then seeded with 50 μL of cells at a density of $3.0\times10^3$ cells/well in DMEM containing 4% FCS (final DMSO concentration at 0.5%). After 3 days incubation at 37° C., cells were analyzed for Renilla Luciferase activity using the EnduRen as substrate (Promega cat #E6485). The EnduRen substrate was diluted in DMEM and then added to the plates to a final concentration of 7.5 μM. The plates were incubated for 2 hrs at 37° C. and then read immediately for 30 seconds with Viewlux Imager (PerkinElmer) using a luminescence program. To assess cytotoxicity of compounds, $CC_{50}$ values were generated by multiplexing the EnduRen-containing plates with Cell Titer-Blue (Promega, cat #G8082). Cell-Titer Blue (3 μL) was added to each well and incubated for 8 hrs at 37° C. The fluorescence signal from each well was read, with an excitation wavelength at 525/10 nm and an emission wavelength of 598/10 nm, using the Viewlux Imager.

The $EC_{50}$ values for compounds were calculated by using a four-parameter logistic equation:

$$y=A+4B-A)/(1+((C/x)^{\wedge}D))),$$

where A and B denotes minimal and maximal % inhibition, respectively, C is the $EC_{50}$, D is the hill slope and x represents compound concentration.

Table 2 shows the $EC_{50}$ values of representative compounds of the present disclosure. Ranges are as follows: A=0.10 nM-0.50 nM; B=0.51 nM-1.00 nM; C=1.01 nM-5.00 nM; D=5.01 nM-35.00 nM; E=35.01 nM-359.00 nM

TABLE 2

| Compound Number | LE_1a (EC50, nM) | LE_1a (EC50, range) | LE_1b (EC50, nM) | LE_1b (EC50, range) |
|---|---|---|---|---|
| 1001 | | C | | B |
| 1002 | 59.00 | E | 11.64 | D |
| 1003 | | C | | C |
| 1004 | | D | | C |
| 1005 | 1.48 | C | 1.71 | C |
| 1006 | | D | | D |
| 1007 | | C | | C |
| 1008 | | D | | C |
| 1009 | | C | | C |
| 1010 | | D | | D |
| 1011 | | C | | C |
| 1012 | | D | | D |
| 1013 | | C | | C |
| 1014 | | E | | D |
| 1015 | | D | | D |
| 1016 | | E | | E |
| 1017 | 0.95 | B | 0.82 | B |
| 1018 | | D | | C |
| 1019 | | C | | C |
| 1020 | | D | | C |
| 1021 | | C | | B |
| 1022 | | D | | C |
| 1023 | 0.46 | A | 0.40 | A |
| 1024 | | C | | B |
| 1025 | | C | | B |
| 1026 | | D | | D |
| 1027 | | C | | C |
| 1028 | | E | | E |
| 1029 | | C | | C |
| 1030 | | E | | E |
| 1031 | | C | | B |
| 1032 | | D | | D |
| 1033 | | C | | B |
| 1034 | | C | | B |
| 1035 | | B | | B |
| 1036 | | B | | A |
| 1037 | | C | | A |
| 1038 | | C | | B |
| 1039 | | C | | C |
| 1040 | | B | | A |

TABLE 2-continued

| Compound Number | LE_1a (EC50, nM) | LE_1a (EC50, range) | LE_1b (EC50, nM) | LE_1b (EC50, range) |
|---|---|---|---|---|
| 1041 |  | B |  | B |
| 1042 |  |  |  |  |
| 1043 |  | B |  | A |
| 1044 |  | C |  | B |
| 1045 |  | C |  | A |
| 1046 |  | C |  | C |
| 1047 |  | C |  | B |
| 1048 |  | C |  | C |
| 1049 |  | D |  | C |
| 1050 |  | C |  | A |
| 1051 |  | C |  | A |
| 1052 |  | A |  | B |
| 1053 |  | C |  | C |
| 1054 |  | C |  | B |
| 1055 |  | C |  | C |
| 1056 |  | C |  | C |
| 1057 |  | C |  | C |
| 1058 |  |  |  |  |
| 1059 |  | B |  | B |
| 1060 |  | B |  | A |
| 1061 |  | D |  | D |
| 1062 |  | C |  | B |
| 1063 | 16.69 | D | 3.51 | C |
| 1064 |  | C |  | A |
| 1065 |  |  |  | C |
| 1066 |  |  |  | B |
| 1067 |  |  |  | A |
| 1068 |  |  |  | C |
| 1069 |  |  |  | A |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound of formula (I)

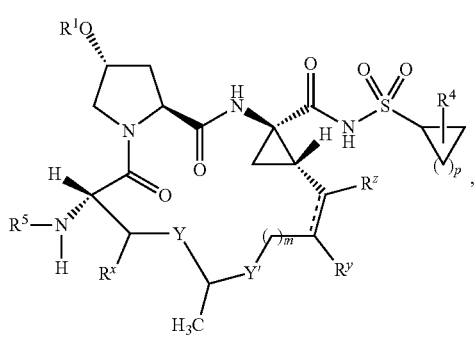

or a pharmaceutically acceptable salt thereof, wherein
p is 1 or 2;
----- is a single or double bond;
$R^1$ is

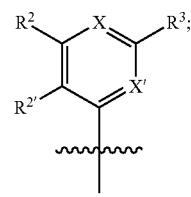

m is 0, 1, or 2;
one of X and X' is N and the other is selected from CH and $CR^{3'}$;
$R^2$, $R^{2'}$, $R^3$, and $R^{3'}$ are independently selected from hydrogen, alkoxy, alkyl, aryl, halo, haloalkyl, and heteroaryl, wherein the aryl and heteroaryl are optionally substituted with one group independently selected from alkoxy and alkyl;
$R^x$ is selected from methyl and ethyl;
$R^y$ and $R^z$ are independently selected from hydrogen and hydroxy; provided that when ----- is a double bond, $R^y$ and $R^z$ are each hydrogen;
$R^4$ is selected from hydrogen, alkyl, and halo, haloalkoxy, haloalkyl, and hydroxyalkyl;
$R^5$ is selected from hydrogen, alkoxyalkoxycarbonyl, alkoxycarbonyl, alkylaminocarbonyl, alkylcarbonyl, cycloalkylalkoxycarbonyl, cycloalkylcarbonyl, cycloalkyloxycarbonyl, deuteroalkoxycarbonyl, deuterohaloalkoxycarbonyl, dialkylaminocarbonyl, dialkylaminocarbonylcarbonyl, haloalkoxycarbonyl, haloalkylaminocarbonyl, haloalkylcarbonyl, heterocyclylcarbonyl, heterocyclyloxycarbonyl, phenylcarbonyl, and phenyloxycarbonyl, wherein the cycloalkyl part of the cycloalkylalkoxycarbonyl, the cycloalkylcarbonyl, and the cycloalkyloxycarbonyl, the heterocyclyl part of the heterocyclylcarbonyl and the heterocyclyloxycarbonyl, and the phenyl part of the phenylcarbonyl and the phenyloxycarbonyl, is optionally substituted with one, two, or three groups independently selected from alkyl, alkylamino, alkylcarbonyl, cycloalkyl, dialkylamino, halo, haloalkoxy, and haloalkyl;
and
one of Y and Y' is $CH_2$ and the other is selected from $CH_2$ and O.

2. A compound of claim 1, or a pharmaceutically acceptable salt thereof, wherein m is 1.

3. A compound of claim 2, or a pharmaceutically acceptable salt thereof, wherein ----- is a double bond.

4. A compound of claim 1 wherein p is 1.

5. A compound of claim 1 wherein $R^4$ is selected from hydrogen and alkyl.

6. A compound of claim 1 wherein $R^5$ is selected from alkoxycarbonyl, haloalkoxycarbonyl, heterocyclyloxycarbonyl, and phenyloxycarbonyl, wherein the heterocyclyl part of the heterocyclyloxycarbonyl, and the phenyl part of the phenyloxycarbonyl is optionally substituted with one, two, or three groups independently selected from alkyl, halo, haloalkoxy, and haloalkyl.

7. A compound of formula (II)

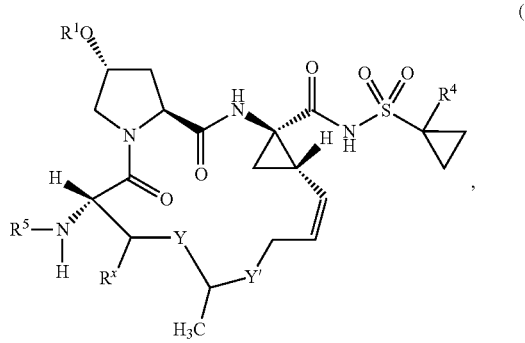

or a pharmaceutically acceptable salt thereof, wherein R¹ is

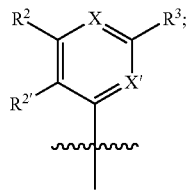

one of X and X' is N and the other is selected from CH and CR³';
R², R²', R³, and R³' are independently selected from hydrogen, alkoxy, alkyl, aryl, halo, haloalkyl, and heteroaryl, wherein the aryl and heteroaryl are optionally substituted with one group independently selected from alkoxy and alkyl;
Rˣ is selected from methyl and ethyl;
R⁴ is selected from hydrogen and alkyl;
R⁵ is selected from alkoxycarbonyl, cycloalkoxycarbonyl, haloalkoxycarbonyl, and heterocyclyloxycarbonyl, wherein heterocyclyl part of the heterocyclyloxycarbonyl is optionally substituted with one haloalkyl group; and
one of Y and Y' is CH₂ and the other is selected from CH₂ and O.

8. A compound selected from 1,1,1-trifluoro-2-methylpropan-2-yl ((2R,6S,7R,9R,13aS,14aR,16aS,Z)-2-((2-(4-isopropoxyphenyl)-6-(pyrazin-2-yl)pyridin-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9S,13aS,14aR,16aS,Z)-2-((2-(4-isopropoxyphenyl)-6-(pyrazin-2-yl)pyridin-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9R,13aS,14aR,16aS,Z)-2-((2-(4-isopropoxyphenyl)-6-(thiazol-5-yl)pyridin-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9S,13aS,14aR,16aS,Z)-2-((2-(4-isopropoxyphenyl)-6-(thiazol-5-yl)pyridin-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9R,13aS,14aR,16aS,Z)-2-((6-(4-isopropoxyphenyl)-[2,3'-bipyridin]-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9S,13aS,14aR,16aS,Z)-2-((6-(4-isopropoxyphenyl)-[2,3'-bipyridin]-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9R,13aS,14aR,16aS,Z)-2-((2-(4-isopropoxyphenyl)-6-(thiazol-2-yl)pyridin-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9S,13aS,14aR,16aS,Z)-2-((2-(4-isopropoxyphenyl)-6-(thiazol-2-yl)pyridin-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9R,13aS,14aR,16aS,Z)-2-((6-(4-isopropoxyphenyl)-[2,4'-bipyridin]-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9S,13aS,14aR,16aS,Z)-2-((6-(4-isopropoxyphenyl)-[2,4'-bipyridin]-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9R,13aS,14aR,16aS,Z)-2-((6-(4-isopropoxyphenyl)-6'-methoxy-[2,2'-bipyridin]-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9R,13aS,14aR,16aS,Z)-2-((6-(4-isopropoxyphenyl)-6'-methoxy-[2,2'-bipyridin]-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9R,13aS,14aR,16aS,Z)-2-((2-(4-isopropoxyphenyl)-6-(1H- pyrazol-1-yl)pyridin-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9S,13aS,14aR,16aS,Z)-2-((2-(4-isopropoxyphenyl)-6-(1H-pyrazol-1-yl)pyridin-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9R,13aS,14aR,16aS,Z)-7,9-dimethyl-2-((2-methyl-6-(thiazol-5-yl)pyridin-4-yl)oxy)-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9S,13aS,14aR,16aS,Z)-7,9-dimethyl-2-((2-methyl-6-(thiazol-5-yl)pyridin-4-yl)oxy)-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

3-(trifluoromethyl)tetrahydro-2H-pyran-3-yl ((2R,6S,7R,9R,13aS,14aR,16aS,Z)-2-((2-(4-isopropoxyphenyl)-6-(thiazol-5-yl)pyridin-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

3-(trifluoromethyl)tetrahydro-2H-pyran-3-yl ((2R,6S,7R,9S,13aS,14aR,16aS,Z)-2-((2-(4-isopropoxyphenyl)-6-(thiazol-5-yl)pyridin-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9R,13aS,14aR,16aS,Z)-2-((2-(4-isopropoxyphenyl)-6-(pyrimidin-2-yl)pyridin-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9S,13aS,14aR,16aS,Z)-2-((2-(4-isopropoxyphenyl)-6-(pyrimidin-2-yl)pyridin-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9R,13aS,14aR,16aS,Z)-2-((6-(4-isopropoxyphenyl)-[2,2'-bipyridin]-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9S,13aS,14aR,16aS,Z)-2-((6-(4-isopropoxyphenyl)-[2,2'-bipyridin]-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9R,13aS,14aR,16aS,Z)-2-((2,6-di(thiazol-2-yl)pyridin-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9S,13aS,14aR,16aS,Z)-2-((2,6-di(thiazol-2-yl)pyridin-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9R,13aS,14aR,16aS,Z)-7,9-dimethyl-14a-(((1-methylcyclopropyl)sulfonyl)carbamoyl)-5,16-dioxo-2-((2-(thiazol-2-yl)pyridin-4-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9R,13aS,14aR,16aS,Z)-2-((4-chloropyridin-2-yl)oxy)-14a-((cyclopropylsulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9R,13aS,14aR,16aS,Z)-2-((4-chloro-6-(4-isopropoxyphenyl)pyridin-2-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9S,13aS,14aR,16aS,Z)-2-((4-chloro-6-(4-isopropoxyphenyl)pyridin-2-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

tert-butyl ((2R,6S,7R,9R,13aS,14aR,16aS,Z)-2-((4-chloro-6-(4-isopropoxyphenyl)pyridin-2-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

tert-butyl ((2R,6S,7R,9S,13aS,14aR,16aS,Z)-2-((4-chloro-6-(4-isopropoxyphenyl)pyridin-2-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9R,13aS,14aR,16aS,Z)-7,9-dimethyl-14a-(((1-methylcyclopropyl)sulfonyl)carbamoyl)-5,16-dioxo-2-((4-(thiazol-2-yl)pyridin-2-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9S,13aS,14aR,16aS,Z)-7,9-dimethyl-14a-(((1-methylcyclopropyl)sulfonyl)carbamoyl)-5,16-dioxo-2-((4-(thiazol-2-yl)pyridin-2-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7S,9R,13aS,14aR,16aS,Z)-7-ethyl-2-((2-(4-isopropoxyphenyl)-6-(thiazol-5-yl)pyridin-4-yl)oxy)-9-methyl-14a-(((1-methylcyclopropyl)sulfonyl)carbamoyl)-5,16-dioxo-2,3,
5,6,7,9,10,11,13a,14,14a,15,16,16a-tetradecahydro-
1H-cyclopropa[i]pyrrolo[1,2-e][1,5,8]
oxadiazacyclopentadecin-6-yl)carbamate;

3-(trifluoromethyl)tetrahydro-2H-pyran-3-yl ((2R,6S,7S,
9R,13aS,14aR,16aS,Z)-7-ethyl-2-((2-(4-isopro-
poxyphenyl)-6-(thiazol-5-yl)pyridin-4-yl)oxy)-9-me-
thyl-14a-(((1-methylcyclopropyl)sulfonyl)carbamoyl)-
5,16-dioxo-2,3,5,6,7,9,10,11,13a,14,14a,15,16,16a-
tetradecahydro-1H-cyclopropa[i]pyrrolo[1,2-e][1,5,8]
oxadiazacyclopentadecin-6-yl)carbamate;

3-(trifluoromethyl)tetrahydro-2H-pyran-3-yl ((2R,6S,7S,
9R,13aS,14aR,16aS,Z)-7-ethyl-2-((2-(4-isopro-
poxyphenyl)-6-(thiazol-2-yl)pyridin-4-yl)oxy)-9-me-
thyl-14a-(((1-methylcyclopropyl)sulfonyl)carbamoyl)-
5,16-dioxo-2,3,5,6,7,9,10,11,13a,14,14a,15,16,16a-
tetradecahydro-1H-cyclopropa[i]pyrrolo[1,2-e][1,5,8]
oxadiazacyclopentadecin-6-yl)carbamate;

3-(trifluoromethyl)tetrahydro-2H-pyran-3-yl ((2R,6S,7S,
9R,13aS,14aR,16aS,Z)-7-ethyl-2-((2-(4-isopro-
poxyphenyl)-6-(thiazol-4-yl)pyridin-4-yl)oxy)-9-me-
thyl-14a-(((1-methylcyclopropyl)sulfonyl)carbamoyl)-
5,16-dioxo-2,3,5,6,7,9,10,11,13a,14,14a,15,16,16a-
tetradecahydro-1H-cyclopropa[i]pyrrolo[1,2-e][1,5,8]
oxadiazacyclopentadecin-6-yl)carbamate;

3-(trifluoromethyl)tetrahydro-2H-pyran-3-yl ((2R,6S,7S,
9R,13aS,14aR,16aS,Z)-7-ethyl-2-((6-(4-isopro-
poxyphenyl)-[2,2'-bipyridin]-4-yl)oxy)-9-methyl-14a-
(((1-methylcyclopropyl)sulfonyl)carbamoyl)-5,16-
dioxo-2,3,5,6,7,9,10,11,13a,14,14a,15,16,16a-
tetradecahydro-1H-cyclopropa[i]pyrrolo[1,2-e][1,5,8]
oxadiazacyclopentadecin-6-yl)carbamate;

1,1,1-trifluoro-2-methylpropan-2-yl ((2R,6S,7S,9R,13aS,
14aR,16aS,Z)-7-ethyl-9-methyl-14a-(((1-methylcyclo-
propyl)sulfonyl)carbamoyl)-5,16-dioxo-2-((2-(thiazol-
2-yl)-6-(4-(trifluoromethyl)phenyl)pyridin-4-yl)oxy)-
2,3,5,6,7,9,10,11,13a,14,14a,15,16,16a-
tetradecahydro-1H-cyclopropa[i]pyrrolo[1,2-e][1,5,8]
oxadiazacyclopentadecin-6-yl)carbamate;

3-(trifluoromethyl)tetrahydro-2H-pyran-3-yl ((2R,6S,7S,
9R,13aS,14aR,16aS,Z)-7-ethyl-9-methyl-14a-(((1-me-
thylcyclopropyl)sulfonyl)carbamoyl)-5,16-dioxo-2-
((2-(thiazol-2-yl)-6-(4-(trifluoromethyl)phenyl)
pyridin-4-yl)oxy)-2,3,5,6,7,9,10,11,13a,14,14a,15,16,
16a-tetradecahydro-1H-cyclopropa[i]pyrrolo[1,2-e][1,
5,8]oxadiazacyclopentadecin-6-yl)carbamate;

3-(trifluoromethyl)tetrahydro-2H-pyran-3-yl ((2R,6S,7R,
9R,13aS,14aR,16aS,Z)-2-((2-(4-isopropoxyphenyl)-6-
(thiazol-2-yl)pyridin-4-yl)oxy)-7,9-dimethyl-14a-(((1-
methylcyclopropyl)sulfonyl)carbamoyl)-5,16-dioxo-1,
2,3,5,6,7,8,9,10,11,13a,14,14a,15,16,16a-
hexadecahydrocyclopropa[e]pyrrolo[1,2-a][1,4]
diazacyclopentadecin-6-yl)carbamate;

3-(trifluoromethyl)tetrahydro-2H-pyran-3-yl ((2R,6S,7R,
9S,13aS,14aR,16aS,Z)-2-((2-(4-isopropoxyphenyl)-6-
(thiazol-2-yl)pyridin-4-yl)oxy)-7,9-dimethyl-14a-(((1-
methylcyclopropyl)sulfonyl)carbamoyl)-5,16-dioxo-1,
2,3,5,6,7,8,9,10,11,13a,14,14a,15,16,16a-
hexadecahydrocyclopropa[e]pyrrolo[1,2-a][1,4]
diazacyclopentadecin-6-yl)carbamate;

1,1,1-trifluoro-2-methylpropan-2-yl ((2R,6S,7R,9R,13aS,
14aR,16aS,Z)-7,9-dimethyl-14a-(((1-methylcyclopro-
pyl)sulfonyl)carbamoyl)-2-((2-(5-methylthiazol-2-yl)
pyridin-4-yl)oxy)-5,16-dioxo-1,2,3,5,6,7,8,9,10,11,
13a,14,14a,15,16,16a-hexadecahydrocyclopropa[e]
pyrrolo[1,2-a][1,4]diazacyclopentadecin-6-yl)
carbamate;

3-(trifluoromethyl)tetrahydro-2H-pyran-3-yl ((2R,6S,7R,
9R,13aS,14aR,16aS,Z)-7,9-dimethyl-14a-(((1-methyl-
cyclopropyl)sulfonyl)carbamoyl)-2-((2-(5-methylthi-
azol-2-yl)pyridin-4-yl)oxy)-5,16-dioxo-1,2,3,5,6,7,8,9,
10,11,13a,14,14a,15,16,16a-hexadecahydrocyclopropa
[e]pyrrolo[1,2-a][1,4]diazacyclopentadecin-6-yl)
carbamate;

1,1,1-trifluoro-2-methylpropan-2-yl ((2R,6S,7R,9R,13aS,
14aR,16aS,Z)-7,9-dimethyl-14a-(((1-methylcyclopro-
pyl)sulfonyl)carbamoyl)-2-((2-(4-methylthiazol-2-yl)
pyridin-4-yl)oxy)-5,16-dioxo-1,2,3,5,6,7,8,9,10,11,
13a,14,14a,15,16,16a-hexadecahydrocyclopropa[e]
pyrrolo[1,2-a][1,4]diazacyclopentadecin-6-yl)
carbamate;

1,1,1-trifluoro-2-methylpropan-2-yl ((2R,6S,7R,9R,13aS,
14aR,16aS,Z)-2-((6'-isopropoxy-6-(thiazol-2-yl)-[2,3'-
bipyridin]-4-yl)oxy)-7,9-dimethyl-14a-(((1-methylcy-
clopropyl)sulfonyl)carbamoyl)-5,16-dioxo-1,2,3,5,6,7,
8,9,10,11,13a,14,14a,15,16,16a-
hexadecahydrocyclopropa[e]pyrrolo[1,2-a][1,4]
diazacyclopentadecin-6-yl)carbamate;

3-(trifluoromethyl)tetrahydro-2H-pyran-3-yl ((2R,6S,7R,
9R,13aS,14aR,16aS,Z)-2-((6'-isopropoxy-6-(thiazol-2-
yl)-[2,3'-bipyridin]-4-yl)oxy)-7,9-dimethyl-14a-(((1-
methylcyclopropyl)sulfonyl)carbamoyl)-5,16-dioxo-1,
2,3,5,6,7,8,9,10,11,13a,14,14a,15,16,16a-
hexadecahydrocyclopropa[e]pyrrolo[1,2-a][1,4]
diazacyclopentadecin-6-yl)carbamate;

3-(trifluoromethyl)tetrahydro-2H-pyran-3-yl ((2R,6S,7R,
9R,13aS,14aR,16aS,Z)-2-((2-(4-isopropoxyphenyl)-6-
(pyrimidin-2-yl)pyridin-4-yl)oxy)-7,9-dimethyl-14a-
(((1-methylcyclopropyl)sulfonyl)carbamoyl)-5,16-
dioxo-1,2,3,5,6,7,8,9,10,11,13a,14,14a,15,16,16a-
hexadecahydrocyclopropa[e]pyrrolo[1,2-a][1,4]
diazacyclopentadecin-6-yl)carbamate;

3-(trifluoromethyl)tetrahydro-2H-pyran-3-yl ((2R,6S,7R,
9R,13aS,14aR,16aS,Z)-7,9-dimethyl-14a-(((1-methyl-
cyclopropyl)sulfonyl)carbamoyl)-5,16-dioxo-2-((6-
(thiazol-2-yl)-[2,3'-bipyridin]-4-yl)oxy)-1,2,3,5,6,7,8,
9,10,11,13a,14,14a,15,16,16a-
hexadecahydrocyclopropa[e]pyrrolo[1,2-a][1,4]
diazacyclopentadecin-6-yl)carbamate;

1,1,1-trifluoro-2-methylpropan-2-yl ((2R,6S,7R,9R,13aS,
14aR,16aS,Z)-7,9-dimethyl-14a-(((1-methylcyclopro-
pyl)sulfonyl)carbamoyl)-5,16-dioxo-2-((6-(thiazol-2-
yl)-[2,3'-bipyridin]-4-yl)oxy)-1,2,3,5,6,7,8,9,10,11,
13a,14,14a,15,16,16a-hexadecahydrocyclopropa[e]
pyrrolo[1,2-a][1,4]diazacyclopentadecin-6-yl)
carbamate;

3-(trifluoromethyl)tetrahydro-2H-pyran-3-yl ((2R,6S,7R,
9R,13aS,14aR,16aS,Z)-2-((6-(4-isopropoxyphenyl)-
[2,2'-bipyridin]-4-yl)oxy)-7,9-dimethyl-14a-(((1-meth-
ylcyclopropyl)sulfonyl)carbamoyl)-5,16-dioxo-1,2,3,
5,6,7,8,9,10,11,13a,14,14a,15,16,16a-
hexadecahydrocyclopropa[e]pyrrolo[1,2-a][1,4]
diazacyclopentadecin-6-yl)carbamate;

3-(trifluoromethyl)tetrahydro-2H-pyran-3-yl ((2R,6S,7R,
9R,13aS,14aR,16aS,Z)-2-((2-(4-isopropoxyphenyl)-6-
(thiazol-4-yl)pyridin-4-yl)oxy)-7,9-dimethyl-14a-(((1-
methylcyclopropyl)sulfonyl)carbamoyl)-5,16-dioxo-1,
2,3,5,6,7,8,9,10,11,13a,14,14a,15,16,16a-
hexadecahydrocyclopropa [e]pyrrolo[1,2-a][1,4]
diazacyclopentadecin-6-yl)carbamate;

1,1,1-trifluoro-2-methylpropan-2-yl ((2R,6S,7R,9R,13aS,
14aR,16aS,Z)-14a-((cyclopropylsulfonyl)carbamoyl)-
7-ethyl-9-methyl-5,16-dioxo-2-((2-(thiazol-2-yl)-6-(4-
(trifluoromethyl)phenyl)pyridin-4-yl)oxy)-1,2,3,5,6,7, 8,9,10,11,13a,14,14a,15,16,16a-hexadecahydrocyclopropa[e]pyrrolo[1,2-a][1,4]diazacyclopentadecin-6-yl)carbamate;

3-(trifluoromethyl)tetrahydro-2H-pyran-3-yl ((2R,6S,7R,9R,13aS,14aR,16aS,Z)-14a-((cyclopropylsulfonyl)carbamoyl)-7-ethyl-9-methyl-5,16-dioxo-2-((2-(thiazol-2-yl)-6-(4-(trifluoromethyl)phenyl)pyridin-4-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9R,13aS,14aR,16aS,Z)-7-ethyl-9-methyl-14a-(((1-methylcyclopropyl)sulfonyl)carbamoyl)-2-((2-(4-methylthiazol-2-yl)pyridin-4-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9R,13aS,14aR,16aS,Z)-14a-((cyclopropylsulfonyl)carbamoyl)-7-ethyl-2-((2-methoxy-6-(thiazol-2-yl)pyridin-4-yl)oxy)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

(1R,3r,5 S)-bicyclo[3.1.0]hexan-3-yl ((2R,6S,7R,9R,13aS,14aR,16aS,Z)-14a-((cyclopropylsulfonyl)carbamoyl)-7-ethyl-2-((2-(4-isopropoxyphenyl)-6-(thiazol-2-yl)pyridin-4-yl)oxy)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9R,13aS,14aR,16aS,Z)-2-((2,6-bis(5-methylthiazol-2-yl)pyridin-4-yl)oxy)-14a-((cyclopropylsulfonyl)carbamoyl)-7-ethyl-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9R,13aS,14aR,16aS,Z)-7,9-dimethyl-14a-(((1-methylcyclopropyl)sulfonyl)carbamoyl)-5,16-dioxo-2-((2-(thiazol-2-yl)-6-(p-tolyl)pyridin-4-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9R,13aS,14aR,16aS,Z)-7,9-dimethyl-14a-(((1-methylcyclopropyl)sulfonyl)carbamoyl)-5,16-dioxo-2-((2-phenyl-6-(thiazol-2-yl)pyridin-4-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9S,13aS,14aR,16aS,Z)-7,9-dimethyl-14a-(((1-methylcyclopropyl)sulfonyl)carbamoyl)-5,16-dioxo-2-((4-(thiazol-2-yl)pyridin-2-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9R,13aS,14aR,16aS,Z)-7,9-dimethyl-14a-(((1-methylcyclopropyl)sulfonyl)carbamoyl)-5,16-dioxo-2-((4-(thiazol-2-yl)pyridin-2-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9R,13aS,14aR,16aS,Z)-14a-((cyclopropylsulfonyl)carbamoyl)-7-ethyl-9-methyl-5,16-dioxo-2-((5-(thiazol-2-yl)pyridin-2-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9R,13aS,14aR,16aS,Z)-7,9-dimethyl-14a-(((1-methylcyclopropyl)sulfonyl)carbamoyl)-5,16-dioxo-2-((5-(thiazol-2-yl)pyridin-2-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

tert-butyl ((2R,6S,7R,9R,13aS,14aR,16aS,Z)-7,9-dimethyl-14a-(((1-methylcyclopropyl)sulfonyl)carbamoyl)-5,16-dioxo-2-((3-(trifluoromethyl)pyridin-2-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9R,13aS,14aR,16aS,Z)-7,9-dimethyl-14a-(((1-methylcyclopropyl)sulfonyl)carbamoyl)-5,16-dioxo-2-((3-(trifluoromethyl)pyridin-2-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9R,13aS,14aR,16aS,Z)-2-((4-chloro-3-(trifluoromethyl)pyridin-2-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9R,13aS,14aR,16aS,Z)-2-((6-methoxypyridin-2-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; and 1,1,1-trifluoro-2-methylpropan-2-yl ((2R,6S,7R,9R,13aS,14aR,16aS,Z)-2-((3-chloropyridin-2-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

or a pharmaceutically acceptable salt thereof.

9. A composition comprising a compound of formula (I), or a pharmaceutically acceptable salt thereof, and a pharmaceutically acceptable carrier.

10. The composition of claim 9 further comprising at least one additional compound having anti-HCV activity.

11. The composition of claim 10 wherein at least one of the additional compounds is an interferon or a ribavirin.

12. The composition of claim 11 wherein the interferon is selected from interferon alpha 2B, pegylated interferon alpha, pegylated interferon lambda, consensus interferon, interferon alpha 2A, and lymphoblastiod interferon tau.

13. The composition of claim 10 wherein at least one of the additional compounds is selected from interleukin 2, interleukin 6, interleukin 12, Imiquimod, ribavirin, an inosine 5'-monophosphate dehydrogenase inhibitor, amantadine, and rimantadine.

14. The composition of claim 10 wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

15. A method of treating an HCV infection in a patient, comprising administering to the patient a therapeutically effective amount of a compound of formula (I), or a pharmaceutically acceptable salt thereof.

16. The method of claim 15 further comprising administering at least one additional compound having anti-HCV activity prior to, after, or simultaneously with the compound of formula (I), or a pharmaceutically acceptable salt thereof.

17. The method of claim 16 wherein at least one of the additional compounds is an interferon or a ribavirin.

18. The method of claim 17 wherein the interferon is selected from interferon alpha 2B, pegylated interferon alpha, pegylated interferon lambda, consensus interferon, interferon alpha 2A, and lymphoblastiod interferon tau.

19. The method of claim 16 wherein at least one of the additional compounds is selected from interleukin 2, interleukin 6, interleukin 12, Imiquimod, ribavirin, an inosine 5'-monophosphate dehydrogenase inhibitor, amantadine, and rimantadine.

20. The method of claim 16 wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

* * * * *